(12) United States Patent
Jylhä et al.

(10) Patent No.: US 9,261,511 B2
(45) Date of Patent: Feb. 16, 2016

(54) ALLERGEN-BINDING IGE MONOCLONAL ANTIBODIES AND METHOD FOR PREPARING HYPOALLERGENS

(75) Inventors: Sirpa Jylhä, Espoo (FI); Merja Niemi, Joensuu (FI); Juha Rouvinen, Joensuu (FI); Marja-Leena Laukkanen, Espoo (FI); Kristiina Takkinen, Espoo (FI); Hans Söderlund, Espoo (FI); Soili Mäkinen-Kiljunen, Helsinki (FI); Tari Haahtela, Helsinki (FI)

(73) Assignee: DESENTUM OY, Espoo (FI)

( * ) Notice: Subject to any disclaimer, the term of this patent is extended or adjusted under 35 U.S.C. 154(b) by 962 days.

(21) Appl. No.: 12/523,151

(22) PCT Filed: Jan. 29, 2008

(86) PCT No.: PCT/FI2008/050026
§ 371 (c)(1),
(2), (4) Date: Oct. 27, 2009

(87) PCT Pub. No.: WO2008/092992
PCT Pub. Date: Aug. 7, 2008

(65) Prior Publication Data
US 2010/0086552 A1    Apr. 8, 2010

Related U.S. Application Data

(60) Provisional application No. 60/887,862, filed on Feb. 2, 2007.

(30) Foreign Application Priority Data

Jan. 29, 2007  (FI) .................................... 20075059

(51) Int. Cl.
*C12N 15/09*    (2006.01)
*G01N 33/53*    (2006.01)
*G01N 33/68*    (2006.01)
*C07K 16/18*    (2006.01)

(52) U.S. Cl.
CPC ............ *G01N 33/6854* (2013.01); *C07K 16/18* (2013.01); *G01N 33/6878* (2013.01); *C07K 2299/00* (2013.01); *G01N 2333/795* (2013.01); *G01N 2500/02* (2013.01); *G01N 2800/24* (2013.01)

(58) Field of Classification Search
None
See application file for complete search history.

(56) References Cited

U.S. PATENT DOCUMENTS

| | | |
|---|---|---|
| 2003/0175312 A1 | 9/2003 | Holm et al. |
| 2003/0207336 A1 | 11/2003 | Jardieu et al. |
| 2005/0181446 A1 | 8/2005 | Roggen et al. |

FOREIGN PATENT DOCUMENTS

| | | |
|---|---|---|
| EP | 1 512 695 A1 | 3/2005 |
| JP | 8-70866 A | 3/1996 |
| WO | WO-03/054216 A2 | 7/2003 |
| WO | WO-03/096869 A2 | 11/2003 |
| WO | WO-2006/125201 A3 | 11/2006 |

OTHER PUBLICATIONS

Bridges et al. 'Somatic mutation and CDR3 lengths of immunoglobulin kappa light chains expressed in patients with rheumatoid arthritis and in normal individuals.' J. Clin. Invest. 96:831-841, 1995.*
Kundrot et al. 'Which strategy for protein crystallization project?' Cell. Mol. Life Scio 61:525-53, 2004.*
Ngo et, al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Lebecque et al. 'Immunologic characterization of monoclonal antibodies that modulate human IgE binding to the major birch pollen allergen Bet v 1.' J. Aller. Clin. Immunol. 99(3):374-384, 1997.*
Gajhede et al. 'X-ray and NMR structure of Bet v 1, the origin of birch pollen allergy.' Nat. Struct. Biol. 3(12):1040-1045, 1996.*
Elsayed et al. 'Purification and N-Terminal Amino Acid Sequence of Two Birch Pollen Isoallergens (Bet v I and Bet v II).' Int. Arch. Allergy Appl. Immunol. 93:378-384, 1990.*
Blumenthal et al. 'Definition of an Allergen.' Allergens and Allergen Immunotherapy. Ed. R Lockey, S. Bukantz and J. Bousquet. New York: Marcel Decker, 37-50, 2004.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473.*
Spangfort, M D et al., "Dominating IgE-Binding Epitope of Bet v 1, the Major Allergen of Birch Pollen, Characterized by X-ray Crystallography and Site-Directed Mutagenesis", The Journal of Immunology 2003, vol. 171, pp. 3084-3090.
Swoboda, I et al., "Mutants of the major ryegrass pollen allergen, Lol p 5, with reduced IgE-binding capacity: candidates for grass pollen-specific immunotherapy", Eur. J. Immunol. 2002, vol. 32, pp. 270-280.
Venien, A et al., "Production and Epitopic Characterization of Monoclonal Antibodies Against Bovine β-Lactoglobulin", J. Dairy, Sci. 1997, vol. 80, No. 9, pp. 1977-1987.
Clement G et al., "Epitopic characterization of native bovine β-lactoglobulin", Journal of Immunological Methods 2002, vol. 266, pp. 67-78.

(Continued)

*Primary Examiner* — Nora Rooney
(74) *Attorney, Agent, or Firm* — Birch, Stewart, Kolasch & Birch, LLP

(57) ABSTRACT

The present invention relates to human IgE antibodies and derivatives thereof, which bind non-continuous planar allergenic epitope, such as in β-lactoglobulin, with high affinity and specificity. The present invention also relates to processes for making and engineering such allergen binding monoclonal antibodies and to methods for using these antibodies and derivatives thereof in the field of immunodiagnostics and immunotherapy.

7 Claims, 23 Drawing Sheets

(56) References Cited

OTHER PUBLICATIONS

Cho Y et al., "Probing the Retinol-binding Site of Bovine β-Lactoglobulin" The Journal of Biological Chemistry, Apr. 15 1994, vol. 269, No. 15, pp. 11102-11107.

Laver, W G et al., "Epitopes on Protein Antigens: Misconceptions and Realities", Cell, May 18, 1990, vol. 61, pp. 553-556.

Laukkanen, Marja-Leena et al., "Hevein-specific recombinant IgE antibodies from human single-chain antibody phage display libraries", Journal of Immunological Methods 2003, vol. 278, pp. 271-281.

Niemi, Merja et al., "Molecular Interactions between a Recombinant IgE Antibody and the β-Lactoglobulin Allergen", Structure Nov. 2007, vol. 15, pp. 1413-1421.

Jenkins, J. A. et al., "Structure relatedness of plant food allergens with specific reference to cross-reactive allergens: An in silico analysis", J. Allergy Clin. Immunol. Jan. 2005, vol. 115, pp. 163-170.

Hantusch, B et al., "Mapping of conformational IgE epitopes on Phl p 5a using mimotopes from a phage display library", J. Allergy Clin. Immunol. Dec. 2004, vol. 114, No. 6, pp. 1294-1300.

MacCallum, R. M. et al., "Antibody-antigen Interactions: Contact Analysis and Binding Site Technology", J. Mol. Biol. 1996, vol. 262, pp. 732-745.

* cited by examiner

Supplemental Figure 1: The flat IgE-binding epitope of D1-antibody. A) The dimensions of the flat face is measured by using a common molecular graphics program Pymol. The residues of BLG allergen making direct contacts with D1 antibody are in red, the residues of BLG allergen buried completeley or partially are in dark yellow. B) The similar view than in A but residues are coloured according to the secondary structure. Residues which are part of b-sheet are in purple, a-helices are in cyan, loops are in light brown. C) Side view of the flat epitope of BLG. The colouring is similar than in A. Antibody is shown as a ribbon model (H-chain in blue, L-chain in green). The average depth variation (rough) of the flat epitope is 6 Å, the maximum is 9 Å. D) For comparison, IgG binding convex epitope of Bet v 1 allergen (BDB code 1BV1) is shown in similar orientation than in C.

Figure 4

```
              10         20         30
D1VH     QVSLRESGGGLVQPGRSLRLSCTASGFTFR
              40         50         60
         HHGMTWVRQAPGKGLEWVASLSGSGTKTHF
              70         80         90
         ADSVKGRFTISRDNSNNTLYLQMDNVRDED
             100        110        120
         TAIYYCAKAKRVGATGYFDLWGRGTLVTVSS
```

Figure 5

```
              10         20         30
D1VL    DIVMTQSPSSLSASVGDRVTITCRASQGIS 40         50         60
        SRLAWYQQKPGKAPKLLIYAASSLQSGVPS 70         80         90
        RFSGSGSGTEFTLTISSLQPEDFATYYCQQ

100
        YHSYPWTFGQGTKVEIKR
```

IgE-Fab    β-lactoglobulin    IgE-Fab

SEQUENCE LISTING

<160> NUMBER OF SEQ ID NOS: 128

<210> SEQ ID NO 1
<211> LENGTH: 363
<212> TYPE: DNA
<213> ORGANISM: Homo sapiens

<400> SEQUENCE: 1

```
caggtcagct taagggagtc tgggggaggc ttggtgcagc ctgggaggtc cctgagactc    60
tcatgtacag cctctggatt caccttagg catcatggca tgacttgggt ccgccaggct   120
ccagggaagg gactggagtg ggtcgcatca ttaagtggga gtggtactaa aacacacttc   180
gcagactccg tgaagggccg attcaccatc tccagagaca actcgaacaa caccctgtat   240
```

```
ctccaaatgg acaacgtgag agacgaggac acggccatat attactgtgc gaaggctaag    300
agagtgggag ctactggata cttcgatctc tggggccgtg gcaccctggt caccgtctcc    360
tca                                                                  363
```

<210> SEQ ID NO 2
<211> LENGTH: 121
<212> TYPE: PRT
<213> ORGANISM: Homo sapiens

<400> SEQUENCE: 2

```
Gln Val Ser Leu Arg Glu Ser Gly Gly Leu Val Gln Pro Gly Arg
1               5                   10                  15

Ser Leu Arg Leu Ser Cys Thr Ala Ser Gly Phe Thr Phe Arg His His
            20                  25                  30

Gly Met Thr Trp Val Arg Gln Ala Pro Gly Lys Gly Leu Glu Trp Val
        35                  40                  45

Ala Ser Leu Ser Gly Ser Gly Thr Lys Thr His Phe Ala Asp Ser Val
    50                  55                  60

Lys Gly Arg Phe Thr Ile Ser Arg Asp Asn Ser Asn Asn Thr Leu Tyr
65                  70                  75                  80

Leu Gln Met Asp Asn Val Arg Asp Glu Asp Thr Ala Ile Tyr Tyr Cys
                85                  90                  95

Ala Lys Ala Lys Arg Val Gly Ala Thr Gly Tyr Phe Asp Leu Trp Gly
            100                 105                 110

Arg Gly Thr Leu Val Thr Val Ser Ser
        115                 120
```

<210> SEQ ID NO 3
<211> LENGTH: 324
<212> TYPE: DNA
<213> ORGANISM: Homo sapiens

<400> SEQUENCE: 3

```
gacatcgtga tgacccagtc tccatcctcc ctgtctgcat ctgtaggaga cagagtcacc    60
atcacttgcc gggccagtca gggtattagc agccggttag cctggtatca gcagaaacca    120
gggaaagccc ctaaactcct gatctacgct gcatccagtt tgcaaagtgg ggtcccatca    180
aggttcagcg gcagtggatc tgggacagag ttcactctca caatcagcag cctgcagcct    240
gaagattttg caacttatta ctgccaacag tatcatagtt acccgtggac gttcggccag    300
gggaccaagg tggagatcaa acgt                                           324
```

<210> SEQ ID NO 4
<211> LENGTH: 108
<212> TYPE: PRT
<213> ORGANISM: Homo sapiens

<400> SEQUENCE: 4

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
```

```
               65                  70                  75                  80
Glu Asp Phe Ala Thr Tyr Tyr Cys Gln Gln Tyr His Ser Tyr Pro Trp
                    85                  90                  95
Thr Phe Gly Gln Gly Thr Lys Val Glu Ile Lys Arg
            100                 105
```

<210> SEQ ID NO 5
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: x is any amino acid
<220> FEATURE:
<221> NAME/KEY: MISC_FEATURE
<222> LOCATION: (8)..(8)
<223> OTHER INFORMATION: x is Ser or Thr

<400> SEQUENCE: 5

```
Leu Leu Ile Tyr Xaa Ala Ser Xaa
1               5
```

<210> SEQ ID NO 6
<211> LENGTH: 11
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: X is any amino acid
<220> FEATURE:
<221> NAME/KEY: MISC_FEATURE
<222> LOCATION: (8)..(8)
<223> OTHER INFORMATION: X is Ser or Thr
<220> FEATURE:
<221> NAME/KEY: MISC_FEATURE
<222> LOCATION: (9)..(11)
<223> OTHER INFORMATION: X is any amino acid

<400> SEQUENCE: 6

```
Leu Leu Xaa Xaa Xaa Ala Ser Xaa Xaa Xaa Xaa
1               5                   10
```

<210> SEQ ID NO 7
<211> LENGTH: 11
<212> TYPE: PRT
<213> ORGANISM: Homo sapiens

<400> SEQUENCE: 7

```
Leu Leu Ile Tyr Ala Ala Ser Ser Leu Gln Ser
1               5                   10
```

<210> SEQ ID NO 8
<211> LENGTH: 162
<212> TYPE: PRT
<213> ORGANISM: Homo sapiens
<220> FEATURE:
<221> NAME/KEY: MISC_FEATURE
<223> OTHER INFORMATION: amino acid sequence of Beta-lactoglobulin

<400> SEQUENCE: 8

```
Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
            20                  25                  30

Asp Ala Gln Ser Ala Pro Leu Arg Val Tyr Val Glu Glu Leu Lys Pro
```

```
                35                  40                  45
Thr Pro Glu Gly Asp Leu Glu Ile Leu Leu Gln Lys Trp Glu Asn Gly
     50                  55                  60

Glu Cys Ala Gln Lys Lys Ile Ile Ala Glu Lys Thr Lys Ile Pro Ala
 65                  70                  75                  80

Val Phe Lys Ile Asp Ala Leu Asn Glu Asn Lys Val Leu Val Leu Asp
                 85                  90                  95

Thr Asp Tyr Lys Lys Tyr Leu Leu Phe Cys Met Glu Asn Ser Ala Glu
                100                 105                 110

Pro Glu Gln Ser Leu Ala Cys Gln Cys Leu Val Arg Thr Pro Glu Val
                115                 120                 125

Asp Asp Glu Ala Leu Glu Lys Phe Asp Lys Ala Leu Lys Ala Leu Pro
    130                 135                 140

Met His Ile Arg Leu Ser Phe Asn Pro Thr Gln Leu Glu Glu Gln Cys
145                 150                 155                 160

His Ile

<210> SEQ ID NO 9
<211> LENGTH: 168
<212> TYPE: PRT
<213> ORGANISM: Artificial Sequence
<220> FEATURE:
<223> OTHER INFORMATION: bovine recombinant BLG

<400> SEQUENCE: 9

Leu Ile Val Thr Gln Thr Met Lys Gly Leu Asp Ile Gln Lys Val Ala
 1               5                  10                  15

Gly Thr Trp Tyr Ser Leu Ala Met Ala Ala Ser Asp Ile Ser Leu Leu
                 20                  25                  30

Asp Ala Gln Ser Ala Pro Leu Arg Val Tyr Val Glu Glu Leu Lys Pro
             35                  40                  45

Thr Pro Glu Gly Asp Leu Glu Ile Leu Leu Gln Lys Trp Glu Asn Gly
     50                  55                  60

Glu Cys Ala Gln Lys Lys Ile Ile Ala Glu Lys Thr Lys Ile Pro Ala
 65                  70                  75                  80

Val Phe Lys Ile Asp Ala Leu Asn Glu Asn Lys Val Leu Val Leu Asp
                 85                  90                  95

Thr Asp Tyr Lys Lys Tyr Leu Leu Phe Cys Met Glu Asn Ser Ala Glu
                100                 105                 110

Pro Glu Gln Ser Leu Val Cys Gln Cys Leu Val Arg Thr Pro Glu Val
                115                 120                 125

Asp Asp Glu Ala Leu Glu Lys Phe Asp Lys Ala Leu Lys Ala Leu Pro
    130                 135                 140

Met His Ile Arg Leu Ser Phe Asn Pro Thr Gln Leu Glu Glu Gln Cys
145                 150                 155                 160

His Ile His His His His His His
                165

<210> SEQ ID NO 10
<211> LENGTH: 168
<212> TYPE: PRT
<213> ORGANISM: Artificial Sequence
<220> FEATURE:
<223> OTHER INFORMATION: bovine recombinant BLG mutant

<400> SEQUENCE: 10

Leu Ile Val Thr Gln Thr Met Lys Gly Leu Asp Ile Gln Lys Val Ala
```

```
            1               5                  10                 15
Gly Tyr Trp Tyr Ser Leu Ala Met Ala Ala Ser Asp Ile Ser Leu Leu
            20                 25                 30

Asp Ala Gln Ser Ala Pro Leu Arg Val Tyr Val Glu Glu Leu Lys Pro
            35                 40                 45

Thr Pro Glu Gly Asp Leu Glu Ile Leu Leu Gln Lys Trp Glu Asn Gly
            50                 55                 60

Glu Cys Ala Gln Lys Lys Ile Ile Ala Glu Lys Thr Lys Ile Pro Ala
 65                 70                 75                 80

Val Phe Lys Ile Asp Ala Leu Asn Glu Asn Lys Val Leu Val Leu Asp
                    85                 90                 95

Thr Asp Tyr Lys Lys Tyr Leu Leu Phe Cys Met Glu Asn Ser Ala Glu
                    100                105                110

Pro Glu Gln Ser Leu Val Cys Gln Cys Leu Val Arg Thr Pro Glu Val
                    115                120                125

Asp Asp Glu Ala Leu Glu Lys Phe Asp Lys Ala Leu Lys Ala Leu Pro
                    130                135                140

Met His Ile Arg Leu Ser Phe Asn Pro Thr Gln Leu Glu Glu Gln Cys
145                 150                155                160

His Ile His His His His His His
                    165
```

<210> SEQ ID NO 11
<211> LENGTH: 168
<212> TYPE: PRT
<213> ORGANISM: Artificial Sequence
<220> FEATURE:
<223> OTHER INFORMATION: bovine recombinant BLG mutant

<400> SEQUENCE: 11

```
Leu Ile Val Thr Gln Thr Met Lys Gly Leu Asp Ile Gln Lys Val Ala
 1              5                  10                 15

Gly Tyr Trp Tyr Ser Leu Ala Met Ala Ala Ser Asp Ile Ser Leu Leu
            20                 25                 30

Asp Ala Gln Ser Ala Pro Leu Arg Val Tyr Val Glu Tyr Leu Lys Pro
            35                 40                 45

Thr Pro Glu Gly Asp Leu Glu Ile Tyr Leu Gln Lys Trp Glu Asn Gly
            50                 55                 60

Glu Cys Ala Gln Lys Lys Ile Ile Ala Glu Lys Thr Lys Ile Pro Ala
 65                 70                 75                 80

Val Phe Lys Ile Asp Ala Leu Asn Glu Asn Lys Val Leu Val Leu Asp
                    85                 90                 95

Thr Asp Tyr Lys Lys Tyr Leu Leu Phe Cys Met Glu Asn Ser Ala Glu
                    100                105                110

Pro Glu Gln Ser Leu Val Cys Gln Cys Leu Val Arg Thr Pro Glu Val
                    115                120                125

Asp Asp Glu Ala Leu Glu Lys Phe Asp Lys Ala Leu Lys Ala Leu Pro
                    130                135                140

Met His Ile Arg Leu Ser Phe Asn Pro Thr Gln Leu Glu Glu Gln Cys
145                 150                155                160

His Ile His His His His His
                    165
```

<210> SEQ ID NO 12
<211> LENGTH: 27
<212> TYPE: DNA

```
<213> ORGANISM: Homo sapiens

<400> SEQUENCE: 12
gctgaaggtt ttgttgtcga cccagtc                                        27

<210> SEQ ID NO 13
<211> LENGTH: 34
<212> TYPE: DNA
<213> ORGANISM: Homo sapiens

<400> SEQUENCE: 13
gaatggtgcg gccgcgctga aggttttgtt gtcg                                34

<210> SEQ ID NO 14
<211> LENGTH: 30
<212> TYPE: DNA
<213> ORGANISM: Homo sapiens

<400> SEQUENCE: 14
atggccgcag ctcaggtkca gctggtgcag                                     30

<210> SEQ ID NO 15
<211> LENGTH: 30
<212> TYPE: DNA
<213> ORGANISM: Homo sapiens

<400> SEQUENCE: 15
atggccgcag ctcaggtcca gcttgtgcag                                     30

<210> SEQ ID NO 16
<211> LENGTH: 30
<212> TYPE: DNA
<213> ORGANISM: Homo sapiens

<400> SEQUENCE: 16
atggccgcag ctsaggtcca gctggtacag                                     30

<210> SEQ ID NO 17
<211> LENGTH: 30
<212> TYPE: DNA
<213> ORGANISM: Homo sapiens

<400> SEQUENCE: 17
atggccgcag ctcaratgca gctggtgcag                                     30

<210> SEQ ID NO 18
<211> LENGTH: 30
<212> TYPE: DNA
<213> ORGANISM: Homo sapiens

<400> SEQUENCE: 18
atggccgcag ctcagatcac cttgaaggag                                     30

<210> SEQ ID NO 19
<211> LENGTH: 30
<212> TYPE: DNA
<213> ORGANISM: Homo sapiens

<400> SEQUENCE: 19
atggccgcag ctcaggtcac cttgarggag                                     30

<210> SEQ ID NO 20
<211> LENGTH: 30
```

```
<212> TYPE: DNA
<213> ORGANISM: Homo sapiens

<400> SEQUENCE: 20
atggccgcag ctgargtgca gctggtggag                                  30

<210> SEQ ID NO 21
<211> LENGTH: 30
<212> TYPE: DNA
<213> ORGANISM: Homo sapiens

<400> SEQUENCE: 21
atggccgcag ctcaggtgca gctggtggag                                  30

<210> SEQ ID NO 22
<211> LENGTH: 30
<212> TYPE: DNA
<213> ORGANISM: Homo sapiens

<400> SEQUENCE: 22
atggccgcag ctgaggtgca gctgttggag                                  30

<210> SEQ ID NO 23
<211> LENGTH: 30
<212> TYPE: DNA
<213> ORGANISM: Homo sapiens

<400> SEQUENCE: 23
atggccgcag ctcagstgca gctgcaggag                                  30

<210> SEQ ID NO 24
<211> LENGTH: 30
<212> TYPE: DNA
<213> ORGANISM: Homo sapiens

<400> SEQUENCE: 24
atggccgcag ctcaggtgca gctacagcag                                  30

<210> SEQ ID NO 25
<211> LENGTH: 30
<212> TYPE: DNA
<213> ORGANISM: Homo sapiens

<400> SEQUENCE: 25
atggccgcag ctgargtgca gctggtgcag                                  30

<210> SEQ ID NO 26
<211> LENGTH: 30
<212> TYPE: DNA
<213> ORGANISM: Homo sapiens

<400> SEQUENCE: 26
atggccgcag ctcaggtaca gctgcagcag                                  30

<210> SEQ ID NO 27
<211> LENGTH: 30
<212> TYPE: DNA
<213> ORGANISM: Homo sapiens

<400> SEQUENCE: 27
atggccgcag ctcaggtsca gctggtgcaa                                  30

<210> SEQ ID NO 28
```

```
<211> LENGTH: 33
<212> TYPE: DNA
<213> ORGANISM: Homo sapiens

<400> SEQUENCE: 28
ttactcgcgg cccagccggc catggccgca gct                                33

<210> SEQ ID NO 29
<211> LENGTH: 37
<212> TYPE: DNA
<213> ORGANISM: Homo sapiens

<400> SEQUENCE: 29
aggtagggcg cgccttaaca ctctcccctg ttgaagc                            37

<210> SEQ ID NO 30
<211> LENGTH: 30
<212> TYPE: DNA
<213> ORGANISM: Homo sapiens

<400> SEQUENCE: 30
atggcagcgg ctracatcca gatgacccag                                    30

<210> SEQ ID NO 31
<211> LENGTH: 30
<212> TYPE: DNA
<213> ORGANISM: Homo sapiens

<400> SEQUENCE: 31
atggcagcgg ctgmcatcca gttgacccag                                    30

<210> SEQ ID NO 32
<211> LENGTH: 30
<212> TYPE: DNA
<213> ORGANISM: Homo sapiens

<400> SEQUENCE: 32
atggcagcgg ctgccatccr gatgacccag                                    30

<210> SEQ ID NO 33
<211> LENGTH: 30
<212> TYPE: DNA
<213> ORGANISM: Homo sapiens

<400> SEQUENCE: 33
atggcagcgg ctgtcatctg gatgacccag                                    30

<210> SEQ ID NO 34
<211> LENGTH: 30
<212> TYPE: DNA
<213> ORGANISM: Homo sapiens

<400> SEQUENCE: 34
atggcagcgg ctgatattgt gatgacccag                                    30

<210> SEQ ID NO 35
<211> LENGTH: 30
<212> TYPE: DNA
<213> ORGANISM: Homo sapiens

<400> SEQUENCE: 35
atggcagcgg ctgatrttgt gatgactcag                                    30
```

```
<210> SEQ ID NO 36
<211> LENGTH: 30
<212> TYPE: DNA
<213> ORGANISM: Homo sapiens

<400> SEQUENCE: 36
atggcagcgg ctgaaattgt gttgacrcag                                   30

<210> SEQ ID NO 37
<211> LENGTH: 30
<212> TYPE: DNA
<213> ORGANISM: Homo sapiens

<400> SEQUENCE: 37
atggcagcgg ctgaaatagt gatgacgcag                                   30

<210> SEQ ID NO 38
<211> LENGTH: 30
<212> TYPE: DNA
<213> ORGANISM: Homo sapiens

<400> SEQUENCE: 38
atggcagcgg ctgaaattgt aatgacacag                                   30

<210> SEQ ID NO 39
<211> LENGTH: 30
<212> TYPE: DNA
<213> ORGANISM: Homo sapiens

<400> SEQUENCE: 39
atggcagcgg ctgacatcgt gatgacccag                                   30

<210> SEQ ID NO 40
<211> LENGTH: 30
<212> TYPE: DNA
<213> ORGANISM: Homo sapiens

<400> SEQUENCE: 40
atggcagcgg ctgaaacgac actcacgcag                                   30

<210> SEQ ID NO 41
<211> LENGTH: 30
<212> TYPE: DNA
<213> ORGANISM: Homo sapiens

<400> SEQUENCE: 41
atggcagcgg ctgaaattgt gctgactcag                                   30

<210> SEQ ID NO 42
<211> LENGTH: 30
<212> TYPE: DNA
<213> ORGANISM: Homo sapiens

<400> SEQUENCE: 42
atggcagcgg ctgatgttgt gatgacacag                                   30

<210> SEQ ID NO 43
<211> LENGTH: 39
<212> TYPE: DNA
<213> ORGANISM: Homo sapiens

<400> SEQUENCE: 43
ttgttattgc tagctgcaca accagcaatg gcagcggct                         39
```

```
<210> SEQ ID NO 44
<211> LENGTH: 35
<212> TYPE: DNA
<213> ORGANISM: Homo sapiens

<400> SEQUENCE: 44
aggtagggcg cgccttatga acattcygya ggggc                              35

<210> SEQ ID NO 45
<211> LENGTH: 30
<212> TYPE: DNA
<213> ORGANISM: Homo sapiens

<400> SEQUENCE: 45
atggcagcgg ctcagtctgt gctgactcag                                    30

<210> SEQ ID NO 46
<211> LENGTH: 30
<212> TYPE: DNA
<213> ORGANISM: Homo sapiens

<400> SEQUENCE: 46
atggcagcgg ctcagtctgt gytgacgcag                                    30

<210> SEQ ID NO 47
<211> LENGTH: 30
<212> TYPE: DNA
<213> ORGANISM: Homo sapiens

<400> SEQUENCE: 47
atggcagcgg ctcagtctgt cgtgacgcag                                    30

<210> SEQ ID NO 48
<211> LENGTH: 30
<212> TYPE: DNA
<213> ORGANISM: Homo sapiens

<400> SEQUENCE: 48
atggcagcgg ctcagtctgc cctgactcag                                    30

<210> SEQ ID NO 49
<211> LENGTH: 30
<212> TYPE: DNA
<213> ORGANISM: Homo sapiens

<400> SEQUENCE: 49
atggcagcgg cttcctatgw gctgactcag                                    30

<210> SEQ ID NO 50
<211> LENGTH: 30
<212> TYPE: DNA
<213> ORGANISM: Homo sapiens

<400> SEQUENCE: 50
atggcagcgg cttcctatga gctgacacag                                    30

<210> SEQ ID NO 51
<211> LENGTH: 30
<212> TYPE: DNA
<213> ORGANISM: Homo sapiens

<400> SEQUENCE: 51
atggcagcgg cttcttctga gctgactcag                                    30
```

<210> SEQ ID NO 52
<211> LENGTH: 30
<212> TYPE: DNA
<213> ORGANISM: Homo sapiens

<400> SEQUENCE: 52
atggcagcgg cttcctatga gctgatgcag                                    30

<210> SEQ ID NO 53
<211> LENGTH: 30
<212> TYPE: DNA
<213> ORGANISM: Homo sapiens

<400> SEQUENCE: 53
atggcagcgg ctcagcytgt gctgactcaa                                    30

<210> SEQ ID NO 54
<211> LENGTH: 30
<212> TYPE: DNA
<213> ORGANISM: Homo sapiens

<400> SEQUENCE: 54
atggcagcgg ctcagsctgt gctgactcag                                    30

<210> SEQ ID NO 55
<211> LENGTH: 30
<212> TYPE: DNA
<213> ORGANISM: Homo sapiens

<400> SEQUENCE: 55
atggcagcgg ctaattttat gctgactcag                                    30

<210> SEQ ID NO 56
<211> LENGTH: 30
<212> TYPE: DNA
<213> ORGANISM: Homo sapiens

<400> SEQUENCE: 56
atggcagcgg ctcagrctgt ggtgactcag                                    30

<210> SEQ ID NO 57
<211> LENGTH: 30
<212> TYPE: DNA
<213> ORGANISM: Homo sapiens

<400> SEQUENCE: 57
atggcagcgg ctcagactgt ggtgacccag                                    30

<210> SEQ ID NO 58
<211> LENGTH: 30
<212> TYPE: DNA
<213> ORGANISM: Homo sapiens

<400> SEQUENCE: 58
atggcagcgg ctcwgcctgt gctgactcag                                    30

<210> SEQ ID NO 59
<211> LENGTH: 30
<212> TYPE: DNA
<213> ORGANISM: Homo sapiens

<400> SEQUENCE: 59

```
atggcagcgg ctcaggcagg gctgactcag                                    30
```

<210> SEQ ID NO 60
<211> LENGTH: 35
<212> TYPE: DNA
<213> ORGANISM: Homo sapiens

<400> SEQUENCE: 60

```
atttactcga gtgaggagac ggtgaccagg gtgcc                              35
```

<210> SEQ ID NO 61
<211> LENGTH: 35
<212> TYPE: DNA
<213> ORGANISM: Homo sapiens

<400> SEQUENCE: 61

```
atttactcga gtgaagagac ggtgaccatt gtccc                              35
```

<210> SEQ ID NO 62
<211> LENGTH: 35
<212> TYPE: DNA
<213> ORGANISM: Homo sapiens

<400> SEQUENCE: 62

```
atttactcga gtgaggagac ggtgaccagg gttcc                              35
```

<210> SEQ ID NO 63
<211> LENGTH: 35
<212> TYPE: DNA
<213> ORGANISM: Homo sapiens

<400> SEQUENCE: 63

```
atttactcga gtgaggagac ggtgaccgtg gtccc                              35
```

<210> SEQ ID NO 64
<211> LENGTH: 33
<212> TYPE: DNA
<213> ORGANISM: Homo sapiens

<400> SEQUENCE: 64

```
ttactcgcgg cccagccggc catggccgca gct                                33
```

<210> SEQ ID NO 65
<211> LENGTH: 34
<212> TYPE: DNA
<213> ORGANISM: Homo sapiens

<400> SEQUENCE: 65

```
ttatagagct cgacatccag atgacccagt ctcc                               34
```

<210> SEQ ID NO 66
<211> LENGTH: 34
<212> TYPE: DNA
<213> ORGANISM: Homo sapiens

<400> SEQUENCE: 66

```
ttatagagct cgatgttgtg atgactcagt ctcc                               34
```

<210> SEQ ID NO 67
<211> LENGTH: 34
<212> TYPE: DNA
<213> ORGANISM: Homo sapiens

<400> SEQUENCE: 67

```
ttatagagct cgaaattgtg ttgacgcagt ctcc                                    34
```

<210> SEQ ID NO 68
<211> LENGTH: 34
<212> TYPE: DNA
<213> ORGANISM: Homo sapiens

<400> SEQUENCE: 68

```
ttatagagct cgacatcgtg atgacccagt ctcc                                    34
```

<210> SEQ ID NO 69
<211> LENGTH: 34
<212> TYPE: DNA
<213> ORGANISM: Homo sapiens

<400> SEQUENCE: 69

```
ttatagagct cgaaacgaca ctcacgcagt ctcc                                    34
```

<210> SEQ ID NO 70
<211> LENGTH: 34
<212> TYPE: DNA
<213> ORGANISM: Homo sapiens

<400> SEQUENCE: 70

```
ttatagagct cgaaattgtg ctgactcagt ctcc                                    34
```

<210> SEQ ID NO 71
<211> LENGTH: 37
<212> TYPE: DNA
<213> ORGANISM: Homo sapiens

<400> SEQUENCE: 71

```
tataagcggc cgcacgtttg atttccacct tggtccc                                 37
```

<210> SEQ ID NO 72
<211> LENGTH: 37
<212> TYPE: DNA
<213> ORGANISM: Homo sapiens

<400> SEQUENCE: 72

```
tataagcggc cgcacgtttg atctccagct tggtccc                                 37
```

<210> SEQ ID NO 73
<211> LENGTH: 37
<212> TYPE: DNA
<213> ORGANISM: Homo sapiens

<400> SEQUENCE: 73

```
tataagcggc cgcacgtttg atatccactt tggtccc                                 37
```

<210> SEQ ID NO 74
<211> LENGTH: 37
<212> TYPE: DNA
<213> ORGANISM: Homo sapiens

<400> SEQUENCE: 74

```
tataagcggc cgcacgtttg atctccacct tggtccc                                 37
```

<210> SEQ ID NO 75
<211> LENGTH: 37
<212> TYPE: DNA
<213> ORGANISM: Homo sapiens

<400> SEQUENCE: 75
tataagcggc cgcacgttta atctccagtc gtgtccc                                37

<210> SEQ ID NO 76
<211> LENGTH: 34
<212> TYPE: DNA
<213> ORGANISM: Homo sapiens

<400> SEQUENCE: 76
atttagagct ccagtctgtg ttgacgcagc cgcc                                   34

<210> SEQ ID NO 77
<211> LENGTH: 34
<212> TYPE: DNA
<213> ORGANISM: Homo sapiens

<400> SEQUENCE: 77
atttagagct ccagtctgcc ctgactcagc ctgc                                   34

<210> SEQ ID NO 78
<211> LENGTH: 34
<212> TYPE: DNA
<213> ORGANISM: Homo sapiens

<400> SEQUENCE: 78
atttagagct ctcctatgtg ctgactcagc cacc                                   34

<210> SEQ ID NO 79
<211> LENGTH: 34
<212> TYPE: DNA
<213> ORGANISM: Homo sapiens

<400> SEQUENCE: 79
atttagagct ctcttctgag ctgactcagg accc                                   34

<210> SEQ ID NO 80
<211> LENGTH: 34
<212> TYPE: DNA
<213> ORGANISM: Homo sapiens

<400> SEQUENCE: 80
atttagagct ccacgttata ctgactcaac cgcc                                   34

<210> SEQ ID NO 81
<211> LENGTH: 34
<212> TYPE: DNA
<213> ORGANISM: Homo sapiens

<400> SEQUENCE: 81
atttagagct ccaggctgtg ctcactcagc cgtc                                   34

<210> SEQ ID NO 82
<211> LENGTH: 34
<212> TYPE: DNA
<213> ORGANISM: Homo sapiens

<400> SEQUENCE: 82
atttagagct caattttatg ctgactcagc ccca                                   34

<210> SEQ ID NO 83
<211> LENGTH: 37
<212> TYPE: DNA
<213> ORGANISM: Homo sapiens

<400> SEQUENCE: 83
atattgcggc cgcacctagg acggtgacct tggtccc                                37

<210> SEQ ID NO 84
<211> LENGTH: 37
<212> TYPE: DNA
<213> ORGANISM: Homo sapiens

<400> SEQUENCE: 84
atattgcggc cgcacctagg acggtcagct tggtccc                                37

<210> SEQ ID NO 85
<211> LENGTH: 37
<212> TYPE: DNA
<213> ORGANISM: Homo sapiens

<400> SEQUENCE: 85
atattgcggc cgcacctaaa acggtgagct gggtccc                                37

<210> SEQ ID NO 86
<211> LENGTH: 38
<212> TYPE: DNA
<213> ORGANISM: Homo sapiens

<400> SEQUENCE: 86
gctcaccgtc tcctcagcct ccacacagag cccatccg                               38

<210> SEQ ID NO 87
<211> LENGTH: 62
<212> TYPE: DNA
<213> ORGANISM: Homo sapiens

<400> SEQUENCE: 87
gcattgcatt gcggccgctt aatggtgatg gtgatgatgg ctgaaggttt tgttgtcgac       60
cc                                                                      62

<210> SEQ ID NO 88
<211> LENGTH: 33
<212> TYPE: DNA
<213> ORGANISM: Homo sapiens

<400> SEQUENCE: 88
ggtcaccgtc tcctcagcct ccaccaaggg ccc                                    33

<210> SEQ ID NO 89
<211> LENGTH: 57
<212> TYPE: DNA
<213> ORGANISM: Homo sapiens

<400> SEQUENCE: 89
tttagtttat gcggccgctt aatggtgatg atgatggtga caagatttgg gctctgc          57

<210> SEQ ID NO 90
<211> LENGTH: 20
<212> TYPE: DNA
<213> ORGANISM: Homo sapiens

<400> SEQUENCE: 90
actcattagg caccccaggc                                                   20

<210> SEQ ID NO 91

```
<211> LENGTH: 16
<212> TYPE: DNA
<213> ORGANISM: Homo sapiens

<400> SEQUENCE: 91
tgaggagacg gtgacc                                                    16

<210> SEQ ID NO 92
<211> LENGTH: 17
<212> TYPE: DNA
<213> ORGANISM: Homo sapiens

<400> SEQUENCE: 92
cgaactgtgg ctgcacc                                                   17

<210> SEQ ID NO 93
<211> LENGTH: 37
<212> TYPE: DNA
<213> ORGANISM: Homo sapiens

<400> SEQUENCE: 93
aggtagggcg cgccttaaca ctctcccctg ttgaagc                              37

<210> SEQ ID NO 94
<211> LENGTH: 56
<212> TYPE: DNA
<213> ORGANISM: Homo sapiens

<400> SEQUENCE: 94
ttgttattgc tagctgcaca accagcaatg gcagacatcg tgatgaccca gtctcc         56

<210> SEQ ID NO 95
<211> LENGTH: 38
<212> TYPE: DNA
<213> ORGANISM: Homo sapiens

<400> SEQUENCE: 95
ggtgcagcca cagttcgttt gatytccasc ttggtccc                             38

<210> SEQ ID NO 96
<211> LENGTH: 11
<212> TYPE: PRT
<213> ORGANISM: artificial sequence
<220> FEATURE:
<223> OTHER INFORMATION: synthetic peptide

<400> SEQUENCE: 96

Ser Gln Ser Ile Gly Asn Tyr Leu Asn Trp Tyr
1               5                   10

<210> SEQ ID NO 97
<211> LENGTH: 11
<212> TYPE: PRT
<213> ORGANISM: Artificial Sequence
<220> FEATURE:
<223> OTHER INFORMATION: synthetic sequence

<400> SEQUENCE: 97

Ser Gln Thr Phe Asn Asn Tyr Leu Asn Trp Tyr
1               5                   10

<210> SEQ ID NO 98
<211> LENGTH: 11
<212> TYPE: PRT
<213> ORGANISM: Artificial Sequence
```

```
<220> FEATURE:
<223> OTHER INFORMATION: synthetic peptide

<400> SEQUENCE: 98

Ser Arg Thr Ile Tyr Asn Tyr Leu Asn Trp Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: synthetic peptide

<400> SEQUENCE: 99

Ser Gln Ser Ile Ser Ser Tyr Leu Asn Trp Tyr
1               5                   10

<210> SEQ ID NO 100
<211> LENGTH: 11
<212> TYPE: PRT
<213> ORGANISM: Artificial Sequence
<220> FEATURE:
<223> OTHER INFORMATION: synthetic peptide

<400> SEQUENCE: 100

Ser His Ser Ile Ser Asn Tyr Leu Asn Trp Tyr
1               5                   10

<210> SEQ ID NO 101
<211> LENGTH: 11
<212> TYPE: PRT
<213> ORGANISM: Artificial Sequence
<220> FEATURE:
<223> OTHER INFORMATION: synthetic peptide

<400> SEQUENCE: 101

Ser Gln Ser Ile Leu Gly Tyr Leu Asn Trp Tyr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: artificial sequence

<400> SEQUENCE: 102

Ser Gln Gly Ile Ser Ser Trp Leu Ala Trp Tyr
1               5                   10

<210> SEQ ID NO 103
<211> LENGTH: 12
<212> TYPE: PRT
<213> ORGANISM: Artificial Sequence
<220> FEATURE:
<223> OTHER INFORMATION: synthetic sequence

<400> SEQUENCE: 103

Ser Gln Ser Val Ser Ser Ser Tyr Leu Ala Trp Tyr
1               5                   10

<210> SEQ ID NO 104
<211> LENGTH: 11
<212> TYPE: PRT
<213> ORGANISM: Artificial Sequence
<220> FEATURE:
```

```
<223> OTHER INFORMATION: synthetic sequence

<400> SEQUENCE: 104

Ser Gln Ser Ile Ser Ser Tyr Leu Asn Trp Tyr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: synthetic sequence

<400> SEQUENCE: 105

Ser Gln Gly Ile Ser Ser Arg Leu Ala Trp Tyr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: synthetic sequence

<400> SEQUENCE: 106

Leu Leu Ile Tyr Ala Ala Ser Thr Leu Arg Arg
1               5                   10

<210> SEQ ID NO 107
<211> LENGTH: 11
<212> TYPE: PRT
<213> ORGANISM: Artificial Sequence
<220> FEATURE:
<223> OTHER INFORMATION: synthetic sequence

<400> SEQUENCE: 107

Leu Leu Ile His Ala Ala Ser Thr Leu Gln Asp
1               5                   10

<210> SEQ ID NO 108
<211> LENGTH: 11
<212> TYPE: PRT
<213> ORGANISM: Artificial Sequence
<220> FEATURE:
<223> OTHER INFORMATION: synthetic sequence

<400> SEQUENCE: 108

Leu Leu Ile Tyr Ala Ala Ser Thr Leu Gln Ser
1               5                   10

<210> SEQ ID NO 109
<211> LENGTH: 11
<212> TYPE: PRT
<213> ORGANISM: Artificial Sequence
<220> FEATURE:
<223> OTHER INFORMATION: synthetic sequence

<400> SEQUENCE: 109

Leu Leu Ile Tyr Ser Ala Ser Ser Leu Gln Ser
1               5                   10

<210> SEQ ID NO 110
<211> LENGTH: 11
<212> TYPE: PRT
<213> ORGANISM: Artificial Sequence
<220> FEATURE:
<223> OTHER INFORMATION: synthetic sequence
```

<400> SEQUENCE: 110

Leu Leu Ile Tyr Gly Ala Ser Ser Arg Ala Thr
1               5                   10

<210> SEQ ID NO 111
<211> LENGTH: 9
<212> TYPE: PRT
<213> ORGANISM: Artificial Sequence
<220> FEATURE:
<223> OTHER INFORMATION: synthetic sequence

<400> SEQUENCE: 111

Gln Gln Ser Tyr Ser Thr Pro Arg Thr
1               5

<210> SEQ ID NO 112
<211> LENGTH: 12
<212> TYPE: PRT
<213> ORGANISM: Artificial Sequence
<220> FEATURE:
<223> OTHER INFORMATION: synthetic sequence

<400> SEQUENCE: 112

Ala Ala Trp Asp Asp Ser Leu Ser Gly Arg Val Val
1               5                   10

<210> SEQ ID NO 113
<211> LENGTH: 10
<212> TYPE: PRT
<213> ORGANISM: Artificial Sequence
<220> FEATURE:
<223> OTHER INFORMATION: synthetic sequence

<400> SEQUENCE: 113

Gln Gln Arg Ser Asn Trp Pro Pro Leu Thr
1               5                   10

<210> SEQ ID NO 114
<211> LENGTH: 10
<212> TYPE: PRT
<213> ORGANISM: Artificial Sequence
<220> FEATURE:
<223> OTHER INFORMATION: synthetic sequence

<400> SEQUENCE: 114

Gln Gln Ser Asn Arg Thr Pro Ile Thr Phe
1               5                   10

<210> SEQ ID NO 115
<211> LENGTH: 10
<212> TYPE: PRT
<213> ORGANISM: Artificial Sequence
<220> FEATURE:
<223> OTHER INFORMATION: synthetic sequence

<400> SEQUENCE: 115

Gln Gln Ser Tyr Ser Thr Pro Leu Thr Phe
1               5                   10

<210> SEQ ID NO 116
<211> LENGTH: 10
<212> TYPE: PRT
<213> ORGANISM: Artificial Sequence
<220> FEATURE:
<223> OTHER INFORMATION: synthetic sequence

```
<400> SEQUENCE: 116

Gln Gln Ser His Gly Thr Pro Leu Thr Phe
1               5                   10

<210> SEQ ID NO 117
<211> LENGTH: 10
<212> TYPE: PRT
<213> ORGANISM: Artificial Sequence
<220> FEATURE:
<223> OTHER INFORMATION: synthetic sequence

<400> SEQUENCE: 117

Gln Gln Ser His Ser Thr Pro Tyr Thr Phe
1               5                   10

<210> SEQ ID NO 118
<211> LENGTH: 10
<212> TYPE: PRT
<213> ORGANISM: Artificial Sequence
<220> FEATURE:
<223> OTHER INFORMATION: synthetic sequence

<400> SEQUENCE: 118

Gln Glu Ser Phe Ser Pro Ser Gly Thr Phe
1               5                   10

<210> SEQ ID NO 119
<211> LENGTH: 10
<212> TYPE: PRT
<213> ORGANISM: Artificial Sequence
<220> FEATURE:
<223> OTHER INFORMATION: synthetic sequence

<400> SEQUENCE: 119

Gln Gln Ser Tyr Ile Thr Pro Arg Thr Phe
1               5                   10

<210> SEQ ID NO 120
<211> LENGTH: 10
<212> TYPE: PRT
<213> ORGANISM: Artificial Sequence
<220> FEATURE:
<223> OTHER INFORMATION: synthetic sequence

<400> SEQUENCE: 120

Gln Gln Ala Asn Ser Phe Pro Tyr Thr Phe
1               5                   10

<210> SEQ ID NO 121
<211> LENGTH: 10
<212> TYPE: PRT
<213> ORGANISM: Artificial Sequence
<220> FEATURE:
<223> OTHER INFORMATION: synthetic sequence

<400> SEQUENCE: 121

Gln Gln Tyr Gly Ser Ser Pro Leu Thr Phe
1               5                   10

<210> SEQ ID NO 122
<211> LENGTH: 10
<212> TYPE: PRT
<213> ORGANISM: Artificial Sequence
<220> FEATURE:
<223> OTHER INFORMATION: synthetic sequence

<400> SEQUENCE: 122
```

```
Gln Gln Ser Tyr Ser Thr Pro Arg Thr Phe
1               5                   10

<210> SEQ ID NO 123
<211> LENGTH: 10
<212> TYPE: PRT
<213> ORGANISM: Artificial Sequence
<220> FEATURE:
<223> OTHER INFORMATION: synthetic sequence

<400> SEQUENCE: 123

Gln Gln Tyr His Ser Tyr Pro Trp Thr Phe
1               5                   10

<210> SEQ ID NO 124
<211> LENGTH: 39
<212> TYPE: DNA
<213> ORGANISM: Artificial Sequence
<220> FEATURE:
<223> OTHER INFORMATION: bovine primer

<400> SEQUENCE: 124
gaatccgcgg cccagccggc catggccctg attgtgacc                          39

<210> SEQ ID NO 125
<211> LENGTH: 55
<212> TYPE: DNA
<213> ORGANISM: Artificial Sequence
<220> FEATURE:
<223> OTHER INFORMATION: bovine primer

<400> SEQUENCE: 125
ttactcaagc ttttaatggt gatggtgatg atgaatatgg cactgttctt ccagc        55

<210> SEQ ID NO 126
<211> LENGTH: 48
<212> TYPE: DNA
<213> ORGANISM: Artificial Sequence
<220> FEATURE:
<223> OTHER INFORMATION: bovine primer

<400> SEQUENCE: 126
ccatgaaagg cctggatatt cagaaagtgg cgggctactg gtatagcc                48

<210> SEQ ID NO 127
<211> LENGTH: 55
<212> TYPE: DNA
<213> ORGANISM: Artificial Sequence
<220> FEATURE:
<223> OTHER INFORMATION: bovine primer

<400> SEQUENCE: 127
ataaatttcc agatcgcctt ccggggtcgg tttcagatat tccacataca cacgc        55

<210> SEQ ID NO 128
<211> LENGTH: 31
<212> TYPE: DNA
<213> ORGANISM: Artificial Sequence
<220> FEATURE:
<223> OTHER INFORMATION: bovine primer

<400> SEQUENCE: 128
ggcgatctgg aaatttatct gcagaaatgg g                                  31
```

ALLERGEN-BINDING IGE MONOCLONAL ANTIBODIES AND METHOD FOR PREPARING HYPOALLERGENS

This application is the National Phase of PCT/FI2008/050026 filed on Jan. 29, 2008, which claims priority under 35 U.S.C. 119(e) to U.S. Provisional Application No. 60/887,862 filed on Feb. 2, 2007, and under 35 U.S.C. 119(a) to Patent Application No. 20075059 filed in Finland on Jan. 29, 2007, all of which are hereby expressly incorporated by reference into the present application.

FIELD OF THE INVENTION

This invention relates to protein engineering technology. More particularly, the present invention relates to human IgE antibodies and derivatives thereof, which bind non-continuous allergenic epitope, a planar surface with the area of 600-900 Å$^2$, e.g. IgE antibodies binding to bovine milk β-lactoglobulin with high affinity and specificity. The present invention also relates to processes for making and engineering such allergen-binding monoclonal antibodies with Type I interaction and to methods for using these antibodies and derivatives thereof in the field of immunodiagnostics, enabling qualitative and quantitative determination and removal of allergenic substances in biological and raw material samples, as well as the construction of focused IgE libraries towards allergens, enabling the development of allergen-specific antibodies. In immunotherapy, the present invention enables blocking the Type I surface interaction of allergenic substances by modifying amino acid residues of allergens. Hypoallergen variant can be obtained by mutating some (1-5) amino acid residues on the planar (flat) epitope surface with bulky residues (such as Arg, Tyr, Lys, Trp). The mutated residues are those which side chains are pointing outside towards solvent thus causing minimal change to the basic structure of the allergen. The purpose of the mutagenesis is to modify the flat surface to convex surface which prevent the binding of IgE-antibodies. The resulting modified allergen can be used to evoke tolerance against particular allergens in allergic patients. The present invention allows the development of human IgE VH-region derived antibodies for those therapeutic and diagnostic targets where the binding specificity is towards areas of protein structures that are not located on the protruding regions of the surface. The invention also provides means for screening or molecular modelling of substances capable of blocking the binding of an antibody to the Type I allergenic epitope. In this invention, the development, characterisation and structure determination of the human IgE antibody fragment and derivatives thereof that binds allergenic β-lactoglobulin with affinity and specificity high enough to be utilised as reagents in immunoassays are also described.

BACKGROUND OF THE INVENTION

Almost 20% of the population world-wide are suffering from allergy. Consequently, it is a health problem of increasing seriousness. Allergy is a hypersensitivity reaction against substances in air, food or water, which are normally harmless (Corry and Kheradmand, 1999). A new and foreign external agent triggers an allergic reaction, which aims at disposal of that agent from the body. In IgE-mediated allergic reactions, also called immediate or type I hypersensitivity reactions, under the first exposure of a foreign substance, allergen, to the body, IgE-bearing B-cells begin to produce soluble IgE molecules which will then bind to high-affinity IgE receptors present on the surface of a wide variety of cells, most importantly to mast cells and basophils. If the same foreign substance is encountered again, the cross-linking of the receptor-bound IgE molecules by the allergen occurs, resulting in cellular activation followed by the release of toxic products such as histamine, which will elicit the signs and symptoms of an allergic reaction.

Cow's milk allergy (CMA) is a most common cause of clinically important adverse food reactions with infants and children during the first 2 years of life (Savilahti, 1981; Host and Halken, 1990; Saarinen et al., 1999). It is characterized by a strong IgE response to milk proteins and clinical symptoms in skin and gastrointestinal tract such as atopic eczema, vomiting and diarrhoea (Vaarala et al., 1995; Saarinen, 2000). Symptoms in respiratory ducts and anaphylactic shock are also possible (Host and Halken, 1990; Schrander et al., 1993; Hill et al., 1999; Vanto et al., 1999; Saarinen, 2000). CMA is a serious problem with children, because milk is an important source of energy (up to 50%) for young children and is not very easily replaceable with non-dairy products. Nearly 85% of the milk allergic children will outgrow of their allergy by the age of 3, but remission of CMA may occur in up to one-third of older children (Sampson and Scanlon, 1989)

One of the major allergens in cow's milk is β-lactoglobulin, which belongs to the protein family known as lipocalins. Lipocalins consists a group of a small ligand binding proteins, mostly respiratory allergens such as Mus m1, Rat n1 (mouse and rat urinary proteins) and a German cockroach allergen Bla g4 (Rouvinen et al. 2001). β-lactoglobulin occurs naturally in the form of a 36 kD dimer with each subunit corresponding 162 amino acids. Totally six genetic variants of the β-lactoglobulin has been identified based on the sequence differences. The most prevalent variants A and B differ only at the position 64 (Asp→Gly) and 118 (Val→Ala) (Godovac-Zimmermann and Braunitzer, 1987). The 3D-structure of the β-lactoglobulin has been determined by X-ray diffraction (Sawyer L. et al, 1985, Brownlow, S. et al, 1997)

IgE antibodies distinctively recognise allergenic epitopes, which would be useful in clinics and immunodiagnostics for detecting and determining allergen concentrations of complex materials. Further, according to this invention, allergenic epitopes are usually different from the immunogenic epitopes of proteins. This fact has hampered the production of monoclonal antibodies capable of specific binding of allergenic epitopes by conventional methodology such as hybridoma technology. It has been recently shown that the development of allergen-specific IgE antibodies is possible by the phage display technology (Steinberger et al., 1996). This methodology is giving new tools to produce allergen-specific recombinant antibodies that can be produced in consistent quality for clinical and diagnostic applications.

The technical problem to which the present invention is related is the detection of actual binding sites of IgE antibodies in allergenic polypeptides and use of this information, e.g., to modify these polypeptides to decrease their allergenicity. Previous solutions for this problem are disclosed in U.S. Patent Application No. 2003/0175312 (Holm et al.), WO 03/096869 (Alk Abello A/S) and Jenkins et al. 2005 (J. Allergy Clin. Immunol. 115:163-170). In these documents, it is described that the putative IgE binding sites in allergenic polypeptides may be detected by sequence analysis of conserved surface structures of allergenic polypeptides. Further, in US 2005/0181446 (Roggen et al.) and Hantusch et al. 2004 (J. Allergy Clin. Immunol.) a peptide-scan approach is used to find IgE binding epitopes. However, none of these documents discloses the method of the present invention wherein an IgE binding site on an allergenic polypeptide is found based on the experimental 3D and molecular modelling data of a novel type of IgE epitope having essentially planar or flat nature. MacCallum et al. 1996 (J. Mol. Biol. 262:732-745) disclose the presence of planar surfaces on antibodies, but teach only modification of antibody structures not antigen structures. Further, the disclosure of MacCallum et al. is directed to antibodies and different kinds of antigens, such as carbohydrates and peptides, in general and does not teach anything particular on the binding between IgE antibodies and allergenic polypeptides or the surface structures of these polypeptides.

SUMMARY OF THE INVENTION

The present invention relates to human IgE antibodies and derivatives thereof, which bind to non-continuous allergenic epitope, a planar Type I surface with the area of 600-900 Å$^2$, e.g. to IgE antibodies binding to bovine milk β-lactoglobulin with high affinity and specificity. The present invention also enables blocking the Type I surface interaction of allergenic substances by modifying amino acid residues of said surface structure or by producing a mimetope binding said surface.

We also describe in this application the development, characterisation and structure determination of the human IgE antibody fragment and derivatives thereof that binds allergenic β-lactoglobulin with affinity and specificity high enough to be utilised as reagents in immunoassays designed for the qualitative and quantitative measurement of β-lactoglobulin in biological samples, in removal of the β-lactoglobulin, in immunotherapy of allergic patients and in the construction of focused antibody libraries based on the structural data. Specifically, the present invention describes selection of human IgE antibodies specific to β-lactoglobulin by the phage display technique, the characterisation of the binding properties of the engineered antibody fragments produced in *E. coli*, and structure determination of the antibody-allergen immunocomplex.

This invention thus provides new reagents to be utilised in different kinds of immunoassay protocols, as well as in human immunotherapy and construction of focused antibody libraries. The invention also permits guaranteed continuous supply of these specific reagents of uniform quality, eliminating inherent batch-to-batch variation of polyclonal antisera. These advantageous effects permit the manufacture of new, specific and economical immunodiagnostic assays of uniform quality.

Consequently, one specific object of the present invention is to provide human IgE monoclonal antibodies, fragments thereof, or other derivatives of such antibodies, which bind β-lactoglobulin with affinity and specificity high enough to allow qualitative and quantitative measurement of β-lactoglobulin in biological samples, as well as their use in immunotherapy. The monovalent antibodies of the present invention demonstrate a specific binding to allergenic β-lactoglobulin.

Another object of the present invention is to provide cDNA clones encoding β-lactoglobulin-specific antibody chains, as well as constructs and methods for expression of such clones to produce β-lactoglobulin-binding antibodies, fragments thereof or other derivatives of such antibodies.

A further object of this invention is to provide methods of using such β-lactoglobulin-binding antibodies, fragments thereof or other derivatives of such antibodies, or combinations of them for qualitative and quantitative measurement of β-lactoglobulin in biological samples. Additionally, this invention provides β-lactoglobulin-binding antibodies, fragments thereof or other derivatives of such antibodies, or combinations of them for immunotherapy in allergic patients.

A further object of this invention is to provide methods of using structural data obtained for constructing focused IgE antibody libraries towards allergens for diagnostics and human IgE VH-region derived antibody libraries for therapeutic and diagnostic targets where the binding specificity is towards areas of protein structures that are not located on the protruding regions of the surface.

Other objects, features and advantages of the present invention will be become apparent from the following drawings and detailed description. It should be understood, however, that the detailed description and the specific examples, while indicating preferred embodiments of the invention, are given for illustration only, since various changes and modifications within the spirit and scope of the invention will become apparent to those skilled in the art from this detailed description.

BRIEF DESCRIPTION OF THE DRAWINGS

FIG. 1 shows a schematic presentation of an intact human IgE subclass antibody, Fab fragment and single-chain antibody (scFv). The antigen-binding site is indicated by a triangle.

FIG. 4 shows the deduced amino acid and nucleotide sequence of the heavy chain variable region of the D1 IgE Fab (SEQ ID NO: 2). The Complementarity Determining Regions (CDRs) are underlined. Numbering is according to Kabat (Kabat et al., 1991).

FIG. 5 shows the deduced amino acid and nucleotide sequence of the light chain variable region of the D1 IgE Fab (SEQ ID NO: 4). CDRs are underlined. Numbering is according to Kabat (Kabat et al., 1991).

Figure 2:
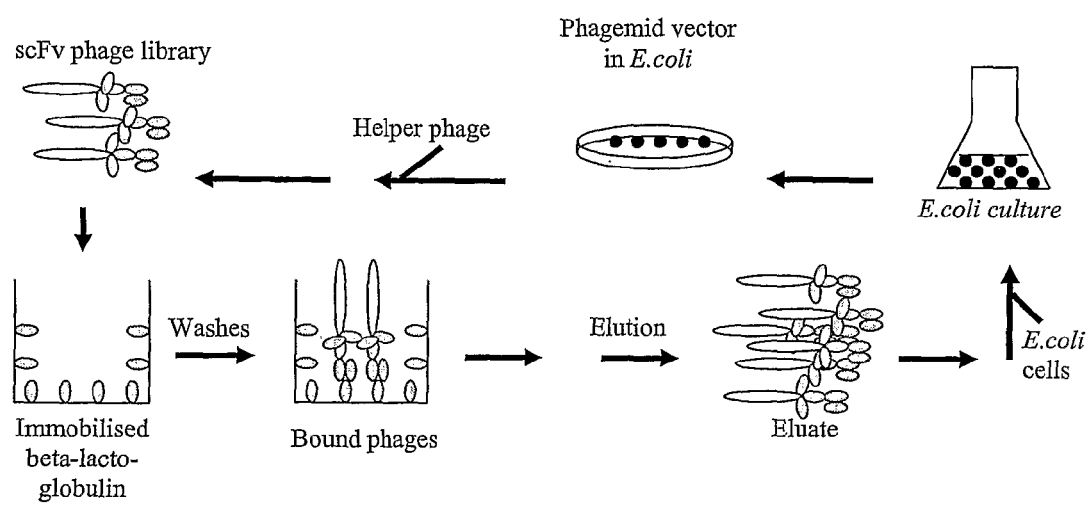
FIG. 2 shows schematically the panning procedure.

The figures of the constructions are not in scale.

ABBREVIATIONS cDNA complementary deoxyribonucleic acid
CDR complementarity determining region
DNA deoxyribonucleic acid
*E. coli Escherichia coli*
ELISA enzyme-linked immunosorbent assay
Fab fragment with specific antigen binding
Fd variable and first constant domain of a heavy chain
Fv variable regions of an antibody with specific antigen binding
IgE immunoglobulin E
mRNA messenger ribonucleic acid
NMR nuclear magnetic resonance
PCR polymerase chain reaction
RNA ribonucleic acid
scFv single-chain antibody
supE$^-$ a genotype of bacterial strain carrying a glutamine-inserting amber suppressor tRNA
$V_H$ variable region of a heavy chain
$V_L$ variable region of a light chain

DETAILED DESCRIPTION OF THE INVENTION

The following definitions are provided for some terms used in this specification. The terms, "immunoglobulin", "heavy chain", "light chain" and "Fab" are used in the same way as in the European Patent Application No. 0125023.

"Antibody" in its various grammatical forms is used herein as a collective noun that refers to a population of immunoglobulin molecules and/or immunologically active portions of immunoglobulin molecules, i.e., molecules that contain an antigen binding site or a paratope.

An "antigen-binding site", a "paratope", is the structural portion of an antibody molecule that specifically binds an antigen.

Exemplary antibodies are those portions of an immunoglobulin molecule that contain the paratope, including those portions known as Fab and Fv.

"Fab" (fragment with specific antigen binding), a portion of antibodies can be prepared by the proteolytic reaction of papain on substantially intact antibodies by methods that are well known. See for example, U.S. Pat. No. 4,342,566. Fab fragments can also be produced by recombinant methods, which are well known to those skilled in the art. See, for example, U.S. Pat. No. 4,949,778.

"Domain" is used to describe an independently folding part of a protein. General structural definitions for domain borders in natural proteins are given in Argos, 1988.

A "variable domain" or "Fv" is used to describe those regions of the immunoglobulin molecule, which are responsible for antigen or hapten binding. Usually these consist of approximately the first 100 amino acids of the N-termini of the light and the heavy chain of the immunoglobulin molecule.

"Single-chain antibody" (scFv) is used to define a molecule in which the variable domains of the heavy and light chain of an antibody are joined together via a linker peptide to form a continuous amino acid chain synthesised from a single mRNA molecule (transcript).

"Linker" or "linker peptide" is used to describe an amino acid sequence that extends between adjacent domains in a natural or engineered protein.

A "β-lactoglobulin-binding antibody" is an antibody, which specifically recognises β-lactoglobulin and binds to it, due to interaction mediated by its variable domains. As used herein, the term "specifically binding" or "specifically recognizing" or the expression "having binding specificity to an allergenic epitope of β-lactoglobulin" refers to a low background and high affinity binding between an antibody or a fragment or derivative thereof and its target molecule (i.e. lack of non-specific binding). One of the embodiments of the present invention is a monoclonal antibody having binding specificity to an allergenic epitope of β-lactoglobulin (SEQ ID NO:8), or a functional fragment or derivative thereof having said specificity.

The term "planar (or flat) surface" refers to the surface structure as defined in Example 8.

As examples of fragments of such antibodies falling within the scope of the invention we disclose here scFv fragments of D1 IgE fab as shown in FIGS. 4 and 5. In one preferred embodiment, the present invention thus provides derivatives of β-lactoglobulin-binding antibodies, e.g. Fab fragments or scFv fragments. It will be appreciated that mutant versions of the CDR sequences or complete $V_L$ and $V_H$ sequences having one or more conservative substitutions which do not substantially affect binding capability, may alternatively be employed and are included into the scope of the invention.

For use in immunoassay, e.g. for qualitative or quantitative determination of β-lactoglobulin in biological samples, antibodies and antibody derivatives of the invention may be labelled. For these purposes, any type of label conventionally employed for antibody labelling is acceptable.

For use in immunotherapy, e.g. for blocking allergenic β-lactoglobulin in allergic patients, antibodies and antibody derivatives of the invention may be labelled. For these purposes, any pharmaceutically acceptable label conventionally employed for antibody labelling is appropriate (see, e.g., US 2007/0003579).

In another aspect, the present invention also provides DNA molecules encoding an antibody or antibody derivative of the invention, and fragments of such DNAs, which encode the CDRs of the $V_L$ and/or $V_H$ region. Such a DNA may be cloned in a vector, more particularly, for example, an expression vector which is capable of directing expression of antibody derivatives of the invention, or at least one antibody chain or a part of one antibody chain.

In a further aspect of the invention, host cells are provided, selected from bacterial cells, yeast cells, fungal cells, insect cells, plant cells and mammalian cells, containing a DNA molecule of the invention, including host cells capable of expressing an antibody or antibody derivative of the invention. Thus, antibody derivatives of the invention may be prepared by culturing host cells of the invention expressing the required antibody chain(s), and either directly recovering the desired protein or, if necessary, initially recovering and combining individual chains.

The above-indicated scFv fragments were obtained by biopanning of a human IgE scFv-phage library using allergenic recombinant β-lactoglobulin. The human IgE scFv-phage library was constructed from mRNAs isolated from lymphocytes of a milk-allergic patient. The variable region of the light and heavy chain cDNAs were synthesised using human IgE-specific primers for Fd cDNAs and human kappa (κ) and lambda (λ) light chains using human κ and λ chain specific primers. The variable regions of the light and heavy chains were amplified by PCR using human κ and λ chain specific primers for Vκ and Vλ cDNAs and human IgE specific primers for $V_H$ cDNAs, respectively. The human IgE scFv library was constructed by cloning the variable region cDNAs into a scFv phage display vector using restriction sites introduced into the PCR primers.

The human IgE scFv library was selected by phage display using a panning procedure. The human IgE scFv phage library was screened by a biotinylated allergenic native β-lactoglobulin in solution and the binders were captured on streptavidin. The elution of phages was done with 100 μM non biotinylated native β-lactoglobulin AB dimer. The phage eluate was amplified in *E. coli* cells. After 2 rounds of biopanning, soluble scFv fragments were produced from isolated phages. The binding specificity of the selected scFv fragments was analysed by ELISA. Several β-lactoglobulin-specific scFv fragment clones were obtained.

As described herein, the phage display technique is an efficient and feasible approach to develop human IgE recombinant anti-β-lactoglobulin antibodies for diagnostic and therapeutic applications.

While one successful selection strategy for obtaining antibody fragments of the invention has been described, numerous variations, by which antibody fragments of the invention may be obtained, will be apparent to those skilled in the art. It may prove possible to select scFv fragments of the invention directly from a phage or microbial display library of scFv fragment or its derivatives. A phage or microbial cell, which presents a scFv fragment or other antibody fragment of the invention as a fusion protein with a surface protein, represents a still further aspect of the invention.

While microbial expression of antibodies and antibody derivatives of the invention offers means for efficient and economical production of highly specific reagents of uniform quality suitable for use in immunodiagnostic assays and immunotherapy, alternatively it may prove possible to produce such a reagent, or at least a portion thereof, synthetically. By applying conventional genetic engineering techniques, initially obtained antibody fragments of the invention may be altered, e.g. new sequences linked, without substantially altering the binding characteristics. Such techniques may be employed to produce novel β-lactoglobulin-binding hybrid proteins, which retain both affinity and specificity for β-lactoglobulin as defined hereinbefore.

Planar Surface of Allergens and Production and Use of Hypoallergens

The present invention enables blocking the Type I surface interaction of allergenic substances by modifying amino acid residues on non-continuous allergenic epitope, i.e. a planar surface with the area of 600-900 $Å^2$ on the allergenic substance (see FIGS. 14 and 16). The planar (flat) surface may contain a β-sheet on the surface of the protein such as in β-lactoglobulin and Bet v 1, or α-helixes packed near to each other such as in Fel d 1. Other allergens with the planar structure are Equ c 1 (horse skin), Bos d 2 (bovine dander), Cyp c 1 (carp parvalbumin), and Hey b 6 (latex).

Hypoallergen variant can be obtained by mutating some (1-5) amino acid residues on the planar (flat) epitope surface with bulky residues (e.g. Arg, Tyr, Lys, Trp can be mutated to Ala). The mutated residues are those which side chains are pointing outside towards solvent thus causing minimal change to the basic structure of the allergen. The purpose of the mutagenesis is to modify the flat surface to convex surface which prevent the binding of IgE-antibodies. The effect of the mutation on the planar surface can be seen as lower affinity of the allergen specific IgE-antibody towards the modified allergen, preferably the mutation decreases the affinity of the specific antibody at least tenfold, more preferably more than tenfold. The resulting modified allergen can be used to evoke tolerance against particular allergens in allergic patients.

Thus, the present invention provides a modified allergen carrying the type I planar epitope which has been distorted by the directed introduction of one or several mutations thereby decreasing the affinity towards the recombinant IgE molecule at least tenfold, preferably more than tenfold.

The present invention also provides a method to create tolerance in a patient for a specific allergen with a planar allergenic epitope comprising the steps of
a) disrupting the planar surface of the allergen with a mutation decreasing the affinity of the IgE towards the epitope more than ten folds;
b) producing the mutated allergen (i.e. hypoallergen);
c) administering, preferably parentally, the mutated allergen into the patient one or several times.

The present invention also provides a method for the isolation of recombinant IgE monoclonal antibodies comprising the steps of
a) isolating mRNA from IgE producing cells from a human derived sample;
b) synthesizing of the cDNAs encoding the IgE Fd gene region and kappa/lambda light chain genes to create an IgE expression library;
c) screening the expressed library against a polypeptide or protein carrying the planar (flat) type I surface typical for allergens and isolating clones showing medium or high affinity (over $10^7 M^{-1}$) towards the planar surface;
d) isolating the DNA encoding the IgE antibody obtained from step c).

Preferably said polypeptide is β-lactoglobulin and said planar surface is defined by the structure or 3D-coordinates of β-lactoglobulin amino acids Val43-Lys47 and Leu57-Gln59 and/or amino acids around these amino acids in an antibody-β-lactoglobulin immunocomplex (see Table VIII).

The present invention further provides a method for producing a modified allergenic polypeptide, the method comprising the steps of (a) modifying nucleic acid sequence encoding said polypeptide so that in the polypeptide expressed from the modified nucleic acid the structure of allergenic epitope of said polypeptide is altered, and (b) expressing or producing the modified allergenic polypeptide from the modified nucleic acid. Preferably step (b) comprises the steps of expressing said modified nucleic acid in a suitable host in a culture system and isolating said modified polypeptide from the culture, or producing synthetically of said modified polypeptide. Preferably said modified allergenic polypeptide is β-lactoglobulin, and/or said allergenic epitope is the planar surface as defined above, more preferably planar surface is defined by the structure or 3D-coordinates of β-lactoglobulin amino acids Val43-Lys47 and Leu57-Gln59 and/or amino acids around these amino acids, in an antibody-β-lactoglobulin immunocomplex. Said allergenic epitope can also be the epitope defined by structure coordinates of β-lactoglobulin amino acids Trp19 and Tyr20 from beta-strand A and Glu44 from beta-strand B in an antibody-β-lactoglobulin immunocomplex.

The present invention further provides a method for identifying a molecule binding to an allergenic epitope of an allergen; comprising the steps of: (a) contacting a particle, such as a virus particle, comprising the allergenic epitope and a candidate binder molecule; (b) isolating those candidate binder molecules which were able to bind to said allergenic epitope. Preferably said allergen is β-lactoglobulin, said molecule is a peptide, and said allergenic epitope is the planar surface as defined above; more preferably planar surface is defined by the structure or 3D-coordinates of β-lactoglobulin amino acids Val43-Lys47, and Leu57-Gln59 and/or amino acids around these amino acids in an antibody-β-lactoglobulin immunocomplex. A good approach in this method is the use of affinity chromatography.

Crystallographic and in Silico Screening

The three-dimensional structure of the allergenic epitope of β-lactoglobulin is defined by a set of structure coordinates as set forth below. The term "structure coordinates" refers to Cartesian coordinates derived from mathematical equations related to the patterns obtained on diffraction of a monochromatic beam of X-rays by the atoms (scattering centers) of the allergenic epitope of β-lactoglobulin in crystal form of an antibody-allergen immunocomplex. The diffraction data are used to calculate an electron density map of the repeating unit of the crystal. The electron density maps are then used to establish the positions of the individual atoms of the allergenic epitope of β-lactoglobulin.

Those of skill in the art will understand that a set of structure coordinates for a protein or a protein-complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The variations in coordinates discussed above may be generated because of mathematical manipulations of the structure coordinates. For example, the structure coordinates set forth below could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same.

Various computational analyses are therefore necessary to determine whether a molecule or molecular complex or a portion thereof is sufficiently similar to all or parts of the allergenic epitope of β-lactoglobulin described herein as to be considered the same. Such analyses may be carried out in current software applications, such as the Molecular Similarity application of QUANTA (Molecular Simulations Inc., San Diego, Calif.) version 4.1, and as described in the accompanying User's Guide.

Once the structure coordinates of a protein crystal have been determined they are useful in solving the structures of other crystals, especially crystals of other similar proteins.

Thus, in accordance with the present invention, the structure coordinates of the allergenic epitope of β-lactoglobulin, and portions thereof is stored in a machine-readable storage medium. Such data may be used for a variety of purposes, such as drug discovery and x-ray crystallographic analysis or protein crystal.

Accordingly, in one embodiment of this invention is provided a machine-readable data storage medium comprising a data storage material encoded with the structure coordinates set forth below.

For the first time, the present invention permits the use of structure-based or rational drug design techniques to design, select, and synthesize chemical entities, including inhibitory compounds that are capable of binding to the allergenic epitope of β-lactoglobulin, or any portion thereof.

Those of skill in the art will realize that association of natural ligands or substrates with the binding pockets of their corresponding receptors or enzymes is the basis of many biological mechanisms of action. The term "binding site", as used herein, refers to a region of a molecule or molecular complex that, as a result of its shape, favourably associates with another chemical entity or compound. Similarly, many drugs exert their biological effects through association with the binding pockets of receptors and enzymes. Such associations may occur with all or any parts of the binding pockets. An understanding of such associations will help lead to the design of molecules such as drugs having more favourable associations with their target receptor or enzyme, and thus, improved biological effects. Therefore, this information is valuable in designing potential ligands or inhibitors of receptors or enzymes.

The term "associating with" or "interacting with" refers to a condition of proximity between chemical entities or compounds, or portions thereof. The association or interaction may be non-covalent, wherein the juxtaposition is energetically favoured by hydrogen bonding or van der Waals or electrostatic interactions, or it may be covalent.

In iterative molecular design, crystals of a series of protein/compound complexes are obtained and then the three-dimensional structures of each complex are solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative molecular design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, the allergenic epitope of β-lactoglobulin crystals, may be soaked in the presence of a compound or compounds, such as antibodies, to provide β-lactoglobulin/antibody crystal complexes.

As used herein, the term "soaked" refers to a process in which the crystal is transferred to a solution containing the compound of interest.

The Storage Medium

The storage medium in which the atomic co-ordinates are provided is preferably random access memory (RAM), but may also be read-only memory (ROM e.g. CDROM), or a diskette. The storage medium may be local to the computer, or may be remote (e.g. a networked storage medium, including the internet).

The invention also provides a computer-readable medium for a computer, characterised in that the medium contains atomic co-ordinates of the allergenic epitope of β-lactoglobulin.

The atomic co-ordinates are preferably those set forth below, or variants thereof.

Any suitable computer can be used in the present invention.

Molecular Modelling Techniques

Molecular modelling techniques can be applied to the atomic co-ordinates of the allergenic epitope of β-lactoglobulin to derive a range of 3D models and to investigate the structure of ligand binding sites. A variety of molecular modelling methods are available to the skilled person for use according to the invention.

At the simplest level, visual inspection of a computer model of the allergenic epitope of β-lactoglobulin can be used, in association with manual docking of models of functional groups into its binding sites.

Software for implementing molecular modelling techniques may also be used. These molecular modelling techniques allow the construction of structural models that can be used for in silico drug design and modelling.

De Novo Compound Design

The molecular modelling steps used in the methods of the invention may use the atomic co-ordinates of the allergenic epitope of β-lactoglobulin, and models derived therefrom, to determine binding surfaces.

This preferably reveals van der Waals contacts, electrostatic interactions, and/or hydrogen bonding opportunities.

These binding surfaces will typically be used by grid-based techniques (e.g. GRID [Goodford (1985) J. Med. Chem. 28: 849-857], CERIUS2) and/or multiple copy simultaneous search (MCSS) techniques to map favourable interaction positions for functional groups. This preferably reveals positions in the allergenic epitope of β-lactoglobulin for interactions such as, but not limited to, those with protons, hydroxyl groups, amine groups, hydrophobic groups (e.g. methyl, ethyl, benzyl) and/or divalent cations.

Once functional groups or small molecule fragments which can interact with specific sites in the binding surface of the allergenic epitope of β-lactoglobulin have been identified, they can be linked in a single compound using either bridging fragments with the correct size and geometry or frameworks which can support the functional groups at favourable orientations, thereby providing a compound according to the invention. Whilst linking of functional groups in this way can be done manually, perhaps with the help of software such as QUANTA or SYBYL, the following software may be used for assistance: HOOK [Available from Molecular Simulations Inc], which links multiple functional groups with molecular templates taken from a database, and/or CAVEAT [Lauri & Bartlett (1994) Comp. Aided Mol. Design. 8: 51-66], which designs linking units to constrain acyclic molecules.

Docking

Compounds in known in silico libraries can also be screened for their ability to interact with the allergenic epitope of β-lactoglobulin by using their respective atomic co-ordinates in automated docking algorithms.

Suitable docking algorithms include: DOCK [Kuntz et al. (1982) J. Mol. Biol. 161: 269-288], AUTODOCK [Available from Oxford Molecular], MOE-DOCK [Available from Chemical Computing Group Inc.] or FLEXX [Available from Tripos Inc.]. Docking algorithms can also be used to verify interactions with ligands designed de novo.

Focused IgE-Antibody Library Towards Allergens

The amino acid sequence comparison of published IgE sequences reveals that the light chains of the known IgE antibodies binding to diverse groups of allergens are strikingly conserved (see Table VII). This gives tools to construct focused allergen specific libraries that can be utilised for the isolation of allergen specific antibodies applicable in the diagnosis of allergens. The conserved light chain sequence information is used to construct a limited pool of light chains or a single light chain with the characteristic amino acid sequences identified in the IgE antibodies. This light chain sequence information is combined with a diverse pool of IgE heavy chain genes isolated from lymphocytes of several allergic patients. The resulting antibody phage display library, in either scFv or Fab display format, is used to select allergen specific IgE antibodies essentially as described in Example 1/II and Hoogenboom et al. (1998).

Human Antibody (scFv, Fab or Whole Antibody) Libraries Containing the Human IgE VH-Regions The IgE VH-region of the D1 IgE Fab and especially the HCDR3 loop are structurally different when compared to IgG antibodies. It is forming a loop structure that is recognizing a cleft on the BLG-allergen structure. Based on this observation it should be possible to develop human IgE VH-region containing antibodies for those therapeutic targets where the binding specificity is required towards protein structures that are not exposed on the surface, e.g., substrate binding sites of enzymes and drug resistance pumps (De Genst et al. 2006). A diverse IgE VH-pool from human lymphocytes is used as a building block to construct a functional human antibody library in a scFv, Fab or whole antibody format. Resulting libraries are selected against therapeutic targets requiring specific recognition of cleft structures.

The development and characterisation of the human β-lactoglobulin-binding recombinant antibodies and their usefulness in immunoassays is now described in more detail in the following examples.

EXAMPLE 1

The Recombinant β-Lactoglobulin-Specific scfv Fragment by Phage Display Selection In this example the human IgE scFv library was constructed and selected by allergenic β-lactoglobulin in order to isolate scFv fragments with affinity and specificity to β-lactoglobulin (BLG). Construction of human IgE scFv phage library was prepared indirectly by constructing IgE Fab-κ and Fab-λ, libraries first, and then the particular library DNAs were used for PCR amplification of variable domains of heavy and light chains.

I. Construction of the Human IgE scFv Phage Libraries 50 ml of heparinised blood was obtained from a milk-allergic patient. Lymphocytes were isolated according to an Ig-Prime kit protocol (Novagen). Per 10 ml of blood 30 ml of lysis buffer (155 mM $NH_4Cl$, 10 mM $NH_4HCO_3$, 0.1 mM EDTA, pH 7.4) was added and incubated on ice for 15 min with shaking occasionally. After centrifugation at 450 g for 10 min the lymphocytes, i.e. the white blood cell pellet, were collected. The pellet was washed twice with lysis buffer and after the final centrifugation the lymphocyte pellet was resuspended in D-solution. Lymphocyte RNAs were isolated using Promega's RNAgents Total RNA Isolation kit according to the manufacturer's protocol. The first strand cDNA synthesis was carried out using Promega's Reverse Transcription system kit. For the synthesis of Fd-fragment cDNA and light chain cDNAs the primers of the constant region of the epsilon (ε) chain (Cε1) and the primer of the kappa (Cκ1) and lambda (Cλ1) chain were used, respectively. Primers used for the cDNA synthesis and PCR amplifications of human IgE Fd region and light chains are showed in Table I and Table II.

PCR amplifications were carried out in two steps: a primary PCR for amplifying Fd and light chains from cDNA templates and a secondary PCR for adding restriction sites to the 5'-end of the DNA fragments obtained after a primary PCR. First the Fd region was amplified by PCR using the primers specific for the variable region of the heavy chains (VH1a-VH7a) and Cε1primer. Accordingly, the kappa and lambda light chains were amplified using specific primers for variable region of the light chains (Vκ1a-Vκ6b and Vλ1a-Vλ10) and Cκ/λ1 primer, respectively. Primers for the secondary PCR were Cκ1 and Vκ/λ1 and Cκ for the kappa light region, Vκ/λ1 and Cλ1 for the kappa light chain and Vλ1A and Cκ/λ1 for the lambda light chain. The primary PCR amplification was done at the following conditions: 1 cycle of 3 min at 93° C. for denaturation, 7 cycles of 1 min at 93° C., 30 s at 63° C. and 50 s at 58° C. for annealing and 1 min at 72° C. for elongation, 23 cycles of 1 min at 93° C., 30 s at 63° C. and 1 min at 72° C. followed by 1 cycle of 10 min at 72° C. For the secondary PCR the amplification conditions were as follows: 1 cycle of 3 min at 95° C. for denaturation, 25 cycles of 1.5 min at 94° C., 1 min at 65° C. for annealing and 1.5 min at 72° C. for elongation followed by 1 cycle of 10 min at 72° C. Between the primary and the secondary PCR and after the secondary PCR the amplified DNA fragments were purified.

The final PCR products of the different antibody fragments were pooled and digested with appropriate restriction enzymes. Digested DNA fragments, encoding IgE Fd region and κ and λ light chains, were ligated into a phagemid vector and transformed into *E. coli* XL-1 Blue cells to yield an Fab-κ and Fab-λ libraries of $10^6$ independent clones. To avoid possible problems on the expression of Fab fragments on a phage particle an antibody library in scFv format was constructed. Phagemid DNAs from different libraries were isolated and used as template DNAs for amplifying the variable regions of the human IgE heavy and human light chains in order to construct human IgE scFv-κ and scFv-λ libraries.

Figure 3:
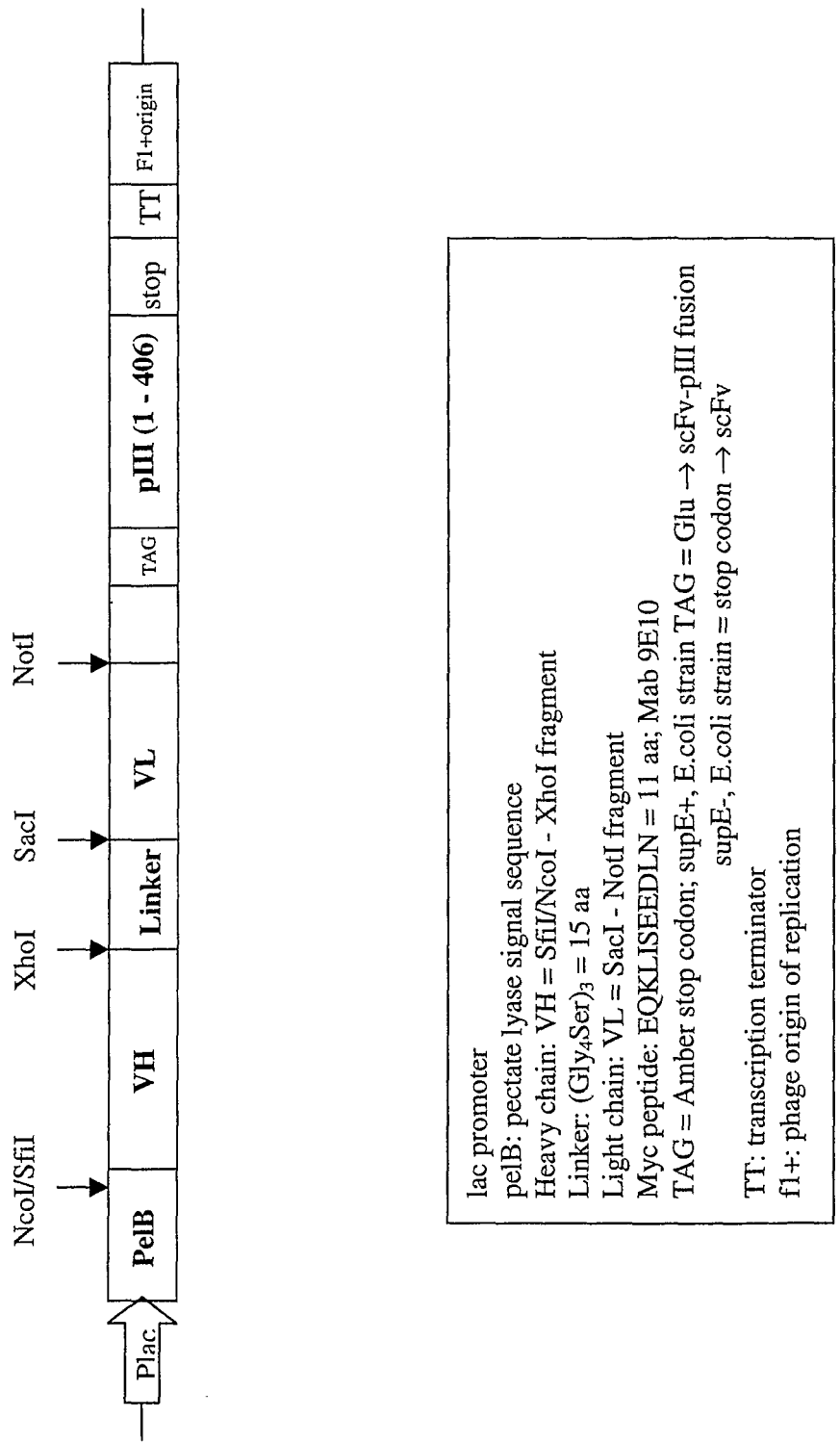
FIG. 3 shows a schematic presentation of the scFv phage display vector used for the construction of scFv phage libraries.

PCR amplification of the variable region of the heavy chain was carried out using human $V_H$ specific primers (VH1-VH4 and VH1A). Amplification of the variable region of the light chains was done using the following primer pairs: Vκ1-Vκ7, Vκ2-Vκ8, Vκ3-Vκ9, Vκ-4-Vκ10, Vκ5-Vκ11 and Vκ6-Vκ11 for human kappa chain and Vλ1-Vλ8, Vλ2-Vλ9, Vλ3-Vλ9, Vλ4-Vλ9, Vλ5-Vλ10, Vλ6-Vλ10 and Vλ7-Vλ10 for human lambda chain (see Tables III and IV). The amplified DNA fragments were purified and digested in order to ligate into a scFv phage display vector (FIG. 3). Ligation mixtures were transformed into *E. coli* XL-1 Blue cells resulting in the human IgE scFv-κ and scFv-λ libraries with approximately $10^5$ independent clones.

II. Selection of the Human scFv-Libraries

The human scFv-κ and scFv-λ, libraries were selected by the phage display technique (McCafferty et al., 1990, Barbas et al., 1991). To isolate β-lactoglobulin-binding antibody fragments, the human IgE scFv-κ and scFv-λ, libraries displayed on the surface of the bacteriophage were panned using an affinity panning procedure (FIG. 2). First the phage pools were allowed to react either with biotinylated, immunoreactive β-lactoglobulin or as a negative control, without antigen for 1.5 h. Thereafter, the phage pools were transferred to microtitre plate wells coated with biotin binding streptavidin. After a 30-min incubation, the wells were washed 3 times with PBS+0.05% Tween20 and the binders were eluted with soluble antigen (100 µM nonbiotinylated β-lactoglobulin AB dimer). For the next panning round the eluted phage pools were amplified by infecting *E. coli* XL-1 Blue cells. Two rounds of panning were performed.

III. Characterisation of the β-Lactoglobulin-Binders

After the last panning cycle scFv phage display DNA was isolated and transformed into *E. coli* HB2151 (supE⁻) cells in order to express soluble scFv fragments. Between the scFv sequence and the phage gene III sequence the scFv phage display vector contains TAG-amber stop codon which will be translated as glutamate in *E. coli* strains with supE⁺ genotype but as a stop codon in *E. coli* strains with supE⁻ genotype. Sixty-two individual clones were grown in a small scale to produce soluble scFv fragments for preliminary characterisation. Clones were analysed on ELISA test using β-lactoglobulin-coated wells to catch the β-lactoglobulin-specific binders and control protein wells to see non-specific binding (data not shown). Most of the clones bound with high affinity to β-lactoglobulin. Clones were analyzed first by DNA-fingerprinting and six of the clones were sequenced (Sanger et al., 1977). Finally, one of the clones was selected for further characterisation (FIGS. 4 and 5).

EXAMPLE 2

Cloning and Characterisation of Human Fab Fragment with β-Lactoglobulin-Binding Specificity In this example the human IgE scFvs with β-lactoglobulin-binding specificity was converted to human Fab fragments with IgG1 subtype. Due to known difficulties in forming multimers, the D1 scFv, obtained from the scFv antibody library, was cloned and bacterially expressed as Fab fragments (Holliger et al., 1993, Desplancq et al., 1994). The resulting antibody fragments were further characterised by a competitive ELISA.

I. Cloning of the Human Fab Fragments with β-Lactoglobulin-Binding Specificity

The Fd regions were amplified by overlapping PCR. The primers used for the PCR are given in Table V.

The resulting cDNAs of the Fd region and light chains were cloned into the bacterial expression vector, pKKtac and then transformed into E. coli RV308. Soluble Fab fragment designated to D1 IgE Fab was produced by fermentation (Nevanen et al, 2001) and the Fab fragment was purified by an introduced C-terminal hexahistidinyl tag on a Sepharose column with immobilised nickel to a substantial purity (data not shown).

II. Characterisation of the Human IgE Fab Fragments

Figure 6:
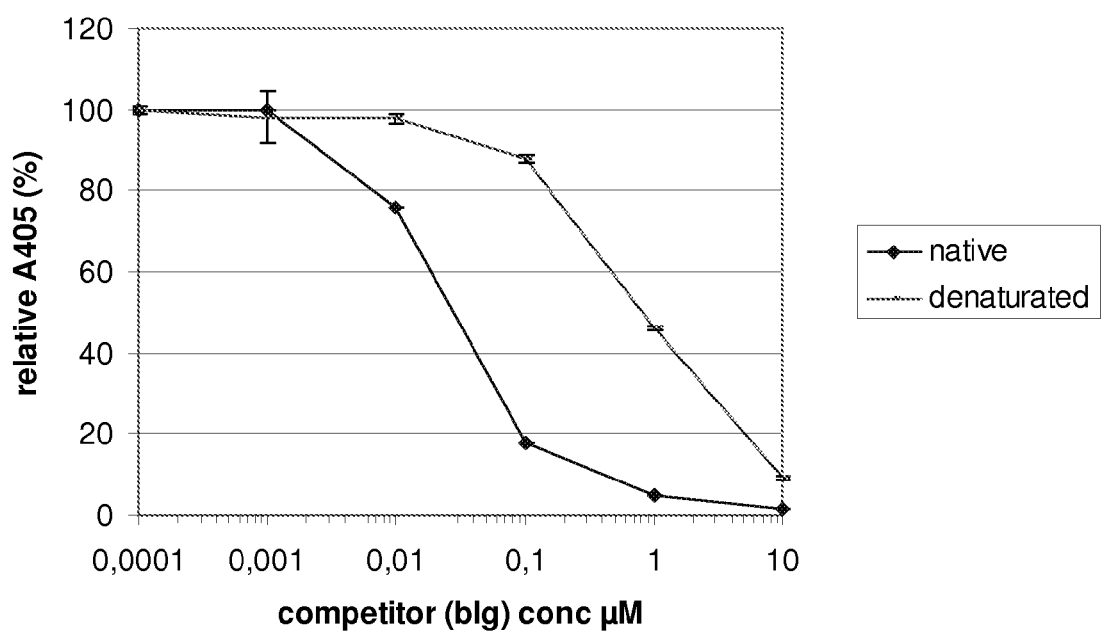
FIG. 6 shows the curve obtained from the competitive ELISA of D1 IgE Fab fragment with human IgG1 subtype whose binding to immobilized, biotinylated β-lactoglobulin has been inhibited by soluble native β-lactoglobulin.

The characterisation of the purified D1 IgE Fab was performed by competitive ELISA. First, increasing amounts of the soluble, non-biotinylated β-lactoglobulin was incubated with the D1 IgE Fab, and then the reaction mixtures were applied onto Streptavidin microtitre plate wells coated with allergenic, biotinylated β-lactoglobulin. FIG. 6 shows the result of the competitive ELISA. The binding of the D1 IgE Fab (FIG. 6) to biotinylated β-lactoglobulin could be inhibited by adding increasing amounts of native β-lactoglobulin.

Figure 7:
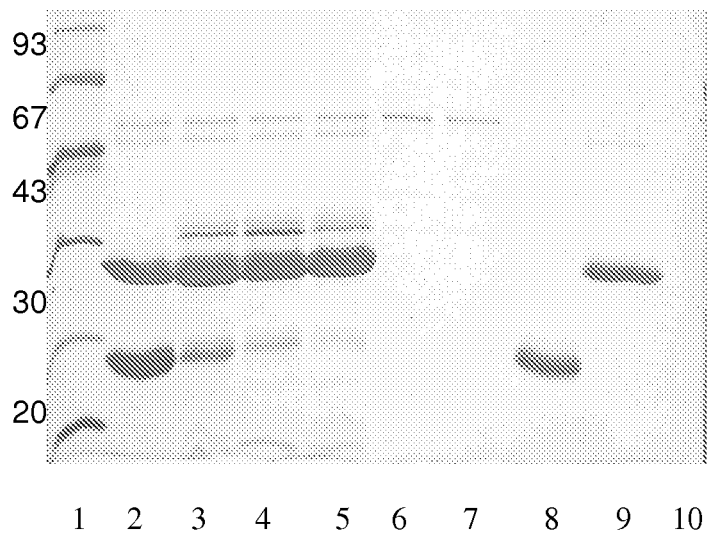
FIG. 7 shows the result from immunoprecipitation assay. The D1 IgE Fab binds the native β-lactoglobulin from cow milk. 1=Low molecular weight marker, 2-5=D1 IgE fab immobilized in proteinL beads+untreated milk sample, milk sample, heated 15 min+95° C., 30 min+95° C., 60 min+95° C. 6-7=negative controls (=empty proteinL beads+untreated milk sample or heated 60 min+95° C.) 8=purified β-lactoglobulin from Sigma 0.59=purified D1 IgE Fab 0.5 µg.
Figure 8:
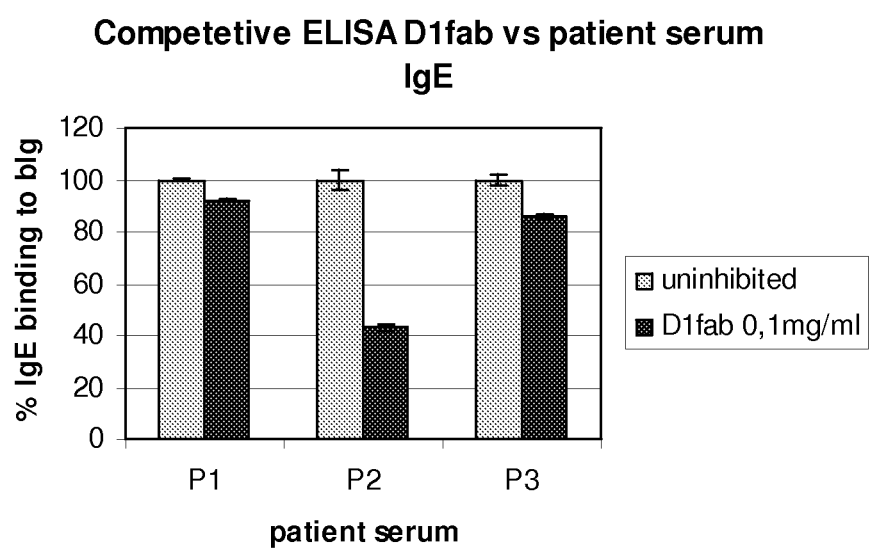
FIG. 8 shows the result of the competitive ELISA. The binding of D1 IgE Fab fragments with human IgG1 subtype to β-lactoglobulin is inhibited by patient sera.

To study if the D1 IgE Fab is able to bind β-lactoglobulin from milk samples, the immunoprecipitation assay was performed (FIG. 7). The D1 IgE Fab was immobilized via kappa light chain to protein L beads and this complex was introduced to milk samples, which were heated for various times (0, 15, 30 and 60 min). The D1 IgE Fab bound to the protein L beads was incubated with milk samples 1 hour at room temperature and after this, the beads were washed several times with PBS+0.05% Tween20 to remove unspecific binding of the milk proteins to protein L beads. The D1 IgE Fab β-lactoglobulin complex was eluted from protein L-beads with low pH (0.1 M Glycine, pH 2.1) and the eluted fraction was neutralized with 3 M Tris, pH 8.8. A small portion of the elution fraction was analyzed with 15% SDS-PAGE followed by silver staining. The correct size bands were cut out from the SDS-PAGE gel and further analyzed by mass spectrometry to confirm that the protein, which D1 IgE Fab recognised from cow milk was β-lactoglobulin.

To study if the D1 IgE Fab recognizes the same allergenic epitope as the IgE antibodies from patient serum, the biotinylated β-lactoglobulin was first immobilised to a microtitre plate wells coated with streptavidin. The patient serum samples were incubated in the wells together with increasing concentrations of D1 IgE Fab and the amount of the bound patient serum IgE was detected with alkaline phosphatase labelled secondary antibody, which specifically recognizes the human IgE isotype. A slight inhibition can be seen in the case of each patient tested, suggesting that the epitope which D1 IgE Fab recognizes is the same as the IgE from the patient serum. The reason why the binding of the patient serum IgE is not totally blocked, might be that the β-lactoglobulin harbours a multiple IgE-epitopes.

EXAMPLE 3

I. Crystallisation of the Antibody-Allergen Immunocomplex

Crystallization and data collection Microcrystals (about 70×50×50 µm) of BLG-D1 IgE Fab were obtained with vapour diffusion method by mixing 2 µl of D1/Fab solution (concentration 1.4 mg/ml in 20 mM phosphate buffer, pH 7.0), 1 µl BLG solution (2 mg/ml in pure water), 0.5 µl of n-dodecyl-β-D-maltoside solution, and 2.5 µl of reservoir solution (14% (w/v) polyethylene glycol 3350, 0.1 M BTP (1,3-bis[tris(hydroxymethyl)methylamino]propane-hydrochloric acid) buffer, pH 5.5). The diffraction data set was collected from single crystal at the beamline ID29 in ESRF (wavelength 1.000 Å) at 100 K. The crystal belonged to the space group $P2_12_12_1$ with unit-cell dimensions a=67.0, b=100.6, c=168.1 Å. The data set was collected at 2.8 Å resolution.

II. Structure Determination of Antibody-Allergen Immunocomplex

The structure was solved with the molecular replacement method using Molrep program implemented in CCP4 program package. BLG monomer (PDB code 1B8E) and Fab fragment of IgG antibody against GP41 of HW virus (1DFB) (identity 92% for light and 79% for heavy chain) were used as search models. The final structure contained one dimer of BLG complexed with two Fab fragments. Model building and refinement were done with the programs O and CNS. Because of low number of reflections restraints were used to keep both Fab/D1 fragments and BLG monomers similar. BLG exist in two isomers, the electron density suggested that we have glycine at position 64 and alanine at position 118. No water molecules were added but the elongated electron density in the lipid binding cavity of BLG was modelled as an n-dodecyl-β-D-maltoside. The final structure has an R value 24.5% and an $R_{free}$ value of 29.9%. 83.5% of the residues are in the most favoured regions and 0.6% of the residues in the disallowed regions in the Ramachandran plot. All figures were generated with Pymol (Delano, W. L. The PyMol Molecular Graphics System, http://www.pymol.org).

EXAMPLE 4

Figure 15:
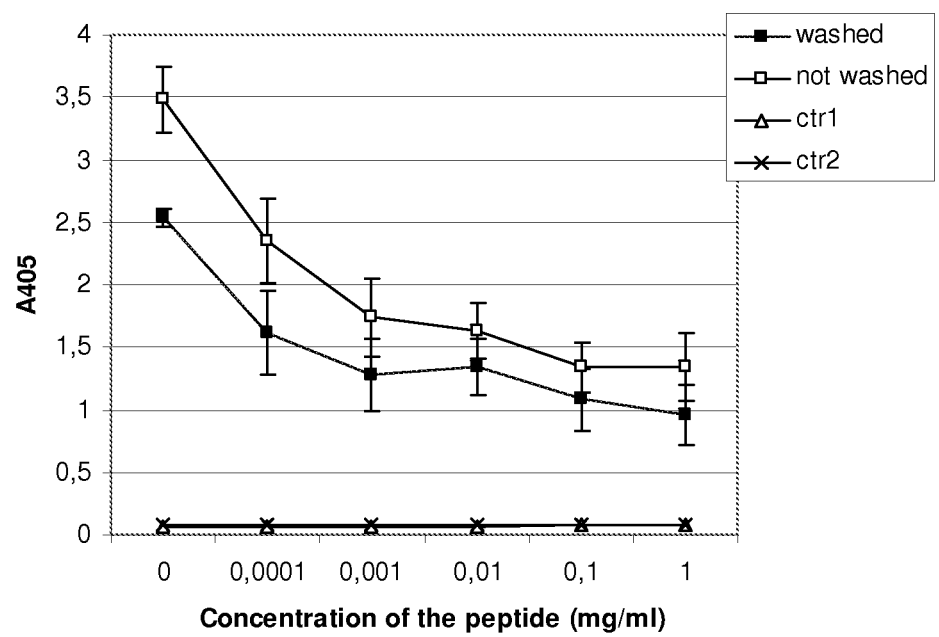
FIG. 15 shows the result of competition ELISA. The binding of the D1 IgE Fab to BLG is inhibited by a short peptide, KRVG. Ctr 1 and ctr2 are the background controls where ctr1 is the result obtained after incubation without D1 IgE Fab and ctr2 without the BLG (see Example 4).
Figure 16:
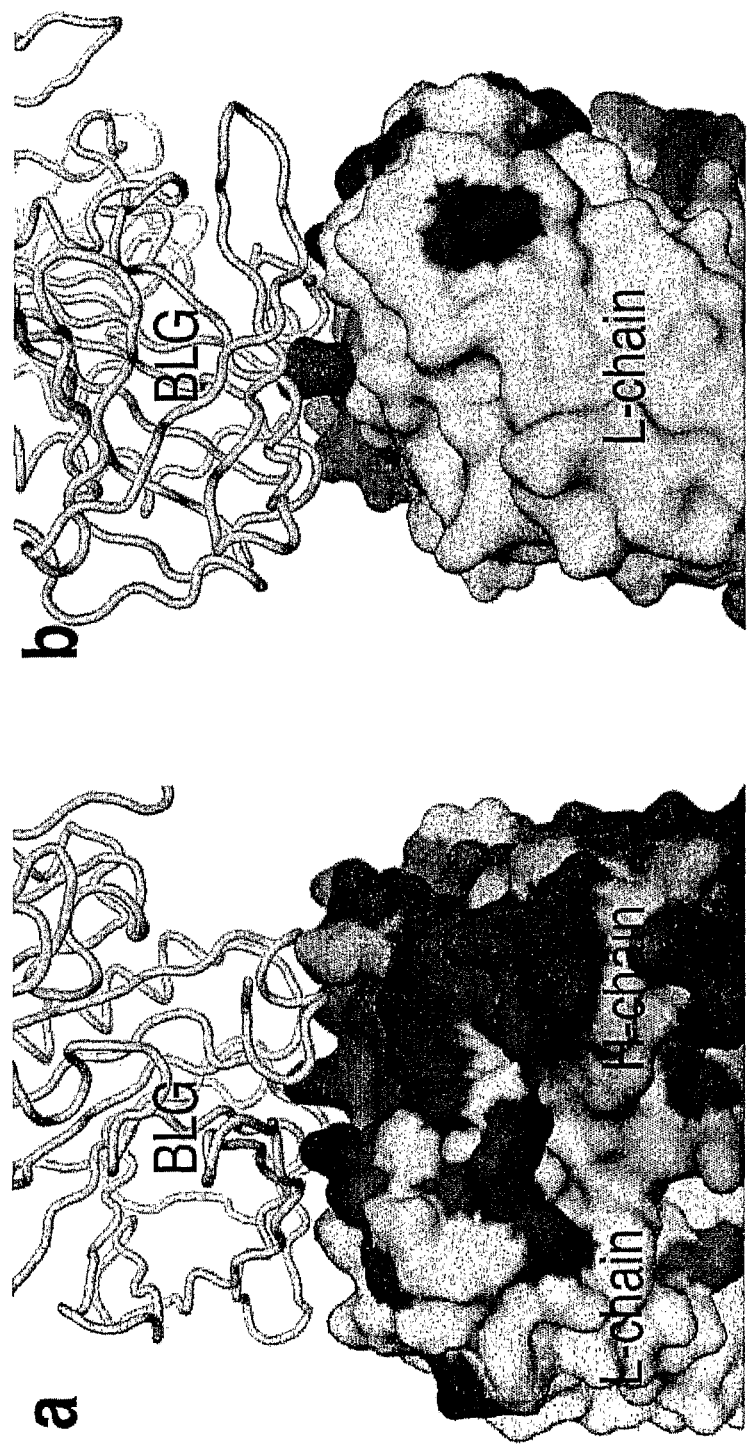
FIG. 16 shows the surface of D1/Fab antibody and ribbon model of allergen BLG. In this figure identical residues of the D1/Fab with hevein-binding IgE-antibody (clone IC2) are shown in light grey, different residues are in dark grey; a) front view, b) side view showing extensive similarity between the light chains of two IgE antibodies binding structurally very different allergens.

Inhibition of the D1 IgE Fab binding to BLG was carried out using a short peptide, KRVG that is the longest linear BLG binding peptide in the HCDR3. In competitive ELISA the biotinylated AB dimer of BLG was immobilised onto streptavidin-coated microtitre wells. First the peptide (an inhibitor) was dissolved into 0.5% BSA-PBS and then different amounts of it were incubated with the immobilised BLG. After that the wells were either washed trice with PBS or not. D1 IgE Fab was added and followed by the washings with PBS. The bound antibody was detected with AFOS-conjugated goat anti-human kappa antibody. After addition of the substrate, p-nitrophenylphosphatase, the absorbance values were read at 405 nm. The results are shown in FIG. 15.

EXAMPLE 5

The Identification of a Flat Epitope by Calculation of Molecular Surface and Curvature In this example we have used commercial AMIRA program (with AmiraMol module) to calculate the solvent excluded surface (probe radius 10 Å). The surfaces are coloured according to the Gaussian curvature which is the product of the two principal curvatures. It is negative in surface areas with hyperbolic geometry (convex-concave, like near saddle points) and positive in areas with elliptic geometry (strictly convex or strictly concave).

Figure 17:
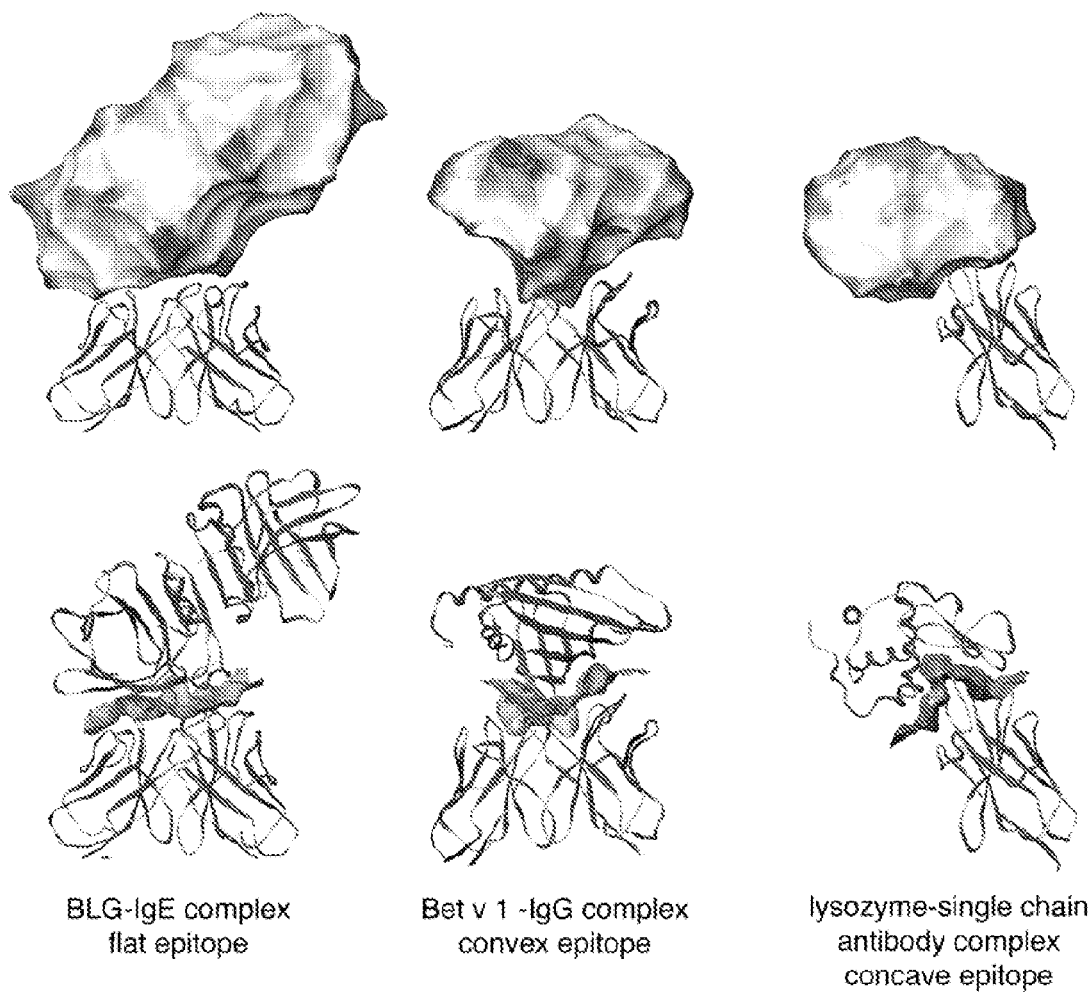
FIG. 17. Antibody binding to flat, convex and concave epitopes. In the first row the solvent excluded surface (probe radius 10 Å) is shown. Because of a large probe sphere the surface show more large scale features. The surface is coloured according to the Gaussian curvature. Flat areas are in white. Antibody is shown as a ribbon model. The second row shows similar structures but now the surfaces represent interaction surface which corresponds epitope.

We have also used AMIRA program to calculate molecular interface area (cutoff 3 Å). The program shows a surface which is located exactly in the middle between two proteins. In FIG. 17 examples for antibody binding to flat (BLG D1(IgE/Fab)), convex (Bet v 1-IgG/Fab; 1BV1) and concave (lysozyme-single chain camel antibody; 1MEL) epitopes are shown.

Figure 18:
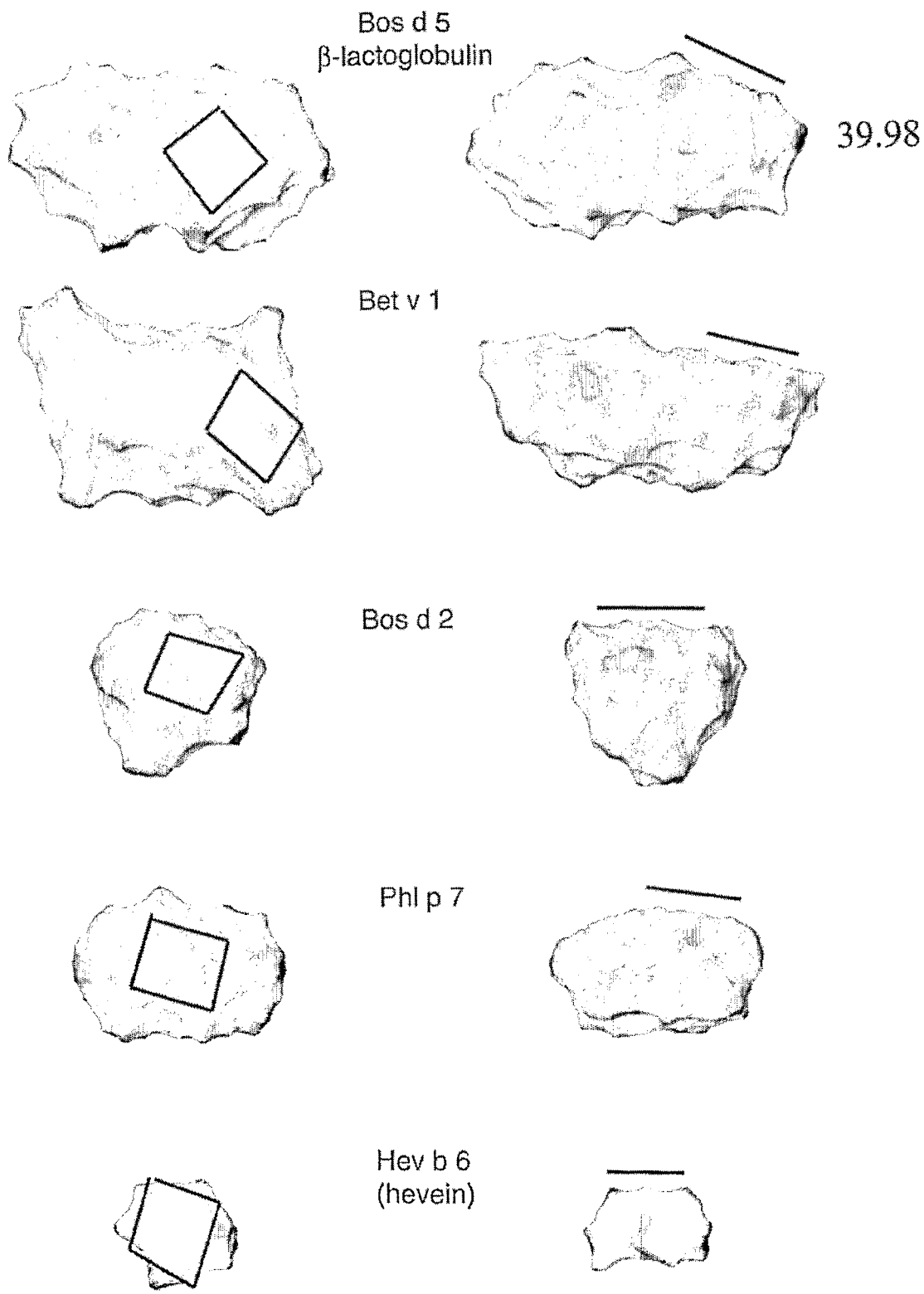
FIG. 18. The molecular surfaces (probe radius 10 Å) of five different allergens in two orientations. The surface is coloured according to the curvature, flat areas are in white. The putative flat area for IgE-binding are shown as a rectangle on the left. The side view is on the right and the position of the same area are shown as a line.

It is thus possible to calculate the molecular surface by using a large probe value (preferably 8-12 Å) for allergens if their three-dimensional structure is available. Such molecular surfaces can be rotated and looked in all directions and with the aid of curvature coloured surfaces a large flat area (600-900 $Å^2$) can be identified. In FIG. 18 we represent molecular surfaces for five allergens. The first one is BLG (Bos d 5) and the flat epitope is shown in two orientations. In the following pictures similar flat areas from four other allergens, Bet v 1, Bos d 2, Phl p 7, and Hev b 6 are identified. These are suggested flat epitopes for IgE binding. The four allergens represent structurally very different classes. Bos d 5 and Bos d 2 are β-proteins (consisting mainly of β-strands). Bet v 1 has both β-strands and α-helices. Phl p 7 has only α-helices and Hev b 6 is a small protein with low secondary structure content.

EXAMPLE 6

Characterisation of Recombinant β-Lactoglobulin and its Mutants

Based on the D1 IgE and the BLG immunocomplex structure, mutations were designed to the flat surface epitope on the BLG in order to produce hypoallergenic variants. Two different recombinant BLG (rBLG) mutants, T18Y and T18Y/E45Y/L57Y, were constructed (Table IX). The cDNAs encoding the rBLG and its mutants were cloned into bacterial expression vector, produced in *Escherichia coli* cells, chromatographically purified to a substantial purity and finally their properties were characterised.

I. Cloning of the Recombinant BLGs

The bovine recombinant BLG (rBLG) cDNA was purchased from GenScript Corporation (USA) in vector pUC57 and it contained the restriction sites of SfiI/NcoI at the 5'end and HindIII at the 3'end (Table X). The rBLG cDNA was cloned into pKKTac bacterial expression vector with the fusion of the Ervinia carotovora's pectate lyase (pelB) signal sequence (Takkinen et al., 1991) as an SfiI-HindIII fragment. The hexa histidinyl (His6) tag was introduced into 3'end of the rBLG cDNA by PCR amplification using primers 1 and 2 (Table X). Phusion DNA polymerase (Finnzymes) was used in all PCR amplifications. The amplified cDNA of rBLG-His6 was digested with SfiI and HindIII (New England Biolabs) and cloned into pKKTac expression vector. *Escherichia coli* XL-1 Blue was used as a host strain to construct the recombinant BLG (rBLG) and its mutants.

Two different rBLG mutants, T18Y and T18Y/E45Y/L57Y (Table IX), were cloned into pKKtac vector. The cDNAs of the rBLG-His6 T18Y and T18Y/E45Y/L57Y mutant were amplified with PCR using mismatch primers 2, 3, 4 and 5 (Table X) and the original rBLG cDNA in pUC57 vector as a template. The cDNA encoding the T18Y mutant was amplified using primers 2 and 3 and the amplified cDNA was digested with StuI and HindIII (New England Biolabs) and cloned into the pKKtac/rBLG-His6 vector (see above). The cDNA encoding the T18Y/E45Y/L57Y mutant was amplified in two steps using overlapping primers. First, the cDNA fragment of 27-165 bp was amplified using primers 3 and 4 and the cDNA fragment of 147-530 bp with the 2 and 5. Then the resulting DNA fragments were combined by overlapping PCR amplification. The primer 4 and 5 have an overlapping sequence. Finally the cDNA encoding the T18Y/E45Y/L57Y mutant was digested with StuI and HindIII and cloned into pKKTac/rBLGhis expression vector.

The DNA sequences of the rBLG-His6 and its mutants were verified by DNA sequencing (ABI 3100 Genetic Analyzer, Applied Biosystems).

II. Production of the Recombinant BLGs

The rBLG-His6 and its mutants were transformed into *E. coli* RV308 (ATCC 31608) strain for the bacterial expression of the rBLGs. Single colonies of each clone were inoculated into 3 ml LB, 100 µg/ml ampicillin and 1% glucose and cultivated for 16 h at +37° C. with 220 rpm shaking. Then the cultivations were 1:50 diluted into 3 ml LB with ampicillin and cultivated 3 hours at +37° C. After that the protein expression was induced by the addition of IPTG to a final concentration of 1 mM and cells were cultivated for 16 h at +30° C. with 220 rpm shaking. Then the cells were harvested and the supernatants were stored for later use. The periplasmic fraction of the cells was isolated by a freeze-thaw method (Boer et al., 2007). Briefly, cells were resuspended in 20% sucrose, 30 mM Tris, 1 mM EDTA (pH 8.0) and then incubated 5 min in dry ice-ethanol bath followed by the resuspension in 5 mM $MgSO_4$ and incubation for 5 min at +37° C., and this freezing and thawing step was repeated trice. The supernatant and the periplasmic fractions were analysed by western blotting. First the samples were run on a 15% SDS-PAGE gel (with β-mercaptoethanol) and then the proteins were transferred onto the nitrocellulose filter. The rBLGs were detected using rabbit anti-BLG antibody (Mäkinen-Kiljunen and Palosuo, 1992) followed by AFOS-conjugated goat anti-rabbit antibody (Bio-Rad).

During the bacterial production the recombinant BLGs were secreted into the periplasmic space with almost no leakage into culture medium. For the large scale production of the rBLGs the cells containing the rBLG-His6 and its mutants in pKKTac vector in *E. coli* RV308 strain were inoculated TB medium containing 100 µg/ml ampicillin, 1% glucose. The cells were cultivated for 16 h at +37° C. with 220 rpm shaking. Then the cell cultures were 1:50 diluted into TB medium with 100 µg/ml ampicillin. The cells were grown at +37° C. with 220 rpm shaking until the $OD_{600}$ was 4 and IPTG was added to a final concentration of 0.1 mM. The induction of the cells was carried out for 6 h at +28° C. with 220 rpm shaking. Then the cells were harvested by centrifugation with 4000×g for 15 min at +4° C. The periplasmic fractions containing the recombinant BLGs were isolated by freeze-thaw method as above.

III. Purification of the rBLGs

Figure 19:
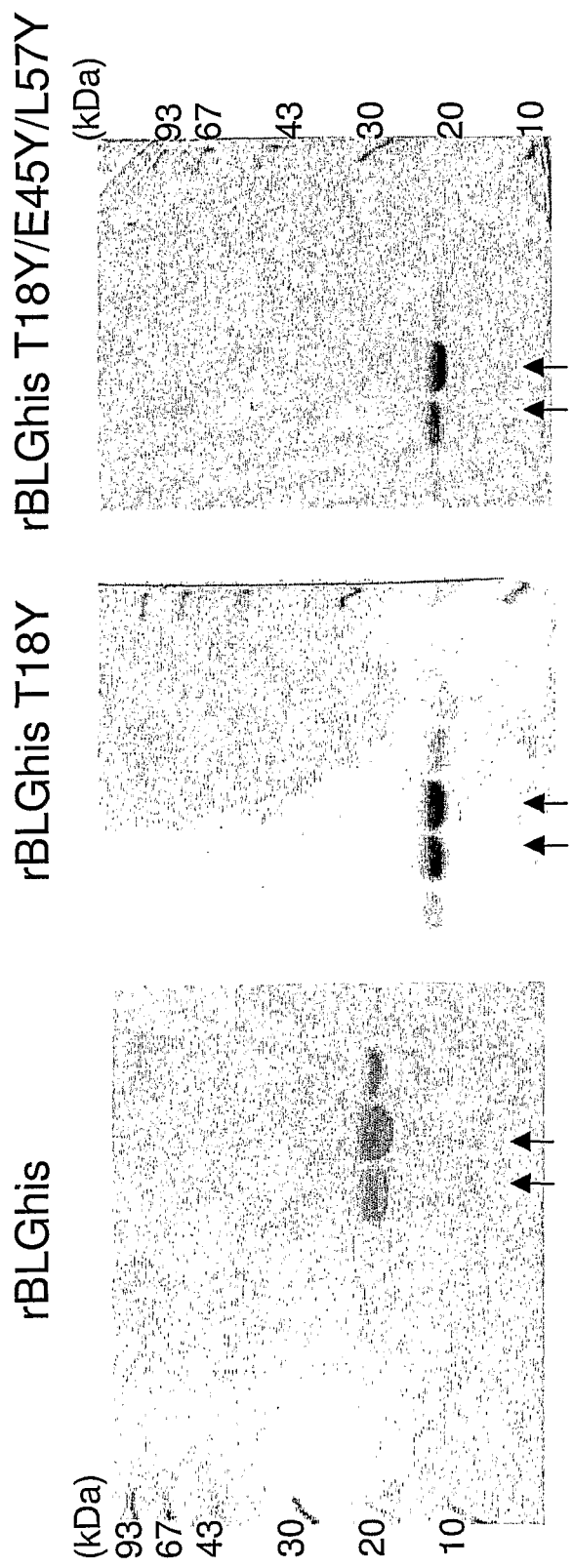
FIG. 19. Purification of the rBLG-His6 and its mutants. After the second IMAC-purification the protein samples were analysed on the Coomassie-stained 15% SDS-PAGE gels (with β-mercaptoethanol). The pooled fractions are shown by arrows.
Figure 20:
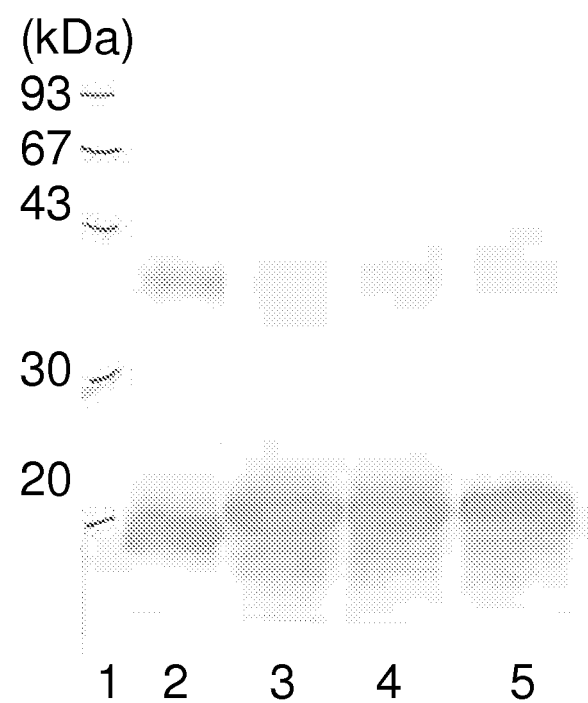
FIG. 20. The purified rBLG-His6 and its mutants were analysed by western blotting followed by the detection with the rabbit anti-BLG antibody and goat AFOS-conjugated anti-rabbit antibody. 3 µg protein were subjected into the well. Lane 1=LMW, lane 2=native BLG(Sigma), lane 3=rBLG-His6, lane 4=rBLG-His6 T18Y, and lane 5=rBLG-His 6 T18Y/E45Y/L57Y.

The purification of recombinant BLGs was performed using immobilised metal affinity chromatography (IMAC) as described earlier (Porath and Olin, 1983). Briefly, periplasmic fractions containing the rBLGs were 1:2 diluted with the binding buffer (10 mM Hepes, 1M NaCl, 10% Glycerol, 1 mM imidazole, pH 7.4) and incubated with Ni$^{2+}$-loaded Chelating Sepharose (Pharmacia) for 16 h at +4° C. The column matrix with bound rBLGs was loaded into the column with gravity flow and washed stepwise with 1 mM, 10 mM, 20 mM and 50 mM imidazole in the binding buffer. Finally, the rBLGs were eluted with 75 mM, 100 mM, 200 mM and 5×500 mM imidazole in the binding buffer and 2 ml fractions were collected. The eluted fractions were analysed on 15% SDS-PAGE gel (with β-mercaptoethanol). The fractions containing the desired proteins were pooled and the IMAC-purification was repeated in a smaller scale. After the second IMAC-purification the fractions were analysed again on a SDS-PAGE gel (FIG. 19). As a result the fractions containing the particular purified BLG were pooled, dialysed against 10 mM HEPES, 0.9% NaCl, pH 7.4 for 16 h at +4° C. The purified proteins were analysed by western blotting using rabbit anti-BLG antibody and AFOS-conjugated goat anti-rabbit antibody detection (FIG. 20).

IV. Circular Dichroism Measurements

Figure 21:
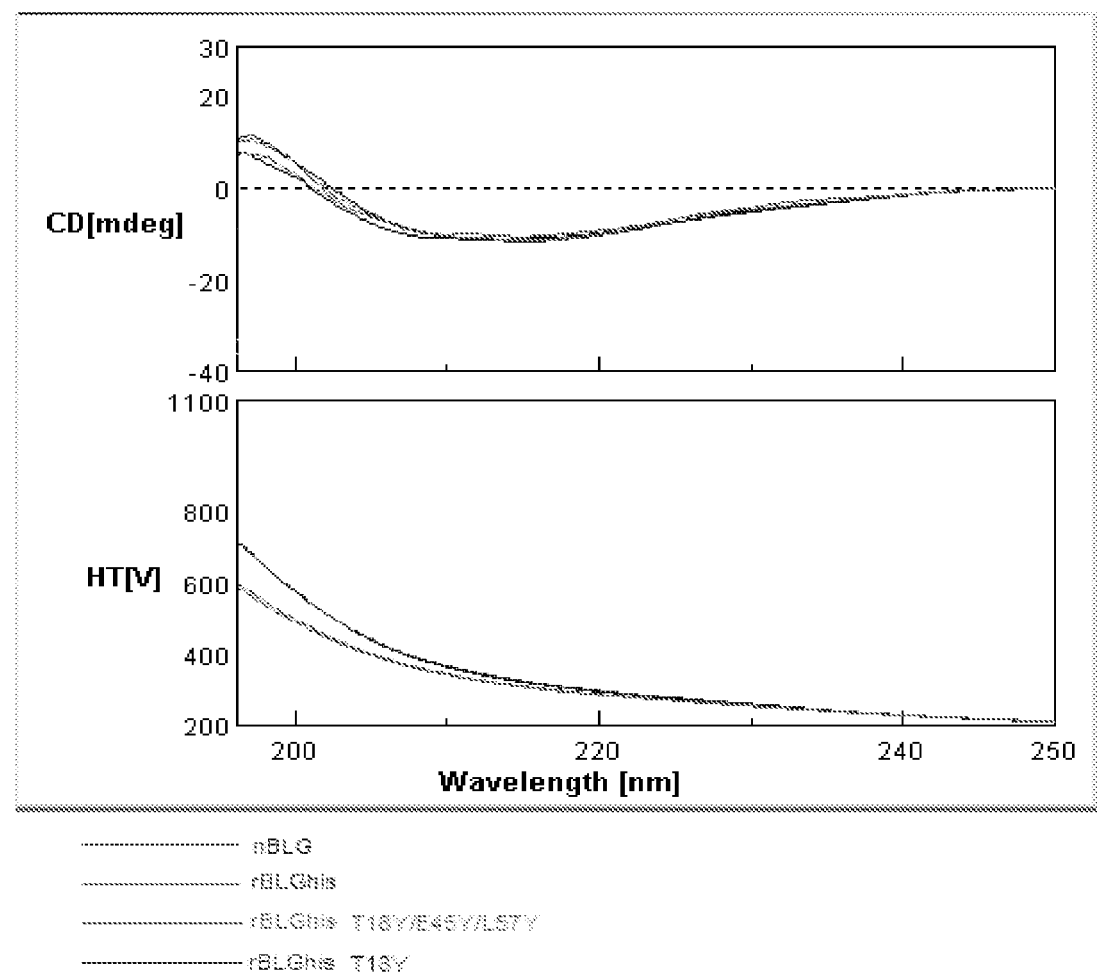
FIG. 21. CD-spectra of the nBLG, rBLG-His6 and its mutants are shown.

For circular dichroism (CD) measurements the buffer of all rBLGs was exchanged into 5 mM Hepes (pH 7.4) using Econo Pac 10DG desalting columns (Bio-Rad) with the cut of 6000 Da. Far-UV spectrum of the native BLG (nBLG, Sigma), rBLG-His6 and the rBLG-His 6 mutants was measured with Jasco J-715 spectropolarimeter at +20° C. controlled with a Peltier thermostat (Jasco PTC-348WI) using a 1-mm quartz cell. The concentrations of the proteins were 1 mg/ml for nBLG, 0.25 mg/ml for rBLG-His6, 1.3 mg/ml for rBLG-His6 T18Y and 0.93 mg/ml for rBLG-His6 T18Y/E45Y/L57Y mutant. The CD-spectra shown are averages of three measurements (FIG. 21).

V. Characterisation of the D1 IgE Fab Binding to rBLGs by ELISA

First the rBLGs were biotinylated. The biotinylation of the rBLGs was performed with Sulfo-NHS-LC-biotin (Pierce) in a molar ratio of 2 mol biotin:1 mol protein in 10 mM Hepes, 0.9% NaCl for 30 min at RT with a gentle shaking. The unreacted biotin was removed using Econo Pac 10 DG desalting columns (Bio-Rad). The incorporation of the biotin to the rBLGs was analysed by western blotting using SA-AFOS detection.

Figure 22:
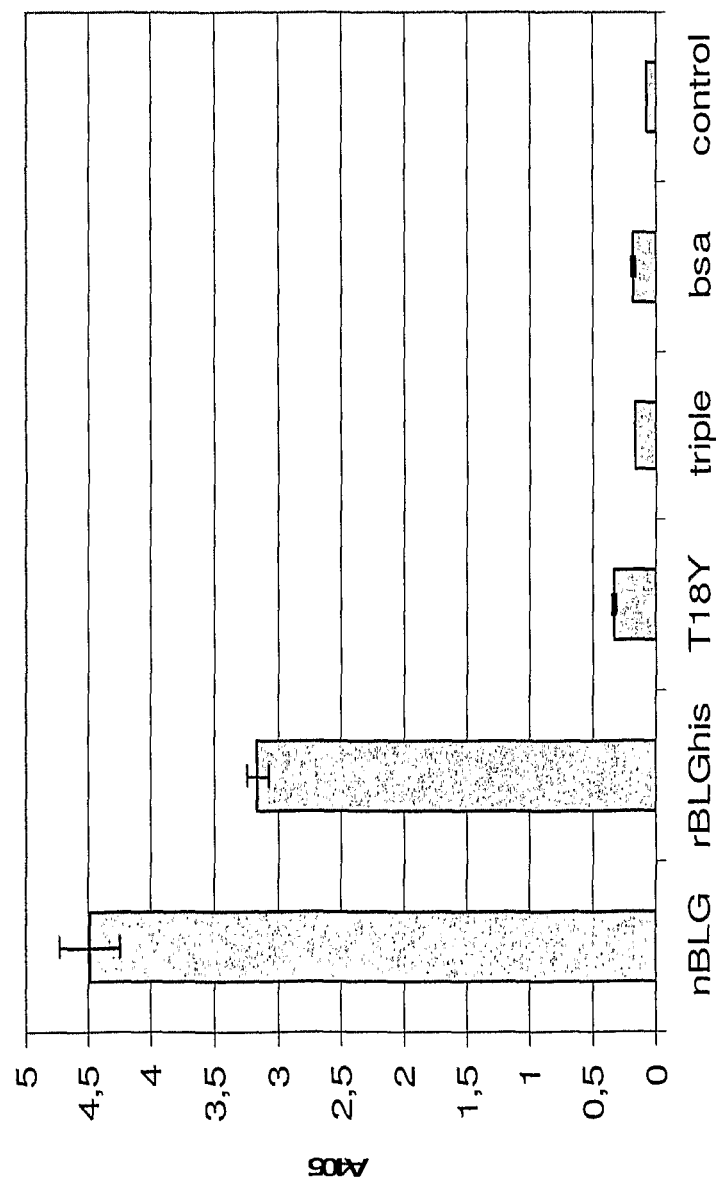
FIG. 22. The binding properties of the D1 IgE Fab to different BLGs were analysed by ELISA. Biotinylated nBLG, rBLG-His6 or its mutants were immobilised on to the SA-microtitre wells. Bound D1 IgE Fab was detected using AFOS-conjugated goat anti-kappa antibody. Triple=rBLG-His6 T18Y/E45Y/L57Y mutant, Bsa=bovine serum albumin, and control-sample shows the background obtained from anti kappa-AFOS conjugate when the BLGs are immobilised but no D1 IgE Fab used.

Then 1 µg biotinylated nBLG, rBLG-His6, rBLG-His6 T18Y mutants in 110 µl 0.5% BSA/PBS were immobilised onto the streptavidin microtitre wells (Roche) for 1 h at RT. After that 100 µl 1:15000 diluted anti-BLG D1 Fab (1.6 mg/ml) in 0.5% BSA, PBS was added to the washed wells. After a 1-h incubation the wells were washed three times with PBS. The detection of the BLGs was carried out using AFOS-conjugated goat anti-human kappa antibody (Southern Biotech). Then p-nitrophenylphosphate substrate (Sigma) was added to the wells (2 mg/ml in diethanolamine buffer). The absorbance at the wavelength 405 nm was measured after 20 minutes of adding the substrate (FIG. 22).

Figure 23:
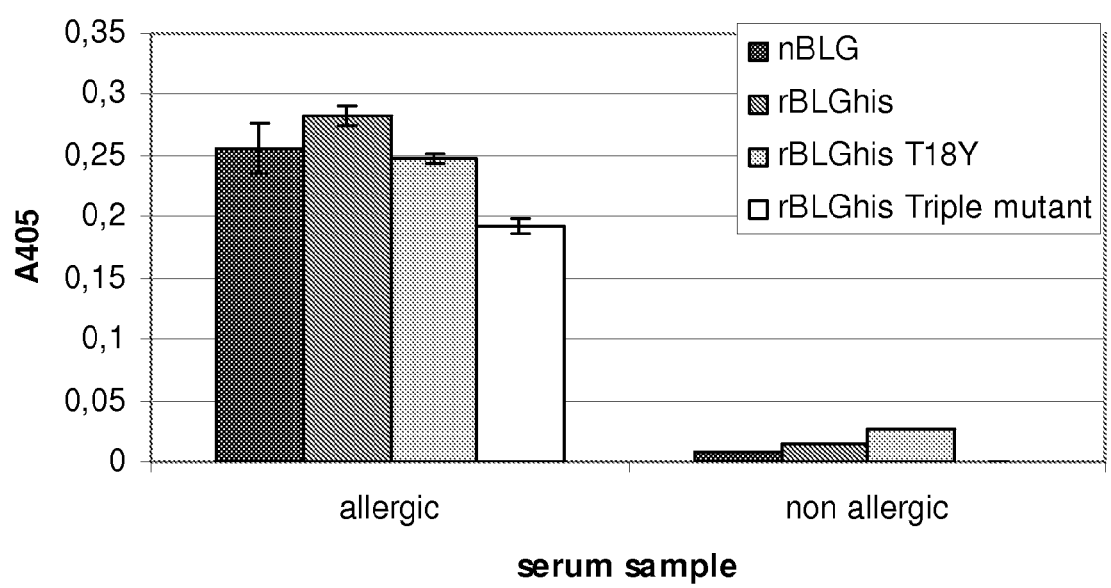
FIG. 23. The binding properties of the IgE serum samples from allergic and non-allergic donor to different BLGs were analysed by ELISA. Biotinylated nBLG, rBLG-His6 or its mutants were immobilised on to the SA-microtitre wells. The bound IgE was detected using AFOS-conjugated goat anti-human IgE.

The ELISA analysis with the serum samples (1:8 dilution in 0.5% BSA, PBS) was performed as above except the bound IgE from allergic patient serum was detected with AFOS-conjugated goat anti-human IgE (Southern Biotech). The absorbances were measured at 405 nm after a 2-h incubation of adding the substrate (FIG. 23).

VI. Analysis of the Binding Kinetics

Figure 24:
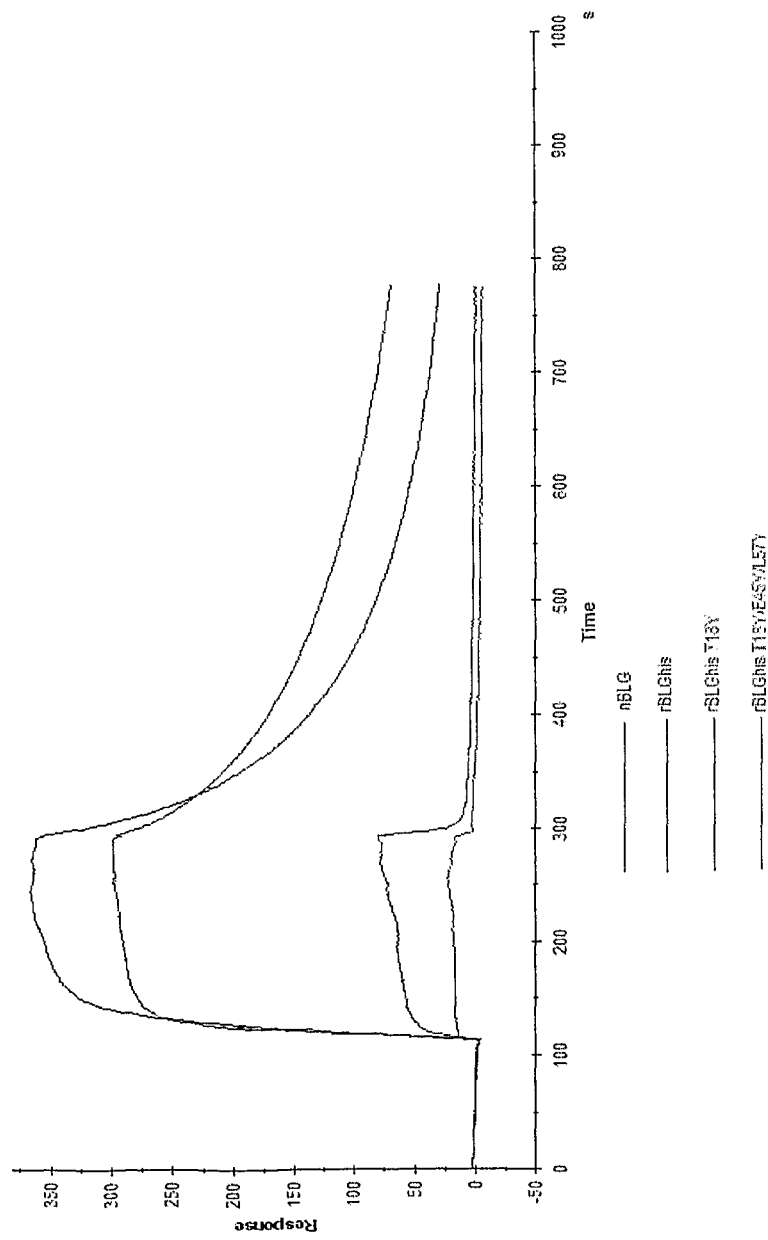
FIG. 24. BIAcore analysis of the nBLG, rBLG-His6 and its mutants. Binding curves of the 69.6 nM D1 IgE Fab solution for binding to different BLGs are shown. The association and dissociation constants of the D1 IgE Fab to nBLG, rBLG-His6 and its mutants are calculated and shown in Table XI.

The association and dissociation constants of the D1 IgE Fab to nBLG, rBLG-His6 and its mutants were measured by BIAcore. The biotinylated BLGs were immobilised in HBS buffer (10 mM Hepes, 0.15M NaCl, 3.4 mM EDTA, 0.005% BIAcore P20 surfactant, pH 7.4) and at a concentration of 1 µg/ml onto the streptavidin biosensor chip resulting in a surface of approximately 400-500 RU. The biotinylated nBLG was immobilised only with 200 RU onto the surface of the SA-chip. The binding kinetics of the purified D1 IgE Fab was analysed at a flow rate of 30 µl/min with the concentrations 138.9 nM, 69.6 nM, 34.8 nM, 17.4 nM, 8.7 nM, 4.3 nM, 2.2 and 1.1 nM. Regeneration of the BLG surface was performed with 100 µM nBLG (Sigma). Binding curves of the 69.6 nM D1 IgE Fab solution are shown in FIG. 24.

TABLE I: Primers used for cDNA synthesis and PCR amplification of the human IgE Fd region.

TABLE I

| Primers used for cDNA synthesis and PCR amplification of the human IgE Fd region. | |
|---|---|
| Cε1: | 5'-GCTGAAGGTTTTGTTGTCGACCCAGTC-3' (SEQ ID NO: 12) |
| CεNotI: | 5'-GAATGGTGCGGCCGCGCTGAAGGTTTTGTTGTCG-3' (SEQ ID NO: 13) |
| VH1a: | 5'-ATGGCCGCAGCTCAGGTKCAGCTGGTGCAG-3' (SEQ ID NO: 14) |
| VH1b: | 5'-ATGGCCGCAGCTCAGGTCCAGCTTGTGCAG-3' (SEQ ID NO: 15) |
| VH1c: | 5'-ATGGCCGCAGCTSAGGTCCAGCTGGTACAG-3' (SEQ ID NO: 16) |
| VH1d: | 5'-ATGGCCGCAGCTCARATGCAGCTGGTGCAG-3' (SEQ ID NO: 17) |
| VH2a: | 5'-ATGGCCGCAGCTCAGATCACCTTGAAGGAG-3' (SEQ ID NO: 18) |
| VH2b: | 5'-ATGGCCGCAGCTCAGGTCACCTTGARGGAG-3' (SEQ ID NO: 19) |
| VH3a: | 5'-ATGGCCGCAGCTGARGTGCAGCTGGTGGAG-3' (SEQ ID NO: 20) |
| VH3b: | 5'-ATGGCCGCAGCTCAGGTGCAGCTGGTGGAG-3' (SEQ ID NO: 21) |
| VH3c: | 5'-ATGGCCGCAGCTGAGGTGCAGCTGTTGGAG-3' (SEQ ID NO: 22) |
| VH4a: | 5'-ATGGCCGCAGCTCAGSTGCAGCTGCAGGAG-3' (SEQ ID NO: 23) |
| VH4b: | 5'-ATGGCCGCAGCTCAGGTGCAGCTACAGCAG-3' (SEQ ID NO: 24) |
| VH5a: | 5'-ATGGCCGCAGCTGARGTGCAGCTGGTGCAG-3' (SEQ ID NO: 25) |
| VH6a: | 5'-ATGGCCGCAGCTCAGGTACAGCTGCAGCAG-3' (SEQ ID NO: 26) |
| VH7a: | 5'-ATGGCCGCAGCTCAGGTSCAGCTGGTGCAA-3' (SEQ ID NO: 27) |
| VH1A: | 5'-TTACTCGCGGCCCAGCCGGCCATGGCCGCAGCT-3' (SEQ ID NO: 28) |

TABLE II: Primers used for cDNA synthesis and PCR amplification of human kappa and lambda chains.

TABLE II

| Primers used for cDNA synthesis and PCR amplification of human kappa and lambda chains. | |
|---|---|
| Cκ1: | 5'-AGGTAGGGCGCGCCTTAACACTCTCCCCTGTTGAAGC-3' (SEQ ID NO: 29) |

TABLE II-continued

Primers used for cDNA synthesis and PCR amplification of human kappa and lambda chains.

```
Vκ1a:   5'-ATGGCAGCGGCTRACATCCAGATGACCCAG-3'
        (SEQ ID NO: 30)

Vκ1b:   5'-ATGGCAGCGGCTGMCATCCAGTTGACCCAG-3'
        (SEQ ID NO: 31)

Vκ1c:   5'-ATGGCAGCGGCTGCCATCCRGATGACCCAG-3'
        (SEQ ID NO: 32)

Vκ1d:   5'-ATGGCAGCGGCTGTCATCTGGATGACCCAG-3'
        (SEQ ID NO: 33)

Vκ2a:   5'-ATGGCAGCGGCTGATATTGTGATGACCCAG-3'
        (SEQ ID NO: 34)

Vκ2b:   5'-ATGGCAGCGGCTGATRTTGTGATGACTCAG-3'
        (SEQ ID NO: 35)

Vκ3a:   5'-ATGGCAGCGGCTGAAATTGTGTTGACRCAG-3'
        (SEQ ID NO: 36)

Vκ3b:   5'-ATGGCAGCGGCTGAAATAGTGATGACGCAG-3'
        (SEQ ID NO: 37)

Vκ3c:   5'-ATGGCAGCGGCTGAAATTGTAATGACACAG-3'
        (SEQ ID NO: 38)

Vκ4a:   5'-ATGGCAGCGGCTGACATCGTGATGACCCAG-3'
        (SEQ ID NO: 39)

Vκ5a:   5'-ATGGCAGCGGCTGAAACGACACTCACGCAG-3'
        (SEQ ID NO: 40)

Vκ6a:   5'-ATGGCAGCGGCTGAAATTGTGCTGACTCAG-3'
        (SEQ ID NO: 41)

Vκ6b:   5'-ATGGCAGCGGCTGATGTTGTGATGACACAG-3'
        (SEQ ID NO: 42)

Vk/λ1:  5'-TTGTTATTGCTAGCTGCACAACCAGCAATGGCAGCGGCT-3'
        (SEQ ID NO: 43)

Cλ1:    5'-AGGTAGGGCGCGCCTTATGAACATTCYGYAGGGGC-3'
        (SEQ ID NO: 44)

Vλ1a:   5'-ATGGCAGCGGCTCAGTCTGTGCTGACTCAG-3'
        (SEQ ID NO: 45)

Vλ1b:   5'-ATGGCAGCGGCTCAGTCTGTGYTGACGCAG-3'
        (SEQ ID NO: 46)

Vλ1c:   5'-ATGGCAGCGGCTCAGTCTGTCGTGACGCAG-3'
        (SEQ ID NO: 47)

Vλ2:    5'-ATGGCAGCGGCTCAGTCTGCCCTGACTCAG-3'
        (SEQ ID NO: 48)

Vλ3a:   5'-ATGGCAGCGGCTTCCTATGWGCTGACTCAG-3'
        (SEQ ID NO: 49)

Vλ3b:   5'-ATGGCAGCGGCTTCCTATGAGCTGACACAG-3'
        (SEQ ID NO: 50)

Vλ3c:   5'-ATGGCAGCGGCTTCTTCTGAGCTGACTCAG-3'
        (SEQ ID NO: 51)

Vλ3d:   5'-ATGGCAGCGGCTTCCTATGAGCTGATGCAG-3'
        (SEQ ID NO: 52)

Vλ4C:   5'-ATGGCAGCGGCTCAGCYTGTGCTGACTCAA-3'
        (SEQ ID NO: 53)

Vλ5:    5'-ATGGCAGCGGCTCAGSCTGTGCTGACTCAG-3'
        (SEQ ID NO: 54)
```

TABLE II-continued

Primers used for cDNA synthesis and PCR amplification of human kappa and lambda chains.

```
Vλ6:    5'-ATGGCAGCGGCTAATTTTATGCTGACTCAG-3'
        (SEQ ID NO: 55)

Vλ7:    5'-ATGGCAGCGGCTCAGACTGTGGTGACTCAG-3'
        (SEQ ID NO: 56)

Vλ8:    5'-ATGGCAGCGGCTCAGACTGTGGTGACCCAG-3'
        (SEQ ID NO: 57)

Vλ4/9:  5'-ATGGCAGCGGCTCWGCCTGTGCTGACTCAG-3'
        (SEQ ID NO: 58)

Vλ10:   5'-ATGGCAGCGGCTCAGGCAGGGCTGACTCAG-3'
        (SEQ ID NO: 59)
```

TABLE III: Primers used for PCR amplification of the human variable regions of the heavy chain.

TABLE III

Primers used for PCR amplification of the human variable regions of the heavy chain.

```
VH1:    5'-ATTTACTCGAGTGAGGAGACGGTGACCAGGGTGCC-3'
        (SEQ ID NO: 60)

VH2:    5'-ATTTACTCGAGTGAAGAGACGGTGACCATTGTCCC-3'
        (SEQ ID NO: 61)

VH3:    5'-ATTTACTCGAGTGAGGAGACGGTGACCAGGGTTCC-3'
        (SEQ ID NO: 62)

VH4:    5'-ATTTACTCGAGTGAGGAGACGGTGACCGTGGTCCC-3'
        (SEQ ID NO: 63)

VH1A:   5'-TTACTCGCGGCCCAGCCGGCCATGGCCGCAGCT-3'
        (SEQ ID NO: 64)
```

TABLE IV: Primers used for PCR amplification of the human variable regions of the light chains.

TABLE IV

Primers used for PCR amplification of the human variable regions of the light chains.

```
Vκ1:    5'-TTATAGAGCTCGACATCCAGATGACCCAGTCTCC-3'
        (SEQ ID NO: 65)

Vκ2:    5'-TTATAGAGCTCGATGTTGTGATGACTCAGTCTCC-3'
        (SEQ ID NO: 66)

Vκ3:    5'-TTATAGAGCTCGAAATTGTGTTGACGCAGTCTCC-3'
        (SEQ ID NO: 67)

Vκ4:    5'-TTATAGAGCTCGACATCGTGATGACCCAGTCTCC-3'
        (SEQ ID NO: 68)

Vκ5:    5'-TTATAGAGCTCGAAACGACACTCACGCAGTCTCC-3'
        (SEQ ID NO: 69)

Vκ6:    5'-TTATAGAGCTCGAAATTGTGCTGACTCAGTCTCC-3'
        (SEQ ID NO: 70)

Vκ7:    5'-TATAAGCGGCCGCACGTTTGATTTCCACCTTGGTCCC-3'
        (SEQ ID NO: 71)

Vκ8:    5'-TATAAGCGGCCGCACGTTTGATCTCCAGCTTGGTCCC-3'
        (SEQ ID NO: 72)

Vκ9:    5'-TATAAGCGGCCGCACGTTTGATATCCACTTTGGTCCC-3'
        (SEQ ID NO: 73)
```

TABLE IV-continued

Primers used for PCR amplification of the human variable regions of the light chains.

Vκ10: 5'-TATAAGCGGCCGCACGTTTGATCTCCACCTTGGTCCC-3'
(SEQ ID NO: 74)

Vκ11: 5'-TATAAGCGGCCGCACGTTTAATCTCCAGTCGTGTCCC-3'
(SEQ ID NO: 75)

Vλ1: 5'-ATTTAGAGCTCCAGTCTGTGTTGACGCAGCCGCC-3'
(SEQ ID NO: 76)

Vλ2: 5'-ATTTAGAGCTCCAGTCTGCCCTGACTCAGCCTGC-3'
(SEQ ID NO: 77)

Vλ3: 5'-ATTTAGAGCTCTCCTATGTGCTGACTCAGCCACC-3'
(SEQ ID NO: 78)

Vλ4: 5'-ATTTAGAGCTCTCTTCTGAGCTGACTCAGGACCC-3'
(SEQ ID NO: 79)

Vλ5: 5'-ATTTAGAGCTCCACGTTATACTGACTCAACCGCC-3'
(SEQ ID NO: 80)

Vλ6: 5'-ATTTAGAGCTCCAGGCTGTGCTCACTCAGCCGTC-3'
(SEQ ID NO: 81)

Vλ7: 5'-ATTTAGAGCTCAATTTTATGCTGACTCAGCCCCA-3'
(SEQ ID NO: 82)

Vλ8: 5'-ATATTGCGGCCGCACCTAGGACGGTGACCTTGGTCCC-3'
(SEQ ID NO: 83)

Vλ9: 5'-ATATTGCGGCCGCACCTAGGACGGTCAGCTTGGTCCC-3'
(SEQ ID NO: 84)

Vλ10: 5'-ATATTGCGGCCGCACCTAAAACGGTGAGCTGGGTCCC-3'
(SEQ ID NO: 85)

TABLE V: Primers used for PCR amplification of the human Fd regions with IgE and IgG1 subtype.

TABLE V

Primers used for PCR amplification of the human Fd regions with IgE and IgG1 subtype.

5'Cε: 5'-GCTCACCGTCTCCTCAGCCTCCACACAGAGCCCATCCG-3'
(SEQ ID NO: 86)

TABLE V-continued

Primers used for PCR amplification of the human Fd regions with IgE and IgG1 subtype.

3'Cε: 5'-GCATTGCATTGCGGCCGCTTAATGGTGATGGTGATGATGG
CTGAAGGTTTTGTTGTCGACCC-3' (SEQ ID NO: 87)

5'Cγ: 5'-GGTCACCGTCTCCTCAGCCTCCACCAAGGGCCC-3'
(SEQ ID NO: 88)

3'Cγ: 5'-TTTAGTTTATGCGGCCGCTTAATGGTGATGATGATGGTGA
CAAGATTTGGGCTCTGC-3' (SEQ ID NO: 89)

5'Vε: 5'-ACTCATTAGGCACCCCAGGC-3'
(SEQ ID NO: 90)

3'Vε: 5'-TGAGGAGACGGTGACC-3' (SEQ ID NO: 91)

5'Cκ: 5'-CGAACTGTGGCTGCACC-3' (SEQ ID NO: 92)

3'Cκ: 5'-AGGTAGGGCGCGCCTTAACACTCTCCCCTGTTGAAGC-3'
(SEQ ID NO: 93)

5'Vκ: 5'-TTGTTATTGCTAGCTGCACAACCAGCAATGGCAGACATCG
TGATGACCCAGTCTCC-3' (SEQ ID NO: 94)

3'Vκ: 5'-GGTGCAGCCACAGTTCGTTTGATYTCCASCTTGGTCCC-3'.
(SEQ ID NO: 95)

TABLE VI

Figure 9:
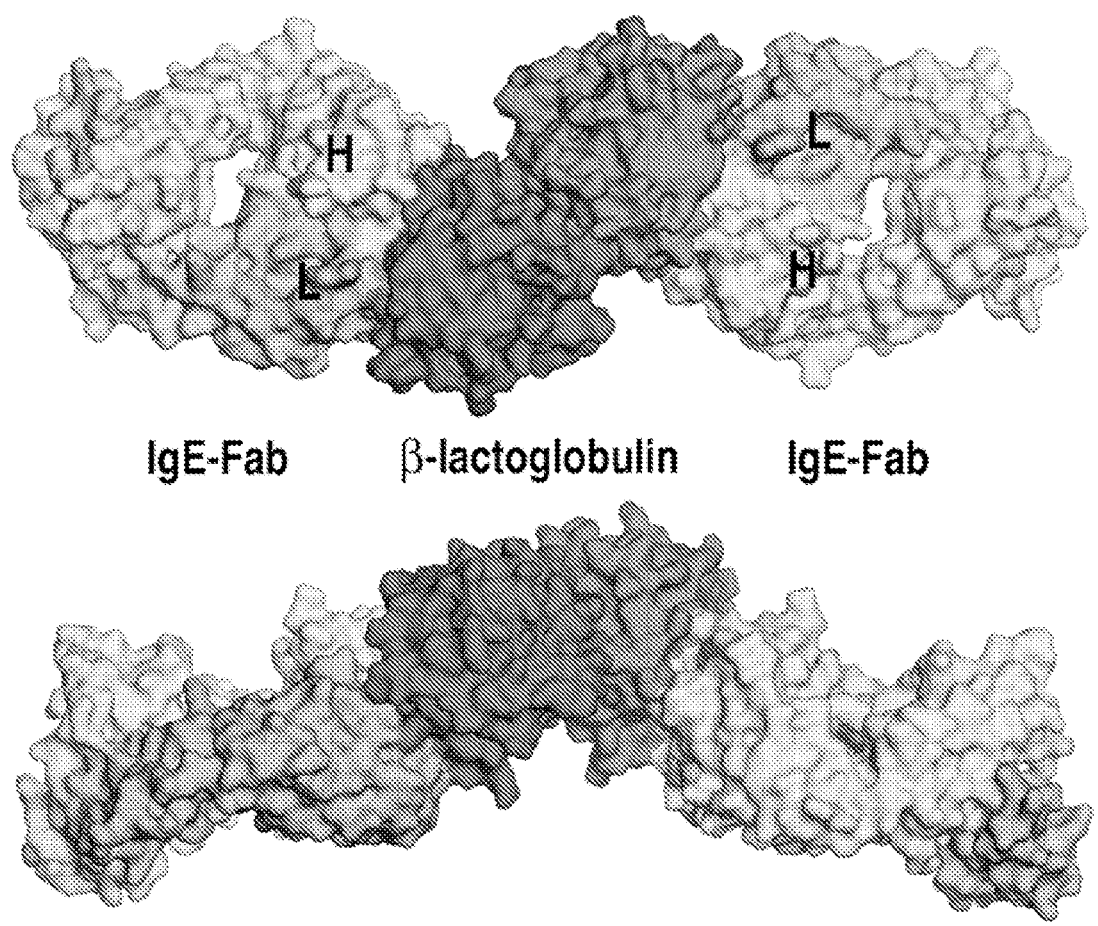
FIG. 9 shows the binding of the D1 IgE Fab-antibody to the β-lactoglobulin. (a), A schematic view of binding an allergen (grey) to two IgE molecules (light chain L, heavy chain H)
Figure 10:
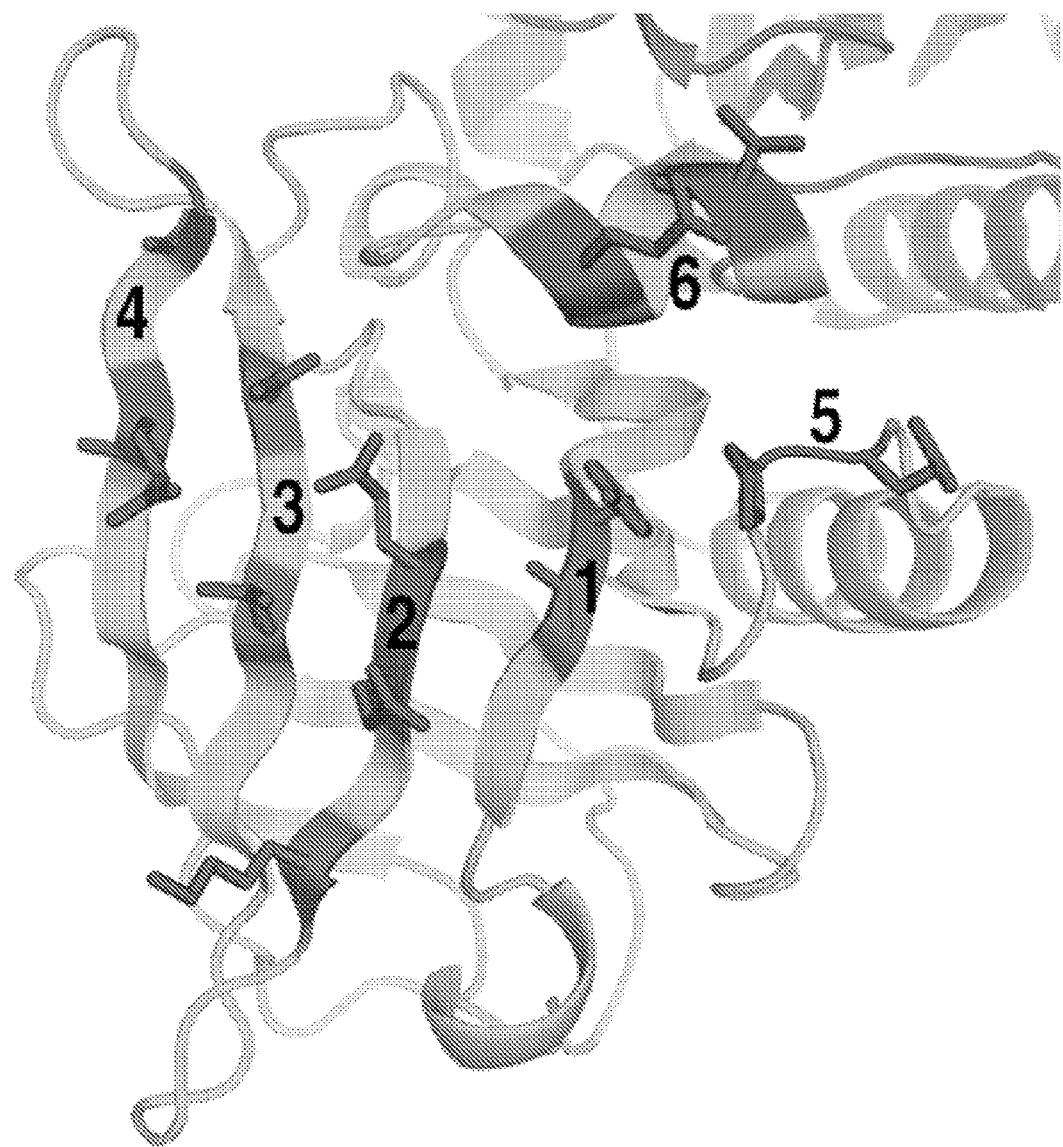
FIG. 10 shows the different segments of the β-lactoglobulin epitope which are numbered 1-6.
Figure 11:
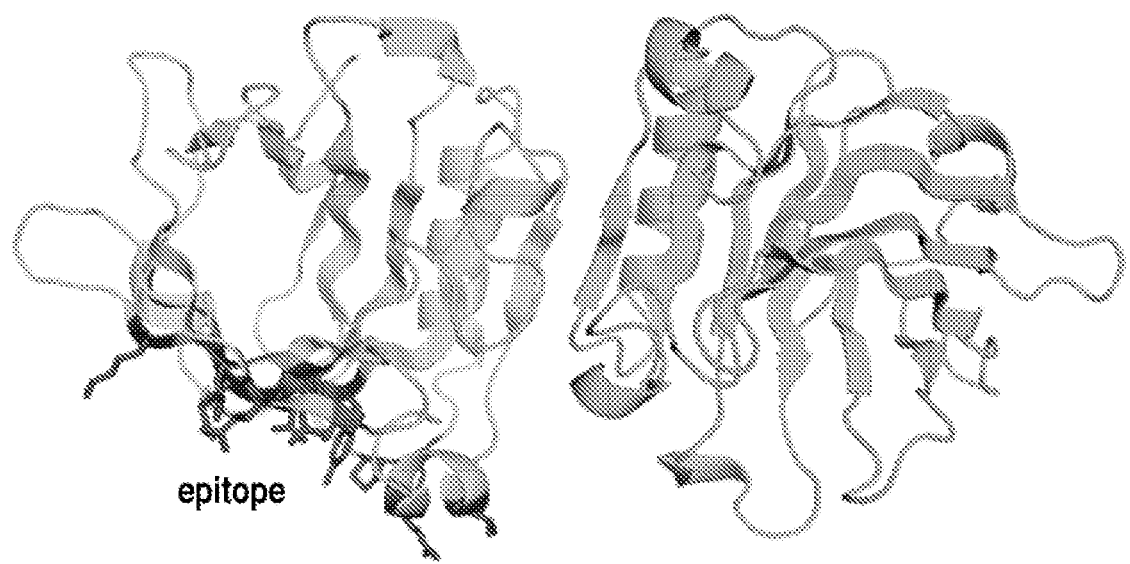
FIG. 11 shows the binding of the D1 IgE Fab to β-lactoglobulin with the side view on the surface of D1/IgE-Fab fragment.
Figure 12:
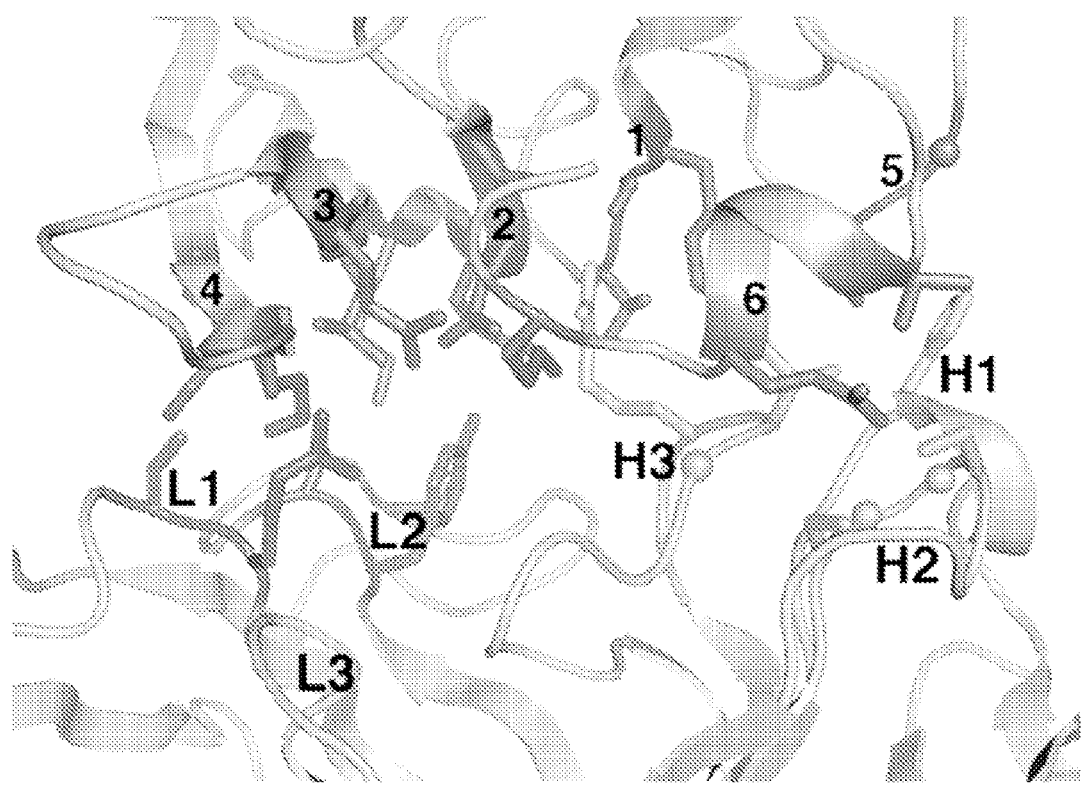
FIG. 12 shows the surface of β-lactoglobulin epitope with the CDR loops of the D1 IgE Fab and the residues of the D1 IgE Fab which make contacts with β-lactoglobulin.
Figure 13:
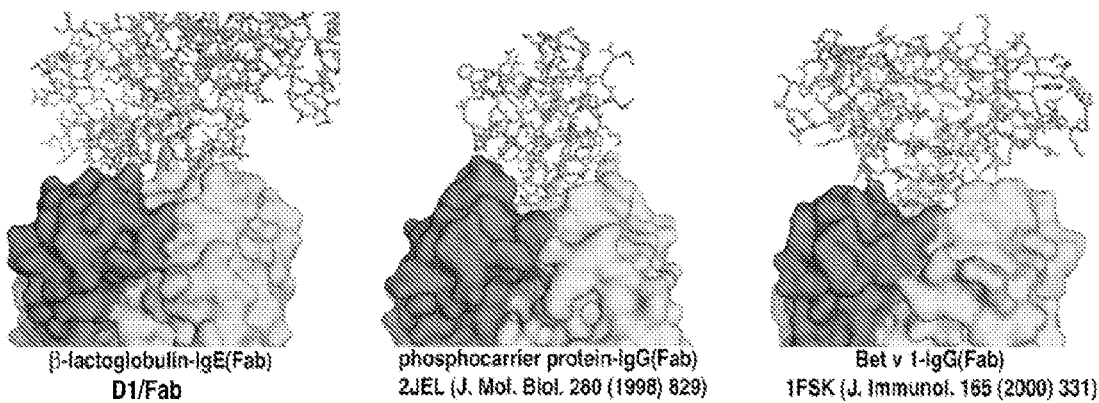
FIG. 13 shows the binding of the D1 IgE Fab to β-lactoglobulin (left), the IgG antibody-antigen type binding IgG Fab 2JEL to phosphocarrier protein (middle) and IgG-allergen type binding of the BV16/Fab to the pollen allergen Bet v 1 (right).
Figure 14:
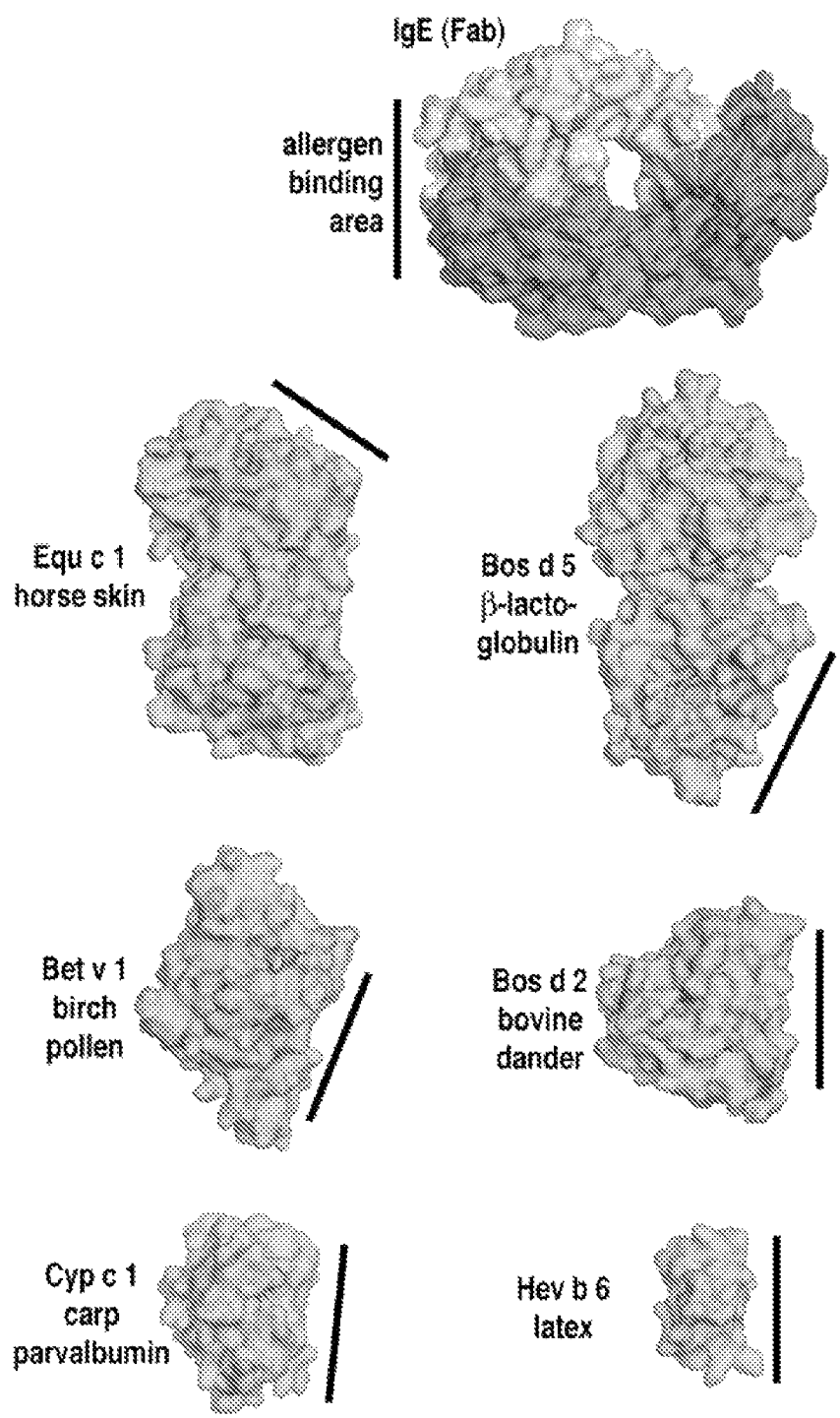
FIG. 14 shows the potential IgE epitope from different allergens: Equ c 1, horse skin (Lascombe et al., 2000, J. Biol. Chem. 275(28):21572-21577); Bos d 5, Beta-lactoglobulin; Bet v 1, birch pollen (Spangfort et al. 2003, J. Immunol. 171(6):3084-3090); Bos d 2, bovine dander (Rautiainen et al., 1998, Biochem. Biophys. Res. Commun. 247:746-750); Cyp c 1, carp parvalbumin (Swoboda et al., 2002, J. Immunol. 168(9):4576-4584); and Hey b 6, latex (see WO02094878). The planar (flat) surfaces are indicated with thick lines/bars.

The D1 IgE Fab binding epitopes of β-lactoglobulin. Core epitope: residues which are making direct contacts with D1 IgE Fab. Extended epitope: includes also residues which mutation may affect binding of D1 IgE Fab. The segments are as shown in FIG. 9d.

| Segment | Core epitope | Extended epitope |
|---|---|---|
| 1 | W19-Y20 | T18-Y20 |
| 2 | V43-K47 | Y42-K47 |
| 3 | L57-Q59 | E55-Q59 |
| 4 | C66-Q68 | E65-K70 |
| 5 | P126-E127 | T125-E127 |
| 6 | T154-E157 | T154-H161 |

TABLE VII

The amino acid sequence comparison of published IgE sequences reveals that the light chains of the known IgE antibodies binding to diverse groups of allergens are strikingly conserved. Conserved amino acids are shown in bold.

| antigen CDR | Ig | clone PDB | CDR-L1 XXXXXXXXXXXXXX.. | (SEQ ID NO) | CDR-L2 ....XXXXXXX | (SEQ ID NO) | CDR-L3 XXXXXXXXXXX. | (SEQ ID NO) |
|---|---|---|---|---|---|---|---|---|
| Bet v 1 | IgE | C-H1 | | | | | QQSYSTP--RT | (111) |
| | | C-H2 | | | | | AAWDDSLS-GRVV | (112) |
| | | C-H3 | | | | | QQRSNWP-PLT | (113) |
| Phl p 1 | IgE | 25 | SQSIGN------YL-NWY | (96) | LLIYAASSLQS | (7) | QQSNRTP--ITF | (114) |
| | | 10 | SQTFNN------YL-NWY | (97) | LLIYAASTLRR | (106) | QQSYSTP--LTF | (115) |
| | | 43 | SRTIYN------YL-NWY | (98) | LLIHAASTLQD | (107) | QQSHGTP--LTF | (116) |
| Phl p 2 | | | | | | | | |
| Phl p 5 | IgE | 31 | SQSISS------YL-NWY | (99) | LLIYAASSLQS | (7) | QQSHSTP--YTF | (117) |
| | | 14 | SHSISN------YL-NWY | (100) | LLIYAASSLQS | (7) | QESFSPS--GTF | (118) |
| | | 28 | SQSILG------YL-NWY | (101) | LLIYAASTLQS | (108) | QQSYITP--RTF | (119) |
| | | 5 | SQGISS------WLAWY | (102) | LLIYSASSLQS | (109) | QQANSFP--YTF | (120) |
| hevein | IgE | 1A4 | SQSVSS-----SY-LAWY | (103) | LLIYGASSRAT | (110) | QQYGSSP--LTF | (121) |
| hevein | IgE | 1C2 | SQSISS------YL-NWY | (104) | LLIYAASSLQS | (7) | QQSYSTP--RTF | (122) |
| Bos d 5 | IgE | D1 | SQGISS------RLAWY | (105) | LLIYAASSLQS | (7) | QQYHSYP--WTF | (123) |

TABLE VIII

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1 | CB | THR | A | 4 | −23.309 | −4.747 | −0.142 | 1.00 | 69.95 | A |
| ATOM | 2 | OG1 | THR | A | 4 | −22.553 | −4.413 | −1.318 | 1.00 | 70.24 | A |
| ATOM | 3 | CG2 | THR | A | 4 | −22.399 | −5.463 | 0.852 | 1.00 | 69.08 | A |
| ATOM | 4 | C | THR | A | 4 | −25.438 | −4.928 | −1.503 | 1.00 | 69.21 | A |
| ATOM | 5 | O | THR | A | 4 | −25.191 | −3.780 | −1.887 | 1.00 | 68.89 | A |
| ATOM | 6 | N | THR | A | 4 | −24.039 | −6.943 | −1.113 | 1.00 | 69.41 | A |
| ATOM | 7 | CA | THR | A | 4 | −24.516 | −5.659 | −0.519 | 1.00 | 69.43 | A |
| ATOM | 8 | N | GLN | A | 5 | −26.503 | −5.615 | −1.909 | 1.00 | 68.87 | A |
| ATOM | 9 | CA | GLN | A | 5 | −27.482 | −5.071 | −2.843 | 1.00 | 68.15 | A |
| ATOM | 10 | CB | GLN | A | 5 | −28.213 | −3.889 | −2.204 | 1.00 | 69.22 | A |
| ATOM | 11 | CG | GLN | A | 5 | −29.389 | −3.378 | −3.017 | 1.00 | 71.17 | A |
| ATOM | 12 | CD | GLN | A | 5 | −30.366 | −4.488 | −3.374 | 1.00 | 72.36 | A |
| ATOM | 13 | OE1 | GLN | A | 5 | −30.836 | −5.225 | −2.499 | 1.00 | 73.05 | A |
| ATOM | 14 | NE2 | GLN | A | 5 | −30.683 | −4.610 | −4.664 | 1.00 | 71.92 | A |
| ATOM | 15 | C | GLN | A | 5 | −26.828 | −4.630 | −4.150 | 1.00 | 67.11 | A |
| ATOM | 16 | O | GLN | A | 5 | −26.732 | −3.435 | −4.438 | 1.00 | 66.95 | A |
| ATOM | 17 | N | THR | A | 6 | −26.374 | −5.604 | −4.934 | 1.00 | 66.26 | A |
| ATOM | 18 | CA | THR | A | 6 | −25.732 | −5.328 | −6.216 | 1.00 | 64.71 | A |
| ATOM | 19 | CB | THR | A | 6 | −24.481 | −6.213 | −6.444 | 1.00 | 64.50 | A |
| ATOM | 20 | OG1 | THR | A | 6 | −24.887 | −7.549 | −6.765 | 1.00 | 63.11 | A |
| ATOM | 21 | CG2 | THR | A | 6 | −23.607 | −6.239 | −5.198 | 1.00 | 64.44 | A |
| ATOM | 22 | C | THR | A | 6 | −26.711 | −5.608 | −7.348 | 1.00 | 63.92 | A |
| ATOM | 23 | O | THR | A | 6 | −27.769 | −6.205 | −7.141 | 1.00 | 63.78 | A |
| ATOM | 24 | N | MET | A | 7 | −26.341 | −5.182 | −8.549 | 1.00 | 63.06 | A |
| ATOM | 25 | CA | MET | A | 7 | −27.172 | −5.377 | −9.728 | 1.00 | 61.96 | A |
| ATOM | 26 | CB | MET | A | 7 | −26.431 | −4.865 | −10.959 | 1.00 | 60.12 | A |
| ATOM | 27 | CG | MET | A | 7 | −27.207 | −4.975 | −12.239 | 1.00 | 58.56 | A |
| ATOM | 28 | SD | MET | A | 7 | −26.235 | −4.362 | −13.595 | 1.00 | 56.18 | A |
| ATOM | 29 | CE | MET | A | 7 | −27.117 | −2.858 | −14.005 | 1.00 | 57.10 | A |
| ATOM | 30 | C | MET | A | 7 | −27.521 | −6.852 | −9.911 | 1.00 | 62.21 | A |
| ATOM | 31 | O | MET | A | 7 | −26.792 | −7.730 | −9.448 | 1.00 | 63.03 | A |
| ATOM | 32 | N | LYS | A | 8 | −28.637 | −7.121 | −10.583 | 1.00 | 61.64 | A |
| ATOM | 33 | CA | LYS | A | 8 | −29.054 | −8.496 | −10.821 | 1.00 | 61.39 | A |
| ATOM | 34 | CB | LYS | A | 8 | −30.516 | −8.542 | −11.274 | 1.00 | 62.21 | A |
| ATOM | 35 | CG | LYS | A | 8 | −31.481 | −7.995 | −10.222 | 1.00 | 64.73 | A |
| ATOM | 36 | CD | LYS | A | 8 | −32.952 | −8.076 | −10.648 | 1.00 | 65.77 | A |

TABLE VIII-continued

Structure coordinates of the epitopes of allergenic beta-lactoglobulin in an antibody-beta-lactoglobulin immunocomplex;

|  |  | Atom type | Resid |  | # | X | Y | Z | OCC | B |  |
|---|---|---|---|---|---|---|---|---|---|---|---|
| ATOM | 37 | CE | LYS | A | 8 | −33.470 | −9.511 | −10.688 | 1.00 | 66.53 | A |
| ATOM | 38 | NZ | LYS | A | 8 | −32.973 | −10.272 | −11.870 | 1.00 | 67.48 | A |
| ATOM | 39 | C | LYS | A | 8 | −28.147 | −9.139 | −11.864 | 1.00 | 60.59 | A |
| ATOM | 40 | O | LYS | A | 8 | −26.924 | −9.122 | −11.720 | 1.00 | 61.07 | A |
| ATOM | 41 | N | GLY | A | 9 | −28.729 | −9.717 | −12.906 | 1.00 | 59.03 | A |
| ATOM | 42 | CA | GLY | A | 9 | −27.899 | −10.326 | −13.932 | 1.00 | 56.96 | A |
| ATOM | 43 | C | GLY | A | 9 | −27.156 | −9.276 | −14.746 | 1.00 | 54.94 | A |
| ATOM | 44 | O | GLY | A | 9 | −27.725 | −8.245 | −15.097 | 1.00 | 55.67 | A |
| ATOM | 45 | N | LEU | A | 10 | −25.889 | −9.531 | −15.049 | 1.00 | 52.32 | A |
| ATOM | 46 | CA | LEU | A | 10 | −25.090 | −8.591 | −15.834 | 1.00 | 50.35 | A |
| ATOM | 47 | CB | LEU | A | 10 | −23.875 | −8.150 | −15.029 | 1.00 | 49.63 | A |
| ATOM | 48 | CG | LEU | A | 10 | −22.872 | −7.298 | −15.807 | 1.00 | 49.13 | A |
| ATOM | 49 | CD1 | LEU | A | 10 | −23.483 | −5.950 | −16.144 | 1.00 | 48.82 | A |
| ATOM | 50 | CD2 | LEU | A | 10 | −21.620 | −7.119 | −14.984 | 1.00 | 49.11 | A |
| ATOM | 51 | C | LEU | A | 10 | −24.619 | −9.172 | −17.177 | 1.00 | 49.26 | A |
| ATOM | 52 | O | LEU | A | 10 | −24.125 | −10.298 | −17.231 | 1.00 | 48.64 | A |
| ATOM | 53 | N | ASP | A | 11 | −24.755 | −8.393 | −18.253 | 1.00 | 48.28 | A |
| ATOM | 54 | CA | ASP | A | 11 | −24.353 | −8.835 | −19.593 | 1.00 | 47.09 | A |
| ATOM | 55 | CB | ASP | A | 11 | −25.218 | −8.166 | −20.666 | 1.00 | 47.90 | A |
| ATOM | 56 | CG | ASP | A | 11 | −24.959 | −8.721 | −22.072 | 1.00 | 48.81 | A |
| ATOM | 57 | OD1 | ASP | A | 11 | −25.713 | −8.359 | −22.999 | 1.00 | 49.16 | A |
| ATOM | 58 | OD2 | ASP | A | 11 | −24.011 | −9.513 | −22.260 | 1.00 | 49.60 | A |
| ATOM | 59 | C | ASP | A | 11 | −22.887 | −8.534 | −19.863 | 1.00 | 45.64 | A |
| ATOM | 60 | O | ASP | A | 11 | −22.542 | −7.556 | −20.525 | 1.00 | 45.05 | A |
| ATOM | 61 | N | ILE | A | 12 | −22.033 | −9.405 | −19.348 | 1.00 | 44.43 | A |
| ATOM | 62 | CA | ILE | A | 12 | −20.590 | −9.279 | −19.493 | 1.00 | 43.31 | A |
| ATOM | 63 | CB | ILE | A | 12 | −19.911 | −10.595 | −19.096 | 1.00 | 43.33 | A |
| ATOM | 64 | CG2 | ILE | A | 12 | −18.408 | −10.420 | −19.082 | 1.00 | 43.02 | A |
| ATOM | 65 | CG1 | ILE | A | 12 | −20.418 | −11.030 | −17.719 | 1.00 | 45.17 | A |
| ATOM | 66 | CD1 | ILE | A | 12 | −20.114 | −12.483 | −17.357 | 1.00 | 46.47 | A |
| ATOM | 67 | C | ILE | A | 12 | −20.135 | −8.893 | −20.907 | 1.00 | 42.33 | A |
| ATOM | 68 | O | ILE | A | 12 | −19.201 | −8.111 | −21.082 | 1.00 | 42.79 | A |
| ATOM | 69 | N | GLN | A | 13 | −20.797 | −9.433 | −21.918 | 1.00 | 40.46 | A |
| ATOM | 70 | CA | GLN | A | 13 | −20.413 | −9.131 | −23.286 | 1.00 | 38.91 | A |
| ATOM | 71 | CB | GLN | A | 13 | −21.223 | −9.984 | −24.266 | 1.00 | 40.33 | A |
| ATOM | 72 | CG | GLN | A | 13 | −21.016 | −11.479 | −24.112 | 1.00 | 41.54 | A |
| ATOM | 73 | CD | GLN | A | 13 | −19.554 | −11.868 | −24.138 | 1.00 | 42.01 | A |
| ATOM | 74 | OE1 | GLN | A | 13 | −18.858 | −11.822 | −23.114 | 1.00 | 40.76 | A |
| ATOM | 75 | NE2 | GLN | A | 13 | −19.070 | −12.230 | −25.321 | 1.00 | 42.60 | A |
| ATOM | 76 | C | GLN | A | 13 | −20.551 | −7.659 | −23.672 | 1.00 | 37.09 | A |
| ATOM | 77 | O | GLN | A | 13 | −19.874 | −7.181 | −24.584 | 1.00 | 37.01 | A |
| ATOM | 78 | N | LYS | A | 14 | −21.410 | −6.923 | −22.980 | 1.00 | 34.35 | A |
| ATOM | 79 | CA | LYS | A | 14 | −21.611 | −5.527 | −23.340 | 1.00 | 30.28 | A |
| ATOM | 80 | CB | LYS | A | 14 | −23.098 | −5.198 | −23.253 | 1.00 | 30.76 | A |
| ATOM | 81 | CG | LYS | A | 14 | −23.960 | −5.988 | −24.226 | 1.00 | 30.07 | A |
| ATOM | 82 | CD | LYS | A | 14 | −25.398 | −5.510 | −24.182 | 1.00 | 31.58 | A |
| ATOM | 83 | CE | LYS | A | 14 | −26.266 | −6.180 | −25.243 | 1.00 | 33.34 | A |
| ATOM | 84 | NZ | LYS | A | 14 | −27.727 | −5.841 | −25.086 | 1.00 | 33.49 | A |
| ATOM | 85 | C | LYS | A | 14 | −20.804 | −4.474 | −22.596 | 1.00 | 28.04 | A |
| ATOM | 86 | O | LYS | A | 14 | −20.754 | −3.332 | −23.028 | 1.00 | 27.31 | A |
| ATOM | 87 | N | VAL | A | 15 | −20.178 | −4.837 | −21.486 | 1.00 | 25.96 | A |
| ATOM | 88 | CA | VAL | A | 15 | −19.381 | −3.861 | −20.752 | 1.00 | 23.39 | A |
| ATOM | 89 | CB | VAL | A | 15 | −19.232 | −4.270 | −19.276 | 1.00 | 23.10 | A |
| ATOM | 90 | CG1 | VAL | A | 15 | −20.589 | −4.329 | −18.632 | 1.00 | 23.40 | A |
| ATOM | 91 | CG2 | VAL | A | 15 | −18.528 | −5.624 | −19.171 | 1.00 | 23.09 | A |
| ATOM | 92 | C | VAL | A | 15 | −17.995 | −3.739 | −21.396 | 1.00 | 22.23 | A |
| ATOM | 93 | O | VAL | A | 15 | −17.168 | −2.929 | −20.991 | 1.00 | 20.60 | A |
| ATOM | 94 | N | ALA | A | 16 | −17.754 | −4.557 | −22.411 | 1.00 | 21.06 | A |
| ATOM | 95 | CA | ALA | A | 16 | −16.475 | −4.547 | −23.095 | 1.00 | 20.08 | A |
| ATOM | 96 | CB | ALA | A | 16 | −16.431 | −5.661 | −24.133 | 1.00 | 18.43 | A |
| ATOM | 97 | C | ALA | A | 16 | −16.181 | −3.204 | −23.757 | 1.00 | 19.05 | A |
| ATOM | 98 | O | ALA | A | 16 | −17.085 | −2.469 | −24.176 | 1.00 | 18.34 | A |
| ATOM | 99 | N | GLY | A | 17 | −14.892 | −2.913 | −23.867 | 1.00 | 16.89 | A |
| ATOM | 100 | CA | GLY | A | 17 | −14.470 | −1.684 | −24.480 | 1.00 | 13.91 | A |
| ATOM | 101 | C | GLY | A | 17 | −13.760 | −0.779 | −23.512 | 1.00 | 14.13 | A |
| ATOM | 102 | O | GLY | A | 17 | −13.420 | −1.165 | −22.389 | 1.00 | 13.58 | A |
| ATOM | 103 | N | THR | A | 18 | −13.558 | 0.449 | −23.980 | 1.00 | 14.39 | A |
| ATOM | 104 | CA | THR | A | 18 | −12.888 | 1.508 | −23.251 | 1.00 | 12.62 | A |
| ATOM | 105 | CB | THR | A | 18 | −12.402 | 2.559 | −24.231 | 1.00 | 12.52 | A |
| ATOM | 106 | OG1 | THR | A | 18 | −11.264 | 2.046 | −24.934 | 1.00 | 15.36 | A |
| ATOM | 107 | CG2 | THR | A | 18 | −12.035 | 3.850 | −23.508 | 1.00 | 13.69 | A |
| ATOM | 108 | C | THR | A | 18 | −13.764 | 2.168 | −22.206 | 1.00 | 12.74 | A |
| ATOM | 109 | O | THR | A | 18 | −14.978 | 2.296 | −22.382 | 1.00 | 13.81 | A |
| ATOM | 110 | N | TRP | A | 19 | −13.128 | 2.570 | −21.111 | 1.00 | 10.41 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 111 | CA | TRP | A | 19 | −13.806 | 3.231 | −20.014 | 1.00 | 8.52 | A |
| ATOM | 112 | CB | TRP | A | 19 | −14.211 | 2.235 | −18.930 | 1.00 | 7.65 | A |
| ATOM | 113 | CG | TRP | A | 19 | −15.284 | 1.302 | −19.337 | 1.00 | 7.67 | A |
| ATOM | 114 | CD2 | TRP | A | 19 | −16.693 | 1.564 | −19.329 | 1.00 | 6.14 | A |
| ATOM | 115 | CE2 | TRP | A | 19 | −17.338 | 0.392 | −19.761 | 1.00 | 6.23 | A |
| ATOM | 116 | CE3 | TRP | A | 19 | −17.470 | 2.677 | −18.995 | 1.00 | 4.83 | A |
| ATOM | 117 | CD1 | TRP | A | 19 | −15.135 | 0.022 | −19.770 | 1.00 | 7.58 | A |
| ATOM | 118 | NE1 | TRP | A | 19 | −16.367 | −0.534 | −20.027 | 1.00 | 7.80 | A |
| ATOM | 119 | CZ2 | TRP | A | 19 | −18.721 | 0.298 | −19.861 | 1.00 | 5.58 | A |
| ATOM | 120 | CZ3 | TRP | A | 19 | −18.844 | 2.583 | −19.095 | 1.00 | 4.02 | A |
| ATOM | 121 | CH2 | TRP | A | 19 | −19.457 | 1.403 | −19.523 | 1.00 | 3.57 | A |
| ATOM | 122 | C | TRP | A | 19 | −12.860 | 4.233 | −19.391 | 1.00 | 8.93 | A |
| ATOM | 123 | O | TRP | A | 19 | −11.666 | 4.215 | −19.651 | 1.00 | 10.27 | A |
| ATOM | 124 | N | TYR | A | 20 | −13.408 | 5.089 | −18.542 | 1.00 | 9.09 | A |
| ATOM | 125 | CA | TYR | A | 20 | −12.628 | 6.076 | −17.841 | 1.00 | 8.07 | A |
| ATOM | 126 | CB | TYR | A | 20 | −12.812 | 7.460 | −18.464 | 1.00 | 9.62 | A |
| ATOM | 127 | CG | TYR | A | 20 | −12.102 | 7.654 | −19.781 | 1.00 | 10.80 | A |
| ATOM | 128 | CD1 | TYR | A | 20 | −12.788 | 7.510 | −21.004 | 1.00 | 9.64 | A |
| ATOM | 129 | CE1 | TYR | A | 20 | −12.127 | 7.683 | −22.222 | 1.00 | 9.99 | A |
| ATOM | 130 | CD2 | TYR | A | 20 | −10.739 | 7.976 | −19.813 | 1.00 | 7.81 | A |
| ATOM | 131 | CE2 | TYR | A | 20 | −10.076 | 8.146 | −21.028 | 1.00 | 9.67 | A |
| ATOM | 132 | CZ | TYR | A | 20 | −10.771 | 7.999 | −22.226 | 1.00 | 9.03 | A |
| ATOM | 133 | OH | TYR | A | 20 | −10.102 | 8.158 | −23.420 | 1.00 | 7.27 | A |
| ATOM | 134 | C | TYR | A | 20 | −13.138 | 6.087 | −16.419 | 1.00 | 8.31 | A |
| ATOM | 135 | O | TYR | A | 20 | −14.338 | 5.909 | −16.185 | 1.00 | 9.09 | A |
| ATOM | 136 | N | SER | A | 21 | −12.227 | 6.279 | −15.470 | 1.00 | 7.65 | A |
| ATOM | 137 | CA | SER | A | 21 | −12.604 | 6.334 | −14.059 | 1.00 | 7.21 | A |
| ATOM | 138 | CB | SER | A | 21 | −11.463 | 5.836 | −13.169 | 1.00 | 7.63 | A |
| ATOM | 139 | OG | SER | A | 21 | −11.239 | 4.436 | −13.360 | 1.00 | 8.81 | A |
| ATOM | 140 | C | SER | A | 21 | −12.891 | 7.792 | −13.745 | 1.00 | 7.24 | A |
| ATOM | 141 | O | SER | A | 21 | −11.968 | 8.573 | −13.525 | 1.00 | 7.82 | A |
| ATOM | 142 | N | LEU | A | 22 | −14.173 | 8.151 | −13.722 | 1.00 | 7.35 | A |
| ATOM | 143 | CA | LEU | A | 22 | −14.608 | 9.525 | −13.458 | 1.00 | 6.56 | A |
| ATOM | 144 | CB | LEU | A | 22 | −16.067 | 9.703 | −13.891 | 1.00 | 6.94 | A |
| ATOM | 145 | CG | LEU | A | 22 | −16.419 | 10.956 | −14.702 | 1.00 | 8.26 | A |
| ATOM | 146 | CD1 | LEU | A | 22 | −17.899 | 11.308 | −14.465 | 1.00 | 10.43 | A |
| ATOM | 147 | CD2 | LEU | A | 22 | −15.548 | 12.118 | −14.299 | 1.00 | 6.27 | A |
| ATOM | 148 | C | LEU | A | 22 | −14.500 | 9.946 | −12.003 | 1.00 | 6.17 | A |
| ATOM | 149 | O | LEU | A | 22 | −14.001 | 11.027 | −11.707 | 1.00 | 6.09 | A |
| ATOM | 150 | N | ALA | A | 23 | −14.981 | 9.081 | −11.112 | 1.00 | 5.52 | A |
| ATOM | 151 | CA | ALA | A | 23 | −15.002 | 9.366 | −9.686 | 1.00 | 5.14 | A |
| ATOM | 152 | CB | ALA | A | 23 | −16.360 | 9.993 | −9.308 | 1.00 | 1.05 | A |
| ATOM | 153 | C | ALA | A | 23 | −14.780 | 8.092 | −8.884 | 1.00 | 6.08 | A |
| ATOM | 154 | O | ALA | A | 23 | −15.039 | 6.983 | −9.372 | 1.00 | 5.25 | A |
| ATOM | 155 | N | MET | A | 24 | −14.293 | 8.244 | −7.654 | 1.00 | 6.12 | A |
| ATOM | 156 | CA | MET | A | 24 | −14.073 | 7.086 | −6.810 | 1.00 | 7.92 | A |
| ATOM | 157 | CB | MET | A | 24 | −12.682 | 6.499 | −7.065 | 1.00 | 10.53 | A |
| ATOM | 158 | CG | MET | A | 24 | −11.538 | 7.490 | −6.968 | 1.00 | 13.91 | A |
| ATOM | 159 | SD | MET | A | 24 | −9.954 | 6.748 | −7.475 | 1.00 | 19.85 | A |
| ATOM | 160 | CE | MET | A | 24 | −10.155 | 6.742 | −9.241 | 1.00 | 16.62 | A |
| ATOM | 161 | C | MET | A | 24 | −14.258 | 7.449 | −5.347 | 1.00 | 7.96 | A |
| ATOM | 162 | O | MET | A | 24 | −14.166 | 8.621 | −4.975 | 1.00 | 7.86 | A |
| ATOM | 163 | N | ALA | A | 25 | −14.543 | 6.440 | −4.525 | 1.00 | 6.87 | A |
| ATOM | 164 | CA | ALA | A | 25 | −14.753 | 6.647 | −3.098 | 1.00 | 5.96 | A |
| ATOM | 165 | CB | ALA | A | 25 | −16.233 | 6.907 | −2.810 | 1.00 | 5.94 | A |
| ATOM | 166 | C | ALA | A | 25 | −14.286 | 5.410 | −2.362 | 1.00 | 5.84 | A |
| ATOM | 167 | O | ALA | A | 25 | −14.196 | 4.337 | −2.949 | 1.00 | 6.04 | A |
| ATOM | 168 | N | ALA | A | 26 | −13.973 | 5.568 | −1.081 | 1.00 | 5.75 | A |
| ATOM | 169 | CA | ALA | A | 26 | −13.513 | 4.456 | −0.264 | 1.00 | 6.01 | A |
| ATOM | 170 | CB | ALA | A | 26 | −12.011 | 4.329 | −0.363 | 1.00 | 3.18 | A |
| ATOM | 171 | C | ALA | A | 26 | −13.927 | 4.664 | 1.185 | 1.00 | 7.89 | A |
| ATOM | 172 | O | ALA | A | 26 | −14.186 | 5.795 | 1.612 | 1.00 | 4.99 | A |
| ATOM | 173 | N | SER | A | 27 | −13.982 | 3.567 | 1.938 | 1.00 | 10.42 | A |
| ATOM | 174 | CA | SER | A | 27 | −14.376 | 3.623 | 3.336 | 1.00 | 12.99 | A |
| ATOM | 175 | CB | SER | A | 27 | −14.720 | 2.216 | 3.850 | 1.00 | 13.33 | A |
| ATOM | 176 | OG | SER | A | 27 | −13.559 | 1.482 | 4.189 | 1.00 | 16.45 | A |
| ATOM | 177 | C | SER | A | 27 | −13.286 | 4.252 | 4.205 | 1.00 | 14.05 | A |
| ATOM | 178 | O | SER | A | 27 | −13.582 | 4.820 | 5.249 | 1.00 | 13.73 | A |
| ATOM | 179 | N | ASP | A | 28 | −12.033 | 4.148 | 3.772 | 1.00 | 16.92 | A |
| ATOM | 180 | CA | ASP | A | 28 | −10.907 | 4.709 | 4.515 | 1.00 | 19.69 | A |
| ATOM | 181 | CB | ASP | A | 28 | −9.980 | 3.601 | 5.011 | 1.00 | 22.47 | A |
| ATOM | 182 | CG | ASP | A | 28 | −10.467 | 2.984 | 6.309 | 1.00 | 27.75 | A |
| ATOM | 183 | OD1 | ASP | A | 28 | −11.704 | 3.020 | 6.564 | 1.00 | 28.49 | A |
| ATOM | 184 | OD2 | ASP | A | 28 | −9.616 | 2.448 | 7.069 | 1.00 | 31.52 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 185 | C | ASP | A | 28 | −10.124 | 5.674 | 3.652 | 1.00 | 19.92 | A |
| ATOM | 186 | O | ASP | A | 28 | −9.742 | 5.342 | 2.531 | 1.00 | 20.07 | A |
| ATOM | 187 | N | ILE | A | 29 | −9.873 | 6.866 | 4.188 | 1.00 | 19.78 | A |
| ATOM | 188 | CA | ILE | A | 29 | −9.152 | 7.909 | 3.468 | 1.00 | 19.41 | A |
| ATOM | 189 | CB | ILE | A | 29 | −8.901 | 9.120 | 4.384 | 1.00 | 18.35 | A |
| ATOM | 190 | CG2 | ILE | A | 29 | −8.030 | 10.140 | 3.671 | 1.00 | 16.12 | A |
| ATOM | 191 | CG1 | ILE | A | 29 | −10.244 | 9.747 | 4.787 | 1.00 | 16.69 | A |
| ATOM | 192 | CD1 | ILE | A | 29 | −10.131 | 10.862 | 5.803 | 1.00 | 13.07 | A |
| ATOM | 193 | C | ILE | A | 29 | −7.820 | 7.431 | 2.901 | 1.00 | 20.55 | A |
| ATOM | 194 | O | ILE | A | 29 | −7.491 | 7.716 | 1.752 | 1.00 | 20.09 | A |
| ATOM | 195 | N | SER | A | 30 | −7.065 | 6.702 | 3.714 | 1.00 | 21.94 | A |
| ATOM | 196 | CA | SER | A | 30 | −5.754 | 6.183 | 3.329 | 1.00 | 23.62 | A |
| ATOM | 197 | CB | SER | A | 30 | −5.203 | 5.341 | 4.461 | 1.00 | 24.48 | A |
| ATOM | 198 | OG | SER | A | 30 | −6.132 | 4.313 | 4.756 | 1.00 | 28.16 | A |
| ATOM | 199 | C | SER | A | 30 | −5.794 | 5.331 | 2.068 | 1.00 | 24.82 | A |
| ATOM | 200 | O | SER | A | 30 | −4.777 | 5.153 | 1.385 | 1.00 | 23.69 | A |
| ATOM | 201 | N | LEU | A | 31 | −6.974 | 4.794 | 1.774 | 1.00 | 26.67 | A |
| ATOM | 202 | CA | LEU | A | 31 | −7.169 | 3.943 | 0.602 | 1.00 | 27.64 | A |
| ATOM | 203 | CB | LEU | A | 31 | −8.567 | 3.303 | 0.645 | 1.00 | 26.50 | A |
| ATOM | 204 | CG | LEU | A | 31 | −8.795 | 2.278 | 1.757 | 1.00 | 26.16 | A |
| ATOM | 205 | CD1 | LEU | A | 31 | −10.266 | 1.929 | 1.859 | 1.00 | 25.35 | A |
| ATOM | 206 | CD2 | LEU | A | 31 | −7.943 | 1.063 | 1.483 | 1.00 | 25.12 | A |
| ATOM | 207 | C | LEU | A | 31 | −6.988 | 4.697 | −0.711 | 1.00 | 28.40 | A |
| ATOM | 208 | O | LEU | A | 31 | −6.503 | 4.136 | −1.696 | 1.00 | 28.86 | A |
| ATOM | 209 | N | LEU | A | 32 | −7.374 | 5.969 | −0.715 | 1.00 | 29.73 | A |
| ATOM | 210 | CA | LEU | A | 32 | −7.286 | 6.821 | −1.907 | 1.00 | 30.99 | A |
| ATOM | 211 | CB | LEU | A | 32 | −8.691 | 7.246 | −2.360 | 1.00 | 30.24 | A |
| ATOM | 212 | CG | LEU | A | 32 | −9.505 | 6.344 | −3.285 | 1.00 | 29.74 | A |
| ATOM | 213 | CD1 | LEU | A | 32 | −9.570 | 4.958 | −2.695 | 1.00 | 30.44 | A |
| ATOM | 214 | CD2 | LEU | A | 32 | −10.907 | 6.919 | −3.502 | 1.00 | 27.92 | A |
| ATOM | 215 | C | LEU | A | 32 | −6.459 | 8.081 | −1.670 | 1.00 | 32.27 | A |
| ATOM | 216 | O | LEU | A | 32 | −6.026 | 8.719 | −2.623 | 1.00 | 31.51 | A |
| ATOM | 217 | N | ASP | A | 33 | −6.275 | 8.447 | −0.403 | 1.00 | 34.56 | A |
| ATOM | 218 | CA | ASP | A | 33 | −5.508 | 9.636 | −0.026 | 1.00 | 37.18 | A |
| ATOM | 219 | CB | ASP | A | 33 | −5.508 | 9.788 | 1.504 | 1.00 | 38.37 | A |
| ATOM | 220 | CG | ASP | A | 33 | −5.076 | 11.178 | 1.973 | 1.00 | 38.48 | A |
| ATOM | 221 | OD1 | ASP | A | 33 | −5.360 | 12.175 | 1.270 | 1.00 | 37.67 | A |
| ATOM | 222 | OD2 | ASP | A | 33 | −4.472 | 11.271 | 3.067 | 1.00 | 38.63 | A |
| ATOM | 223 | C | ASP | A | 33 | −4.086 | 9.502 | −0.553 | 1.00 | 38.68 | A |
| ATOM | 224 | O | ASP | A | 33 | −3.396 | 8.516 | −0.267 | 1.00 | 39.31 | A |
| ATOM | 225 | N | ALA | A | 34 | −3.660 | 10.504 | −1.318 | 1.00 | 40.30 | A |
| ATOM | 226 | CA | ALA | A | 34 | −2.340 | 10.522 | −1.937 | 1.00 | 42.39 | A |
| ATOM | 227 | CB | ALA | A | 34 | −1.280 | 9.999 | −0.971 | 1.00 | 42.13 | A |
| ATOM | 228 | C | ALA | A | 34 | −2.400 | 9.648 | −3.190 | 1.00 | 43.89 | A |
| ATOM | 229 | O | ALA | A | 34 | −2.869 | 8.507 | −3.141 | 1.00 | 43.68 | A |
| ATOM | 230 | N | GLN | A | 35 | −1.927 | 10.193 | −4.309 | 1.00 | 46.04 | A |
| ATOM | 231 | CA | GLN | A | 35 | −1.932 | 9.494 | −5.597 | 1.00 | 47.75 | A |
| ATOM | 232 | CB | GLN | A | 35 | −1.183 | 10.333 | −6.632 | 1.00 | 49.01 | A |
| ATOM | 233 | CG | GLN | A | 35 | −1.860 | 10.368 | −7.996 | 1.00 | 51.86 | A |
| ATOM | 234 | CD | GLN | A | 35 | −1.440 | 11.582 | −8.833 | 1.00 | 53.04 | A |
| ATOM | 235 | OE1 | GLN | A | 35 | −0.302 | 11.662 | −9.323 | 1.00 | 53.42 | A |
| ATOM | 236 | NE2 | GLN | A | 35 | −2.361 | 12.540 | −8.988 | 1.00 | 52.30 | A |
| ATOM | 237 | C | GLN | A | 35 | −1.361 | 8.068 | −5.563 | 1.00 | 48.50 | A |
| ATOM | 238 | O | GLN | A | 35 | −1.853 | 7.183 | −6.278 | 1.00 | 49.53 | A |
| ATOM | 239 | N | SER | A | 36 | −0.342 | 7.847 | −4.732 | 1.00 | 47.82 | A |
| ATOM | 240 | CA | SER | A | 36 | 0.282 | 6.533 | −4.604 | 1.00 | 47.78 | A |
| ATOM | 241 | CB | SER | A | 36 | 1.714 | 6.688 | −4.076 | 1.00 | 49.93 | A |
| ATOM | 242 | OG | SER | A | 36 | 2.479 | 5.493 | −4.271 | 1.00 | 51.54 | A |
| ATOM | 243 | C | SER | A | 36 | −0.535 | 5.662 | −3.644 | 1.00 | 46.74 | A |
| ATOM | 244 | O | SER | A | 36 | 0.005 | 5.062 | −2.717 | 1.00 | 47.36 | A |
| ATOM | 245 | N | ALA | A | 37 | −1.839 | 5.597 | −3.875 | 1.00 | 45.30 | A |
| ATOM | 246 | CA | ALA | A | 37 | −2.715 | 4.820 | −3.022 | 1.00 | 44.15 | A |
| ATOM | 247 | CB | ALA | A | 37 | −4.078 | 5.486 | −2.940 | 1.00 | 45.03 | A |
| ATOM | 248 | C | ALA | A | 37 | −2.855 | 3.373 | −3.492 | 1.00 | 43.52 | A |
| ATOM | 249 | O | ALA | A | 37 | −2.697 | 3.059 | −4.679 | 1.00 | 43.45 | A |
| ATOM | 250 | N | PRO | A | 38 | −3.155 | 2.466 | −2.548 | 1.00 | 42.24 | A |
| ATOM | 251 | CD | PRO | A | 38 | −3.315 | 2.745 | −1.106 | 1.00 | 41.30 | A |
| ATOM | 252 | CA | PRO | A | 38 | −3.322 | 1.038 | −2.821 | 1.00 | 40.88 | A |
| ATOM | 253 | CB | PRO | A | 38 | −3.259 | 0.426 | −1.425 | 1.00 | 41.84 | A |
| ATOM | 254 | CG | PRO | A | 38 | −3.924 | 1.471 | −0.588 | 1.00 | 41.59 | A |
| ATOM | 255 | C | PRO | A | 38 | −4.609 | 0.669 | −3.562 | 1.00 | 39.03 | A |
| ATOM | 256 | O | PRO | A | 38 | −4.761 | −0.460 | −4.028 | 1.00 | 39.26 | A |
| ATOM | 257 | N | LEU | A | 39 | −5.539 | 1.611 | −3.666 | 1.00 | 36.16 | A |
| ATOM | 258 | CA | LEU | A | 39 | −6.793 | 1.334 | −4.357 | 1.00 | 32.67 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 259 | CB | LEU | A | 39 | −7.947 | 1.214 | −3.366 | 1.00 | 34.76 | A |
| ATOM | 260 | CG | LEU | A | 39 | −7.972 | −0.013 | −2.458 | 1.00 | 36.49 | A |
| ATOM | 261 | CD1 | LEU | A | 39 | −9.296 | 0.006 | −1.684 | 1.00 | 39.85 | A |
| ATOM | 262 | CD2 | LEU | A | 39 | −7.859 | −1.289 | −3.285 | 1.00 | 37.68 | A |
| ATOM | 263 | C | LEU | A | 39 | −7.105 | 2.420 | −5.344 | 1.00 | 28.83 | A |
| ATOM | 264 | O | LEU | A | 39 | −8.216 | 2.498 | −5.854 | 1.00 | 28.46 | A |
| ATOM | 265 | N | ARG | A | 40 | −6.116 | 3.262 | −5.615 | 1.00 | 25.66 | A |
| ATOM | 266 | CA | ARG | A | 40 | −6.307 | 4.351 | −6.560 | 1.00 | 22.85 | A |
| ATOM | 267 | CB | ARG | A | 40 | −5.431 | 5.533 | −6.175 | 1.00 | 21.75 | A |
| ATOM | 268 | CG | ARG | A | 40 | −5.740 | 6.803 | −6.931 | 1.00 | 21.09 | A |
| ATOM | 269 | CD | ARG | A | 40 | −5.789 | 7.968 | −5.960 | 1.00 | 22.80 | A |
| ATOM | 270 | NE | ARG | A | 40 | −5.618 | 9.265 | −6.616 | 1.00 | 22.93 | A |
| ATOM | 271 | CZ | ARG | A | 40 | −5.550 | 10.426 | −5.965 | 1.00 | 22.37 | A |
| ATOM | 272 | NH1 | ARG | A | 40 | −5.643 | 10.462 | −4.645 | 1.00 | 19.87 | A |
| ATOM | 273 | NH2 | ARG | A | 40 | −5.373 | 11.551 | −6.634 | 1.00 | 25.01 | A |
| ATOM | 274 | C | ARG | A | 40 | −5.945 | 3.844 | −7.943 | 1.00 | 21.35 | A |
| ATOM | 275 | O | ARG | A | 40 | −4.907 | 4.184 | −8.503 | 1.00 | 21.42 | A |
| ATOM | 276 | N | VAL | A | 41 | −6.822 | 3.016 | −8.489 | 1.00 | 19.98 | A |
| ATOM | 277 | CA | VAL | A | 41 | −6.593 | 2.442 | −9.796 | 1.00 | 17.66 | A |
| ATOM | 278 | CB | VAL | A | 41 | −6.881 | 0.953 | −9.765 | 1.00 | 16.68 | A |
| ATOM | 279 | CG1 | VAL | A | 41 | −6.242 | 0.349 | −8.540 | 1.00 | 16.35 | A |
| ATOM | 280 | CG2 | VAL | A | 41 | −8.355 | 0.716 | −9.769 | 1.00 | 17.46 | A |
| ATOM | 281 | C | VAL | A | 41 | −7.491 | 3.113 | −10.816 | 1.00 | 16.54 | A |
| ATOM | 282 | O | VAL | A | 41 | −8.517 | 3.686 | −10.458 | 1.00 | 17.39 | A |
| ATOM | 283 | N | TYR | A | 42 | −7.092 | 3.049 | −12.081 | 1.00 | 16.55 | A |
| ATOM | 284 | CA | TYR | A | 42 | −7.859 | 3.634 | −13.173 | 1.00 | 15.47 | A |
| ATOM | 285 | CB | TYR | A | 42 | −7.104 | 4.815 | −13.788 | 1.00 | 13.88 | A |
| ATOM | 286 | CG | TYR | A | 42 | −6.574 | 5.785 | −12.751 | 1.00 | 12.95 | A |
| ATOM | 287 | CD1 | TYR | A | 42 | −5.266 | 5.683 | −12.281 | 1.00 | 12.86 | A |
| ATOM | 288 | CE1 | TYR | A | 42 | −4.791 | 6.520 | −11.269 | 1.00 | 11.80 | A |
| ATOM | 289 | CD2 | TYR | A | 42 | −7.400 | 6.756 | −12.183 | 1.00 | 12.39 | A |
| ATOM | 290 | CE2 | TYR | A | 42 | −6.927 | 7.597 | −11.166 | 1.00 | 12.09 | A |
| ATOM | 291 | CZ | TYR | A | 42 | −5.623 | 7.458 | −10.720 | 1.00 | 10.82 | A |
| ATOM | 292 | OH | TYR | A | 42 | −5.168 | 8.232 | −9.694 | 1.00 | 12.77 | A |
| ATOM | 293 | C | TYR | A | 42 | −8.124 | 2.586 | −14.236 | 1.00 | 15.00 | A |
| ATOM | 294 | O | TYR | A | 42 | −7.191 | 2.015 | −14.797 | 1.00 | 13.20 | A |
| ATOM | 295 | N | VAL | A | 43 | −9.407 | 2.329 | −14.480 | 1.00 | 15.77 | A |
| ATOM | 296 | CA | VAL | A | 43 | −9.858 | 1.367 | −15.478 | 1.00 | 16.87 | A |
| ATOM | 297 | CB | VAL | A | 43 | −11.367 | 1.045 | −15.294 | 1.00 | 18.26 | A |
| ATOM | 298 | CG1 | VAL | A | 43 | −11.814 | −0.036 | −16.278 | 1.00 | 18.05 | A |
| ATOM | 299 | CG2 | VAL | A | 43 | −11.628 | 0.610 | −13.866 | 1.00 | 19.17 | A |
| ATOM | 300 | C | VAL | A | 43 | −9.661 | 1.967 | −16.869 | 1.00 | 17.12 | A |
| ATOM | 301 | O | VAL | A | 43 | −9.888 | 3.162 | −17.081 | 1.00 | 18.44 | A |
| ATOM | 302 | N | GLU | A | 44 | −9.233 | 1.144 | −17.817 | 1.00 | 17.63 | A |
| ATOM | 303 | CA | GLU | A | 44 | −9.023 | 1.628 | −19.175 | 1.00 | 18.37 | A |
| ATOM | 304 | CB | GLU | A | 44 | −7.540 | 1.600 | −19.526 | 1.00 | 17.78 | A |
| ATOM | 305 | CG | GLU | A | 44 | −6.700 | 2.474 | −18.632 | 1.00 | 19.02 | A |
| ATOM | 306 | CD | GLU | A | 44 | −5.327 | 2.720 | −19.212 | 1.00 | 22.11 | A |
| ATOM | 307 | OE1 | GLU | A | 44 | −4.657 | 1.733 | −19.630 | 1.00 | 22.53 | A |
| ATOM | 308 | OE2 | GLU | A | 44 | −4.912 | 3.905 | −19.239 | 1.00 | 22.89 | A |
| ATOM | 309 | C | GLU | A | 44 | −9.776 | 0.792 | −20.180 | 1.00 | 17.64 | A |
| ATOM | 310 | O | GLU | A | 44 | −10.422 | 1.325 | −21.078 | 1.00 | 16.88 | A |
| ATOM | 311 | N | GLU | A | 45 | −9.704 | −0.519 | −19.994 | 1.00 | 18.74 | A |
| ATOM | 312 | CA | GLU | A | 45 | −10.335 | −1.452 | −20.898 | 1.00 | 20.81 | A |
| ATOM | 313 | CB | GLU | A | 45 | −9.283 | −1.935 | −21.902 | 1.00 | 21.48 | A |
| ATOM | 314 | CG | GLU | A | 45 | −9.777 | −2.219 | −23.312 | 1.00 | 25.33 | A |
| ATOM | 315 | CD | GLU | A | 45 | −9.527 | −1.059 | −24.264 | 1.00 | 27.54 | A |
| ATOM | 316 | OE1 | GLU | A | 45 | −8.411 | −0.490 | −24.239 | 1.00 | 27.39 | A |
| ATOM | 317 | OE2 | GLU | A | 45 | −10.440 | −0.720 | −25.050 | 1.00 | 29.46 | A |
| ATOM | 318 | C | GLU | A | 45 | −10.932 | −2.658 | −20.163 | 1.00 | 21.59 | A |
| ATOM | 319 | O | GLU | A | 45 | −10.384 | −3.141 | −19.163 | 1.00 | 20.49 | A |
| ATOM | 320 | N | LEU | A | 46 | −12.065 | −3.129 | −20.673 | 1.00 | 23.36 | A |
| ATOM | 321 | CA | LEU | A | 46 | −12.732 | −4.308 | −20.138 | 1.00 | 25.89 | A |
| ATOM | 322 | CB | LEU | A | 46 | −14.129 | −3.968 | −19.595 | 1.00 | 24.67 | A |
| ATOM | 323 | CG | LEU | A | 46 | −14.163 | −3.256 | −18.243 | 1.00 | 22.90 | A |
| ATOM | 324 | CD1 | LEU | A | 46 | −15.589 | −3.016 | −17.823 | 1.00 | 22.10 | A |
| ATOM | 325 | CD2 | LEU | A | 46 | −13.418 | −4.094 | −17.209 | 1.00 | 23.07 | A |
| ATOM | 326 | C | LEU | A | 46 | −12.831 | −5.297 | −21.301 | 1.00 | 27.65 | A |
| ATOM | 327 | O | LEU | A | 46 | −13.572 | −5.079 | −22.255 | 1.00 | 27.18 | A |
| ATOM | 328 | N | LYS | A | 47 | −12.058 | −6.373 | −21.213 | 1.00 | 31.02 | A |
| ATOM | 329 | CA | LYS | A | 47 | −12.015 | −7.396 | −22.240 | 1.00 | 34.48 | A |
| ATOM | 330 | CB | LYS | A | 47 | −10.571 | −7.543 | −22.731 | 1.00 | 35.53 | A |
| ATOM | 331 | CG | LYS | A | 47 | −10.313 | −8.672 | −23.702 | 1.00 | 37.60 | A |
| ATOM | 332 | CD | LYS | A | 47 | −8.938 | −8.510 | −24.347 | 1.00 | 38.84 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 333 | CE | LYS | A | 47 | −8.324 | −9.851 | −24.708 | 1.00 | 39.57 | A |
| ATOM | 334 | NZ | LYS | A | 47 | −6.998 | −9.685 | −25.365 | 1.00 | 40.23 | A |
| ATOM | 335 | C | LYS | A | 47 | −12.529 | −8.730 | −21.701 | 1.00 | 36.80 | A |
| ATOM | 336 | O | LYS | A | 47 | −11.854 | −9.400 | −20.910 | 1.00 | 36.52 | A |
| ATOM | 337 | N | PRO | A | 48 | −13.743 | −9.122 | −22.117 | 1.00 | 38.18 | A |
| ATOM | 338 | CD | PRO | A | 48 | −14.620 | −8.395 | −23.048 | 1.00 | 38.61 | A |
| ATOM | 339 | CA | PRO | A | 48 | −14.376 | −10.372 | −21.701 | 1.00 | 39.51 | A |
| ATOM | 340 | CB | PRO | A | 48 | −15.811 | −10.197 | −22.178 | 1.00 | 39.56 | A |
| ATOM | 341 | CG | PRO | A | 48 | −15.619 | −9.461 | −23.448 | 1.00 | 38.54 | A |
| ATOM | 342 | C | PRO | A | 48 | −13.698 | −11.561 | −22.361 | 1.00 | 40.34 | A |
| ATOM | 343 | O | PRO | A | 48 | −13.371 | −11.511 | −23.541 | 1.00 | 39.26 | A |
| ATOM | 344 | N | THR | A | 49 | −13.491 | −12.622 | −21.588 | 1.00 | 42.45 | A |
| ATOM | 345 | CA | THR | A | 49 | −12.851 | −13.831 | −22.088 | 1.00 | 43.91 | A |
| ATOM | 346 | CB | THR | A | 49 | −11.982 | −14.493 | −21.028 | 1.00 | 43.45 | A |
| ATOM | 347 | OG1 | THR | A | 49 | −12.820 | −14.990 | −19.981 | 1.00 | 43.90 | A |
| ATOM | 348 | CG2 | THR | A | 49 | −10.988 | −13.510 | −20.461 | 1.00 | 43.33 | A |
| ATOM | 349 | C | THR | A | 49 | −13.923 | −14.839 | −22.466 | 1.00 | 45.42 | A |
| ATOM | 350 | O | THR | A | 49 | −15.070 | −14.753 | −22.012 | 1.00 | 45.06 | A |
| ATOM | 351 | N | PRO | A | 50 | −13.555 | −15.825 | −23.290 | 1.00 | 46.42 | A |
| ATOM | 352 | CD | PRO | A | 50 | −12.200 | −16.122 | −23.785 | 1.00 | 46.56 | A |
| ATOM | 353 | CA | PRO | A | 50 | −14.503 | −16.851 | −23.721 | 1.00 | 47.28 | A |
| ATOM | 354 | CB | PRO | A | 50 | −13.664 | −17.721 | −24.651 | 1.00 | 46.60 | A |
| ATOM | 355 | CG | PRO | A | 50 | −12.292 | −17.599 | −24.079 | 1.00 | 46.90 | A |
| ATOM | 356 | C | PRO | A | 50 | −15.078 | −17.634 | −22.539 | 1.00 | 48.52 | A |
| ATOM | 357 | O | PRO | A | 50 | −16.274 | −17.939 | −22.506 | 1.00 | 48.29 | A |
| ATOM | 358 | N | GLU | A | 51 | −14.233 | −17.944 | −21.559 | 1.00 | 49.18 | A |
| ATOM | 359 | CA | GLU | A | 51 | −14.702 | −18.694 | −20.400 | 1.00 | 49.93 | A |
| ATOM | 360 | CB | GLU | A | 51 | −13.520 | −19.151 | −19.542 | 1.00 | 50.20 | A |
| ATOM | 361 | CG | GLU | A | 51 | −12.405 | −18.147 | −19.450 | 1.00 | 52.19 | A |
| ATOM | 362 | CD | GLU | A | 51 | −11.193 | −18.543 | −20.287 | 1.00 | 54.81 | A |
| ATOM | 363 | OE1 | GLU | A | 51 | −10.460 | −19.478 | −19.886 | 1.00 | 55.81 | A |
| ATOM | 364 | OE2 | GLU | A | 51 | −10.972 | −17.930 | −21.355 | 1.00 | 54.93 | A |
| ATOM | 365 | C | GLU | A | 51 | −15.698 | −17.910 | −19.541 | 1.00 | 50.04 | A |
| ATOM | 366 | O | GLU | A | 51 | −16.178 | −18.410 | −18.521 | 1.00 | 51.24 | A |
| ATOM | 367 | N | GLY | A | 52 | −16.017 | −16.685 | −19.952 | 1.00 | 48.90 | A |
| ATOM | 368 | CA | GLY | A | 52 | −16.967 | −15.882 | −19.192 | 1.00 | 46.90 | A |
| ATOM | 369 | C | GLY | A | 52 | −16.353 | −14.928 | −18.179 | 1.00 | 45.73 | A |
| ATOM | 370 | O | GLY | A | 52 | −17.063 | −14.220 | −17.454 | 1.00 | 44.51 | A |
| ATOM | 371 | N | ASP | A | 53 | −15.024 | −14.912 | −18.119 | 1.00 | 44.59 | A |
| ATOM | 372 | CA | ASP | A | 53 | −14.325 | −14.026 | −17.198 | 1.00 | 42.64 | A |
| ATOM | 373 | CB | ASP | A | 53 | −12.937 | −14.574 | −16.846 | 1.00 | 43.41 | A |
| ATOM | 374 | CG | ASP | A | 53 | −12.996 | −15.915 | −16.139 | 1.00 | 44.82 | A |
| ATOM | 375 | OD1 | ASP | A | 53 | −13.850 | −16.091 | −15.237 | 1.00 | 44.78 | A |
| ATOM | 376 | OD2 | ASP | A | 53 | −12.168 | −16.794 | −16.477 | 1.00 | 46.39 | A |
| ATOM | 377 | C | ASP | A | 53 | −14.172 | −12.653 | −17.833 | 1.00 | 40.68 | A |
| ATOM | 378 | O | ASP | A | 53 | −14.540 | −12.445 | −18.988 | 1.00 | 39.21 | A |
| ATOM | 379 | N | LEU | A | 54 | −13.612 | −11.721 | −17.073 | 1.00 | 39.63 | A |
| ATOM | 380 | CA | LEU | A | 54 | −13.411 | −10.364 | −17.555 | 1.00 | 37.71 | A |
| ATOM | 381 | CB | LEU | A | 54 | −14.402 | −9.437 | −16.858 | 1.00 | 37.78 | A |
| ATOM | 382 | CG | LEU | A | 54 | −14.543 | −8.033 | −17.426 | 1.00 | 38.04 | A |
| ATOM | 383 | CD1 | LEU | A | 54 | −14.949 | −8.112 | −18.888 | 1.00 | 38.98 | A |
| ATOM | 384 | CD2 | LEU | A | 54 | −15.575 | −7.277 | −16.618 | 1.00 | 38.45 | A |
| ATOM | 385 | C | LEU | A | 54 | −11.980 | −9.874 | −17.314 | 1.00 | 36.15 | A |
| ATOM | 386 | O | LEU | A | 54 | −11.547 | −9.725 | −16.170 | 1.00 | 35.39 | A |
| ATOM | 387 | N | GLU | A | 55 | −11.241 | −9.639 | −18.395 | 1.00 | 33.89 | A |
| ATOM | 388 | CA | GLU | A | 55 | −9.880 | −9.144 | −18.267 | 1.00 | 31.45 | A |
| ATOM | 389 | CB | GLU | A | 55 | −9.063 | −9.455 | −19.513 | 1.00 | 33.59 | A |
| ATOM | 390 | CG | GLU | A | 55 | −7.566 | −9.428 | −19.278 | 1.00 | 36.34 | A |
| ATOM | 391 | CD | GLU | A | 55 | −6.790 | −9.078 | −20.532 | 1.00 | 39.61 | A |
| ATOM | 392 | OE1 | GLU | A | 55 | −7.034 | −9.707 | −21.586 | 1.00 | 41.88 | A |
| ATOM | 393 | OE2 | GLU | A | 55 | −5.930 | −8.169 | −20.470 | 1.00 | 41.11 | A |
| ATOM | 394 | C | GLU | A | 55 | −9.993 | −7.636 | −18.096 | 1.00 | 28.49 | A |
| ATOM | 395 | O | GLU | A | 55 | −10.872 | −7.001 | −18.677 | 1.00 | 27.60 | A |
| ATOM | 396 | N | ILE | A | 56 | −9.108 | −7.064 | −17.295 | 1.00 | 25.67 | A |
| ATOM | 397 | CA | ILE | A | 56 | −9.154 | −5.639 | −17.045 | 1.00 | 22.66 | A |
| ATOM | 398 | CB | ILE | A | 56 | −9.662 | −5.362 | −15.632 | 1.00 | 21.92 | A |
| ATOM | 399 | CG2 | ILE | A | 56 | −9.571 | −3.875 | −15.312 | 1.00 | 20.65 | A |
| ATOM | 400 | CG1 | ILE | A | 56 | −11.087 | −5.857 | −15.508 | 1.00 | 20.67 | A |
| ATOM | 401 | CD1 | ILE | A | 56 | −11.338 | −6.533 | −14.224 | 1.00 | 20.88 | A |
| ATOM | 402 | C | ILE | A | 56 | −7.812 | −4.976 | −17.202 | 1.00 | 21.00 | A |
| ATOM | 403 | O | ILE | A | 56 | −6.832 | −5.376 | −16.579 | 1.00 | 19.63 | A |
| ATOM | 404 | N | LEU | A | 57 | −7.783 | −3.945 | −18.038 | 1.00 | 20.06 | A |
| ATOM | 405 | CA | LEU | A | 57 | −6.563 | −3.191 | −18.266 | 1.00 | 19.69 | A |
| ATOM | 406 | CB | LEU | A | 57 | −6.454 | −2.789 | −19.733 | 1.00 | 16.44 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 407 | CG | LEU | A | 57 | −5.166 | −2.067 | −20.075 | 1.00 | 14.61 | A |
| ATOM | 408 | CD1 | LEU | A | 57 | −4.000 | −2.961 | −19.751 | 1.00 | 12.30 | A |
| ATOM | 409 | CD2 | LEU | A | 57 | −5.170 | −1.661 | −21.537 | 1.00 | 13.35 | A |
| ATOM | 410 | C | LEU | A | 57 | −6.667 | −1.948 | −17.396 | 1.00 | 20.13 | A |
| ATOM | 411 | O | LEU | A | 57 | −7.624 | −1.187 | −17.529 | 1.00 | 19.45 | A |
| ATOM | 412 | N | LEU | A | 58 | −5.702 | −1.742 | −16.502 | 1.00 | 20.63 | A |
| ATOM | 413 | CA | LEU | A | 58 | −5.752 | −0.578 | −15.632 | 1.00 | 22.21 | A |
| ATOM | 414 | CB | LEU | A | 58 | −6.504 | −0.928 | −14.350 | 1.00 | 21.17 | A |
| ATOM | 415 | CG | LEU | A | 58 | −5.911 | −2.034 | −13.479 | 1.00 | 20.12 | A |
| ATOM | 416 | CD1 | LEU | A | 58 | −4.774 | −1.473 | −12.644 | 1.00 | 20.35 | A |
| ATOM | 417 | CD2 | LEU | A | 58 | −6.988 | −2.595 | −12.557 | 1.00 | 20.30 | A |
| ATOM | 418 | C | LEU | A | 58 | −4.398 | 0.017 | −15.285 | 1.00 | 24.46 | A |
| ATOM | 419 | O | LEU | A | 58 | −3.354 | −0.557 | −15.597 | 1.00 | 22.97 | A |
| ATOM | 420 | N | GLN | A | 59 | −4.435 | 1.179 | −14.632 | 1.00 | 27.45 | A |
| ATOM | 421 | CA | GLN | A | 59 | −3.225 | 1.893 | −14.215 | 1.00 | 29.95 | A |
| ATOM | 422 | CB | GLN | A | 59 | −3.066 | 3.199 | −15.014 | 1.00 | 30.32 | A |
| ATOM | 423 | CG | GLN | A | 59 | −3.110 | 3.066 | −16.533 | 1.00 | 29.93 | A |
| ATOM | 424 | CD | GLN | A | 59 | −1.849 | 2.471 | −17.121 | 1.00 | 31.13 | A |
| ATOM | 425 | OE1 | GLN | A | 59 | −1.779 | 2.205 | −18.322 | 1.00 | 31.40 | A |
| ATOM | 426 | NE2 | GLN | A | 59 | −0.839 | 2.265 | −16.283 | 1.00 | 30.58 | A |
| ATOM | 427 | C | GLN | A | 59 | −3.297 | 2.234 | −12.723 | 1.00 | 31.07 | A |
| ATOM | 428 | O | GLN | A | 59 | −4.370 | 2.495 | −12.190 | 1.00 | 29.29 | A |
| ATOM | 429 | N | LYS | A | 60 | −2.146 | 2.228 | −12.063 | 1.00 | 35.25 | A |
| ATOM | 430 | CA | LYS | A | 60 | −2.064 | 2.563 | −10.648 | 1.00 | 40.05 | A |
| ATOM | 431 | CB | LYS | A | 60 | −2.547 | 1.406 | −9.772 | 1.00 | 41.46 | A |
| ATOM | 432 | CG | LYS | A | 60 | −1.838 | 0.098 | −10.010 | 1.00 | 44.79 | A |
| ATOM | 433 | CD | LYS | A | 60 | −2.453 | −1.010 | −9.156 | 1.00 | 47.46 | A |
| ATOM | 434 | CE | LYS | A | 60 | −1.904 | −2.379 | −9.554 | 1.00 | 49.65 | A |
| ATOM | 435 | NZ | LYS | A | 60 | −2.316 | −3.473 | −8.616 | 1.00 | 51.45 | A |
| ATOM | 436 | C | LYS | A | 60 | −0.633 | 2.919 | −10.297 | 1.00 | 42.65 | A |
| ATOM | 437 | O | LYS | A | 60 | 0.304 | 2.379 | −10.884 | 1.00 | 42.07 | A |
| ATOM | 438 | N | TRP | A | 61 | −0.471 | 3.837 | −9.347 | 1.00 | 46.96 | A |
| ATOM | 439 | CA | TRP | A | 61 | 0.852 | 4.285 | −8.938 | 1.00 | 51.03 | A |
| ATOM | 440 | CB | TRP | A | 61 | 0.742 | 5.554 | −8.081 | 1.00 | 53.76 | A |
| ATOM | 441 | CG | TRP | A | 61 | 1.987 | 6.403 | −8.115 | 1.00 | 57.70 | A |
| ATOM | 442 | CD2 | TRP | A | 61 | 2.192 | 7.602 | −8.887 | 1.00 | 59.81 | A |
| ATOM | 443 | CE2 | TRP | A | 61 | 3.526 | 8.021 | −8.660 | 1.00 | 60.30 | A |
| ATOM | 444 | CE3 | TRP | A | 61 | 1.380 | 8.357 | −9.752 | 1.00 | 61.20 | A |
| ATOM | 445 | CD1 | TRP | A | 61 | 3.169 | 6.160 | −7.467 | 1.00 | 57.99 | A |
| ATOM | 446 | NE1 | TRP | A | 61 | 4.095 | 7.127 | −7.790 | 1.00 | 59.69 | A |
| ATOM | 447 | CZ2 | TRP | A | 61 | 4.069 | 9.170 | −9.267 | 1.00 | 61.29 | A |
| ATOM | 448 | CZ3 | TRP | A | 61 | 1.921 | 9.503 | −10.359 | 1.00 | 62.02 | A |
| ATOM | 449 | CH2 | TRP | A | 61 | 3.254 | 9.892 | −10.112 | 1.00 | 61.97 | A |
| ATOM | 450 | C | TRP | A | 61 | 1.588 | 3.181 | −8.192 | 1.00 | 52.67 | A |
| ATOM | 451 | O | TRP | A | 61 | 0.991 | 2.420 | −7.428 | 1.00 | 52.42 | A |
| ATOM | 452 | N | GLU | A | 62 | 2.892 | 3.093 | −8.438 | 1.00 | 55.20 | A |
| ATOM | 453 | CA | GLU | A | 62 | 3.733 | 2.075 | −7.817 | 1.00 | 57.16 | A |
| ATOM | 454 | CB | GLU | A | 62 | 3.580 | 0.762 | −8.579 | 1.00 | 57.04 | A |
| ATOM | 455 | CG | GLU | A | 62 | 3.574 | −0.464 | −7.708 | 1.00 | 58.73 | A |
| ATOM | 456 | CD | GLU | A | 62 | 3.273 | −1.727 | −8.494 | 1.00 | 60.57 | A |
| ATOM | 457 | OE1 | GLU | A | 62 | 4.126 | −2.144 | −9.315 | 1.00 | 61.75 | A |
| ATOM | 458 | OE2 | GLU | A | 62 | 2.179 | −2.305 | −8.296 | 1.00 | 60.52 | A |
| ATOM | 459 | C | GLU | A | 62 | 5.205 | 2.506 | −7.812 | 1.00 | 58.20 | A |
| ATOM | 460 | O | GLU | A | 62 | 5.873 | 2.520 | −8.851 | 1.00 | 58.37 | A |
| ATOM | 461 | N | ASN | A | 63 | 5.695 | 2.856 | −6.625 | 1.00 | 59.00 | A |
| ATOM | 462 | CA | ASN | A | 63 | 7.072 | 3.309 | −6.426 | 1.00 | 59.09 | A |
| ATOM | 463 | CB | ASN | A | 63 | 8.057 | 2.146 | −6.601 | 1.00 | 60.08 | A |
| ATOM | 464 | CG | ASN | A | 63 | 9.464 | 2.490 | −6.111 | 1.00 | 61.16 | A |
| ATOM | 465 | OD1 | ASN | A | 63 | 10.420 | 1.746 | −6.347 | 1.00 | 62.06 | A |
| ATOM | 466 | ND2 | ASN | A | 63 | 9.591 | 3.620 | −5.416 | 1.00 | 60.90 | A |
| ATOM | 467 | C | ASN | A | 63 | 7.468 | 4.452 | −7.366 | 1.00 | 58.34 | A |
| ATOM | 468 | O | ASN | A | 63 | 8.341 | 4.293 | −8.216 | 1.00 | 58.61 | A |
| ATOM | 469 | N | GLY | A | 64 | 6.824 | 5.601 | −7.206 | 1.00 | 57.66 | A |
| ATOM | 470 | CA | GLY | A | 64 | 7.147 | 6.745 | −8.035 | 1.00 | 57.23 | A |
| ATOM | 471 | C | GLY | A | 64 | 7.081 | 6.503 | −9.532 | 1.00 | 56.69 | A |
| ATOM | 472 | O | GLY | A | 64 | 7.988 | 6.892 | −10.271 | 1.00 | 57.24 | A |
| ATOM | 473 | N | GLU | A | 65 | 6.014 | 5.852 | −9.982 | 1.00 | 55.45 | A |
| ATOM | 474 | CA | GLU | A | 65 | 5.816 | 5.581 | −11.407 | 1.00 | 53.27 | A |
| ATOM | 475 | CB | GLU | A | 65 | 6.940 | 4.700 | −11.956 | 1.00 | 54.85 | A |
| ATOM | 476 | CG | GLU | A | 65 | 6.771 | 4.365 | −13.442 | 1.00 | 57.62 | A |
| ATOM | 477 | CD | GLU | A | 65 | 7.591 | 3.152 | −13.876 | 1.00 | 59.68 | A |
| ATOM | 478 | OE1 | GLU | A | 65 | 8.808 | 3.316 | −14.166 | 1.00 | 60.24 | A |
| ATOM | 479 | OE2 | GLU | A | 65 | 7.012 | 2.032 | −13.913 | 1.00 | 59.19 | A |
| ATOM | 480 | C | GLU | A | 65 | 4.473 | 4.904 | −11.675 | 1.00 | 50.57 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 481 | O | GLU | A | 65 | 4.070 | 3.987 | −10.961 | 1.00 | 48.97 | A |
| ATOM | 482 | N | CYS | A | 66 | 3.787 | 5.367 | −12.714 | 1.00 | 47.19 | A |
| ATOM | 483 | CA | CYS | A | 66 | 2.503 | 4.803 | −13.084 | 1.00 | 43.59 | A |
| ATOM | 484 | C | CYS | A | 66 | 2.756 | 3.455 | −13.762 | 1.00 | 40.51 | A |
| ATOM | 485 | O | CYS | A | 66 | 3.625 | 3.345 | −14.632 | 1.00 | 40.39 | A |
| ATOM | 486 | CB | CYS | A | 66 | 1.767 | 5.752 | −14.033 | 1.00 | 44.83 | A |
| ATOM | 487 | SG | CYS | A | 66 | −0.027 | 5.451 | −14.082 | 1.00 | 47.82 | A |
| ATOM | 488 | N | ALA | A | 67 | 2.022 | 2.424 | −13.346 | 1.00 | 36.07 | A |
| ATOM | 489 | CA | ALA | A | 67 | 2.194 | 1.093 | −13.927 | 1.00 | 32.69 | A |
| ATOM | 490 | CB | ALA | A | 67 | 2.661 | 0.127 | −12.860 | 1.00 | 31.43 | A |
| ATOM | 491 | C | ALA | A | 67 | 0.930 | 0.550 | −14.599 | 1.00 | 30.95 | A |
| ATOM | 492 | O | ALA | A | 67 | −0.175 | 0.772 | −14.116 | 1.00 | 30.29 | A |
| ATOM | 493 | N | GLN | A | 68 | 1.096 | −0.160 | −15.714 | 1.00 | 29.19 | A |
| ATOM | 494 | CA | GLN | A | 68 | −0.039 | −0.736 | −16.433 | 1.00 | 28.43 | A |
| ATOM | 495 | CB | GLN | A | 68 | 0.202 | −0.729 | −17.954 | 1.00 | 27.45 | A |
| ATOM | 496 | CG | GLN | A | 68 | −1.040 | −1.062 | −18.789 | 1.00 | 26.69 | A |
| ATOM | 497 | CD | GLN | A | 68 | −0.746 | −1.378 | −20.248 | 1.00 | 26.54 | A |
| ATOM | 498 | OE1 | GLN | A | 68 | −0.308 | −2.480 | −20.575 | 1.00 | 25.60 | A |
| ATOM | 499 | NE2 | GLN | A | 68 | −0.986 | −0.410 | −21.131 | 1.00 | 25.13 | A |
| ATOM | 500 | C | GLN | A | 68 | −0.198 | −2.170 | −15.960 | 1.00 | 28.78 | A |
| ATOM | 501 | O | GLN | A | 68 | 0.779 | −2.908 | −15.856 | 1.00 | 30.77 | A |
| ATOM | 502 | N | LYS | A | 69 | −1.424 | −2.575 | −15.668 | 1.00 | 28.41 | A |
| ATOM | 503 | CA | LYS | A | 69 | −1.637 | −3.932 | −15.211 | 1.00 | 27.79 | A |
| ATOM | 504 | CB | LYS | A | 69 | −1.709 | −3.942 | −13.680 | 1.00 | 29.08 | A |
| ATOM | 505 | CG | LYS | A | 69 | −0.407 | −3.533 | −12.974 | 1.00 | 29.62 | A |
| ATOM | 506 | CD | LYS | A | 69 | −0.279 | −4.243 | −11.611 | 1.00 | 32.13 | A |
| ATOM | 507 | CE | LYS | A | 69 | 0.997 | −3.868 | −10.829 | 1.00 | 32.54 | A |
| ATOM | 508 | NZ | LYS | A | 69 | 0.984 | −4.540 | −9.486 | 1.00 | 33.14 | A |
| ATOM | 509 | C | LYS | A | 69 | −2.883 | −4.575 | −15.832 | 1.00 | 27.00 | A |
| ATOM | 510 | O | LYS | A | 69 | −3.878 | −3.904 | −16.121 | 1.00 | 26.83 | A |
| ATOM | 511 | N | LYS | A | 70 | −2.801 | −5.877 | −16.068 | 1.00 | 26.65 | A |
| ATOM | 512 | CA | LYS | A | 70 | −3.911 | −6.629 | −16.644 | 1.00 | 27.65 | A |
| ATOM | 513 | CB | LYS | A | 70 | −3.465 | −7.395 | −17.883 | 1.00 | 28.88 | A |
| ATOM | 514 | CG | LYS | A | 70 | −3.161 | −6.516 | −19.080 | 1.00 | 29.87 | A |
| ATOM | 515 | CD | LYS | A | 70 | −2.682 | −7.330 | −20.275 | 1.00 | 31.48 | A |
| ATOM | 516 | CE | LYS | A | 70 | −1.275 | −7.868 | −20.062 | 1.00 | 33.90 | A |
| ATOM | 517 | NZ | LYS | A | 70 | −0.764 | −8.550 | −21.295 | 1.00 | 34.28 | A |
| ATOM | 518 | C | LYS | A | 70 | −4.412 | −7.608 | −15.599 | 1.00 | 28.24 | A |
| ATOM | 519 | O | LYS | A | 70 | −3.702 | −8.539 | −15.206 | 1.00 | 28.11 | A |
| ATOM | 520 | N | ILE | A | 71 | −5.646 | −7.393 | −15.163 | 1.00 | 28.75 | A |
| ATOM | 521 | CA | ILE | A | 71 | −6.256 | −8.217 | −14.139 | 1.00 | 29.38 | A |
| ATOM | 522 | CB | ILE | A | 71 | −6.784 | −7.342 | −12.995 | 1.00 | 29.74 | A |
| ATOM | 523 | CG2 | ILE | A | 71 | −7.449 | −8.201 | −11.945 | 1.00 | 29.87 | A |
| ATOM | 524 | CG1 | ILE | A | 71 | −5.634 | −6.519 | −12.406 | 1.00 | 31.07 | A |
| ATOM | 525 | CD1 | ILE | A | 71 | −4.411 | −7.320 | −12.037 | 1.00 | 29.99 | A |
| ATOM | 526 | C | ILE | A | 71 | −7.402 | −9.028 | −14.688 | 1.00 | 30.07 | A |
| ATOM | 527 | O | ILE | A | 71 | −8.092 | −8.594 | −15.601 | 1.00 | 30.69 | A |
| ATOM | 528 | N | ILE | A | 72 | −7.598 | −10.215 | −14.126 | 1.00 | 31.03 | A |
| ATOM | 529 | CA | ILE | A | 72 | −8.684 | −11.094 | −14.543 | 1.00 | 31.39 | A |
| ATOM | 530 | CB | ILE | A | 72 | −8.157 | −12.481 | −15.016 | 1.00 | 30.67 | A |
| ATOM | 531 | CG2 | ILE | A | 72 | −7.592 | −12.374 | −16.420 | 1.00 | 29.84 | A |
| ATOM | 532 | CG1 | ILE | A | 72 | −7.117 | −13.031 | −14.025 | 1.00 | 31.46 | A |
| ATOM | 533 | CD1 | ILE | A | 72 | −5.791 | −12.272 | −13.964 | 1.00 | 30.80 | A |
| ATOM | 534 | C | ILE | A | 72 | −9.681 | −11.297 | −13.395 | 1.00 | 31.89 | A |
| ATOM | 535 | O | ILE | A | 72 | −9.339 | −11.822 | −12.344 | 1.00 | 31.15 | A |
| ATOM | 536 | N | ALA | A | 73 | −10.911 | −10.843 | −13.601 | 1.00 | 33.09 | A |
| ATOM | 537 | CA | ALA | A | 73 | −11.961 | −10.990 | −12.608 | 1.00 | 34.36 | A |
| ATOM | 538 | CB | ALA | A | 73 | −12.854 | −9.756 | −12.592 | 1.00 | 32.94 | A |
| ATOM | 539 | C | ALA | A | 73 | −12.763 | −12.218 | −13.018 | 1.00 | 36.37 | A |
| ATOM | 540 | O | ALA | A | 73 | −13.492 | −12.180 | −14.012 | 1.00 | 35.78 | A |
| ATOM | 541 | N | GLU | A | 74 | −12.612 | −13.307 | −12.264 | 1.00 | 38.55 | A |
| ATOM | 542 | CA | GLU | A | 74 | −13.311 | −14.559 | −12.554 | 1.00 | 40.60 | A |
| ATOM | 543 | CB | GLU | A | 74 | −12.599 | −15.720 | −11.853 | 1.00 | 42.50 | A |
| ATOM | 544 | CG | GLU | A | 74 | −11.126 | −15.861 | −12.232 | 1.00 | 46.59 | A |
| ATOM | 545 | CD | GLU | A | 74 | −10.349 | −16.791 | −11.301 | 1.00 | 48.06 | A |
| ATOM | 546 | OE1 | GLU | A | 74 | −10.349 | −16.548 | −10.074 | 1.00 | 49.47 | A |
| ATOM | 547 | OE2 | GLU | A | 74 | −9.732 | −17.754 | −11.803 | 1.00 | 48.88 | A |
| ATOM | 548 | C | GLU | A | 74 | −14.765 | −14.505 | −12.106 | 1.00 | 41.17 | A |
| ATOM | 549 | O | GLU | A | 74 | −15.062 | −14.102 | −10.983 | 1.00 | 40.92 | A |
| ATOM | 550 | N | LYS | A | 75 | −15.676 | −14.910 | −12.983 | 1.00 | 42.54 | A |
| ATOM | 551 | CA | LYS | A | 75 | −17.086 | −14.895 | −12.630 | 1.00 | 43.98 | A |
| ATOM | 552 | CB | LYS | A | 75 | −17.962 | −15.093 | −13.872 | 1.00 | 44.43 | A |
| ATOM | 553 | CG | LYS | A | 75 | −17.430 | −16.091 | −14.874 | 1.00 | 45.71 | A |
| ATOM | 554 | CD | LYS | A | 75 | −18.037 | −17.459 | −14.685 | 1.00 | 46.72 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 555 | CE | LYS | A | 75 | −17.517 | −18.420 | −15.743 | 1.00 | 48.20 | A |
| ATOM | 556 | NZ | LYS | A | 75 | −16.030 | −18.585 | −15.686 | 1.00 | 48.26 | A |
| ATOM | 557 | C | LYS | A | 75 | −17.373 | −15.962 | −11.589 | 1.00 | 44.70 | A |
| ATOM | 558 | O | LYS | A | 75 | −16.731 | −17.012 | −11.561 | 1.00 | 45.03 | A |
| ATOM | 559 | N | THR | A | 76 | −18.335 | −15.673 | −10.720 | 1.00 | 45.79 | A |
| ATOM | 560 | CA | THR | A | 76 | −18.704 | −16.594 | −9.656 | 1.00 | 46.49 | A |
| ATOM | 561 | CB | THR | A | 76 | −18.482 | −15.931 | −8.265 | 1.00 | 46.29 | A |
| ATOM | 562 | OG1 | THR | A | 76 | −19.386 | −14.829 | −8.099 | 1.00 | 44.95 | A |
| ATOM | 563 | CG2 | THR | A | 76 | −17.043 | −15.425 | −8.139 | 1.00 | 44.80 | A |
| ATOM | 564 | C | THR | A | 76 | −20.163 | −17.048 | −9.784 | 1.00 | 47.70 | A |
| ATOM | 565 | O | THR | A | 76 | −20.834 | −16.742 | −10.771 | 1.00 | 48.25 | A |
| ATOM | 566 | N | LYS | A | 77 | −20.638 | −17.777 | −8.775 | 1.00 | 48.61 | A |
| ATOM | 567 | CA | LYS | A | 77 | −22.004 | −18.290 | −8.735 | 1.00 | 49.17 | A |
| ATOM | 568 | CB | LYS | A | 77 | −22.063 | −19.543 | −7.853 | 1.00 | 49.66 | A |
| ATOM | 569 | CG | LYS | A | 77 | −21.293 | −20.737 | −8.418 | 1.00 | 50.61 | A |
| ATOM | 570 | CD | LYS | A | 77 | −21.051 | −21.797 | −7.360 | 1.00 | 51.96 | A |
| ATOM | 571 | CE | LYS | A | 77 | −20.127 | −22.895 | −7.867 | 1.00 | 52.72 | A |
| ATOM | 572 | NZ | LYS | A | 77 | −19.518 | −23.679 | −6.741 | 1.00 | 52.80 | A |
| ATOM | 573 | C | LYS | A | 77 | −22.947 | −17.220 | −8.201 | 1.00 | 49.74 | A |
| ATOM | 574 | O | LYS | A | 77 | −24.022 | −17.513 | −7.675 | 1.00 | 50.02 | A |
| ATOM | 575 | N | ILE | A | 78 | −22.516 | −15.971 | −8.333 | 1.00 | 50.28 | A |
| ATOM | 576 | CA | ILE | A | 78 | −23.296 | −14.818 | −7.895 | 1.00 | 50.17 | A |
| ATOM | 577 | CB | ILE | A | 78 | −22.618 | −14.092 | −6.746 | 1.00 | 51.47 | A |
| ATOM | 578 | CG2 | ILE | A | 78 | −23.550 | −13.013 | −6.193 | 1.00 | 50.83 | A |
| ATOM | 579 | CG1 | ILE | A | 78 | −22.241 | −15.099 | −5.659 | 1.00 | 51.83 | A |
| ATOM | 580 | CD1 | ILE | A | 78 | −21.526 | −14.477 | −4.487 | 1.00 | 53.00 | A |
| ATOM | 581 | C | ILE | A | 78 | −23.394 | −13.860 | −9.072 | 1.00 | 49.78 | A |
| ATOM | 582 | O | ILE | A | 78 | −22.386 | −13.481 | −9.656 | 1.00 | 50.43 | A |
| ATOM | 583 | N | PRO | A | 79 | −24.613 | −13.438 | −9.416 | 1.00 | 49.21 | A |
| ATOM | 584 | CD | PRO | A | 79 | −25.782 | −13.560 | −8.530 | 1.00 | 48.92 | A |
| ATOM | 585 | CA | PRO | A | 79 | −24.913 | −12.530 | −10.524 | 1.00 | 48.42 | A |
| ATOM | 586 | CB | PRO | A | 79 | −26.114 | −11.762 | −10.004 | 1.00 | 48.75 | A |
| ATOM | 587 | CG | PRO | A | 79 | −26.860 | −12.841 | −9.308 | 1.00 | 49.27 | A |
| ATOM | 588 | C | PRO | A | 79 | −23.803 | −11.611 | −11.039 | 1.00 | 47.58 | A |
| ATOM | 589 | O | PRO | A | 79 | −23.015 | −11.999 | −11.917 | 1.00 | 48.27 | A |
| ATOM | 590 | N | ALA | A | 80 | −23.751 | −10.394 | −10.504 | 1.00 | 44.81 | A |
| ATOM | 591 | CA | ALA | A | 80 | −22.765 | −9.417 | −10.938 | 1.00 | 41.38 | A |
| ATOM | 592 | CB | ALA | A | 80 | −23.427 | −8.058 | −11.109 | 1.00 | 40.61 | A |
| ATOM | 593 | C | ALA | A | 80 | −21.599 | −9.312 | −9.978 | 1.00 | 39.63 | A |
| ATOM | 594 | O | ALA | A | 80 | −21.166 | −8.219 | −9.625 | 1.00 | 39.74 | A |
| ATOM | 595 | N | VAL | A | 81 | −21.076 | −10.457 | −9.567 | 1.00 | 37.52 | A |
| ATOM | 596 | CA | VAL | A | 81 | −19.950 | −10.479 | −8.646 | 1.00 | 35.26 | A |
| ATOM | 597 | CB | VAL | A | 81 | −20.380 | −11.038 | −7.276 | 1.00 | 34.98 | A |
| ATOM | 598 | CG1 | VAL | A | 81 | −19.193 | −11.110 | −6.337 | 1.00 | 32.95 | A |
| ATOM | 599 | CG2 | VAL | A | 81 | −21.473 | −10.175 | −6.692 | 1.00 | 34.19 | A |
| ATOM | 600 | C | VAL | A | 81 | −18.815 | −11.328 | −9.204 | 1.00 | 34.49 | A |
| ATOM | 601 | O | VAL | A | 81 | −19.012 | −12.490 | −9.559 | 1.00 | 34.64 | A |
| ATOM | 602 | N | PHE | A | 82 | −17.628 | −10.742 | −9.286 | 1.00 | 33.80 | A |
| ATOM | 603 | CA | PHE | A | 82 | −16.471 | −11.457 | −9.805 | 1.00 | 34.10 | A |
| ATOM | 604 | CB | PHE | A | 82 | −15.909 | −10.758 | −11.049 | 1.00 | 32.25 | A |
| ATOM | 605 | CG | PHE | A | 82 | −16.919 | −10.533 | −12.134 | 1.00 | 30.18 | A |
| ATOM | 606 | CD1 | PHE | A | 82 | −17.829 | −9.492 | −12.048 | 1.00 | 28.63 | A |
| ATOM | 607 | CD2 | PHE | A | 82 | −16.967 | −11.367 | −13.245 | 1.00 | 29.67 | A |
| ATOM | 608 | CE1 | PHE | A | 82 | −18.764 | −9.286 | −13.051 | 1.00 | 28.96 | A |
| ATOM | 609 | CE2 | PHE | A | 82 | −17.903 | −11.162 | −14.248 | 1.00 | 29.77 | A |
| ATOM | 610 | CZ | PHE | A | 82 | −18.803 | −10.121 | −14.151 | 1.00 | 29.10 | A |
| ATOM | 611 | C | PHE | A | 82 | −15.401 | −11.508 | −8.735 | 1.00 | 35.20 | A |
| ATOM | 612 | O | PHE | A | 82 | −15.527 | −10.872 | −7.695 | 1.00 | 35.28 | A |
| ATOM | 613 | N | LYS | A | 83 | −14.344 | −12.261 | −8.988 | 1.00 | 37.28 | A |
| ATOM | 614 | CA | LYS | A | 83 | −13.281 | −12.354 | −8.014 | 1.00 | 40.61 | A |
| ATOM | 615 | CB | LYS | A | 83 | −13.354 | −13.689 | −7.282 | 1.00 | 41.61 | A |
| ATOM | 616 | CG | LYS | A | 83 | −12.383 | −13.787 | −6.118 | 1.00 | 44.64 | A |
| ATOM | 617 | CD | LYS | A | 83 | −12.342 | −15.182 | −5.500 | 1.00 | 45.25 | A |
| ATOM | 618 | CE | LYS | A | 83 | −11.773 | −16.211 | −6.467 | 1.00 | 46.11 | A |
| ATOM | 619 | NZ | LYS | A | 83 | −11.737 | −17.558 | −5.854 | 1.00 | 45.81 | A |
| ATOM | 620 | C | LYS | A | 83 | −11.917 | −12.198 | −8.667 | 1.00 | 42.61 | A |
| ATOM | 621 | O | LYS | A | 83 | −11.716 | −12.622 | −9.801 | 1.00 | 41.97 | A |
| ATOM | 622 | N | ILE | A | 84 | −10.989 | −11.582 | −7.941 | 1.00 | 45.99 | A |
| ATOM | 623 | CA | ILE | A | 84 | −9.634 | −11.357 | −8.422 | 1.00 | 50.16 | A |
| ATOM | 624 | CB | ILE | A | 84 | −9.173 | −9.929 | −8.133 | 1.00 | 50.06 | A |
| ATOM | 625 | CG2 | ILE | A | 84 | −7.789 | −9.706 | −8.719 | 1.00 | 50.61 | A |
| ATOM | 626 | CG1 | ILE | A | 84 | −10.159 | −8.929 | −8.724 | 1.00 | 49.73 | A |
| ATOM | 627 | CD1 | ILE | A | 84 | −10.097 | −7.572 | −8.059 | 1.00 | 50.68 | A |
| ATOM | 628 | C | ILE | A | 84 | −8.713 | −12.309 | −7.682 | 1.00 | 53.84 | A |

TABLE VIII-continued

Structure coordinates of the epitopes of allergenic beta-lactoglobulin in an antibody-beta-lactoglobulin immunocomplex;

|      | # | Atom type | Resid | | # | X | Y | Z | OCC | B | |
|---|---|---|---|---|---|---|---|---|---|---|---|
| ATOM | 629 | O   | ILE | A | 84 | −8.653  | −12.295 | −6.453  | 1.00 | 54.52 | A |
| ATOM | 630 | N   | ASP | A | 85 | −7.989  | −13.127 | −8.437  | 1.00 | 58.42 | A |
| ATOM | 631 | CA  | ASP | A | 85 | −7.077  | −14.110 | −7.855  | 1.00 | 62.83 | A |
| ATOM | 632 | CB  | ASP | A | 85 | −6.543  | −15.030 | −8.960  | 1.00 | 64.60 | A |
| ATOM | 633 | CG  | ASP | A | 85 | −6.508  | −16.494 | −8.540  | 1.00 | 66.46 | A |
| ATOM | 634 | OD1 | ASP | A | 85 | −6.292  | −17.364 | −9.421  | 1.00 | 67.24 | A |
| ATOM | 635 | OD2 | ASP | A | 85 | −6.695  | −16.771 | −7.330  | 1.00 | 67.13 | A |
| ATOM | 636 | C   | ASP | A | 85 | −5.909  | −13.512 | −7.052  | 1.00 | 64.82 | A |
| ATOM | 637 | O   | ASP | A | 85 | −5.184  | −14.243 | −6.373  | 1.00 | 65.69 | A |
| ATOM | 638 | N   | ALA | A | 86 | −5.725  | −12.195 | −7.129  | 1.00 | 66.46 | A |
| ATOM | 639 | CA  | ALA | A | 86 | −4.655  | −11.533 | −6.386  | 1.00 | 68.14 | A |
| ATOM | 640 | CB  | ALA | A | 86 | −4.686  | −10.028 | −6.644  | 1.00 | 67.64 | A |
| ATOM | 641 | C   | ALA | A | 86 | −4.843  | −11.817 | −4.896  | 1.00 | 69.84 | A |
| ATOM | 642 | O   | ALA | A | 86 | −5.910  | −12.273 | −4.477  | 1.00 | 71.12 | A |
| ATOM | 643 | N   | LEU | A | 87 | −3.814  | −11.551 | −4.097  | 1.00 | 71.20 | A |
| ATOM | 644 | CA  | LEU | A | 87 | −3.893  | −11.792 | −2.655  | 1.00 | 71.87 | A |
| ATOM | 645 | CB  | LEU | A | 87 | −2.572  | −11.406 | −1.967  | 1.00 | 72.10 | A |
| ATOM | 646 | CG  | LEU | A | 87 | −2.329  | −11.877 | −0.520  | 1.00 | 72.35 | A |
| ATOM | 647 | CD1 | LEU | A | 87 | −2.150  | −13.388 | −0.499  | 1.00 | 71.46 | A |
| ATOM | 648 | CD2 | LEU | A | 87 | −1.084  | −11.201 | 0.051   | 1.00 | 72.25 | A |
| ATOM | 649 | C   | LEU | A | 87 | −5.043  | −10.989 | −2.045  | 1.00 | 72.03 | A |
| ATOM | 650 | O   | LEU | A | 87 | −5.599  | −10.086 | −2.683  | 1.00 | 71.30 | A |
| ATOM | 651 | N   | ASN | A | 88 | −5.383  | −11.326 | −0.802  | 1.00 | 71.95 | A |
| ATOM | 652 | CA  | ASN | A | 88 | −6.457  | −10.664 | −0.064  | 1.00 | 71.65 | A |
| ATOM | 653 | CB  | ASN | A | 88 | −6.299  | −9.132  | −0.143  | 1.00 | 73.05 | A |
| ATOM | 654 | CG  | ASN | A | 88 | −4.849  | −8.670  | 0.032   | 1.00 | 73.75 | A |
| ATOM | 655 | OD1 | ASN | A | 88 | −4.164  | −9.051  | 0.989   | 1.00 | 74.21 | A |
| ATOM | 656 | ND2 | ASN | A | 88 | −4.387  | −7.831  | −0.891  | 1.00 | 73.03 | A |
| ATOM | 657 | C   | ASN | A | 88 | −7.838  | −11.067 | −0.606  | 1.00 | 70.43 | A |
| ATOM | 658 | O   | ASN | A | 88 | −8.851  | −10.913 | 0.084   | 1.00 | 70.57 | A |
| ATOM | 659 | N   | GLU | A | 89 | −7.863  | −11.582 | −1.839  | 1.00 | 68.18 | A |
| ATOM | 660 | CA  | GLU | A | 89 | −9.100  | −11.997 | −2.511  | 1.00 | 65.08 | A |
| ATOM | 661 | CB  | GLU | A | 89 | −9.798  | −13.114 | −1.728  | 1.00 | 67.04 | A |
| ATOM | 662 | CG  | GLU | A | 89 | −9.172  | −14.497 | −1.905  | 1.00 | 69.48 | A |
| ATOM | 663 | CD  | GLU | A | 89 | −9.208  | −14.972 | −3.357  | 1.00 | 70.72 | A |
| ATOM | 664 | OE1 | GLU | A | 89 | −8.437  | −14.439 | −4.191  | 1.00 | 71.05 | A |
| ATOM | 665 | OE2 | GLU | A | 89 | −10.024 | −15.869 | −3.664  | 1.00 | 71.34 | A |
| ATOM | 666 | C   | GLU | A | 89 | −10.076 | −10.844 | −2.719  | 1.00 | 61.80 | A |
| ATOM | 667 | O   | GLU | A | 89 | −11.203 | −10.870 | −2.224  | 1.00 | 62.02 | A |
| ATOM | 668 | N   | ASN | A | 90 | −9.630  | −9.829  | −3.448  | 1.00 | 57.36 | A |
| ATOM | 669 | CA  | ASN | A | 90 | −10.460 | −8.671  | −3.727  | 1.00 | 52.67 | A |
| ATOM | 670 | CB  | ASN | A | 90 | −9.647  | −7.646  | −4.533  | 1.00 | 52.48 | A |
| ATOM | 671 | CG  | ASN | A | 90 | −8.928  | −6.634  | −3.646  | 1.00 | 52.32 | A |
| ATOM | 672 | OD1 | ASN | A | 90 | −9.508  | −5.631  | −3.216  | 1.00 | 53.38 | A |
| ATOM | 673 | ND2 | ASN | A | 90 | −7.663  | −6.899  | −3.364  | 1.00 | 52.47 | A |
| ATOM | 674 | C   | ASN | A | 90 | −11.715 | −9.096  | −4.501  | 1.00 | 49.56 | A |
| ATOM | 675 | O   | ASN | A | 90 | −11.625 | −9.859  | −5.458  | 1.00 | 48.05 | A |
| ATOM | 676 | N   | LYS | A | 91 | −12.886 | −8.639  | −4.061  | 1.00 | 46.27 | A |
| ATOM | 677 | CA  | LYS | A | 91 | −14.127 | −8.960  | −4.756  | 1.00 | 42.55 | A |
| ATOM | 678 | CB  | LYS | A | 91 | −15.196 | −9.528  | −3.816  | 1.00 | 43.88 | A |
| ATOM | 679 | CG  | LYS | A | 91 | −15.043 | −11.009 | −3.467  | 1.00 | 46.95 | A |
| ATOM | 680 | CD  | LYS | A | 91 | −16.307 | −11.537 | −2.772  | 1.00 | 49.01 | A |
| ATOM | 681 | CE  | LYS | A | 91 | −16.120 | −12.957 | −2.226  | 1.00 | 48.98 | A |
| ATOM | 682 | NZ  | LYS | A | 91 | −17.356 | −13.517 | −1.586  | 1.00 | 47.83 | A |
| ATOM | 683 | C   | LYS | A | 91 | −14.667 | −7.697  | −5.394  | 1.00 | 39.10 | A |
| ATOM | 684 | O   | LYS | A | 91 | −14.642 | −6.621  | −4.797  | 1.00 | 38.37 | A |
| ATOM | 685 | N   | VAL | A | 92 | −15.150 | −7.839  | −6.619  | 1.00 | 35.12 | A |
| ATOM | 686 | CA  | VAL | A | 92 | −15.703 | −6.721  | −7.356  | 1.00 | 31.05 | A |
| ATOM | 687 | CB  | VAL | A | 92 | −15.035 | −6.638  | −8.732  | 1.00 | 30.40 | A |
| ATOM | 688 | CG1 | VAL | A | 92 | −15.487 | −5.402  | −9.460  | 1.00 | 30.11 | A |
| ATOM | 689 | CG2 | VAL | A | 92 | −13.526 | −6.647  | −8.558  | 1.00 | 29.54 | A |
| ATOM | 690 | C   | VAL | A | 92 | −17.210 | −6.939  | −7.502  | 1.00 | 28.12 | A |
| ATOM | 691 | O   | VAL | A | 92 | −17.658 | −8.058  | −7.731  | 1.00 | 27.38 | A |
| ATOM | 692 | N   | LEU | A | 93 | −17.991 | −5.875  | −7.348  | 1.00 | 25.32 | A |
| ATOM | 693 | CA  | LEU | A | 93 | −19.442 | −5.972  | −7.470  | 1.00 | 23.52 | A |
| ATOM | 694 | CB  | LEU | A | 93 | −20.109 | −5.806  | −6.107  | 1.00 | 24.09 | A |
| ATOM | 695 | CG  | LEU | A | 93 | −19.510 | −6.500  | −4.880  | 1.00 | 22.89 | A |
| ATOM | 696 | CD1 | LEU | A | 93 | −19.306 | −7.960  | −5.154  | 1.00 | 23.08 | A |
| ATOM | 697 | CD2 | LEU | A | 93 | −18.197 | −5.831  | −4.513  | 1.00 | 24.87 | A |
| ATOM | 698 | C   | LEU | A | 93 | −19.955 | −4.875  | −8.392  | 1.00 | 22.06 | A |
| ATOM | 699 | O   | LEU | A | 93 | −19.679 | −3.699  | −8.169  | 1.00 | 22.62 | A |
| ATOM | 700 | N   | VAL | A | 94 | −20.700 | −5.250  | −9.423  | 1.00 | 20.24 | A |
| ATOM | 701 | CA  | VAL | A | 94 | −21.234 | −4.262  | −10.359 | 1.00 | 19.43 | A |
| ATOM | 702 | CB  | VAL | A | 94 | −21.402 | −4.869  | −11.785 | 1.00 | 18.31 | A |

TABLE VIII-continued

Structure coordinates of the epitopes of allergenic beta-lactoglobulin in an antibody-beta-lactoglobulin immunocomplex;

|  |  | Atom type | Resid |  | # | X | Y | Z | OCC | B |  |
|---|---|---|---|---|---|---|---|---|---|---|---|
| ATOM | 703 | CG1 | VAL | A | 94 | −21.967 | −3.841 | −12.735 | 1.00 | 16.47 | A |
| ATOM | 704 | CG2 | VAL | A | 94 | −20.072 | −5.368 | −12.291 | 1.00 | 14.46 | A |
| ATOM | 705 | C | VAL | A | 94 | −22.582 | −3.795 | −9.823 | 1.00 | 19.37 | A |
| ATOM | 706 | O | VAL | A | 94 | −23.565 | −4.536 | −9.843 | 1.00 | 19.85 | A |
| ATOM | 707 | N | LEU | A | 95 | −22.618 | −2.563 | −9.333 | 1.00 | 18.93 | A |
| ATOM | 708 | CA | LEU | A | 95 | −23.838 | −2.009 | −8.766 | 1.00 | 18.77 | A |
| ATOM | 709 | CB | LEU | A | 95 | −23.502 | −0.785 | −7.915 | 1.00 | 20.01 | A |
| ATOM | 710 | CG | LEU | A | 95 | −22.774 | −1.051 | −6.591 | 1.00 | 20.85 | A |
| ATOM | 711 | CD1 | LEU | A | 95 | −22.627 | 0.263 | −5.844 | 1.00 | 20.24 | A |
| ATOM | 712 | CD2 | LEU | A | 95 | −23.576 | −2.041 | −5.738 | 1.00 | 21.51 | A |
| ATOM | 713 | C | LEU | A | 95 | −24.898 | −1.639 | −9.793 | 1.00 | 18.28 | A |
| ATOM | 714 | O | LEU | A | 95 | −26.080 | −1.907 | −9.591 | 1.00 | 16.17 | A |
| ATOM | 715 | N | ASP | A | 96 | −24.477 | −1.024 | −10.889 | 1.00 | 19.53 | A |
| ATOM | 716 | CA | ASP | A | 96 | −25.413 | −0.623 | −11.926 | 1.00 | 21.52 | A |
| ATOM | 717 | CB | ASP | A | 96 | −26.225 | 0.582 | −11.460 | 1.00 | 21.47 | A |
| ATOM | 718 | CG | ASP | A | 96 | −27.412 | 0.850 | −12.350 | 1.00 | 22.85 | A |
| ATOM | 719 | OD1 | ASP | A | 96 | −28.132 | −0.126 | −12.655 | 1.00 | 25.16 | A |
| ATOM | 720 | OD2 | ASP | A | 96 | −27.635 | 2.020 | −12.733 | 1.00 | 23.28 | A |
| ATOM | 721 | C | ASP | A | 96 | −24.667 | −0.269 | −13.204 | 1.00 | 22.80 | A |
| ATOM | 722 | O | ASP | A | 96 | −23.461 | −0.023 | −13.169 | 1.00 | 24.06 | A |
| ATOM | 723 | N | THR | A | 97 | −25.383 | −0.247 | −14.326 | 1.00 | 22.38 | A |
| ATOM | 724 | CA | THR | A | 97 | −24.776 | 0.095 | −15.600 | 1.00 | 22.34 | A |
| ATOM | 725 | CB | THR | A | 97 | −23.696 | −0.931 | −16.006 | 1.00 | 22.56 | A |
| ATOM | 726 | OG1 | THR | A | 97 | −23.116 | −0.553 | −17.264 | 1.00 | 22.90 | A |
| ATOM | 727 | CG2 | THR | A | 97 | −24.303 | −2.319 | −16.139 | 1.00 | 20.01 | A |
| ATOM | 728 | C | THR | A | 97 | −25.803 | 0.143 | −16.707 | 1.00 | 22.52 | A |
| ATOM | 729 | O | THR | A | 97 | −26.726 | −0.659 | −16.711 | 1.00 | 23.66 | A |
| ATOM | 730 | N | ASP | A | 98 | −25.642 | 1.083 | −17.637 | 1.00 | 22.22 | A |
| ATOM | 731 | CA | ASP | A | 98 | −26.544 | 1.203 | −18.780 | 1.00 | 21.65 | A |
| ATOM | 732 | CB | ASP | A | 98 | −26.949 | 2.671 | −19.004 | 1.00 | 22.77 | A |
| ATOM | 733 | CG | ASP | A | 98 | −25.814 | 3.527 | −19.532 | 1.00 | 24.72 | A |
| ATOM | 734 | OD1 | ASP | A | 98 | −24.658 | 3.311 | −19.127 | 1.00 | 27.27 | A |
| ATOM | 735 | OD2 | ASP | A | 98 | −26.075 | 4.434 | −20.347 | 1.00 | 26.48 | A |
| ATOM | 736 | C | ASP | A | 98 | −25.819 | 0.635 | −20.007 | 1.00 | 21.37 | A |
| ATOM | 737 | O | ASP | A | 98 | −26.393 | 0.538 | −21.086 | 1.00 | 20.79 | A |
| ATOM | 738 | N | TYR | A | 99 | −24.555 | 0.252 | −19.815 | 1.00 | 20.65 | A |
| ATOM | 739 | CA | TYR | A | 99 | −23.708 | −0.330 | −20.864 | 1.00 | 19.29 | A |
| ATOM | 740 | CB | TYR | A | 99 | −24.451 | −1.454 | −21.601 | 1.00 | 16.84 | A |
| ATOM | 741 | CG | TYR | A | 99 | −24.856 | −2.627 | −20.750 | 1.00 | 14.61 | A |
| ATOM | 742 | CD1 | TYR | A | 99 | −23.946 | −3.617 | −20.406 | 1.00 | 12.54 | A |
| ATOM | 743 | CE1 | TYR | A | 99 | −24.328 | −4.698 | −19.614 | 1.00 | 12.07 | A |
| ATOM | 744 | CD2 | TYR | A | 99 | −26.156 | −2.742 | −20.280 | 1.00 | 13.65 | A |
| ATOM | 745 | CE2 | TYR | A | 99 | −26.547 | −3.814 | −19.492 | 1.00 | 13.03 | A |
| ATOM | 746 | CZ | TYR | A | 99 | −25.631 | −4.792 | −19.157 | 1.00 | 13.13 | A |
| ATOM | 747 | OH | TYR | A | 99 | −26.036 | −5.856 | −18.365 | 1.00 | 12.49 | A |
| ATOM | 748 | C | TYR | A | 99 | −23.194 | 0.667 | −21.902 | 1.00 | 20.53 | A |
| ATOM | 749 | O | TYR | A | 99 | −22.073 | 0.530 | −22.379 | 1.00 | 20.58 | A |
| ATOM | 750 | N | LYS | A | 100 | −24.005 | 1.670 | −22.238 | 1.00 | 21.61 | A |
| ATOM | 751 | CA | LYS | A | 100 | −23.649 | 2.654 | −23.258 | 1.00 | 21.03 | A |
| ATOM | 752 | CB | LYS | A | 100 | −24.891 | 3.004 | −24.085 | 1.00 | 23.12 | A |
| ATOM | 753 | CG | LYS | A | 100 | −25.705 | 1.800 | −24.531 | 1.00 | 26.96 | A |
| ATOM | 754 | CD | LYS | A | 100 | −24.896 | 0.871 | −25.424 | 1.00 | 29.57 | A |
| ATOM | 755 | CE | LYS | A | 100 | −25.436 | −0.584 | −25.398 | 1.00 | 33.09 | A |
| ATOM | 756 | NZ | LYS | A | 100 | −26.875 | −0.751 | −25.800 | 1.00 | 33.75 | A |
| ATOM | 757 | C | LYS | A | 100 | −23.046 | 3.946 | −22.718 | 1.00 | 20.25 | A |
| ATOM | 758 | O | LYS | A | 100 | −22.413 | 4.689 | −23.461 | 1.00 | 20.17 | A |
| ATOM | 759 | N | LYS | A | 101 | −23.236 | 4.228 | −21.435 | 1.00 | 19.04 | A |
| ATOM | 760 | CA | LYS | A | 101 | −22.701 | 5.467 | −20.874 | 1.00 | 17.66 | A |
| ATOM | 761 | CB | LYS | A | 101 | −23.837 | 6.492 | −20.704 | 1.00 | 17.25 | A |
| ATOM | 762 | CG | LYS | A | 101 | −24.408 | 7.018 | −22.017 | 1.00 | 18.59 | A |
| ATOM | 763 | CD | LYS | A | 101 | −25.507 | 8.052 | −21.803 | 1.00 | 21.15 | A |
| ATOM | 764 | CE | LYS | A | 101 | −26.614 | 7.492 | −20.892 | 1.00 | 25.51 | A |
| ATOM | 765 | NZ | LYS | A | 101 | −27.841 | 8.354 | −20.716 | 1.00 | 25.35 | A |
| ATOM | 766 | C | LYS | A | 101 | −21.927 | 5.328 | −19.552 | 1.00 | 16.29 | A |
| ATOM | 767 | O | LYS | A | 101 | −20.783 | 5.767 | −19.457 | 1.00 | 16.64 | A |
| ATOM | 768 | N | TYR | A | 102 | −22.541 | 4.723 | −18.539 | 1.00 | 13.96 | A |
| ATOM | 769 | CA | TYR | A | 102 | −21.884 | 4.579 | −17.250 | 1.00 | 12.20 | A |
| ATOM | 770 | CB | TYR | A | 102 | −22.552 | 5.485 | −16.221 | 1.00 | 13.37 | A |
| ATOM | 771 | CG | TYR | A | 102 | −23.967 | 5.074 | −15.913 | 1.00 | 14.80 | A |
| ATOM | 772 | CD1 | TYR | A | 102 | −25.026 | 5.452 | −16.743 | 1.00 | 15.56 | A |
| ATOM | 773 | CE1 | TYR | A | 102 | −26.332 | 5.040 | −16.473 | 1.00 | 16.40 | A |
| ATOM | 774 | CD2 | TYR | A | 102 | −24.245 | 4.275 | −14.810 | 1.00 | 14.91 | A |
| ATOM | 775 | CE2 | TYR | A | 102 | −25.537 | 3.852 | −14.533 | 1.00 | 16.83 | A |
| ATOM | 776 | CZ | TYR | A | 102 | −26.574 | 4.231 | −15.362 | 1.00 | 17.72 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 777 | OH | TYR | A | 102 | −27.843 | 3.776 | −15.086 | 1.00 | 19.73 | A |
| ATOM | 778 | C | TYR | A | 102 | −21.870 | 3.163 | −16.691 | 1.00 | 11.60 | A |
| ATOM | 779 | O | TYR | A | 102 | −22.555 | 2.272 | −17.194 | 1.00 | 11.84 | A |
| ATOM | 780 | N | LEU | A | 103 | −21.081 | 2.973 | −15.636 | 1.00 | 9.56 | A |
| ATOM | 781 | CA | LEU | A | 103 | −20.979 | 1.690 | −14.954 | 1.00 | 8.12 | A |
| ATOM | 782 | CB | LEU | A | 103 | −20.022 | 0.743 | −15.694 | 1.00 | 8.06 | A |
| ATOM | 783 | CG | LEU | A | 103 | −19.983 | −0.682 | −15.115 | 1.00 | 7.72 | A |
| ATOM | 784 | CD1 | LEU | A | 103 | −19.586 | −1.676 | −16.152 | 1.00 | 8.20 | A |
| ATOM | 785 | CD2 | LEU | A | 103 | −19.049 | −0.720 | −13.930 | 1.00 | 7.20 | A |
| ATOM | 786 | C | LEU | A | 103 | −20.488 | 1.948 | −13.526 | 1.00 | 9.01 | A |
| ATOM | 787 | O | LEU | A | 103 | −19.541 | 2.692 | −13.313 | 1.00 | 8.51 | A |
| ATOM | 788 | N | LEU | A | 104 | −21.136 | 1.319 | −12.551 | 1.00 | 9.89 | A |
| ATOM | 789 | CA | LEU | A | 104 | −20.773 | 1.513 | −11.158 | 1.00 | 10.66 | A |
| ATOM | 790 | CB | LEU | A | 104 | −21.958 | 2.088 | −10.398 | 1.00 | 10.47 | A |
| ATOM | 791 | CG | LEU | A | 104 | −22.586 | 3.339 | −11.002 | 1.00 | 9.11 | A |
| ATOM | 792 | CD1 | LEU | A | 104 | −23.833 | 3.732 | −10.219 | 1.00 | 8.12 | A |
| ATOM | 793 | CD2 | LEU | A | 104 | −21.576 | 4.465 | −10.984 | 1.00 | 8.64 | A |
| ATOM | 794 | C | LEU | A | 104 | −20.354 | 0.225 | −10.485 | 1.00 | 11.23 | A |
| ATOM | 795 | O | LEU | A | 104 | −21.083 | −0.758 | −10.534 | 1.00 | 13.70 | A |
| ATOM | 796 | N | PHE | A | 105 | −19.202 | 0.232 | −9.829 | 1.00 | 10.76 | A |
| ATOM | 797 | CA | PHE | A | 105 | −18.748 | −0.969 | −9.153 | 1.00 | 11.87 | A |
| ATOM | 798 | CB | PHE | A | 105 | −17.829 | −1.782 | −10.068 | 1.00 | 10.16 | A |
| ATOM | 799 | CG | PHE | A | 105 | −16.489 | −1.140 | −10.292 | 1.00 | 9.81 | A |
| ATOM | 800 | CD1 | PHE | A | 105 | −16.337 | −0.129 | −11.249 | 1.00 | 8.87 | A |
| ATOM | 801 | CD2 | PHE | A | 105 | −15.391 | −1.494 | −9.482 | 1.00 | 8.20 | A |
| ATOM | 802 | CE1 | PHE | A | 105 | −15.118 | 0.521 | −11.394 | 1.00 | 9.90 | A |
| ATOM | 803 | CE2 | PHE | A | 105 | −14.164 | −0.857 | −9.606 | 1.00 | 6.67 | A |
| ATOM | 804 | CZ | PHE | A | 105 | −14.016 | 0.156 | −10.563 | 1.00 | 9.33 | A |
| ATOM | 805 | C | PHE | A | 105 | −17.996 | −0.615 | −7.877 | 1.00 | 14.65 | A |
| ATOM | 806 | O | PHE | A | 105 | −17.598 | 0.535 | −7.675 | 1.00 | 13.84 | A |
| ATOM | 807 | N | CYS | A | 106 | −17.809 | −1.620 | −7.028 | 1.00 | 17.88 | A |
| ATOM | 808 | CA | CYS | A | 106 | −17.085 | −1.469 | −5.774 | 1.00 | 21.18 | A |
| ATOM | 809 | C | CYS | A | 106 | −16.159 | −2.660 | −5.649 | 1.00 | 24.19 | A |
| ATOM | 810 | O | CYS | A | 106 | −16.388 | −3.698 | −6.272 | 1.00 | 24.79 | A |
| ATOM | 811 | CB | CYS | A | 106 | −18.026 | −1.484 | −4.571 | 1.00 | 20.47 | A |
| ATOM | 812 | SG | CYS | A | 106 | −19.182 | −0.095 | −4.399 | 1.00 | 22.55 | A |
| ATOM | 813 | N | MET | A | 107 | −15.115 | −2.521 | −4.846 | 1.00 | 27.17 | A |
| ATOM | 814 | CA | MET | A | 107 | −14.205 | −3.625 | −4.652 | 1.00 | 32.34 | A |
| ATOM | 815 | CB | MET | A | 107 | −12.999 | −3.483 | −5.575 | 1.00 | 31.11 | A |
| ATOM | 816 | CG | MET | A | 107 | −12.201 | −2.228 | −5.382 | 1.00 | 30.90 | A |
| ATOM | 817 | SD | MET | A | 107 | −11.147 | −1.907 | −6.805 | 1.00 | 30.75 | A |
| ATOM | 818 | CE | MET | A | 107 | −11.313 | −0.129 | −6.939 | 1.00 | 30.73 | A |
| ATOM | 819 | C | MET | A | 107 | −13.779 | −3.692 | −3.202 | 1.00 | 36.20 | A |
| ATOM | 820 | O | MET | A | 107 | −13.458 | −2.670 | −2.606 | 1.00 | 36.17 | A |
| ATOM | 821 | N | GLU | A | 108 | −13.806 | −4.894 | −2.625 | 1.00 | 41.42 | A |
| ATOM | 822 | CA | GLU | A | 108 | −13.416 | −5.086 | −1.225 | 1.00 | 45.26 | A |
| ATOM | 823 | CB | GLU | A | 108 | −14.655 | −5.281 | −0.344 | 1.00 | 45.70 | A |
| ATOM | 824 | CG | GLU | A | 108 | −15.475 | −6.512 | −0.691 | 1.00 | 47.75 | A |
| ATOM | 825 | CD | GLU | A | 108 | −16.441 | −6.901 | 0.412 | 1.00 | 48.53 | A |
| ATOM | 826 | OE1 | GLU | A | 108 | −17.331 | −6.087 | 0.742 | 1.00 | 48.20 | A |
| ATOM | 827 | OE2 | GLU | A | 108 | −16.303 | −8.024 | 0.948 | 1.00 | 50.31 | A |
| ATOM | 828 | C | GLU | A | 108 | −12.500 | −6.287 | −1.055 | 1.00 | 47.65 | A |
| ATOM | 829 | O | GLU | A | 108 | −12.474 | −7.181 | −1.894 | 1.00 | 47.55 | A |
| ATOM | 830 | N | ASN | A | 109 | −11.744 | −6.297 | 0.034 | 1.00 | 51.81 | A |
| ATOM | 831 | CA | ASN | A | 109 | −10.852 | −7.408 | 0.310 | 1.00 | 56.91 | A |
| ATOM | 832 | CB | ASN | A | 109 | −9.469 | −6.900 | 0.729 | 1.00 | 58.54 | A |
| ATOM | 833 | CG | ASN | A | 109 | −8.779 | −6.089 | −0.373 | 1.00 | 60.68 | A |
| ATOM | 834 | OD1 | ASN | A | 109 | −9.271 | −5.030 | −0.790 | 1.00 | 61.57 | A |
| ATOM | 835 | ND2 | ASN | A | 109 | −7.636 | −6.590 | −0.853 | 1.00 | 60.43 | A |
| ATOM | 836 | C | ASN | A | 109 | −11.451 | −8.258 | 1.415 | 1.00 | 59.35 | A |
| ATOM | 837 | O | ASN | A | 109 | −11.616 | −7.800 | 2.544 | 1.00 | 59.16 | A |
| ATOM | 838 | N | SER | A | 110 | −11.789 | −9.494 | 1.072 | 1.00 | 63.16 | A |
| ATOM | 839 | CA | SER | A | 110 | −12.367 | −10.425 | 2.034 | 1.00 | 66.90 | A |
| ATOM | 840 | CB | SER | A | 110 | −12.335 | −11.850 | 1.471 | 1.00 | 66.79 | A |
| ATOM | 841 | OG | SER | A | 110 | −12.800 | −12.790 | 2.426 | 0.00 | 67.03 | A |
| ATOM | 842 | C | SER | A | 110 | −11.629 | −10.390 | 3.378 | 1.00 | 68.96 | A |
| ATOM | 843 | O | SER | A | 110 | −12.247 | −10.508 | 4.442 | 1.00 | 69.21 | A |
| ATOM | 844 | N | ALA | A | 111 | −10.309 | −10.228 | 3.324 | 1.00 | 70.87 | A |
| ATOM | 845 | CA | ALA | A | 111 | −9.497 | −10.182 | 4.534 | 1.00 | 73.10 | A |
| ATOM | 846 | CB | ALA | A | 111 | −8.041 | −9.886 | 4.178 | 1.00 | 74.11 | A |
| ATOM | 847 | C | ALA | A | 111 | −10.027 | −9.127 | 5.502 | 1.00 | 74.80 | A |
| ATOM | 848 | O | ALA | A | 111 | −10.281 | −9.414 | 6.672 | 1.00 | 75.12 | A |
| ATOM | 849 | N | GLU | A | 112 | −10.191 | −7.904 | 5.010 | 1.00 | 76.54 | A |
| ATOM | 850 | CA | GLU | A | 112 | −10.699 | −6.812 | 5.832 | 1.00 | 77.67 | A |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 851 | CB | GLU | A | 112 | −9.578 | −5.812 | 6.142 | 1.00 | 78.60 | A |
| ATOM | 852 | CG | GLU | A | 112 | −8.796 | −6.095 | 7.440 | 1.00 | 79.84 | A |
| ATOM | 853 | CD | GLU | A | 112 | −8.054 | −7.425 | 7.433 | 1.00 | 80.21 | A |
| ATOM | 854 | OE1 | GLU | A | 112 | −7.213 | −7.638 | 6.529 | 1.00 | 80.30 | A |
| ATOM | 855 | OE2 | GLU | A | 112 | −8.305 | −8.248 | 8.344 | 1.00 | 79.95 | A |
| ATOM | 856 | C | GLU | A | 112 | −11.858 | −6.105 | 5.130 | 1.00 | 77.80 | A |
| ATOM | 857 | O | GLU | A | 112 | −11.687 | −5.032 | 4.555 | 1.00 | 77.90 | A |
| ATOM | 858 | N | PRO | A | 113 | −13.060 | −6.710 | 5.164 | 1.00 | 77.88 | A |
| ATOM | 859 | CD | PRO | A | 113 | −13.373 | −8.027 | 5.750 | 1.00 | 77.78 | A |
| ATOM | 860 | CA | PRO | A | 113 | −14.248 | −6.130 | 4.527 | 1.00 | 77.56 | A |
| ATOM | 861 | CB | PRO | A | 113 | −15.233 | −7.294 | 4.526 | 1.00 | 77.90 | A |
| ATOM | 862 | CG | PRO | A | 113 | −14.885 | −8.010 | 5.793 | 1.00 | 78.21 | A |
| ATOM | 863 | C | PRO | A | 113 | −14.791 | −4.909 | 5.275 | 1.00 | 76.94 | A |
| ATOM | 864 | O | PRO | A | 113 | −15.998 | −4.664 | 5.290 | 1.00 | 77.05 | A |
| ATOM | 865 | N | GLU | A | 114 | −13.888 | −4.151 | 5.893 | 1.00 | 75.57 | A |
| ATOM | 866 | CA | GLU | A | 114 | −14.258 | −2.954 | 6.646 | 1.00 | 73.78 | A |
| ATOM | 867 | CB | GLU | A | 114 | −14.203 | −3.244 | 8.151 | 1.00 | 75.45 | A |
| ATOM | 868 | CG | GLU | A | 114 | −15.247 | −4.243 | 8.650 | 1.00 | 78.06 | A |
| ATOM | 869 | CD | GLU | A | 114 | −15.136 | −4.521 | 10.149 | 1.00 | 79.68 | A |
| ATOM | 870 | OE1 | GLU | A | 114 | −15.184 | −3.554 | 10.947 | 1.00 | 80.23 | A |
| ATOM | 871 | OE2 | GLU | A | 114 | −15.006 | −5.709 | 10.529 | 1.00 | 80.56 | A |
| ATOM | 872 | C | GLU | A | 114 | −13.327 | −1.785 | 6.314 | 1.00 | 71.15 | A |
| ATOM | 873 | O | GLU | A | 114 | −13.738 | −0.620 | 6.330 | 1.00 | 70.50 | A |
| ATOM | 874 | N | GLN | A | 115 | −12.071 | −2.110 | 6.017 | 1.00 | 68.29 | A |
| ATOM | 875 | CA | GLN | A | 115 | −11.057 | −1.110 | 5.681 | 1.00 | 64.44 | A |
| ATOM | 876 | CB | GLN | A | 115 | −9.952 | −1.083 | 6.757 | 1.00 | 66.01 | A |
| ATOM | 877 | CG | GLN | A | 115 | −9.552 | −2.450 | 7.325 | 1.00 | 66.72 | A |
| ATOM | 878 | CD | GLN | A | 115 | −10.479 | −2.918 | 8.444 | 1.00 | 67.94 | A |
| ATOM | 879 | OE1 | GLN | A | 115 | −10.572 | −2.282 | 9.497 | 1.00 | 68.73 | A |
| ATOM | 880 | NE2 | GLN | A | 115 | −11.166 | −4.035 | 8.220 | 1.00 | 68.36 | A |
| ATOM | 881 | C | GLN | A | 115 | −10.436 | −1.334 | 4.297 | 1.00 | 59.98 | A |
| ATOM | 882 | O | GLN | A | 115 | −9.217 | −1.230 | 4.120 | 1.00 | 59.29 | A |
| ATOM | 883 | N | SER | A | 116 | −11.289 | −1.638 | 3.322 | 1.00 | 54.28 | A |
| ATOM | 884 | CA | SER | A | 116 | −10.852 | −1.868 | 1.956 | 1.00 | 48.50 | A |
| ATOM | 885 | CB | SER | A | 116 | −10.068 | −3.177 | 1.847 | 1.00 | 49.02 | A |
| ATOM | 886 | OG | SER | A | 116 | −10.929 | −4.299 | 1.952 | 1.00 | 48.61 | A |
| ATOM | 887 | C | SER | A | 116 | −12.041 | −1.914 | 1.009 | 1.00 | 44.48 | A |
| ATOM | 888 | O | SER | A | 116 | −12.159 | −2.826 | 0.200 | 1.00 | 45.41 | A |
| ATOM | 889 | N | LEU | A | 117 | −12.939 | −0.946 | 1.123 | 1.00 | 39.02 | A |
| ATOM | 890 | CA | LEU | A | 117 | −14.085 | −0.894 | 0.233 | 1.00 | 33.21 | A |
| ATOM | 891 | CB | LEU | A | 117 | −15.398 | −0.842 | 1.023 | 1.00 | 32.48 | A |
| ATOM | 892 | CG | LEU | A | 117 | −16.677 | −0.687 | 0.179 | 1.00 | 32.08 | A |
| ATOM | 893 | CD1 | LEU | A | 117 | −16.989 | −1.984 | −0.551 | 1.00 | 32.14 | A |
| ATOM | 894 | CD2 | LEU | A | 117 | −17.843 | −0.320 | 1.073 | 1.00 | 32.82 | A |
| ATOM | 895 | C | LEU | A | 117 | −13.965 | 0.348 | −0.643 | 1.00 | 29.70 | A |
| ATOM | 896 | O | LEU | A | 117 | −14.139 | 1.469 | −0.164 | 1.00 | 29.28 | A |
| ATOM | 897 | N | ALA | A | 118 | −13.640 | 0.152 | −1.917 | 1.00 | 25.59 | A |
| ATOM | 898 | CA | ALA | A | 118 | −13.524 | 1.268 | −2.854 | 1.00 | 21.14 | A |
| ATOM | 899 | CB | ALA | A | 118 | −12.120 | 1.322 | −3.465 | 1.00 | 19.41 | A |
| ATOM | 900 | C | ALA | A | 118 | −14.566 | 1.083 | −3.942 | 1.00 | 17.56 | A |
| ATOM | 901 | O | ALA | A | 118 | −14.859 | −0.038 | −4.351 | 1.00 | 17.34 | A |
| ATOM | 902 | N | CYS | A | 119 | −15.133 | 2.185 | −4.402 | 1.00 | 15.41 | A |
| ATOM | 903 | CA | CYS | A | 119 | −16.147 | 2.127 | −5.447 | 1.00 | 14.62 | A |
| ATOM | 904 | C | CYS | A | 119 | −15.805 | 3.145 | −6.520 | 1.00 | 12.55 | A |
| ATOM | 905 | O | CYS | A | 119 | −15.160 | 4.150 | −6.239 | 1.00 | 12.39 | A |
| ATOM | 906 | CB | CYS | A | 119 | −17.527 | 2.449 | −4.881 | 1.00 | 16.58 | A |
| ATOM | 907 | SG | CYS | A | 119 | −18.118 | 1.399 | −3.507 | 1.00 | 19.89 | A |
| ATOM | 908 | N | GLN | A | 120 | −16.242 | 2.902 | −7.751 | 1.00 | 11.31 | A |
| ATOM | 909 | CA | GLN | A | 120 | −15.931 | 3.837 | −8.826 | 1.00 | 9.34 | A |
| ATOM | 910 | CB | GLN | A | 120 | −14.691 | 3.382 | −9.600 | 1.00 | 8.23 | A |
| ATOM | 911 | CG | GLN | A | 120 | −13.408 | 3.510 | −8.824 | 1.00 | 9.44 | A |
| ATOM | 912 | CD | GLN | A | 120 | −12.192 | 3.228 | −9.666 | 1.00 | 10.28 | A |
| ATOM | 913 | OE1 | GLN | A | 120 | −12.276 | 3.187 | −10.895 | 1.00 | 9.16 | A |
| ATOM | 914 | NE2 | GLN | A | 120 | −11.042 | 3.044 | −9.011 | 1.00 | 11.24 | A |
| ATOM | 915 | C | GLN | A | 120 | −17.055 | 4.029 | −9.808 | 1.00 | 7.85 | A |
| ATOM | 916 | O | GLN | A | 120 | −17.935 | 3.191 | −9.936 | 1.00 | 8.44 | A |
| ATOM | 917 | N | CYS | A | 121 | −17.015 | 5.160 | −10.491 | 1.00 | 6.54 | A |
| ATOM | 918 | CA | CYS | A | 121 | −17.985 | 5.467 | −11.505 | 1.00 | 5.28 | A |
| ATOM | 919 | CB | CYS | A | 121 | −18.684 | 6.774 | −11.200 | 1.00 | 3.98 | A |
| ATOM | 920 | SG | CYS | A | 121 | −19.807 | 7.249 | −12.559 | 1.00 | 6.72 | A |
| ATOM | 921 | C | CYS | A | 121 | −17.230 | 5.594 | −12.829 | 1.00 | 5.88 | A |
| ATOM | 922 | O | CYS | A | 121 | −16.462 | 6.539 | −13.035 | 1.00 | 6.74 | A |
| ATOM | 923 | N | LEU | A | 122 | −17.439 | 4.621 | −13.711 | 1.00 | 4.93 | A |
| ATOM | 924 | CA | LEU | A | 122 | −16.796 | 4.583 | −15.016 | 1.00 | 4.70 | A |

TABLE VIII-continued

Structure coordinates of the epitopes of allergenic beta-lactoglobulin in an antibody-beta-lactoglobulin immunocomplex;

|      |     | Atom type | Resid |   | #   | X       | Y       | Z       | OCC  | B     |   |
|------|-----|-----------|-------|---|-----|---------|---------|---------|------|-------|---|
| ATOM | 925 | CB        | LEU   | A | 122 | −16.472 | 3.133   | −15.390 | 1.00 | 2.79  | A |
| ATOM | 926 | CG        | LEU   | A | 122 | −15.544 | 2.308   | −14.507 | 1.00 | 3.05  | A |
| ATOM | 927 | CD1       | LEU   | A | 122 | −15.272 | 0.946   | −15.164 | 1.00 | 1.00  | A |
| ATOM | 928 | CD2       | LEU   | A | 122 | −14.247 | 3.051   | −14.288 | 1.00 | 2.57  | A |
| ATOM | 929 | C         | LEU   | A | 122 | −17.708 | 5.192   | −16.085 | 1.00 | 4.56  | A |
| ATOM | 930 | O         | LEU   | A | 122 | −18.909 | 5.334   | −15.871 | 1.00 | 3.87  | A |
| ATOM | 931 | N         | VAL   | A | 123 | −17.130 | 5.577   | −17.221 | 1.00 | 5.28  | A |
| ATOM | 932 | CA        | VAL   | A | 123 | −17.908 | 6.131   | −18.327 | 1.00 | 7.18  | A |
| ATOM | 933 | CB        | VAL   | A | 123 | −18.066 | 7.656   | −18.252 | 1.00 | 5.88  | A |
| ATOM | 934 | CG1       | VAL   | A | 123 | −19.103 | 8.011   | −17.226 | 1.00 | 4.32  | A |
| ATOM | 935 | CG2       | VAL   | A | 123 | −16.727 | 8.304   | −17.961 | 1.00 | 5.09  | A |
| ATOM | 936 | C         | VAL   | A | 123 | −17.262 | 5.806   | −19.655 | 1.00 | 8.00  | A |
| ATOM | 937 | O         | VAL   | A | 123 | −16.063 | 5.591   | −19.731 | 1.00 | 9.15  | A |
| ATOM | 938 | N         | ARG   | A | 124 | −18.061 | 5.783   | −20.708 | 1.00 | 9.32  | A |
| ATOM | 939 | CA        | ARG   | A | 124 | −17.546 | 5.467   | −22.024 | 1.00 | 11.59 | A |
| ATOM | 940 | CB        | ARG   | A | 124 | −18.701 | 5.084   | −22.931 | 1.00 | 10.68 | A |
| ATOM | 941 | CG        | ARG   | A | 124 | −19.397 | 3.813   | −22.512 | 1.00 | 9.01  | A |
| ATOM | 942 | CD        | ARG   | A | 124 | −18.512 | 2.641   | −22.744 | 1.00 | 10.13 | A |
| ATOM | 943 | NE        | ARG   | A | 124 | −19.251 | 1.379   | −22.807 | 1.00 | 10.56 | A |
| ATOM | 944 | CZ        | ARG   | A | 124 | −18.684 | 0.222   | −23.122 | 1.00 | 10.23 | A |
| ATOM | 945 | NH1       | ARG   | A | 124 | −17.387 | 0.172   | −23.399 | 1.00 | 11.34 | A |
| ATOM | 946 | NH2       | ARG   | A | 124 | −19.401 | −0.878  | −23.151 | 1.00 | 9.22  | A |
| ATOM | 947 | C         | ARG   | A | 124 | −16.742 | 6.600   | −22.646 | 1.00 | 12.71 | A |
| ATOM | 948 | O         | ARG   | A | 124 | −15.653 | 6.378   | −23.172 | 1.00 | 11.93 | A |
| ATOM | 949 | N         | THR   | A | 125 | −17.265 | 7.817   | −22.598 | 1.00 | 13.65 | A |
| ATOM | 950 | CA        | THR   | A | 125 | −16.533 | 8.934   | −23.177 | 1.00 | 14.62 | A |
| ATOM | 951 | CB        | THR   | A | 125 | −17.445 | 9.802   | −24.041 | 1.00 | 14.21 | A |
| ATOM | 952 | OG1       | THR   | A | 125 | −18.544 | 10.273  | −23.253 | 1.00 | 13.29 | A |
| ATOM | 953 | CG2       | THR   | A | 125 | −17.951 | 8.995   | −25.232 | 1.00 | 12.45 | A |
| ATOM | 954 | C         | THR   | A | 125 | −15.885 | 9.784   | −22.098 | 1.00 | 15.60 | A |
| ATOM | 955 | O         | THR   | A | 125 | −16.376 | 9.859   | −20.977 | 1.00 | 17.35 | A |
| ATOM | 956 | N         | PRO   | A | 126 | −14.757 | 10.427  | −22.422 | 1.00 | 15.78 | A |
| ATOM | 957 | CD        | PRO   | A | 126 | −14.037 | 10.316  | −23.700 | 1.00 | 16.42 | A |
| ATOM | 958 | CA        | PRO   | A | 126 | −14.019 | 11.274  | −21.488 | 1.00 | 16.99 | A |
| ATOM | 959 | CB        | PRO   | A | 126 | −12.689 | 11.472  | −22.203 | 1.00 | 17.41 | A |
| ATOM | 960 | CG        | PRO   | A | 126 | −13.083 | 11.474  | −23.641 | 1.00 | 15.72 | A |
| ATOM | 961 | C         | PRO   | A | 126 | −14.717 | 12.596  | −21.183 | 1.00 | 18.38 | A |
| ATOM | 962 | O         | PRO   | A | 126 | −14.110 | 13.671  | −21.247 | 1.00 | 18.55 | A |
| ATOM | 963 | N         | GLU   | A | 127 | −15.995 | 12.508  | −20.844 | 1.00 | 19.23 | A |
| ATOM | 964 | CA        | GLU   | A | 127 | −16.789 | 13.686  | −20.562 | 1.00 | 19.40 | A |
| ATOM | 965 | CB        | GLU   | A | 127 | −17.916 | 13.797  | −21.595 | 1.00 | 21.19 | A |
| ATOM | 966 | CG        | GLU   | A | 127 | −18.145 | 15.195  | −22.115 | 1.00 | 25.72 | A |
| ATOM | 967 | CD        | GLU   | A | 127 | −17.240 | 15.548  | −23.277 | 1.00 | 28.77 | A |
| ATOM | 968 | OE1       | GLU   | A | 127 | −16.003 | 15.421  | −23.156 | 1.00 | 31.16 | A |
| ATOM | 969 | OE2       | GLU   | A | 127 | −17.774 | 15.970  | −24.319 | 1.00 | 30.40 | A |
| ATOM | 970 | C         | GLU   | A | 127 | −17.362 | 13.511  | −19.176 | 1.00 | 18.77 | A |
| ATOM | 971 | O         | GLU   | A | 127 | −17.372 | 12.399  | −18.644 | 1.00 | 17.85 | A |
| ATOM | 972 | N         | VAL   | A | 128 | −17.816 | 14.609  | −18.581 | 1.00 | 18.87 | A |
| ATOM | 973 | CA        | VAL   | A | 128 | −18.422 | 14.551  | −17.259 | 1.00 | 19.36 | A |
| ATOM | 974 | CB        | VAL   | A | 128 | −18.215 | 15.865  | −16.488 | 1.00 | 19.07 | A |
| ATOM | 975 | CG1       | VAL   | A | 128 | −18.943 | 15.808  | −15.150 | 1.00 | 16.94 | A |
| ATOM | 976 | CG2       | VAL   | A | 128 | −16.731 | 16.100  | −16.285 | 1.00 | 19.94 | A |
| ATOM | 977 | C         | VAL   | A | 128 | −19.925 | 14.274  | −17.392 | 1.00 | 19.92 | A |
| ATOM | 978 | O         | VAL   | A | 128 | −20.694 | 15.098  | −17.885 | 1.00 | 18.96 | A |
| ATOM | 979 | N         | ASP   | A | 129 | −20.335 | 13.095  | −16.952 | 1.00 | 21.31 | A |
| ATOM | 980 | CA        | ASP   | A | 129 | −21.735 | 12.708  | −17.018 | 1.00 | 22.53 | A |
| ATOM | 981 | CB        | ASP   | A | 129 | −21.839 | 11.213  | −17.310 | 1.00 | 22.60 | A |
| ATOM | 982 | CG        | ASP   | A | 129 | −23.247 | 10.784  | −17.628 | 1.00 | 24.84 | A |
| ATOM | 983 | OD1       | ASP   | A | 129 | −24.172 | 11.273  | −16.931 | 1.00 | 25.94 | A |
| ATOM | 984 | OD2       | ASP   | A | 129 | −23.428 | 9.955   | −18.563 | 1.00 | 24.73 | A |
| ATOM | 985 | C         | ASP   | A | 129 | −22.402 | 13.026  | −15.681 | 1.00 | 23.04 | A |
| ATOM | 986 | O         | ASP   | A | 129 | −22.375 | 12.214  | −14.767 | 1.00 | 22.72 | A |
| ATOM | 987 | N         | ASP   | A | 130 | −23.007 | 14.203  | −15.568 | 1.00 | 25.17 | A |
| ATOM | 988 | CA        | ASP   | A | 130 | −23.652 | 14.599  | −14.324 | 1.00 | 27.39 | A |
| ATOM | 989 | CB        | ASP   | A | 130 | −24.307 | 15.967  | −14.483 | 1.00 | 28.36 | A |
| ATOM | 990 | CG        | ASP   | A | 130 | −23.295 | 17.080  | −14.682 | 1.00 | 30.38 | A |
| ATOM | 991 | OD1       | ASP   | A | 130 | −22.407 | 17.253  | −13.811 | 1.00 | 30.27 | A |
| ATOM | 992 | OD2       | ASP   | A | 130 | −23.402 | 17.791  | −15.707 | 1.00 | 31.41 | A |
| ATOM | 993 | C         | ASP   | A | 130 | −24.689 | 13.589  | −13.829 | 1.00 | 28.10 | A |
| ATOM | 994 | O         | ASP   | A | 130 | −24.758 | 13.288  | −12.629 | 1.00 | 27.21 | A |
| ATOM | 995 | N         | GLU   | A | 131 | −25.497 | 13.073  | −14.749 | 1.00 | 28.87 | A |
| ATOM | 996 | CA        | GLU   | A | 131 | −26.528 | 12.098  | −14.396 | 1.00 | 30.34 | A |
| ATOM | 997 | CB        | GLU   | A | 131 | −27.415 | 11.780  | −15.608 | 1.00 | 32.40 | A |
| ATOM | 998 | CG        | GLU   | A | 131 | −28.620 | 10.891  | −15.283 | 1.00 | 36.77 | A |

TABLE VIII-continued

Structure coordinates of the epitopes of allergenic beta-lactoglobulin in an antibody-beta-lactoglobulin immunocomplex;

|      | Atom type | Resid |   | #   | X       | Y      | Z       | OCC  | B     |   |
|------|-----------|-------|---|-----|---------|--------|---------|------|-------|---|
| ATOM | 999 CD    | GLU   | A | 131 | −29.516 | 10.597 | −16.495 | 1.00 | 39.79 | A |
| ATOM | 1000 OE1  | GLU   | A | 131 | −29.391 | 9.498  | −17.097 | 1.00 | 39.74 | A |
| ATOM | 1001 OE2  | GLU   | A | 131 | −30.347 | 11.473 | −16.842 | 1.00 | 41.54 | A |
| ATOM | 1002 C    | GLU   | A | 131 | −25.902 | 10.804 | −13.871 | 1.00 | 29.77 | A |
| ATOM | 1003 O    | GLU   | A | 131 | −26.481 | 10.124 | −13.013 | 1.00 | 30.31 | A |
| ATOM | 1004 N    | ALA   | A | 132 | −24.724 | 10.462 | −14.390 | 1.00 | 27.73 | A |
| ATOM | 1005 CA   | ALA   | A | 132 | −24.022 | 9.261  | −13.961 | 1.00 | 24.94 | A |
| ATOM | 1006 CB   | ALA   | A | 132 | −22.890 | 8.951  | −14.917 | 1.00 | 25.43 | A |
| ATOM | 1007 C    | ALA   | A | 132 | −23.485 | 9.459  | −12.547 | 1.00 | 24.00 | A |
| ATOM | 1008 O    | ALA   | A | 132 | −23.628 | 8.584  | −11.690 | 1.00 | 22.89 | A |
| ATOM | 1009 N    | LEU   | A | 133 | −22.875 | 10.613 | −12.301 | 1.00 | 22.77 | A |
| ATOM | 1010 CA   | LEU   | A | 133 | −22.346 | 10.916 | −10.978 | 1.00 | 23.19 | A |
| ATOM | 1011 CB   | LEU   | A | 133 | −21.685 | 12.293 | −10.977 | 1.00 | 21.08 | A |
| ATOM | 1012 CG   | LEU   | A | 133 | −20.298 | 12.301 | −11.606 | 1.00 | 20.59 | A |
| ATOM | 1013 CD1  | LEU   | A | 133 | −19.737 | 13.703 | −11.645 | 1.00 | 20.36 | A |
| ATOM | 1014 CD2  | LEU   | A | 133 | −19.398 | 11.374 | −10.808 | 1.00 | 20.36 | A |
| ATOM | 1015 C    | LEU   | A | 133 | −23.490 | 10.889 | −9.976  | 1.00 | 23.95 | A |
| ATOM | 1016 O    | LEU   | A | 133 | −23.321 | 10.464 | −8.835  | 1.00 | 24.50 | A |
| ATOM | 1017 N    | GLU   | A | 134 | −24.653 | 11.349 | −10.428 | 1.00 | 24.99 | A |
| ATOM | 1018 CA   | GLU   | A | 134 | −25.855 | 11.383 | −9.619  | 1.00 | 25.76 | A |
| ATOM | 1019 CB   | GLU   | A | 134 | −27.027 | 11.882 | −10.457 | 1.00 | 28.60 | A |
| ATOM | 1020 CG   | GLU   | A | 134 | −27.242 | 13.373 | −10.379 | 1.00 | 34.21 | A |
| ATOM | 1021 CD   | GLU   | A | 134 | −27.894 | 13.791 | −9.068  | 1.00 | 38.01 | A |
| ATOM | 1022 OE1  | GLU   | A | 134 | −29.127 | 13.596 | −8.931  | 1.00 | 40.41 | A |
| ATOM | 1023 OE2  | GLU   | A | 134 | −27.175 | 14.300 | −8.173  | 1.00 | 39.41 | A |
| ATOM | 1024 C    | GLU   | A | 134 | −26.169 | 10.002 | −9.081  | 1.00 | 25.10 | A |
| ATOM | 1025 O    | GLU   | A | 134 | −26.307 | 9.797  | −7.877  | 1.00 | 25.75 | A |
| ATOM | 1026 N    | LYS   | A | 135 | −26.286 | 9.042  | −9.980  | 1.00 | 23.93 | A |
| ATOM | 1027 CA   | LYS   | A | 135 | −26.581 | 7.696  | −9.550  | 1.00 | 22.05 | A |
| ATOM | 1028 CB   | LYS   | A | 135 | −26.738 | 6.789  | −10.767 | 1.00 | 21.87 | A |
| ATOM | 1029 CG   | LYS   | A | 135 | −27.675 | 7.367  | −11.806 | 1.00 | 22.27 | A |
| ATOM | 1030 CD   | LYS   | A | 135 | −28.199 | 6.301  | −12.732 | 1.00 | 23.04 | A |
| ATOM | 1031 CE   | LYS   | A | 135 | −29.081 | 6.926  | −13.792 | 1.00 | 24.13 | A |
| ATOM | 1032 NZ   | LYS   | A | 135 | −29.705 | 5.909  | −14.672 | 1.00 | 25.19 | A |
| ATOM | 1033 C    | LYS   | A | 135 | −25.470 | 7.187  | −8.645  | 1.00 | 20.93 | A |
| ATOM | 1034 O    | LYS   | A | 135 | −25.715 | 6.338  | −7.810  | 1.00 | 22.80 | A |
| ATOM | 1035 N    | PHE   | A | 136 | −24.256 | 7.712  | −8.800  | 1.00 | 19.44 | A |
| ATOM | 1036 CA   | PHE   | A | 136 | −23.123 | 7.276  | −7.986  | 1.00 | 17.59 | A |
| ATOM | 1037 CB   | PHE   | A | 136 | −21.804 | 7.753  | −8.623  | 1.00 | 16.15 | A |
| ATOM | 1038 CG   | PHE   | A | 136 | −20.553 | 7.155  | −8.008  | 1.00 | 12.06 | A |
| ATOM | 1039 CD1  | PHE   | A | 136 | −20.380 | 5.777  | −7.924  | 1.00 | 10.59 | A |
| ATOM | 1040 CD2  | PHE   | A | 136 | −19.523 | 7.986  | −7.562  | 1.00 | 10.64 | A |
| ATOM | 1041 CE1  | PHE   | A | 136 | −19.194 | 5.235  | −7.408  | 1.00 | 8.70  | A |
| ATOM | 1042 CE2  | PHE   | A | 136 | −18.333 | 7.461  | −7.045  | 1.00 | 8.38  | A |
| ATOM | 1043 CZ   | PHE   | A | 136 | −18.170 | 6.080  | −6.970  | 1.00 | 8.38  | A |
| ATOM | 1044 C    | PHE   | A | 136 | −23.263 | 7.820  | −6.575  | 1.00 | 17.94 | A |
| ATOM | 1045 O    | PHE   | A | 136 | −23.060 | 7.094  | −5.610  | 1.00 | 18.11 | A |
| ATOM | 1046 N    | ASP   | A | 137 | −23.608 | 9.097  | −6.454  | 1.00 | 18.56 | A |
| ATOM | 1047 CA   | ASP   | A | 137 | −23.777 | 9.705  | −5.140  | 1.00 | 20.78 | A |
| ATOM | 1048 CB   | ASP   | A | 137 | −24.020 | 11.199 | −5.283  | 1.00 | 21.98 | A |
| ATOM | 1049 CG   | ASP   | A | 137 | −22.761 | 11.933 | −5.650  | 1.00 | 26.64 | A |
| ATOM | 1050 OD1  | ASP   | A | 137 | −22.791 | 13.172 | −5.803  | 1.00 | 28.97 | A |
| ATOM | 1051 OD2  | ASP   | A | 137 | −21.715 | 11.255 | −5.780  | 1.00 | 29.46 | A |
| ATOM | 1052 C    | ASP   | A | 137 | −24.916 | 9.055  | −4.381  | 1.00 | 21.56 | A |
| ATOM | 1053 O    | ASP   | A | 137 | −24.829 | 8.823  | −3.180  | 1.00 | 20.68 | A |
| ATOM | 1054 N    | LYS   | A | 138 | −25.978 | 8.757  | −5.114  | 1.00 | 23.89 | A |
| ATOM | 1055 CA   | LYS   | A | 138 | −27.163 | 8.119  | −4.575  | 1.00 | 24.77 | A |
| ATOM | 1056 CB   | LYS   | A | 138 | −28.201 | 7.983  | −5.685  | 1.00 | 26.49 | A |
| ATOM | 1057 CG   | LYS   | A | 138 | −29.590 | 8.464  | −5.311  | 1.00 | 29.38 | A |
| ATOM | 1058 CD   | LYS   | A | 138 | −30.440 | 8.746  | −6.551  | 1.00 | 31.73 | A |
| ATOM | 1059 CE   | LYS   | A | 138 | −30.787 | 7.464  | −7.309  | 1.00 | 33.18 | A |
| ATOM | 1060 NZ   | LYS   | A | 138 | −31.684 | 6.561  | −6.512  | 1.00 | 32.38 | A |
| ATOM | 1061 C    | LYS   | A | 138 | −26.834 | 6.738  | −4.020  | 1.00 | 24.53 | A |
| ATOM | 1062 O    | LYS   | A | 138 | −27.283 | 6.368  | −2.933  | 1.00 | 25.44 | A |
| ATOM | 1063 N    | ALA   | A | 139 | −26.047 | 5.981  | −4.771  | 1.00 | 23.16 | A |
| ATOM | 1064 CA   | ALA   | A | 139 | −25.684 | 4.640  | −4.365  | 1.00 | 22.42 | A |
| ATOM | 1065 CB   | ALA   | A | 139 | −25.192 | 3.859  | −5.557  | 1.00 | 22.54 | A |
| ATOM | 1066 C    | ALA   | A | 139 | −24.631 | 4.653  | −3.296  | 1.00 | 22.29 | A |
| ATOM | 1067 O    | ALA   | A | 139 | −24.315 | 3.619  | −2.725  | 1.00 | 23.95 | A |
| ATOM | 1068 N    | LEU   | A | 140 | −24.091 | 5.823  | −3.007  | 1.00 | 22.46 | A |
| ATOM | 1069 CA   | LEU   | A | 140 | −23.050 | 5.906  | −2.002  | 1.00 | 22.59 | A |
| ATOM | 1070 CB   | LEU   | A | 140 | −21.923 | 6.819  | −2.494  | 1.00 | 21.49 | A |
| ATOM | 1071 CG   | LEU   | A | 140 | −20.640 | 6.154  | −2.992  | 1.00 | 20.22 | A |
| ATOM | 1072 CD1  | LEU   | A | 140 | −20.962 | 5.055  | −3.974  | 1.00 | 20.98 | A |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1073 CD2 | LEU | A | 140 | −19.746 | 7.196 | −3.618 | 1.00 | 19.16 | A |
| ATOM | 1074 C | LEU | A | 140 | −23.552 | 6.400 | −0.661 | 1.00 | 23.85 | A |
| ATOM | 1075 O | LEU | A | 140 | −22.930 | 6.131 | 0.362 | 1.00 | 24.84 | A |
| ATOM | 1076 N | LYS | A | 141 | −24.684 | 7.098 | −0.660 | 1.00 | 23.81 | A |
| ATOM | 1077 CA | LYS | A | 141 | −25.221 | 7.650 | 0.572 | 1.00 | 23.95 | A |
| ATOM | 1078 CB | LYS | A | 141 | −26.479 | 8.488 | 0.275 | 1.00 | 27.33 | A |
| ATOM | 1079 CG | LYS | A | 141 | −27.732 | 7.679 | −0.062 | 1.00 | 31.67 | A |
| ATOM | 1080 CD | LYS | A | 141 | −28.961 | 8.581 | −0.222 | 1.00 | 34.16 | A |
| ATOM | 1081 CE | LYS | A | 141 | −30.252 | 7.750 | −0.167 | 1.00 | 35.86 | A |
| ATOM | 1082 NZ | LYS | A | 141 | −31.508 | 8.520 | −0.454 | 1.00 | 34.90 | A |
| ATOM | 1083 C | LYS | A | 141 | −25.521 | 6.577 | 1.620 | 1.00 | 22.86 | A |
| ATOM | 1084 O | LYS | A | 141 | −25.814 | 6.886 | 2.776 | 1.00 | 23.16 | A |
| ATOM | 1085 N | ALA | A | 142 | −25.425 | 5.320 | 1.202 | 1.00 | 21.93 | A |
| ATOM | 1086 CA | ALA | A | 142 | −25.673 | 4.164 | 2.058 | 1.00 | 20.55 | A |
| ATOM | 1087 CB | ALA | A | 142 | −26.646 | 3.227 | 1.371 | 1.00 | 20.26 | A |
| ATOM | 1088 C | ALA | A | 142 | −24.373 | 3.399 | 2.385 | 1.00 | 20.23 | A |
| ATOM | 1089 O | ALA | A | 142 | −24.393 | 2.329 | 2.994 | 1.00 | 20.08 | A |
| ATOM | 1090 N | LEU | A | 143 | −23.241 | 3.928 | 1.957 | 1.00 | 19.08 | A |
| ATOM | 1091 CA | LEU | A | 143 | −21.983 | 3.284 | 2.249 | 1.00 | 16.71 | A |
| ATOM | 1092 CB | LEU | A | 143 | −21.222 | 2.995 | 0.957 | 1.00 | 16.66 | A |
| ATOM | 1093 CG | LEU | A | 143 | −21.938 | 2.027 | 0.009 | 1.00 | 14.82 | A |
| ATOM | 1094 CD1 | LEU | A | 143 | −21.160 | 1.904 | −1.280 | 1.00 | 11.61 | A |
| ATOM | 1095 CD2 | LEU | A | 143 | −22.080 | 0.661 | 0.683 | 1.00 | 14.87 | A |
| ATOM | 1096 C | LEU | A | 143 | −21.186 | 4.210 | 3.152 | 1.00 | 16.35 | A |
| ATOM | 1097 O | LEU | A | 143 | −21.389 | 5.427 | 3.138 | 1.00 | 16.52 | A |
| ATOM | 1098 N | PRO | A | 144 | −20.266 | 3.639 | 3.954 | 1.00 | 16.35 | A |
| ATOM | 1099 CD | PRO | A | 144 | −20.060 | 2.183 | 4.085 | 1.00 | 15.80 | A |
| ATOM | 1100 CA | PRO | A | 144 | −19.410 | 4.356 | 4.896 | 1.00 | 14.08 | A |
| ATOM | 1101 CB | PRO | A | 144 | −19.073 | 3.278 | 5.904 | 1.00 | 15.09 | A |
| ATOM | 1102 CG | PRO | A | 144 | −18.889 | 2.090 | 5.023 | 1.00 | 14.40 | A |
| ATOM | 1103 C | PRO | A | 144 | −18.185 | 4.926 | 4.221 | 1.00 | 12.91 | A |
| ATOM | 1104 O | PRO | A | 144 | −17.054 | 4.622 | 4.612 | 1.00 | 11.28 | A |
| ATOM | 1105 N | MET | A | 145 | −18.419 | 5.753 | 3.204 | 1.00 | 11.90 | A |
| ATOM | 1106 CA | MET | A | 145 | −17.332 | 6.378 | 2.456 | 1.00 | 10.38 | A |
| ATOM | 1107 CB | MET | A | 145 | −17.820 | 6.851 | 1.083 | 1.00 | 10.21 | A |
| ATOM | 1108 CG | MET | A | 145 | −18.395 | 5.753 | 0.207 | 1.00 | 12.43 | A |
| ATOM | 1109 SD | MET | A | 145 | −17.224 | 4.412 | −0.200 | 1.00 | 13.28 | A |
| ATOM | 1110 CE | MET | A | 145 | −17.618 | 3.241 | 1.092 | 1.00 | 14.67 | A |
| ATOM | 1111 C | MET | A | 145 | −16.819 | 7.566 | 3.229 | 1.00 | 9.66 | A |
| ATOM | 1112 O | MET | A | 145 | −17.605 | 8.384 | 3.689 | 1.00 | 11.74 | A |
| ATOM | 1113 N | HIS | A | 146 | −15.506 | 7.663 | 3.388 | 1.00 | 9.91 | A |
| ATOM | 1114 CA | HIS | A | 146 | −14.936 | 8.807 | 4.098 | 1.00 | 9.87 | A |
| ATOM | 1115 CB | HIS | A | 146 | −14.282 | 8.358 | 5.403 | 1.00 | 8.49 | A |
| ATOM | 1116 CG | HIS | A | 146 | −15.269 | 7.866 | 6.418 | 1.00 | 9.17 | A |
| ATOM | 1117 CD2 | HIS | A | 146 | −15.920 | 8.512 | 7.415 | 1.00 | 8.75 | A |
| ATOM | 1118 ND1 | HIS | A | 146 | −15.717 | 6.565 | 6.448 | 1.00 | 8.57 | A |
| ATOM | 1119 CE1 | HIS | A | 146 | −16.599 | 6.427 | 7.422 | 1.00 | 7.28 | A |
| ATOM | 1120 NE2 | HIS | A | 146 | −16.738 | 7.592 | 8.024 | 1.00 | 8.13 | A |
| ATOM | 1121 C | HIS | A | 146 | −13.946 | 9.581 | 3.233 | 1.00 | 8.88 | A |
| ATOM | 1122 O | HIS | A | 146 | −13.035 | 10.211 | 3.741 | 1.00 | 9.73 | A |
| ATOM | 1123 N | ILE | A | 147 | −14.158 | 9.542 | 1.923 | 1.00 | 10.01 | A |
| ATOM | 1124 CA | ILE | A | 147 | −13.315 | 10.234 | 0.954 | 1.00 | 9.28 | A |
| ATOM | 1125 CB | ILE | A | 147 | −11.833 | 9.773 | 1.028 | 1.00 | 9.29 | A |
| ATOM | 1126 CG2 | ILE | A | 147 | −11.765 | 8.271 | 1.046 | 1.00 | 10.92 | A |
| ATOM | 1127 CG1 | ILE | A | 147 | −11.054 | 10.332 | −0.163 | 1.00 | 8.05 | A |
| ATOM | 1128 CD1 | ILE | A | 147 | −9.542 | 10.152 | −0.042 | 1.00 | 8.07 | A |
| ATOM | 1129 C | ILE | A | 147 | −13.862 | 9.957 | −0.439 | 1.00 | 9.12 | A |
| ATOM | 1130 O | ILE | A | 147 | −14.181 | 8.812 | −0.772 | 1.00 | 8.68 | A |
| ATOM | 1131 N | ARG | A | 148 | −13.993 | 11.011 | −1.239 | 1.00 | 8.42 | A |
| ATOM | 1132 CA | ARG | A | 148 | −14.501 | 10.878 | −2.607 | 1.00 | 10.40 | A |
| ATOM | 1133 CB | ARG | A | 148 | −15.975 | 11.295 | −2.724 | 1.00 | 13.43 | A |
| ATOM | 1134 CG | ARG | A | 148 | −16.996 | 10.452 | −1.996 | 1.00 | 19.51 | A |
| ATOM | 1135 CD | ARG | A | 148 | −17.301 | 10.971 | −0.586 | 1.00 | 23.86 | A |
| ATOM | 1136 NE | ARG | A | 148 | −18.387 | 10.192 | −0.002 | 1.00 | 27.00 | A |
| ATOM | 1137 CZ | ARG | A | 148 | −19.646 | 10.211 | −0.439 | 1.00 | 29.04 | A |
| ATOM | 1138 NH1 | ARG | A | 148 | −19.986 | 10.987 | −1.461 | 1.00 | 29.76 | A |
| ATOM | 1139 NH2 | ARG | A | 148 | −20.561 | 9.416 | 0.115 | 1.00 | 30.58 | A |
| ATOM | 1140 C | ARG | A | 148 | −13.729 | 11.790 | −3.537 | 1.00 | 9.25 | A |
| ATOM | 1141 O | ARG | A | 148 | −13.368 | 12.896 | −3.151 | 1.00 | 8.09 | A |
| ATOM | 1142 N | LEU | A | 149 | −13.497 | 11.346 | −4.767 | 1.00 | 8.09 | A |
| ATOM | 1143 CA | LEU | A | 149 | −12.792 | 12.171 | −5.741 | 1.00 | 8.72 | A |
| ATOM | 1144 CB | LEU | A | 149 | −11.347 | 11.686 | −5.954 | 1.00 | 9.94 | A |
| ATOM | 1145 CG | LEU | A | 149 | −10.315 | 11.644 | −4.821 | 1.00 | 11.17 | A |
| ATOM | 1146 CD1 | LEU | A | 149 | −10.696 | 10.566 | −3.809 | 1.00 | 13.78 | A |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1147 CD2 | LEU | A | 149 | −8.959 | 11.343 | −5.398 | 1.00 | 11.11 | A |
| ATOM | 1148 C | LEU | A | 149 | −13.520 | 12.142 | −7.088 | 1.00 | 9.46 | A |
| ATOM | 1149 O | LEU | A | 149 | −14.094 | 11.120 | −7.486 | 1.00 | 8.08 | A |
| ATOM | 1150 N | SER | A | 150 | −13.491 | 13.272 | −7.785 | 1.00 | 10.68 | A |
| ATOM | 1151 CA | SER | A | 150 | −14.108 | 13.391 | −9.111 | 1.00 | 12.68 | A |
| ATOM | 1152 CB | SER | A | 150 | −15.379 | 14.239 | −9.041 | 1.00 | 13.11 | A |
| ATOM | 1153 OG | SER | A | 150 | −15.921 | 14.443 | −10.333 | 1.00 | 15.87 | A |
| ATOM | 1154 C | SER | A | 150 | −13.117 | 14.052 | −10.076 | 1.00 | 12.26 | A |
| ATOM | 1155 O | SER | A | 150 | −12.519 | 15.077 | −9.746 | 1.00 | 11.98 | A |
| ATOM | 1156 N | PHE | A | 151 | −12.979 | 13.506 | −11.278 | 1.00 | 12.33 | A |
| ATOM | 1157 CA | PHE | A | 151 | −12.035 | 14.073 | −12.231 | 1.00 | 14.30 | A |
| ATOM | 1158 CB | PHE | A | 151 | −11.174 | 12.934 | −12.804 | 1.00 | 13.88 | A |
| ATOM | 1159 CG | PHE | A | 151 | −10.390 | 12.186 | −11.754 | 1.00 | 14.26 | A |
| ATOM | 1160 CD1 | PHE | A | 151 | −9.346 | 12.800 | −11.068 | 1.00 | 13.10 | A |
| ATOM | 1161 CD2 | PHE | A | 151 | −10.731 | 10.882 | −11.413 | 1.00 | 14.46 | A |
| ATOM | 1162 CE1 | PHE | A | 151 | −8.661 | 12.123 | −10.055 | 1.00 | 12.62 | A |
| ATOM | 1163 CE2 | PHE | A | 151 | −10.049 | 10.203 | −10.402 | 1.00 | 14.91 | A |
| ATOM | 1164 CZ | PHE | A | 151 | −9.017 | 10.824 | −9.723 | 1.00 | 13.40 | A |
| ATOM | 1165 C | PHE | A | 151 | −12.621 | 14.952 | −13.361 | 1.00 | 14.36 | A |
| ATOM | 1166 O | PHE | A | 151 | −13.833 | 14.987 | −13.570 | 1.00 | 13.80 | A |
| ATOM | 1167 N | ASN | A | 152 | −11.736 | 15.671 | −14.053 | 1.00 | 15.86 | A |
| ATOM | 1168 CA | ASN | A | 152 | −12.095 | 16.544 | −15.164 | 1.00 | 16.02 | A |
| ATOM | 1169 CB | ASN | A | 152 | −11.376 | 17.890 | −15.097 | 1.00 | 18.74 | A |
| ATOM | 1170 CG | ASN | A | 152 | −11.397 | 18.498 | −13.740 | 1.00 | 23.20 | A |
| ATOM | 1171 OD1 | ASN | A | 152 | −10.753 | 19.522 | −13.506 | 1.00 | 22.52 | A |
| ATOM | 1172 ND2 | ASN | A | 152 | −12.145 | 17.877 | −12.815 | 1.00 | 27.59 | A |
| ATOM | 1173 C | ASN | A | 152 | −11.596 | 15.925 | −16.447 | 1.00 | 15.17 | A |
| ATOM | 1174 O | ASN | A | 152 | −10.651 | 15.141 | −16.445 | 1.00 | 14.04 | A |
| ATOM | 1175 N | PRO | A | 153 | −12.199 | 16.315 | −17.574 | 1.00 | 15.08 | A |
| ATOM | 1176 CD | PRO | A | 153 | −13.352 | 17.224 | −17.726 | 1.00 | 15.27 | A |
| ATOM | 1177 CA | PRO | A | 153 | −11.778 | 15.791 | −18.864 | 1.00 | 13.73 | A |
| ATOM | 1178 CB | PRO | A | 153 | −12.503 | 16.701 | −19.839 | 1.00 | 12.37 | A |
| ATOM | 1179 CG | PRO | A | 153 | −13.791 | 16.948 | −19.133 | 1.00 | 13.31 | A |
| ATOM | 1180 C | PRO | A | 153 | −10.259 | 15.885 | −18.988 | 1.00 | 13.52 | A |
| ATOM | 1181 O | PRO | A | 153 | −9.603 | 14.920 | −19.377 | 1.00 | 14.15 | A |
| ATOM | 1182 N | THR | A | 154 | −9.684 | 17.029 | −18.629 | 1.00 | 12.52 | A |
| ATOM | 1183 CA | THR | A | 154 | −8.231 | 17.177 | −18.747 | 1.00 | 11.18 | A |
| ATOM | 1184 CB | THR | A | 154 | −7.763 | 18.587 | −18.357 | 1.00 | 9.17 | A |
| ATOM | 1185 OG1 | THR | A | 154 | −8.404 | 19.554 | −19.196 | 1.00 | 12.66 | A |
| ATOM | 1186 CG2 | THR | A | 154 | −6.264 | 18.704 | −18.522 | 1.00 | 6.13 | A |
| ATOM | 1187 C | THR | A | 154 | −7.477 | 16.194 | −17.883 | 1.00 | 9.97 | A |
| ATOM | 1188 O | THR | A | 154 | −6.415 | 15.722 | −18.263 | 1.00 | 9.78 | A |
| ATOM | 1189 N | GLN | A | 155 | −8.015 | 15.900 | −16.709 | 1.00 | 10.79 | A |
| ATOM | 1190 CA | GLN | A | 155 | −7.342 | 14.980 | −15.811 | 1.00 | 11.97 | A |
| ATOM | 1191 CB | GLN | A | 155 | −7.960 | 15.067 | −14.435 | 1.00 | 10.76 | A |
| ATOM | 1192 CG | GLN | A | 155 | −7.894 | 16.455 | −13.894 | 1.00 | 11.68 | A |
| ATOM | 1193 CD | GLN | A | 155 | −8.361 | 16.542 | −12.473 | 1.00 | 11.87 | A |
| ATOM | 1194 OE1 | GLN | A | 155 | −9.539 | 16.324 | −12.169 | 1.00 | 9.48 | A |
| ATOM | 1195 NE2 | GLN | A | 155 | −7.434 | 16.859 | −11.579 | 1.00 | 12.87 | A |
| ATOM | 1196 C | GLN | A | 155 | −7.391 | 13.550 | −16.312 | 1.00 | 13.34 | A |
| ATOM | 1197 O | GLN | A | 155 | −6.529 | 12.742 | −15.978 | 1.00 | 15.38 | A |
| ATOM | 1198 N | LEU | A | 156 | −8.403 | 13.235 | −17.112 | 1.00 | 13.70 | A |
| ATOM | 1199 CA | LEU | A | 156 | −8.532 | 11.904 | −17.662 | 1.00 | 13.24 | A |
| ATOM | 1200 CB | LEU | A | 156 | −9.929 | 11.720 | −18.238 | 1.00 | 10.39 | A |
| ATOM | 1201 CG | LEU | A | 156 | −11.052 | 11.820 | −17.229 | 1.00 | 11.34 | A |
| ATOM | 1202 CD1 | LEU | A | 156 | −12.388 | 11.688 | −17.961 | 1.00 | 11.83 | A |
| ATOM | 1203 CD2 | LEU | A | 156 | −10.913 | 10.747 | −16.157 | 1.00 | 9.95 | A |
| ATOM | 1204 C | LEU | A | 156 | −7.490 | 11.667 | −18.752 | 1.00 | 15.89 | A |
| ATOM | 1205 O | LEU | A | 156 | −7.306 | 10.543 | −19.194 | 1.00 | 16.59 | A |
| ATOM | 1206 N | GLU | A | 157 | −6.824 | 12.733 | −19.184 | 1.00 | 19.18 | A |
| ATOM | 1207 CA | GLU | A | 157 | −5.822 | 12.626 | −20.225 | 1.00 | 23.89 | A |
| ATOM | 1208 CB | GLU | A | 157 | −5.570 | 13.984 | −20.878 | 1.00 | 21.16 | A |
| ATOM | 1209 CG | GLU | A | 157 | −6.829 | 14.699 | −21.299 | 1.00 | 21.05 | A |
| ATOM | 1210 CD | GLU | A | 157 | −6.534 | 15.965 | −22.071 | 1.00 | 20.58 | A |
| ATOM | 1211 OE1 | GLU | A | 157 | −5.525 | 16.629 | −21.756 | 1.00 | 20.06 | A |
| ATOM | 1212 OE2 | GLU | A | 157 | −7.311 | 16.302 | −22.983 | 1.00 | 21.31 | A |
| ATOM | 1213 C | GLU | A | 157 | −4.522 | 12.088 | −19.646 | 1.00 | 28.18 | A |
| ATOM | 1214 O | GLU | A | 157 | −3.538 | 11.905 | −20.362 | 1.00 | 29.82 | A |
| ATOM | 1215 N | GLU | A | 158 | −4.517 | 11.835 | −18.345 | 1.00 | 32.98 | A |
| ATOM | 1216 CA | GLU | A | 158 | −3.330 | 11.319 | −17.681 | 1.00 | 38.78 | A |
| ATOM | 1217 CB | GLU | A | 158 | −2.996 | 12.164 | −16.458 | 1.00 | 39.64 | A |
| ATOM | 1218 CG | GLU | A | 158 | −2.128 | 13.371 | −16.796 | 1.00 | 44.59 | A |
| ATOM | 1219 CD | GLU | A | 158 | −0.665 | 13.000 | −17.086 | 1.00 | 46.03 | A |
| ATOM | 1220 OE1 | GLU | A | 158 | −0.419 | 11.941 | −17.718 | 1.00 | 47.74 | A |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1221 OE2 | GLU | A | 158 | 0.236 | 13.780 | −16.692 | 1.00 | 45.88 | A |
| ATOM | 1222 C | GLU | A | 158 | −3.413 | 9.858 | −17.275 | 1.00 | 42.20 | A |
| ATOM | 1223 O | GLU | A | 158 | −4.325 | 9.435 | −16.551 | 1.00 | 42.84 | A |
| ATOM | 1224 N | GLN | A | 159 | −2.436 | 9.090 | −17.750 | 1.00 | 45.59 | A |
| ATOM | 1225 CA | GLN | A | 159 | −2.349 | 7.664 | −17.463 | 1.00 | 47.67 | A |
| ATOM | 1226 CB | GLN | A | 159 | −0.942 | 7.158 | −17.786 | 1.00 | 48.76 | A |
| ATOM | 1227 CG | GLN | A | 159 | 0.128 | 8.223 | −17.656 | 1.00 | 50.01 | A |
| ATOM | 1228 CD | GLN | A | 159 | 1.465 | 7.645 | −17.258 | 1.00 | 51.72 | A |
| ATOM | 1229 OE1 | GLN | A | 159 | 1.926 | 6.648 | −17.829 | 1.00 | 51.63 | A |
| ATOM | 1230 NE2 | GLN | A | 159 | 2.107 | 8.275 | −16.275 | 1.00 | 52.16 | A |
| ATOM | 1231 C | GLN | A | 159 | −2.664 | 7.412 | −16.001 | 1.00 | 48.11 | A |
| ATOM | 1232 O | GLN | A | 159 | −3.296 | 6.416 | −15.659 | 1.00 | 48.73 | A |
| ATOM | 1233 N | CYS | A | 160 | −2.224 | 8.329 | −15.144 | 1.00 | 48.60 | A |
| ATOM | 1234 CA | CYS | A | 160 | −2.454 | 8.209 | −13.709 | 1.00 | 49.21 | A |
| ATOM | 1235 C | CYS | A | 160 | −3.262 | 9.371 | −13.146 | 1.00 | 50.25 | A |
| ATOM | 1236 O | CYS | A | 160 | −3.207 | 9.640 | −11.947 | 1.00 | 50.25 | A |
| ATOM | 1237 CB | CYS | A | 160 | −1.111 | 8.090 | −12.970 | 1.00 | 48.31 | A |
| ATOM | 1238 SG | CYS | A | 160 | −0.706 | 6.398 | −12.410 | 1.00 | 47.53 | A |
| ATOM | 1239 N | HIS | A | 161 | −4.010 | 10.052 | −14.017 | 1.00 | 52.12 | A |
| ATOM | 1240 CA | HIS | A | 161 | −4.855 | 11.199 | −13.631 | 1.00 | 53.87 | A |
| ATOM | 1241 CB | HIS | A | 161 | −6.062 | 10.722 | −12.801 | 1.00 | 51.81 | A |
| ATOM | 1242 CG | HIS | A | 161 | −7.069 | 9.939 | −13.586 | 1.00 | 50.36 | A |
| ATOM | 1243 CD2 | HIS | A | 161 | −8.422 | 9.928 | −13.542 | 1.00 | 49.28 | A |
| ATOM | 1244 ND1 | HIS | A | 161 | −6.712 | 8.997 | −14.530 | 1.00 | 50.71 | A |
| ATOM | 1245 CE1 | HIS | A | 161 | −7.802 | 8.440 | −15.030 | 1.00 | 49.63 | A |
| ATOM | 1246 NE2 | HIS | A | 161 | −8.853 | 8.987 | −14.446 | 1.00 | 49.13 | A |
| ATOM | 1247 C | HIS | A | 161 | −4.105 | 12.295 | −12.856 | 1.00 | 55.61 | A |
| ATOM | 1248 O | HIS | A | 161 | −3.703 | 12.089 | −11.701 | 1.00 | 55.42 | A |
| ATOM | 1249 N | ILE | A | 162 | −3.938 | 13.455 | −13.504 | 1.00 | 57.43 | A |
| ATOM | 1250 CA | ILE | A | 162 | −3.253 | 14.631 | −12.936 | 1.00 | 58.86 | A |
| ATOM | 1251 CB | ILE | A | 162 | −3.873 | 15.962 | −13.480 | 1.00 | 58.80 | A |
| ATOM | 1252 CG2 | ILE | A | 162 | −3.183 | 17.170 | −12.812 | 1.00 | 58.56 | A |
| ATOM | 1253 CG1 | ILE | A | 162 | −3.750 | 16.023 | −15.012 | 1.00 | 57.83 | A |
| ATOM | 1254 CD1 | ILE | A | 162 | −4.369 | 17.271 | −15.642 | 1.00 | 55.94 | A |
| ATOM | 1255 C | ILE | A | 162 | −3.272 | 14.695 | −11.400 | 1.00 | 59.78 | A |
| ATOM | 1256 OT1 | ILE | A | 162 | −2.170 | 14.685 | −10.788 | 1.00 | 59.36 | A |
| ATOM | 1257 OT2 | ILE | A | 162 | −4.394 | 14.754 | −10.837 | 1.00 | 60.08 | A |
| ATOM | 1258 CB | ASP | L | 1 | 16.550 | 5.554 | −25.535 | 1.00 | 16.37 | L |
| ATOM | 1259 CG | ASP | L | 1 | 16.503 | 7.069 | −25.599 | 1.00 | 19.69 | L |
| ATOM | 1260 OD1 | ASP | L | 1 | 16.752 | 7.733 | −24.551 | 1.00 | 21.13 | L |
| ATOM | 1261 OD2 | ASP | L | 1 | 16.236 | 7.600 | −26.702 | 1.00 | 18.80 | L |
| ATOM | 1262 C | ASP | L | 1 | 15.914 | 3.511 | −24.259 | 1.00 | 13.85 | L |
| ATOM | 1263 O | ASP | L | 1 | 16.895 | 2.773 | −24.238 | 1.00 | 15.08 | L |
| ATOM | 1264 N | ASP | L | 1 | 17.141 | 5.276 | −23.136 | 1.00 | 16.84 | L |
| ATOM | 1265 CA | ASP | L | 1 | 16.101 | 5.010 | −24.177 | 1.00 | 15.47 | L |
| ATOM | 1266 N | ILE | L | 2 | 14.669 | 3.052 | −24.335 | 1.00 | 11.38 | L |
| ATOM | 1267 CA | ILE | L | 2 | 14.423 | 1.626 | −24.435 | 1.00 | 8.80 | L |
| ATOM | 1268 CB | ILE | L | 2 | 12.995 | 1.271 | −23.982 | 1.00 | 8.68 | L |
| ATOM | 1269 CG2 | ILE | L | 2 | 12.795 | −0.225 | −24.067 | 1.00 | 6.83 | L |
| ATOM | 1270 CG1 | ILE | L | 2 | 12.771 | 1.771 | −22.551 | 1.00 | 9.62 | L |
| ATOM | 1271 CD1 | ILE | L | 2 | 11.413 | 1.456 | −21.968 | 1.00 | 8.82 | L |
| ATOM | 1272 C | ILE | L | 2 | 14.643 | 1.214 | −25.886 | 1.00 | 8.52 | L |
| ATOM | 1273 O | ILE | L | 2 | 14.104 | 1.824 | −26.816 | 1.00 | 4.81 | L |
| ATOM | 1274 N | VAL | L | 3 | 15.474 | 0.195 | −26.078 | 1.00 | 8.21 | L |
| ATOM | 1275 CA | VAL | L | 3 | 15.778 | −0.278 | −27.422 | 1.00 | 7.79 | L |
| ATOM | 1276 CB | VAL | L | 3 | 17.284 | −0.578 | −27.549 | 1.00 | 5.49 | L |
| ATOM | 1277 CG1 | VAL | L | 3 | 17.627 | −0.990 | −28.958 | 1.00 | 1.00 | L |
| ATOM | 1278 CG2 | VAL | L | 3 | 18.072 | 0.648 | −27.135 | 1.00 | 5.03 | L |
| ATOM | 1279 C | VAL | L | 3 | 14.959 | −1.520 | −27.769 | 1.00 | 9.17 | L |
| ATOM | 1280 O | VAL | L | 3 | 15.054 | −2.547 | −27.098 | 1.00 | 11.84 | L |
| ATOM | 1281 N | MET | L | 4 | 14.133 | −1.417 | −28.802 | 1.00 | 8.22 | L |
| ATOM | 1282 CA | MET | L | 4 | 13.304 | −2.543 | −29.202 | 1.00 | 7.73 | L |
| ATOM | 1283 CB | MET | L | 4 | 11.923 | −2.055 | −29.655 | 1.00 | 9.47 | L |
| ATOM | 1284 CG | MET | L | 4 | 11.149 | −1.225 | −28.653 | 1.00 | 5.71 | L |
| ATOM | 1285 SD | MET | L | 4 | 10.934 | −2.041 | −27.095 | 1.00 | 9.24 | L |
| ATOM | 1286 CE | MET | L | 4 | 9.556 | −3.115 | −27.385 | 1.00 | 4.45 | L |
| ATOM | 1287 C | MET | L | 4 | 13.978 | −3.286 | −30.350 | 1.00 | 8.02 | L |
| ATOM | 1288 O | MET | L | 4 | 14.298 | −2.685 | −31.382 | 1.00 | 6.96 | L |
| ATOM | 1289 N | THR | L | 5 | 14.196 | −4.586 | −30.173 | 1.00 | 8.30 | L |
| ATOM | 1290 CA | THR | L | 5 | 14.835 | −5.392 | −31.210 | 1.00 | 8.27 | L |
| ATOM | 1291 CB | THR | L | 5 | 16.100 | −6.107 | −30.656 | 1.00 | 8.90 | L |
| ATOM | 1292 OG1 | THR | L | 5 | 16.842 | −5.200 | −29.822 | 1.00 | 10.13 | L |
| ATOM | 1293 CG2 | THR | L | 5 | 16.993 | −6.557 | −31.794 | 1.00 | 7.36 | L |
| ATOM | 1294 C | THR | L | 5 | 13.831 | −6.423 | −31.706 | 1.00 | 8.20 | L |

TABLE VIII-continued

Structure coordinates of the epitopes of allergenic beta-lactoglobulin in an antibody-beta-lactoglobulin immunocomplex;

|  | | Atom type | Resid | | # | X | Y | Z | OCC | B | |
|---|---|---|---|---|---|---|---|---|---|---|---|
| ATOM | 1295 | O | THR | L | 5 | 13.344 | −7.256 | −30.940 | 1.00 | 7.90 | L |
| ATOM | 1296 | N | GLN | L | 6 | 13.484 | −6.333 | −32.984 | 1.00 | 9.47 | L |
| ATOM | 1297 | CA | GLN | L | 6 | 12.533 | −7.268 | −33.580 | 1.00 | 9.71 | L |
| ATOM | 1298 | CB | GLN | L | 6 | 11.683 | −6.576 | −34.635 | 1.00 | 9.96 | L |
| ATOM | 1299 | CG | GLN | L | 6 | 10.217 | −6.389 | −34.283 | 1.00 | 10.83 | L |
| ATOM | 1300 | CD | GLN | L | 6 | 9.560 | −5.379 | −35.227 | 1.00 | 12.71 | L |
| ATOM | 1301 | OE1 | GLN | L | 6 | 9.754 | −4.156 | −35.100 | 1.00 | 11.89 | L |
| ATOM | 1302 | NE2 | GLN | L | 6 | 8.812 | −5.888 | −36.204 | 1.00 | 11.00 | L |
| ATOM | 1303 | C | GLN | L | 6 | 13.283 | −8.409 | −34.223 | 1.00 | 9.95 | L |
| ATOM | 1304 | O | GLN | L | 6 | 14.476 | −8.311 | −34.513 | 1.00 | 9.91 | L |
| ATOM | 1305 | N | SER | L | 7 | 12.580 | −9.501 | −34.460 | 1.00 | 10.84 | L |
| ATOM | 1306 | CA | SER | L | 7 | 13.234 | −10.652 | −35.045 | 1.00 | 10.80 | L |
| ATOM | 1307 | CB | SER | L | 7 | 14.081 | −11.315 | −33.982 | 1.00 | 9.99 | L |
| ATOM | 1308 | OG | SER | L | 7 | 15.047 | −12.144 | −34.575 | 1.00 | 16.72 | L |
| ATOM | 1309 | C | SER | L | 7 | 12.191 | −11.624 | −35.554 | 1.00 | 10.08 | L |
| ATOM | 1310 | O | SER | L | 7 | 11.206 | −11.886 | −34.876 | 1.00 | 12.81 | L |
| ATOM | 1311 | N | PRO | L | 8 | 12.365 | −12.131 | −36.779 | 1.00 | 9.04 | L |
| ATOM | 1312 | CD | PRO | L | 8 | 11.571 | −13.254 | −37.308 | 1.00 | 7.85 | L |
| ATOM | 1313 | CA | PRO | L | 8 | 13.490 | −11.816 | −37.668 | 1.00 | 9.77 | L |
| ATOM | 1314 | CB | PRO | L | 8 | 13.490 | −12.991 | −38.640 | 1.00 | 8.02 | L |
| ATOM | 1315 | CG | PRO | L | 8 | 12.033 | −13.328 | −38.732 | 1.00 | 8.29 | L |
| ATOM | 1316 | C | PRO | L | 8 | 13.241 | −10.474 | −38.377 | 1.00 | 10.57 | L |
| ATOM | 1317 | O | PRO | L | 8 | 12.140 | −9.923 | −38.302 | 1.00 | 10.48 | L |
| ATOM | 1318 | N | SER | L | 9 | 14.251 | −9.939 | −39.052 | 1.00 | 11.09 | L |
| ATOM | 1319 | CA | SER | L | 9 | 14.070 | −8.667 | −39.757 | 1.00 | 13.69 | L |
| ATOM | 1320 | CB | SER | L | 9 | 15.426 | −8.033 | −40.090 | 1.00 | 15.41 | L |
| ATOM | 1321 | OG | SER | L | 9 | 16.465 | −9.001 | −40.081 | 1.00 | 20.93 | L |
| ATOM | 1322 | C | SER | L | 9 | 13.231 | −8.841 | −41.031 | 1.00 | 13.61 | L |
| ATOM | 1323 | O | SER | L | 9 | 12.517 | −7.923 | −41.456 | 1.00 | 11.42 | L |
| ATOM | 1324 | N | SER | L | 10 | 13.316 | −10.024 | −41.636 | 1.00 | 14.50 | L |
| ATOM | 1325 | CA | SER | L | 10 | 12.531 | −10.330 | −42.833 | 1.00 | 16.25 | L |
| ATOM | 1326 | CB | SER | L | 10 | 13.280 | −9.938 | −44.104 | 1.00 | 16.02 | L |
| ATOM | 1327 | OG | SER | L | 10 | 14.253 | −10.900 | −44.437 | 1.00 | 19.67 | L |
| ATOM | 1328 | C | SER | L | 10 | 12.202 | −11.817 | −42.850 | 1.00 | 15.53 | L |
| ATOM | 1329 | O | SER | L | 10 | 13.002 | −12.648 | −42.426 | 1.00 | 15.73 | L |
| ATOM | 1330 | N | LEU | L | 11 | 11.011 | −12.143 | −43.329 | 1.00 | 15.59 | L |
| ATOM | 1331 | CA | LEU | L | 11 | 10.571 | −13.524 | −43.361 | 1.00 | 16.29 | L |
| ATOM | 1332 | CB | LEU | L | 11 | 9.730 | −13.789 | −42.120 | 1.00 | 16.99 | L |
| ATOM | 1333 | CG | LEU | L | 11 | 9.261 | −15.225 | −41.963 | 1.00 | 18.29 | L |
| ATOM | 1334 | CD1 | LEU | L | 11 | 10.338 | −15.994 | −41.199 | 1.00 | 19.78 | L |
| ATOM | 1335 | CD2 | LEU | L | 11 | 7.929 | −15.276 | −41.212 | 1.00 | 17.06 | L |
| ATOM | 1336 | C | LEU | L | 11 | 9.748 | −13.852 | −44.609 | 1.00 | 17.00 | L |
| ATOM | 1337 | O | LEU | L | 11 | 9.089 | −12.978 | −45.171 | 1.00 | 19.02 | L |
| ATOM | 1338 | N | SER | L | 12 | 9.786 | −15.109 | −45.043 | 1.00 | 17.38 | L |
| ATOM | 1339 | CA | SER | L | 12 | 8.999 | −15.533 | −46.200 | 1.00 | 16.83 | L |
| ATOM | 1340 | CB | SER | L | 12 | 9.893 | −15.852 | −47.395 | 1.00 | 16.19 | L |
| ATOM | 1341 | OG | SER | L | 12 | 10.483 | −14.670 | −47.897 | 1.00 | 18.96 | L |
| ATOM | 1342 | C | SER | L | 12 | 8.229 | −16.772 | −45.792 | 1.00 | 15.74 | L |
| ATOM | 1343 | O | SER | L | 12 | 8.820 | −17.778 | −45.395 | 1.00 | 16.18 | L |
| ATOM | 1344 | N | ALA | L | 13 | 6.907 | −16.689 | −45.893 | 1.00 | 14.50 | L |
| ATOM | 1345 | CA | ALA | L | 13 | 6.040 | −17.790 | −45.510 | 1.00 | 13.88 | L |
| ATOM | 1346 | CB | ALA | L | 13 | 5.435 | −17.524 | −44.142 | 1.00 | 11.70 | L |
| ATOM | 1347 | C | ALA | L | 13 | 4.941 | −18.025 | −46.520 | 1.00 | 14.84 | L |
| ATOM | 1348 | O | ALA | L | 13 | 4.414 | −17.080 | −47.098 | 1.00 | 15.89 | L |
| ATOM | 1349 | N | SER | L | 14 | 4.590 | −19.289 | −46.726 | 1.00 | 16.55 | L |
| ATOM | 1350 | CA | SER | L | 14 | 3.548 | −19.653 | −47.686 | 1.00 | 18.52 | L |
| ATOM | 1351 | CB | SER | L | 14 | 3.584 | −21.161 | −47.953 | 1.00 | 21.34 | L |
| ATOM | 1352 | OG | SER | L | 14 | 4.906 | −21.598 | −48.266 | 1.00 | 25.96 | L |
| ATOM | 1353 | C | SER | L | 14 | 2.187 | −19.280 | −47.146 | 1.00 | 17.08 | L |
| ATOM | 1354 | O | SER | L | 14 | 1.926 | −19.420 | −45.954 | 1.00 | 15.37 | L |
| ATOM | 1355 | N | VAL | L | 15 | 1.321 | −18.795 | −48.025 | 1.00 | 18.37 | L |
| ATOM | 1356 | CA | VAL | L | 15 | −0.022 | −18.426 | −47.602 | 1.00 | 20.11 | L |
| ATOM | 1357 | CB | VAL | L | 15 | −0.895 | −17.953 | −48.814 | 1.00 | 19.65 | L |
| ATOM | 1358 | CG1 | VAL | L | 15 | −0.468 | −18.683 | −50.077 | 1.00 | 21.07 | L |
| ATOM | 1359 | CG2 | VAL | L | 15 | −2.386 | −18.191 | −48.526 | 1.00 | 16.68 | L |
| ATOM | 1360 | C | VAL | L | 15 | −0.660 | −19.631 | −46.912 | 1.00 | 20.75 | L |
| ATOM | 1361 | O | VAL | L | 15 | −0.853 | −20.677 | −47.520 | 1.00 | 21.60 | L |
| ATOM | 1362 | N | GLY | L | 16 | −0.957 | −19.483 | −45.628 | 1.00 | 21.09 | L |
| ATOM | 1363 | CA | GLY | L | 16 | −1.554 | −20.579 | −44.901 | 1.00 | 22.33 | L |
| ATOM | 1364 | C | GLY | L | 16 | −0.814 | −20.944 | −43.632 | 1.00 | 23.59 | L |
| ATOM | 1365 | O | GLY | L | 16 | −1.451 | −21.194 | −42.616 | 1.00 | 25.28 | L |
| ATOM | 1366 | N | ASP | L | 17 | 0.514 | −20.979 | −43.657 | 1.00 | 24.99 | L |
| ATOM | 1367 | CA | ASP | L | 17 | 1.230 | −21.341 | −42.436 | 1.00 | 27.99 | L |
| ATOM | 1368 | CB | ASP | L | 17 | 2.693 | −21.717 | −42.723 | 1.00 | 28.83 | L |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1369 CG | ASP | L | 17 | 3.458 | −20.625 | −43.424 | 1.00 | 29.50 | L |
| ATOM | 1370 OD1 | ASP | L | 17 | 3.262 | −19.441 | −43.048 | 1.00 | 31.11 | L |
| ATOM | 1371 OD2 | ASP | L | 17 | 4.271 | −20.954 | −44.329 | 1.00 | 27.86 | L |
| ATOM | 1372 C | ASP | L | 17 | 1.160 | −20.221 | −41.407 | 1.00 | 29.07 | L |
| ATOM | 1373 O | ASP | L | 17 | 0.811 | −19.091 | −41.747 | 1.00 | 30.22 | L |
| ATOM | 1374 N | ARG | L | 18 | 1.473 | −20.540 | −40.150 | 1.00 | 29.29 | L |
| ATOM | 1375 CA | ARG | L | 18 | 1.428 | −19.550 | −39.085 | 1.00 | 28.54 | L |
| ATOM | 1376 CB | ARG | L | 18 | 0.964 | −20.185 | −37.758 | 1.00 | 30.31 | L |
| ATOM | 1377 CG | ARG | L | 18 | 2.046 | −20.954 | −36.997 | 1.00 | 33.86 | L |
| ATOM | 1378 CD | ARG | L | 18 | 1.515 | −21.703 | −35.764 | 1.00 | 35.75 | L |
| ATOM | 1379 NE | ARG | L | 18 | 0.691 | −20.880 | −34.879 | 1.00 | 38.27 | L |
| ATOM | 1380 CZ | ARG | L | 18 | −0.645 | −20.869 | −34.882 | 1.00 | 39.93 | L |
| ATOM | 1381 NH1 | ARG | L | 18 | −1.317 | −21.642 | −35.726 | 1.00 | 39.27 | L |
| ATOM | 1382 NH2 | ARG | L | 18 | −1.316 | −20.085 | −34.037 | 1.00 | 40.51 | L |
| ATOM | 1383 C | ARG | L | 18 | 2.814 | −18.946 | −38.934 | 1.00 | 27.76 | L |
| ATOM | 1384 O | ARG | L | 18 | 3.829 | −19.658 | −38.958 | 1.00 | 27.29 | L |
| ATOM | 1385 N | VAL | L | 19 | 2.858 | −17.623 | −38.810 | 1.00 | 26.27 | L |
| ATOM | 1386 CA | VAL | L | 19 | 4.124 | −16.924 | −38.655 | 1.00 | 24.20 | L |
| ATOM | 1387 CB | VAL | L | 19 | 4.290 | −15.843 | −39.743 | 1.00 | 24.36 | L |
| ATOM | 1388 CG1 | VAL | L | 19 | 3.975 | −16.440 | −41.112 | 1.00 | 25.14 | L |
| ATOM | 1389 CG2 | VAL | L | 19 | 3.387 | −14.671 | −39.464 | 1.00 | 26.02 | L |
| ATOM | 1390 C | VAL | L | 19 | 4.209 | −16.292 | −37.278 | 1.00 | 22.08 | L |
| ATOM | 1391 O | VAL | L | 19 | 3.190 | −15.978 | −36.676 | 1.00 | 20.97 | L |
| ATOM | 1392 N | THR | L | 20 | 5.432 | −16.132 | −36.782 | 1.00 | 21.47 | L |
| ATOM | 1393 CA | THR | L | 20 | 5.671 | −15.541 | −35.469 | 1.00 | 19.88 | L |
| ATOM | 1394 CB | THR | L | 20 | 5.991 | −16.619 | −34.422 | 1.00 | 17.86 | L |
| ATOM | 1395 OG1 | THR | L | 20 | 4.866 | −17.480 | −34.259 | 1.00 | 18.26 | L |
| ATOM | 1396 CG2 | THR | L | 20 | 6.324 | −15.994 | −33.100 | 1.00 | 16.28 | L |
| ATOM | 1397 C | THR | L | 20 | 6.847 | −14.575 | −35.499 | 1.00 | 20.30 | L |
| ATOM | 1398 O | THR | L | 20 | 7.946 | −14.931 | −35.918 | 1.00 | 20.29 | L |
| ATOM | 1399 N | ILE | L | 21 | 6.610 | −13.351 | −35.055 | 1.00 | 20.44 | L |
| ATOM | 1400 CA | ILE | L | 21 | 7.658 | −12.349 | −35.000 | 1.00 | 20.12 | L |
| ATOM | 1401 CB | ILE | L | 21 | 7.236 | −11.072 | −35.736 | 1.00 | 20.69 | L |
| ATOM | 1402 CG2 | ILE | L | 21 | 8.406 | −10.088 | −35.799 | 1.00 | 18.90 | L |
| ATOM | 1403 CG1 | ILE | L | 21 | 6.759 | −11.441 | −37.142 | 1.00 | 21.95 | L |
| ATOM | 1404 CD1 | ILE | L | 21 | 6.285 | −10.252 | −37.972 | 1.00 | 22.52 | L |
| ATOM | 1405 C | ILE | L | 21 | 7.904 | −12.024 | −33.528 | 1.00 | 20.23 | L |
| ATOM | 1406 O | ILE | L | 21 | 6.961 | −11.872 | −32.735 | 1.00 | 19.59 | L |
| ATOM | 1407 N | THR | L | 22 | 9.174 | −11.915 | −33.169 | 1.00 | 19.11 | L |
| ATOM | 1408 CA | THR | L | 22 | 9.534 | −11.605 | −31.801 | 1.00 | 19.72 | L |
| ATOM | 1409 CB | THR | L | 22 | 10.651 | −12.529 | −31.291 | 1.00 | 19.77 | L |
| ATOM | 1410 OG1 | THR | L | 22 | 10.343 | −13.878 | −31.647 | 1.00 | 20.92 | L |
| ATOM | 1411 CG2 | THR | L | 22 | 10.773 | −12.442 | −29.770 | 1.00 | 17.04 | L |
| ATOM | 1412 C | THR | L | 22 | 10.009 | −10.172 | −31.690 | 1.00 | 20.10 | L |
| ATOM | 1413 O | THR | L | 22 | 10.498 | −9.590 | −32.660 | 1.00 | 19.87 | L |
| ATOM | 1414 N | CYS | L | 23 | 9.848 | −9.617 | −30.493 | 1.00 | 20.03 | L |
| ATOM | 1415 CA | CYS | L | 23 | 10.255 | −8.257 | −30.192 | 1.00 | 20.14 | L |
| ATOM | 1416 C | CYS | L | 23 | 10.753 | −8.272 | −28.748 | 1.00 | 20.68 | L |
| ATOM | 1417 O | CYS | L | 23 | 10.063 | −8.777 | −27.861 | 1.00 | 20.07 | L |
| ATOM | 1418 CB | CYS | L | 23 | 9.050 | −7.327 | −30.361 | 1.00 | 19.95 | L |
| ATOM | 1419 SG | CYS | L | 23 | 9.273 | −5.579 | −29.906 | 1.00 | 24.16 | L |
| ATOM | 1420 N | ARG | L | 24 | 11.972 | −7.776 | −28.521 | 1.00 | 20.89 | L |
| ATOM | 1421 CA | ARG | L | 24 | 12.538 | −7.736 | −27.172 | 1.00 | 19.57 | L |
| ATOM | 1422 CB | ARG | L | 24 | 13.771 | −8.629 | −27.042 | 1.00 | 21.13 | L |
| ATOM | 1423 CG | ARG | L | 24 | 13.464 | −10.092 | −27.137 | 1.00 | 23.44 | L |
| ATOM | 1424 CD | ARG | L | 24 | 14.727 | −10.917 | −27.090 | 1.00 | 26.37 | L |
| ATOM | 1425 NE | ARG | L | 24 | 14.457 | −12.270 | −27.558 | 1.00 | 30.08 | L |
| ATOM | 1426 CZ | ARG | L | 24 | 14.080 | −12.559 | −28.794 | 1.00 | 32.01 | L |
| ATOM | 1427 NH1 | ARG | L | 24 | 13.935 | −11.583 | −29.695 | 1.00 | 34.19 | L |
| ATOM | 1428 NH2 | ARG | L | 24 | 13.831 | −13.819 | −29.112 | 1.00 | 32.69 | L |
| ATOM | 1429 C | ARG | L | 24 | 12.927 | −6.335 | −26.809 | 1.00 | 18.40 | L |
| ATOM | 1430 O | ARG | L | 24 | 13.490 | −5.615 | −27.629 | 1.00 | 18.93 | L |
| ATOM | 1431 N | ALA | L | 25 | 12.628 | −5.958 | −25.568 | 1.00 | 17.14 | L |
| ATOM | 1432 CA | ALA | L | 25 | 12.925 | −4.624 | −25.063 | 1.00 | 16.03 | L |
| ATOM | 1433 CB | ALA | L | 25 | 11.804 | −4.169 | −24.158 | 1.00 | 16.46 | L |
| ATOM | 1434 C | ALA | L | 25 | 14.249 | −4.594 | −24.317 | 1.00 | 15.36 | L |
| ATOM | 1435 O | ALA | L | 25 | 14.662 | −5.597 | −23.742 | 1.00 | 14.07 | L |
| ATOM | 1436 N | SER | L | 26 | 14.913 | −3.442 | −24.343 | 1.00 | 16.19 | L |
| ATOM | 1437 CA | SER | L | 26 | 16.195 | −3.277 | −23.668 | 1.00 | 16.76 | L |
| ATOM | 1438 CB | SER | L | 26 | 16.888 | −1.996 | −24.132 | 1.00 | 17.23 | L |
| ATOM | 1439 OG | SER | L | 26 | 16.373 | −0.865 | −23.464 | 1.00 | 20.63 | L |
| ATOM | 1440 C | SER | L | 26 | 16.003 | −3.246 | −22.149 | 1.00 | 16.15 | L |
| ATOM | 1441 O | SER | L | 26 | 16.967 | −3.188 | −21.394 | 1.00 | 15.95 | L |
| ATOM | 1442 N | GLN | L | 27 | 14.749 | −3.260 | −21.711 | 1.00 | 15.84 | L |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1443 CA | GLN | L | 27 | 14.416 | −3.291 | −20.289 | 1.00 | 14.82 | L |
| ATOM | 1444 CB | GLN | L | 27 | 14.690 | −1.950 | −19.615 | 1.00 | 15.42 | L |
| ATOM | 1445 CG | GLN | L | 27 | 13.719 | −0.864 | −19.989 | 1.00 | 17.28 | L |
| ATOM | 1446 CD | GLN | L | 27 | 13.715 | 0.267 | −18.991 | 1.00 | 19.54 | L |
| ATOM | 1447 OE1 | GLN | L | 27 | 14.671 | 1.046 | −18.916 | 1.00 | 19.13 | L |
| ATOM | 1448 NE2 | GLN | L | 27 | 12.647 | 0.345 | −18.184 | 1.00 | 21.52 | L |
| ATOM | 1449 C | GLN | L | 27 | 12.933 | −3.625 | −20.170 | 1.00 | 13.71 | L |
| ATOM | 1450 O | GLN | L | 27 | 12.190 | −3.547 | −21.152 | 1.00 | 11.47 | L |
| ATOM | 1451 N | GLY | L | 28 | 12.507 | −3.998 | −18.970 | 1.00 | 12.79 | L |
| ATOM | 1452 CA | GLY | L | 28 | 11.116 | −4.345 | −18.765 | 1.00 | 11.73 | L |
| ATOM | 1453 C | GLY | L | 28 | 10.230 | −3.167 | −19.092 | 1.00 | 12.33 | L |
| ATOM | 1454 O | GLY | L | 28 | 10.534 | −2.029 | −18.728 | 1.00 | 12.44 | L |
| ATOM | 1455 N | ILE | L | 29 | 9.136 | −3.437 | −19.792 | 1.00 | 11.90 | L |
| ATOM | 1456 CA | ILE | L | 29 | 8.206 | −2.389 | −20.166 | 1.00 | 12.68 | L |
| ATOM | 1457 CB | ILE | L | 29 | 8.252 | −2.078 | −21.664 | 1.00 | 11.70 | L |
| ATOM | 1458 CG2 | ILE | L | 29 | 9.607 | −1.483 | −22.023 | 1.00 | 12.24 | L |
| ATOM | 1459 CG1 | ILE | L | 29 | 7.948 | −3.348 | −22.465 | 1.00 | 12.26 | L |
| ATOM | 1460 CD1 | ILE | L | 29 | 7.626 | −3.110 | −23.937 | 1.00 | 10.24 | L |
| ATOM | 1461 C | ILE | L | 29 | 6.800 | −2.808 | −19.828 | 1.00 | 14.29 | L |
| ATOM | 1462 O | ILE | L | 29 | 5.833 | −2.365 | −20.458 | 1.00 | 14.88 | L |
| ATOM | 1463 N | SER | L | 30 | 6.686 | −3.681 | −18.839 | 1.00 | 15.26 | L |
| ATOM | 1464 CA | SER | L | 30 | 5.373 | −4.129 | −18.422 | 1.00 | 16.96 | L |
| ATOM | 1465 CB | SER | L | 30 | 4.545 | −2.903 | −18.005 | 1.00 | 17.33 | L |
| ATOM | 1466 OG | SER | L | 30 | 3.175 | −3.203 | −17.824 | 1.00 | 18.85 | L |
| ATOM | 1467 C | SER | L | 30 | 4.721 | −4.845 | −19.600 | 1.00 | 17.57 | L |
| ATOM | 1468 O | SER | L | 30 | 5.328 | −5.689 | −20.258 | 1.00 | 18.80 | L |
| ATOM | 1469 N | SER | L | 31 | 3.476 | −4.492 | −19.862 | 1.00 | 16.56 | L |
| ATOM | 1470 CA | SER | L | 31 | 2.737 | −5.081 | −20.956 | 1.00 | 16.37 | L |
| ATOM | 1471 CB | SER | L | 31 | 1.472 | −5.751 | −20.415 | 1.00 | 16.56 | L |
| ATOM | 1472 OG | SER | L | 31 | 0.798 | −4.889 | −19.505 | 1.00 | 17.23 | L |
| ATOM | 1473 C | SER | L | 31 | 2.375 | −3.971 | −21.939 | 1.00 | 15.72 | L |
| ATOM | 1474 O | SER | L | 31 | 1.424 | −4.085 | −22.727 | 1.00 | 14.38 | L |
| ATOM | 1475 N | ARG | L | 32 | 3.137 | −2.886 | −21.882 | 1.00 | 14.57 | L |
| ATOM | 1476 CA | ARG | L | 32 | 2.869 | −1.761 | −22.763 | 1.00 | 12.87 | L |
| ATOM | 1477 CB | ARG | L | 32 | 3.232 | −0.432 | −22.077 | 1.00 | 12.78 | L |
| ATOM | 1478 CG | ARG | L | 32 | 2.545 | −0.190 | −20.731 | 1.00 | 13.17 | L |
| ATOM | 1479 CD | ARG | L | 32 | 2.896 | 1.199 | −20.286 | 1.00 | 16.26 | L |
| ATOM | 1480 NE | ARG | L | 32 | 2.682 | 1.484 | −18.877 | 1.00 | 20.43 | L |
| ATOM | 1481 CZ | ARG | L | 32 | 1.751 | 2.314 | −18.409 | 1.00 | 24.20 | L |
| ATOM | 1482 NH1 | ARG | L | 32 | 0.931 | 2.937 | −19.255 | 1.00 | 23.63 | L |
| ATOM | 1483 NH2 | ARG | L | 32 | 1.669 | 2.550 | −17.095 | 1.00 | 21.89 | L |
| ATOM | 1484 C | ARG | L | 32 | 3.624 | −1.888 | −24.086 | 1.00 | 10.58 | L |
| ATOM | 1485 O | ARG | L | 32 | 4.626 | −1.222 | −24.312 | 1.00 | 11.04 | L |
| ATOM | 1486 N | LEU | L | 33 | 3.135 | −2.759 | −24.950 | 1.00 | 7.55 | L |
| ATOM | 1487 CA | LEU | L | 33 | 3.728 | −2.953 | −26.243 | 1.00 | 5.79 | L |
| ATOM | 1488 CB | LEU | L | 33 | 4.558 | −4.233 | −26.293 | 1.00 | 6.51 | L |
| ATOM | 1489 CG | LEU | L | 33 | 5.261 | −4.460 | −27.669 | 1.00 | 6.68 | L |
| ATOM | 1490 CD1 | LEU | L | 33 | 6.728 | −4.722 | −27.445 | 1.00 | 5.42 | L |
| ATOM | 1491 CD2 | LEU | L | 33 | 4.616 | −5.605 | −28.430 | 1.00 | 3.57 | L |
| ATOM | 1492 C | LEU | L | 33 | 2.613 | −3.045 | −27.273 | 1.00 | 4.13 | L |
| ATOM | 1493 O | LEU | L | 33 | 1.559 | −3.640 | −27.011 | 1.00 | 3.72 | L |
| ATOM | 1494 N | ALA | L | 34 | 2.857 | −2.480 | −28.454 | 1.00 | 3.03 | L |
| ATOM | 1495 CA | ALA | L | 34 | 1.857 | −2.507 | −29.521 | 1.00 | 3.10 | L |
| ATOM | 1496 CB | ALA | L | 34 | 1.245 | −1.114 | −29.712 | 1.00 | 3.61 | L |
| ATOM | 1497 C | ALA | L | 34 | 2.455 | −2.991 | −30.820 | 1.00 | 2.38 | L |
| ATOM | 1498 O | ALA | L | 34 | 3.662 | −2.950 | −31.000 | 1.00 | 2.65 | L |
| ATOM | 1499 N | TRP | L | 35 | 1.594 | −3.455 | −31.715 | 1.00 | 3.03 | L |
| ATOM | 1500 CA | TRP | L | 35 | 2.016 | −3.967 | −33.007 | 1.00 | 4.01 | L |
| ATOM | 1501 CB | TRP | L | 35 | 1.714 | −5.459 | −33.112 | 1.00 | 5.67 | L |
| ATOM | 1502 CG | TRP | L | 35 | 2.557 | −6.314 | −32.225 | 1.00 | 7.10 | L |
| ATOM | 1503 CD2 | TRP | L | 35 | 3.882 | −6.790 | −32.507 | 1.00 | 6.96 | L |
| ATOM | 1504 CE2 | TRP | L | 35 | 4.308 | −7.525 | −31.380 | 1.00 | 7.48 | L |
| ATOM | 1505 CE3 | TRP | L | 35 | 4.751 | −6.663 | −33.604 | 1.00 | 6.37 | L |
| ATOM | 1506 CD1 | TRP | L | 35 | 2.242 | −6.768 | −30.973 | 1.00 | 5.81 | L |
| ATOM | 1507 NE1 | TRP | L | 35 | 3.287 | −7.493 | −30.459 | 1.00 | 7.49 | L |
| ATOM | 1508 CZ2 | TRP | L | 35 | 5.581 | −8.140 | −31.318 | 1.00 | 6.10 | L |
| ATOM | 1509 CZ3 | TRP | L | 35 | 6.012 | −7.271 | −33.541 | 1.00 | 5.88 | L |
| ATOM | 1510 CH2 | TRP | L | 35 | 6.411 | −8.002 | −32.403 | 1.00 | 5.71 | L |
| ATOM | 1511 C | TRP | L | 35 | 1.310 | −3.251 | −34.147 | 1.00 | 4.05 | L |
| ATOM | 1512 O | TRP | L | 35 | 0.074 | −3.220 | −34.209 | 1.00 | 2.57 | L |
| ATOM | 1513 N | TYR | L | 36 | 2.099 | −2.693 | −35.055 | 1.00 | 2.93 | L |
| ATOM | 1514 CA | TYR | L | 36 | 1.522 | −1.981 | −36.169 | 1.00 | 3.86 | L |
| ATOM | 1515 CB | TYR | L | 36 | 2.035 | −0.544 | −36.209 | 1.00 | 1.42 | L |
| ATOM | 1516 CG | TYR | L | 36 | 1.701 | 0.264 | −34.970 | 1.00 | 2.49 | L |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1517 CD1 | TYR | L | 36 | 0.469 | 0.885 | −34.829 | 1.00 | 1.00 | L |
| ATOM | 1518 CE1 | TYR | L | 36 | 0.178 | 1.650 | −33.715 | 1.00 | 1.00 | L |
| ATOM | 1519 CD2 | TYR | L | 36 | 2.635 | 0.427 | −33.944 | 1.00 | 2.52 | L |
| ATOM | 1520 CE2 | TYR | L | 36 | 2.342 | 1.196 | −32.819 | 1.00 | 1.93 | L |
| ATOM | 1521 CZ | TYR | L | 36 | 1.109 | 1.807 | −32.722 | 1.00 | 1.00 | L |
| ATOM | 1522 OH | TYR | L | 36 | 0.838 | 2.597 | −31.632 | 1.00 | 1.00 | L |
| ATOM | 1523 C | TYR | L | 36 | 1.851 | −2.671 | −37.464 | 1.00 | 5.39 | L |
| ATOM | 1524 O | TYR | L | 36 | 2.844 | −3.388 | −37.575 | 1.00 | 5.41 | L |
| ATOM | 1525 N | GLN | L | 37 | 1.002 | −2.455 | −38.453 | 1.00 | 7.83 | L |
| ATOM | 1526 CA | GLN | L | 37 | 1.207 | −3.054 | −39.754 | 1.00 | 9.39 | L |
| ATOM | 1527 CB | GLN | L | 37 | 0.046 | −3.980 | −40.097 | 1.00 | 11.00 | L |
| ATOM | 1528 CG | GLN | L | 37 | 0.086 | −4.527 | −41.501 | 1.00 | 9.81 | L |
| ATOM | 1529 CD | GLN | L | 37 | −1.129 | −5.339 | −41.803 | 1.00 | 10.26 | L |
| ATOM | 1530 OE1 | GLN | L | 37 | −2.238 | −4.815 | −41.847 | 1.00 | 12.94 | L |
| ATOM | 1531 NE2 | GLN | L | 37 | −0.941 | −6.637 | −41.983 | 1.00 | 13.63 | L |
| ATOM | 1532 C | GLN | L | 37 | 1.274 | −1.933 | −40.766 | 1.00 | 10.97 | L |
| ATOM | 1533 O | GLN | L | 37 | 0.415 | −1.056 | −40.787 | 1.00 | 11.76 | L |
| ATOM | 1534 N | GLN | L | 38 | 2.296 | −1.966 | −41.609 | 1.00 | 13.25 | L |
| ATOM | 1535 CA | GLN | L | 38 | 2.443 | −0.946 | −42.622 | 1.00 | 15.72 | L |
| ATOM | 1536 CB | GLN | L | 38 | 3.562 | 0.023 | −42.258 | 1.00 | 16.17 | L |
| ATOM | 1537 CG | GLN | L | 38 | 3.619 | 1.227 | −43.194 | 1.00 | 17.87 | L |
| ATOM | 1538 CD | GLN | L | 38 | 4.854 | 2.054 | −43.000 | 1.00 | 18.58 | L |
| ATOM | 1539 OE1 | GLN | L | 38 | 4.887 | 3.241 | −43.360 | 1.00 | 18.70 | L |
| ATOM | 1540 NE2 | GLN | L | 38 | 5.896 | 1.436 | −42.437 | 1.00 | 18.33 | L |
| ATOM | 1541 C | GLN | L | 38 | 2.739 | −1.530 | −43.991 | 1.00 | 17.75 | L |
| ATOM | 1542 O | GLN | L | 38 | 3.618 | −2.372 | −44.144 | 1.00 | 17.47 | L |
| ATOM | 1543 N | LYS | L | 39 | 2.003 | −1.051 | −44.984 | 1.00 | 19.94 | L |
| ATOM | 1544 CA | LYS | L | 39 | 2.172 | −1.466 | −46.360 | 1.00 | 20.60 | L |
| ATOM | 1545 CB | LYS | L | 39 | 0.843 | −1.990 | −46.911 | 1.00 | 19.44 | L |
| ATOM | 1546 CG | LYS | L | 39 | 0.372 | −3.242 | −46.214 | 1.00 | 18.77 | L |
| ATOM | 1547 CD | LYS | L | 39 | −1.043 | −3.641 | −46.559 | 1.00 | 18.38 | L |
| ATOM | 1548 CE | LYS | L | 39 | −1.314 | −5.039 | −45.989 | 1.00 | 19.75 | L |
| ATOM | 1549 NZ | LYS | L | 39 | −2.760 | −5.437 | −45.970 | 1.00 | 19.42 | L |
| ATOM | 1550 C | LYS | L | 39 | 2.615 | −0.225 | −47.142 | 1.00 | 23.17 | L |
| ATOM | 1551 O | LYS | L | 39 | 2.320 | 0.916 | −46.762 | 1.00 | 22.18 | L |
| ATOM | 1552 N | PRO | L | 40 | 3.319 | −0.440 | −48.258 | 1.00 | 25.17 | L |
| ATOM | 1553 CD | PRO | L | 40 | 3.543 | −1.778 | −48.829 | 1.00 | 25.97 | L |
| ATOM | 1554 CA | PRO | L | 40 | 3.846 | 0.591 | −49.157 | 1.00 | 25.55 | L |
| ATOM | 1555 CB | PRO | L | 40 | 4.172 | −0.194 | −50.417 | 1.00 | 25.75 | L |
| ATOM | 1556 CG | PRO | L | 40 | 4.583 | −1.491 | −49.863 | 1.00 | 26.38 | L |
| ATOM | 1557 C | PRO | L | 40 | 2.863 | 1.705 | −49.444 | 1.00 | 25.25 | L |
| ATOM | 1558 O | PRO | L | 40 | 1.775 | 1.467 | −49.973 | 1.00 | 25.17 | L |
| ATOM | 1559 N | GLY | L | 41 | 3.262 | 2.923 | −49.101 | 1.00 | 24.69 | L |
| ATOM | 1560 CA | GLY | L | 41 | 2.419 | 4.082 | −49.343 | 1.00 | 23.52 | L |
| ATOM | 1561 C | GLY | L | 41 | 1.056 | 4.091 | −48.665 | 1.00 | 21.83 | L |
| ATOM | 1562 O | GLY | L | 41 | 0.195 | 4.900 | −49.004 | 1.00 | 20.85 | L |
| ATOM | 1563 N | LYS | L | 42 | 0.848 | 3.200 | −47.708 | 1.00 | 21.05 | L |
| ATOM | 1564 CA | LYS | L | 42 | −0.418 | 3.159 | −47.017 | 1.00 | 20.64 | L |
| ATOM | 1565 CB | LYS | L | 42 | −1.022 | 1.758 | −47.112 | 1.00 | 23.78 | L |
| ATOM | 1566 CG | LYS | L | 42 | −1.251 | 1.276 | −48.549 | 1.00 | 27.37 | L |
| ATOM | 1567 CD | LYS | L | 42 | −1.686 | −0.178 | −48.582 | 1.00 | 29.55 | L |
| ATOM | 1568 CE | LYS | L | 42 | −1.463 | −0.807 | −49.960 | 1.00 | 31.53 | L |
| ATOM | 1569 NZ | LYS | L | 42 | −1.924 | −2.247 | −50.023 | 1.00 | 30.21 | L |
| ATOM | 1570 C | LYS | L | 42 | −0.235 | 3.567 | −45.561 | 1.00 | 19.67 | L |
| ATOM | 1571 O | LYS | L | 42 | 0.888 | 3.642 | −45.057 | 1.00 | 22.24 | L |
| ATOM | 1572 N | ALA | L | 43 | −1.353 | 3.831 | −44.895 | 1.00 | 17.35 | L |
| ATOM | 1573 CA | ALA | L | 43 | −1.379 | 4.238 | −43.500 | 1.00 | 14.73 | L |
| ATOM | 1574 CB | ALA | L | 43 | −2.707 | 4.896 | −43.197 | 1.00 | 13.07 | L |
| ATOM | 1575 C | ALA | L | 43 | −1.166 | 3.061 | −42.561 | 1.00 | 13.46 | L |
| ATOM | 1576 O | ALA | L | 43 | −1.844 | 2.044 | −42.655 | 1.00 | 13.73 | L |
| ATOM | 1577 N | PRO | L | 44 | −0.206 | 3.177 | −41.639 | 1.00 | 11.50 | L |
| ATOM | 1578 CD | PRO | L | 44 | 0.860 | 4.180 | −41.480 | 1.00 | 9.68 | L |
| ATOM | 1579 CA | PRO | L | 44 | −0.007 | 2.050 | −40.730 | 1.00 | 11.04 | L |
| ATOM | 1580 CB | PRO | L | 44 | 1.101 | 2.552 | −39.805 | 1.00 | 10.36 | L |
| ATOM | 1581 CG | PRO | L | 44 | 1.920 | 3.409 | −40.739 | 1.00 | 9.88 | L |
| ATOM | 1582 C | PRO | L | 44 | −1.307 | 1.721 | −39.975 | 1.00 | 10.49 | L |
| ATOM | 1583 O | PRO | L | 44 | −2.161 | 2.583 | −39.759 | 1.00 | 9.88 | L |
| ATOM | 1584 N | LYS | L | 45 | −1.453 | 0.459 | −39.599 | 1.00 | 11.44 | L |
| ATOM | 1585 CA | LYS | L | 45 | −2.631 | −0.005 | −38.881 | 1.00 | 12.22 | L |
| ATOM | 1586 CB | LYS | L | 45 | −3.368 | −1.063 | −39.698 | 1.00 | 15.28 | L |
| ATOM | 1587 CG | LYS | L | 45 | −4.045 | −0.532 | −40.955 | 1.00 | 18.72 | L |
| ATOM | 1588 CD | LYS | L | 45 | −4.689 | −1.651 | −41.789 | 1.00 | 23.99 | L |
| ATOM | 1589 CE | LYS | L | 45 | −5.758 | −2.410 | −40.990 | 1.00 | 28.70 | L |
| ATOM | 1590 NZ | LYS | L | 45 | −6.539 | −3.436 | −41.781 | 1.00 | 30.44 | L |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1591 C | LYS | L | 45 | −2.243 | −0.599 | −37.542 | 1.00 | 10.66 | L |
| ATOM | 1592 O | LYS | L | 45 | −1.270 | −1.343 | −37.433 | 1.00 | 11.06 | L |
| ATOM | 1593 N | LEU | L | 46 | −3.011 | −0.271 | −36.517 | 1.00 | 9.86 | L |
| ATOM | 1594 CA | LEU | L | 46 | −2.738 | −0.780 | −35.185 | 1.00 | 8.87 | L |
| ATOM | 1595 CB | LEU | L | 46 | −3.336 | 0.180 | −34.147 | 1.00 | 9.27 | L |
| ATOM | 1596 CG | LEU | L | 46 | −3.140 | 0.020 | −32.631 | 1.00 | 9.63 | L |
| ATOM | 1597 CD1 | LEU | L | 46 | −4.354 | −0.644 | −32.037 | 1.00 | 9.45 | L |
| ATOM | 1598 CD2 | LEU | L | 46 | −1.857 | −0.768 | −32.330 | 1.00 | 10.10 | L |
| ATOM | 1599 C | LEU | L | 46 | −3.382 | −2.150 | −35.103 | 1.00 | 8.10 | L |
| ATOM | 1600 O | LEU | L | 46 | −4.573 | −2.287 | −35.357 | 1.00 | 8.98 | L |
| ATOM | 1601 N | LEU | L | 47 | −2.593 | −3.160 | −34.757 | 1.00 | 7.67 | L |
| ATOM | 1602 CA | LEU | L | 47 | −3.109 | −4.525 | −34.662 | 1.00 | 6.84 | L |
| ATOM | 1603 CB | LEU | L | 47 | −2.148 | −5.527 | −35.320 | 1.00 | 5.42 | L |
| ATOM | 1604 CG | LEU | L | 47 | −1.750 | −5.328 | −36.793 | 1.00 | 6.34 | L |
| ATOM | 1605 CD1 | LEU | L | 47 | −0.631 | −6.286 | −37.139 | 1.00 | 3.93 | L |
| ATOM | 1606 CD2 | LEU | L | 47 | −2.960 | −5.530 | −37.695 | 1.00 | 5.28 | L |
| ATOM | 1607 C | LEU | L | 47 | −3.298 | −4.949 | −33.224 | 1.00 | 6.82 | L |
| ATOM | 1608 O | LEU | L | 47 | −4.347 | −5.457 | −32.860 | 1.00 | 6.11 | L |
| ATOM | 1609 N | ILE | L | 48 | −2.263 | −4.732 | −32.417 | 1.00 | 7.58 | L |
| ATOM | 1610 CA | ILE | L | 48 | −2.261 | −5.145 | −31.015 | 1.00 | 7.30 | L |
| ATOM | 1611 CB | ILE | L | 48 | −1.351 | −6.420 | −30.815 | 1.00 | 6.26 | L |
| ATOM | 1612 CG2 | ILE | L | 48 | −1.227 | −6.758 | −29.342 | 1.00 | 2.73 | L |
| ATOM | 1613 CG1 | ILE | L | 48 | −1.879 | −7.611 | −31.641 | 1.00 | 3.91 | L |
| ATOM | 1614 CD1 | ILE | L | 48 | −3.265 | −8.085 | −31.244 | 1.00 | 5.88 | L |
| ATOM | 1615 C | ILE | L | 48 | −1.709 | −4.047 | −30.119 | 1.00 | 9.05 | L |
| ATOM | 1616 O | ILE | L | 48 | −0.800 | −3.313 | −30.513 | 1.00 | 9.25 | L |
| ATOM | 1617 N | TYR | L | 49 | −2.267 | −3.930 | −28.918 | 1.00 | 9.07 | L |
| ATOM | 1618 CA | TYR | L | 49 | −1.796 | −2.955 | −27.936 | 1.00 | 7.79 | L |
| ATOM | 1619 CB | TYR | L | 49 | −2.663 | −1.698 | −27.928 | 1.00 | 8.17 | L |
| ATOM | 1620 CG | TYR | L | 49 | −4.122 | −1.920 | −27.631 | 1.00 | 8.50 | L |
| ATOM | 1621 CD1 | TYR | L | 49 | −4.986 | −2.388 | −28.610 | 1.00 | 8.58 | L |
| ATOM | 1622 CE1 | TYR | L | 49 | −6.343 | −2.525 | −28.351 | 1.00 | 9.02 | L |
| ATOM | 1623 CD2 | TYR | L | 49 | −4.650 | −1.604 | −26.383 | 1.00 | 6.91 | L |
| ATOM | 1624 CE2 | TYR | L | 49 | −6.000 | −1.739 | −26.117 | 1.00 | 5.94 | L |
| ATOM | 1625 CZ | TYR | L | 49 | −6.843 | −2.194 | −27.102 | 1.00 | 7.73 | L |
| ATOM | 1626 OH | TYR | L | 49 | −8.196 | −2.299 | −26.855 | 1.00 | 8.78 | L |
| ATOM | 1627 C | TYR | L | 49 | −1.884 | −3.647 | −26.586 | 1.00 | 8.45 | L |
| ATOM | 1628 O | TYR | L | 49 | −2.469 | −4.723 | −26.476 | 1.00 | 7.21 | L |
| ATOM | 1629 N | ALA | L | 50 | −1.306 | −3.042 | −25.556 | 1.00 | 8.94 | L |
| ATOM | 1630 CA | ALA | L | 50 | −1.332 | −3.661 | −24.243 | 1.00 | 10.42 | L |
| ATOM | 1631 CB | ALA | L | 50 | −2.751 | −3.633 | −23.674 | 1.00 | 10.58 | L |
| ATOM | 1632 C | ALA | L | 50 | −0.837 | −5.114 | −24.366 | 1.00 | 11.72 | L |
| ATOM | 1633 O | ALA | L | 50 | −1.317 | −6.023 | −23.677 | 1.00 | 12.15 | L |
| ATOM | 1634 N | ALA | L | 51 | 0.117 | −5.322 | −25.273 | 1.00 | 11.70 | L |
| ATOM | 1635 CA | ALA | L | 51 | 0.727 | −6.631 | −25.523 | 1.00 | 9.42 | L |
| ATOM | 1636 CB | ALA | L | 51 | 1.330 | −7.173 | −24.234 | 1.00 | 7.05 | L |
| ATOM | 1637 C | ALA | L | 51 | −0.173 | −7.694 | −26.159 | 1.00 | 9.55 | L |
| ATOM | 1638 O | ALA | L | 51 | 0.275 | −8.458 | −27.015 | 1.00 | 8.26 | L |
| ATOM | 1639 N | SER | L | 52 | −1.439 | −7.753 | −25.763 | 1.00 | 9.60 | L |
| ATOM | 1640 CA | SER | L | 52 | −2.315 | −8.771 | −26.328 | 1.00 | 10.62 | L |
| ATOM | 1641 CB | SER | L | 52 | −2.398 | −9.948 | −25.363 | 1.00 | 10.40 | L |
| ATOM | 1642 OG | SER | L | 52 | −2.708 | −9.513 | −24.050 | 1.00 | 10.76 | L |
| ATOM | 1643 C | SER | L | 52 | −3.735 | −8.345 | −26.704 | 1.00 | 11.70 | L |
| ATOM | 1644 O | SER | L | 52 | −4.538 | −9.179 | −27.112 | 1.00 | 12.32 | L |
| ATOM | 1645 N | SER | L | 53 | −4.063 | −7.070 | −26.542 | 1.00 | 12.45 | L |
| ATOM | 1646 CA | SER | L | 53 | −5.392 | −6.620 | −26.887 | 1.00 | 12.61 | L |
| ATOM | 1647 CB | SER | L | 53 | −5.735 | −5.353 | −26.127 | 1.00 | 12.98 | L |
| ATOM | 1648 OG | SER | L | 53 | −6.024 | −5.669 | −24.770 | 1.00 | 11.76 | L |
| ATOM | 1649 C | SER | L | 53 | −5.434 | −6.384 | −28.380 | 1.00 | 14.27 | L |
| ATOM | 1650 O | SER | L | 53 | −4.563 | −5.711 | −28.961 | 1.00 | 16.33 | L |
| ATOM | 1651 N | LEU | L | 54 | −6.448 | −6.972 | −28.998 | 1.00 | 12.16 | L |
| ATOM | 1652 CA | LEU | L | 54 | −6.631 | −6.882 | −30.426 | 1.00 | 12.45 | L |
| ATOM | 1653 CB | LEU | L | 54 | −7.256 | −8.181 | −30.925 | 1.00 | 12.18 | L |
| ATOM | 1654 CG | LEU | L | 54 | −7.643 | −8.244 | −32.395 | 1.00 | 11.41 | L |
| ATOM | 1655 CD1 | LEU | L | 54 | −6.376 | −8.187 | −33.226 | 1.00 | 14.26 | L |
| ATOM | 1656 CD2 | LEU | L | 54 | −8.408 | −9.519 | −32.662 | 1.00 | 10.12 | L |
| ATOM | 1657 C | LEU | L | 54 | −7.505 | −5.699 | −30.821 | 1.00 | 13.60 | L |
| ATOM | 1658 O | LEU | L | 54 | −8.662 | −5.606 | −30.419 | 1.00 | 16.51 | L |
| ATOM | 1659 N | GLN | L | 55 | −6.944 | −4.798 | −31.616 | 1.00 | 13.48 | L |
| ATOM | 1660 CA | GLN | L | 55 | −7.668 | −3.627 | −32.096 | 1.00 | 14.51 | L |
| ATOM | 1661 CB | GLN | L | 55 | −6.766 | −2.832 | −33.036 | 1.00 | 14.61 | L |
| ATOM | 1662 CG | GLN | L | 55 | −7.487 | −1.838 | −33.930 | 1.00 | 14.24 | L |
| ATOM | 1663 CD | GLN | L | 55 | −8.269 | −0.805 | −33.149 | 1.00 | 12.97 | L |
| ATOM | 1664 OE1 | GLN | L | 55 | −7.943 | −0.504 | −32.002 | 1.00 | 11.02 | L |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1665 NE2 | GLN | L | 55 | −9.292 | −0.236 | −33.777 | 1.00 | 13.96 | L |
| ATOM | 1666 C | GLN | L | 55 | −8.942 | −4.053 | −32.829 | 1.00 | 15.51 | L |
| ATOM | 1667 O | GLN | L | 55 | −8.971 | −5.097 | −33.496 | 1.00 | 16.22 | L |
| ATOM | 1668 N | SER | L | 56 | −9.994 | −3.254 | −32.714 | 1.00 | 15.89 | L |
| ATOM | 1669 CA | SER | L | 56 | −11.232 | −3.609 | −33.386 | 1.00 | 17.33 | L |
| ATOM | 1670 CB | SER | L | 56 | −12.354 | −2.646 | −33.030 | 1.00 | 17.45 | L |
| ATOM | 1671 OG | SER | L | 56 | −13.505 | −2.971 | −33.799 | 1.00 | 20.41 | L |
| ATOM | 1672 C | SER | L | 56 | −11.052 | −3.599 | −34.889 | 1.00 | 17.72 | L |
| ATOM | 1673 O | SER | L | 56 | −10.285 | −2.807 | −35.428 | 1.00 | 18.29 | L |
| ATOM | 1674 N | GLY | L | 57 | −11.779 | −4.477 | −35.566 | 1.00 | 19.09 | L |
| ATOM | 1675 CA | GLY | L | 57 | −11.685 | −4.542 | −37.011 | 1.00 | 19.73 | L |
| ATOM | 1676 C | GLY | L | 57 | −10.493 | −5.311 | −37.551 | 1.00 | 20.28 | L |
| ATOM | 1677 O | GLY | L | 57 | −10.216 | −5.259 | −38.749 | 1.00 | 22.53 | L |
| ATOM | 1678 N | VAL | L | 58 | −9.779 | −6.001 | −36.672 | 1.00 | 20.10 | L |
| ATOM | 1679 CA | VAL | L | 58 | −8.639 | −6.796 | −37.080 | 1.00 | 20.30 | L |
| ATOM | 1680 CB | VAL | L | 58 | −7.386 | −6.488 | −36.211 | 1.00 | 21.32 | L |
| ATOM | 1681 CG1 | VAL | L | 58 | −6.265 | −7.495 | −36.511 | 1.00 | 19.34 | L |
| ATOM | 1682 CG2 | VAL | L | 58 | −6.904 | −5.074 | −36.495 | 1.00 | 19.12 | L |
| ATOM | 1683 C | VAL | L | 58 | −9.009 | −8.264 | −36.925 | 1.00 | 19.94 | L |
| ATOM | 1684 O | VAL | L | 58 | −9.526 | −8.678 | −35.889 | 1.00 | 18.67 | L |
| ATOM | 1685 N | PRO | L | 59 | −8.757 | −9.065 | −37.966 | 1.00 | 21.08 | L |
| ATOM | 1686 CD | PRO | L | 59 | −8.083 | −8.678 | −39.214 | 1.00 | 20.13 | L |
| ATOM | 1687 CA | PRO | L | 59 | −9.054 | −10.500 | −37.963 | 1.00 | 21.74 | L |
| ATOM | 1688 CB | PRO | L | 59 | −8.499 | −10.964 | −39.306 | 1.00 | 21.19 | L |
| ATOM | 1689 CG | PRO | L | 59 | −7.436 | −9.961 | −39.603 | 1.00 | 21.70 | L |
| ATOM | 1690 C | PRO | L | 59 | −8.437 | −11.242 | −36.770 | 1.00 | 22.49 | L |
| ATOM | 1691 O | PRO | L | 59 | −7.299 | −10.991 | −36.380 | 1.00 | 22.11 | L |
| ATOM | 1692 N | SER | L | 60 | −9.207 | −12.164 | −36.207 | 1.00 | 22.49 | L |
| ATOM | 1693 CA | SER | L | 60 | −8.785 | −12.928 | −35.048 | 1.00 | 22.80 | L |
| ATOM | 1694 CB | SER | L | 60 | −9.923 | −13.845 | −34.621 | 1.00 | 25.54 | L |
| ATOM | 1695 OG | SER | L | 60 | −11.097 | −13.085 | −34.367 | 1.00 | 28.03 | L |
| ATOM | 1696 C | SER | L | 60 | −7.510 | −13.747 | −35.223 | 1.00 | 22.02 | L |
| ATOM | 1697 O | SER | L | 60 | −6.896 | −14.162 | −34.227 | 1.00 | 20.07 | L |
| ATOM | 1698 N | ARG | L | 61 | −7.108 | −13.982 | −36.475 | 1.00 | 20.14 | L |
| ATOM | 1699 CA | ARG | L | 61 | −5.897 | −14.768 | −36.735 | 1.00 | 19.34 | L |
| ATOM | 1700 CB | ARG | L | 61 | −5.785 | −15.149 | −38.216 | 1.00 | 19.85 | L |
| ATOM | 1701 CG | ARG | L | 61 | −5.642 | −14.011 | −39.193 | 1.00 | 19.55 | L |
| ATOM | 1702 CD | ARG | L | 61 | −5.201 | −14.557 | −40.548 | 1.00 | 18.85 | L |
| ATOM | 1703 NE | ARG | L | 61 | −4.882 | −13.496 | −41.510 | 1.00 | 18.60 | L |
| ATOM | 1704 CZ | ARG | L | 61 | −5.791 | −12.698 | −42.066 | 1.00 | 18.92 | L |
| ATOM | 1705 NH1 | ARG | L | 61 | −7.071 | −12.843 | −41.760 | 1.00 | 19.33 | L |
| ATOM | 1706 NH2 | ARG | L | 61 | −5.429 | −11.749 | −42.918 | 1.00 | 17.42 | L |
| ATOM | 1707 C | ARG | L | 61 | −4.611 | −14.073 | −36.265 | 1.00 | 18.31 | L |
| ATOM | 1708 O | ARG | L | 61 | −3.560 | −14.716 | −36.123 | 1.00 | 17.76 | L |
| ATOM | 1709 N | PHE | L | 62 | −4.711 | −12.768 | −36.014 | 1.00 | 16.50 | L |
| ATOM | 1710 CA | PHE | L | 62 | −3.591 | −11.994 | −35.502 | 1.00 | 14.82 | L |
| ATOM | 1711 CB | PHE | L | 62 | −3.683 | −10.521 | −35.896 | 1.00 | 13.22 | L |
| ATOM | 1712 CG | PHE | L | 62 | −3.259 | −10.232 | −37.296 | 1.00 | 11.96 | L |
| ATOM | 1713 CD1 | PHE | L | 62 | −4.194 | −10.132 | −38.318 | 1.00 | 11.33 | L |
| ATOM | 1714 CD2 | PHE | L | 62 | −1.914 | −10.060 | −37.597 | 1.00 | 12.51 | L |
| ATOM | 1715 CE1 | PHE | L | 62 | −3.789 | −9.860 | −39.635 | 1.00 | 12.01 | L |
| ATOM | 1716 CE2 | PHE | L | 62 | −1.494 | −9.789 | −38.906 | 1.00 | 12.70 | L |
| ATOM | 1717 CZ | PHE | L | 62 | −2.433 | −9.688 | −39.929 | 1.00 | 11.60 | L |
| ATOM | 1718 C | PHE | L | 62 | −3.708 | −12.094 | −33.996 | 1.00 | 15.02 | L |
| ATOM | 1719 O | PHE | L | 62 | −4.782 | −11.897 | −33.425 | 1.00 | 14.54 | L |
| ATOM | 1720 N | SER | L | 63 | −2.603 | −12.404 | −33.345 | 1.00 | 14.08 | L |
| ATOM | 1721 CA | SER | L | 63 | −2.637 | −12.535 | −31.907 | 1.00 | 13.29 | L |
| ATOM | 1722 CB | SER | L | 63 | −2.785 | −14.020 | −31.547 | 1.00 | 13.93 | L |
| ATOM | 1723 OG | SER | L | 63 | −2.372 | −14.294 | −30.217 | 1.00 | 19.30 | L |
| ATOM | 1724 C | SER | L | 63 | −1.341 | −11.975 | −31.373 | 1.00 | 12.67 | L |
| ATOM | 1725 O | SER | L | 63 | −0.377 | −11.831 | −32.122 | 1.00 | 12.77 | L |
| ATOM | 1726 N | GLY | L | 64 | −1.313 | −11.666 | −30.082 | 1.00 | 11.59 | L |
| ATOM | 1727 CA | GLY | L | 64 | −0.103 | −11.137 | −29.493 | 1.00 | 11.87 | L |
| ATOM | 1728 C | GLY | L | 64 | 0.019 | −11.587 | −28.068 | 1.00 | 12.34 | L |
| ATOM | 1729 O | GLY | L | 64 | −0.988 | −11.691 | −27.376 | 1.00 | 12.02 | L |
| ATOM | 1730 N | SER | L | 65 | 1.242 | −11.885 | −27.638 | 1.00 | 14.21 | L |
| ATOM | 1731 CA | SER | L | 65 | 1.481 | −12.309 | −26.263 | 1.00 | 15.67 | L |
| ATOM | 1732 CB | SER | L | 65 | 1.411 | −13.821 | −26.144 | 1.00 | 17.02 | L |
| ATOM | 1733 OG | SER | L | 65 | 2.436 | −14.431 | −26.905 | 1.00 | 21.04 | L |
| ATOM | 1734 C | SER | L | 65 | 2.855 | −11.853 | −25.844 | 1.00 | 15.90 | L |
| ATOM | 1735 O | SER | L | 65 | 3.612 | −11.325 | −26.653 | 1.00 | 17.42 | L |
| ATOM | 1736 N | GLY | L | 66 | 3.173 | −12.074 | −24.576 | 1.00 | 15.84 | L |
| ATOM | 1737 CA | GLY | L | 66 | 4.464 | −11.678 | −24.061 | 1.00 | 15.61 | L |
| ATOM | 1738 C | GLY | L | 66 | 4.338 | −10.874 | −22.793 | 1.00 | 16.12 | L |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 1739 O | GLY | L | 66 | 3.241 | −10.464 | −22.407 | 1.00 | 16.35 | L |
| ATOM | 1740 N | SER | L | 67 | 5.467 | −10.649 | −22.134 | 1.00 | 17.61 | L |
| ATOM | 1741 CA | SER | L | 67 | 5.458 | −9.888 | −20.898 | 1.00 | 18.73 | L |
| ATOM | 1742 CB | SER | L | 67 | 4.733 | −10.686 | −19.817 | 1.00 | 19.61 | L |
| ATOM | 1743 OG | SER | L | 67 | 4.853 | −10.060 | −18.555 | 1.00 | 24.17 | L |
| ATOM | 1744 C | SER | L | 67 | 6.866 | −9.572 | −20.441 | 1.00 | 18.10 | L |
| ATOM | 1745 O | SER | L | 67 | 7.790 | −10.352 | −20.666 | 1.00 | 19.07 | L |
| ATOM | 1746 N | GLY | L | 68 | 7.023 | −8.430 | −19.786 | 1.00 | 16.86 | L |
| ATOM | 1747 CA | GLY | L | 68 | 8.331 | −8.055 | −19.293 | 1.00 | 15.58 | L |
| ATOM | 1748 C | GLY | L | 68 | 9.251 | −7.559 | −20.389 | 1.00 | 14.93 | L |
| ATOM | 1749 O | GLY | L | 68 | 9.273 | −6.371 | −20.712 | 1.00 | 15.09 | L |
| ATOM | 1750 N | THR | L | 69 | 10.003 | −8.474 | −20.983 | 1.00 | 14.58 | L |
| ATOM | 1751 CA | THR | L | 69 | 10.932 | −8.101 | −22.042 | 1.00 | 13.89 | L |
| ATOM | 1752 CB | THR | L | 69 | 12.358 | −8.443 | −21.664 | 1.00 | 12.62 | L |
| ATOM | 1753 OG1 | THR | L | 69 | 12.695 | −7.784 | −20.444 | 1.00 | 11.61 | L |
| ATOM | 1754 CG2 | THR | L | 69 | 13.309 | −7.978 | −22.739 | 1.00 | 14.73 | L |
| ATOM | 1755 C | THR | L | 69 | 10.695 | −8.740 | −23.398 | 1.00 | 14.85 | L |
| ATOM | 1756 O | THR | L | 69 | 11.043 | −8.165 | −24.421 | 1.00 | 15.44 | L |
| ATOM | 1757 N | GLU | L | 70 | 10.142 | −9.941 | −23.419 | 1.00 | 15.79 | L |
| ATOM | 1758 CA | GLU | L | 70 | 9.921 | −10.589 | −24.698 | 1.00 | 17.69 | L |
| ATOM | 1759 CB | GLU | L | 70 | 10.551 | −11.987 | −24.706 | 1.00 | 19.10 | L |
| ATOM | 1760 CG | GLU | L | 70 | 10.379 | −12.728 | −26.021 | 1.00 | 22.22 | L |
| ATOM | 1761 CD | GLU | L | 70 | 10.928 | −14.127 | −25.957 | 1.00 | 24.82 | L |
| ATOM | 1762 OE1 | GLU | L | 70 | 10.358 | −14.952 | −25.217 | 1.00 | 27.80 | L |
| ATOM | 1763 OE2 | GLU | L | 70 | 11.933 | −14.412 | −26.643 | 1.00 | 27.03 | L |
| ATOM | 1764 C | GLU | L | 70 | 8.435 | −10.656 | −25.035 | 1.00 | 17.15 | L |
| ATOM | 1765 O | GLU | L | 70 | 7.623 | −11.105 | −24.218 | 1.00 | 16.60 | L |
| ATOM | 1766 N | PHE | L | 71 | 8.105 | −10.191 | −26.245 | 1.00 | 15.52 | L |
| ATOM | 1767 CA | PHE | L | 71 | 6.739 | −10.141 | −26.776 | 1.00 | 12.84 | L |
| ATOM | 1768 CB | PHE | L | 71 | 6.292 | −8.694 | −26.866 | 1.00 | 9.40 | L |
| ATOM | 1769 CG | PHE | L | 71 | 6.236 | −8.024 | −25.544 | 1.00 | 9.01 | L |
| ATOM | 1770 CD1 | PHE | L | 71 | 5.043 | −7.994 | −24.816 | 1.00 | 6.35 | L |
| ATOM | 1771 CD2 | PHE | L | 71 | 7.395 | −7.470 | −24.988 | 1.00 | 7.48 | L |
| ATOM | 1772 CE1 | PHE | L | 71 | 5.002 | −7.423 | −23.552 | 1.00 | 7.02 | L |
| ATOM | 1773 CE2 | PHE | L | 71 | 7.368 | −6.895 | −23.721 | 1.00 | 8.02 | L |
| ATOM | 1774 CZ | PHE | L | 71 | 6.168 | −6.867 | −22.990 | 1.00 | 7.39 | L |
| ATOM | 1775 C | PHE | L | 71 | 6.688 | −10.771 | −28.153 | 1.00 | 13.30 | L |
| ATOM | 1776 O | PHE | L | 71 | 7.689 | −10.812 | −28.857 | 1.00 | 14.78 | L |
| ATOM | 1777 N | THR | L | 72 | 5.522 | −11.252 | −28.552 | 1.00 | 11.72 | L |
| ATOM | 1778 CA | THR | L | 72 | 5.449 | −11.884 | −29.837 | 1.00 | 12.93 | L |
| ATOM | 1779 CB | THR | L | 72 | 5.851 | −13.382 | −29.677 | 1.00 | 13.79 | L |
| ATOM | 1780 OG1 | THR | L | 72 | 5.871 | −14.029 | −30.955 | 1.00 | 16.29 | L |
| ATOM | 1781 CG2 | THR | L | 72 | 4.884 | −14.093 | −28.750 | 1.00 | 14.12 | L |
| ATOM | 1782 C | THR | L | 72 | 4.112 | −11.732 | −30.578 | 1.00 | 14.12 | L |
| ATOM | 1783 O | THR | L | 72 | 3.017 | −11.877 | −30.004 | 1.00 | 13.32 | L |
| ATOM | 1784 N | LEU | L | 73 | 4.223 | −11.418 | −31.868 | 1.00 | 13.71 | L |
| ATOM | 1785 CA | LEU | L | 73 | 3.068 | −11.240 | −32.746 | 1.00 | 13.61 | L |
| ATOM | 1786 CB | LEU | L | 73 | 3.288 | −10.048 | −33.681 | 1.00 | 13.61 | L |
| ATOM | 1787 CG | LEU | L | 73 | 2.285 | −9.831 | −34.820 | 1.00 | 12.11 | L |
| ATOM | 1788 CD1 | LEU | L | 73 | 0.937 | −9.387 | −34.247 | 1.00 | 11.81 | L |
| ATOM | 1789 CD2 | LEU | L | 73 | 2.831 | −8.780 | −35.766 | 1.00 | 11.75 | L |
| ATOM | 1790 C | LEU | L | 73 | 2.940 | −12.500 | −33.577 | 1.00 | 13.74 | L |
| ATOM | 1791 O | LEU | L | 73 | 3.887 | −12.902 | −34.252 | 1.00 | 14.87 | L |
| ATOM | 1792 N | THR | L | 74 | 1.773 | −13.124 | −33.531 | 1.00 | 13.00 | L |
| ATOM | 1793 CA | THR | L | 74 | 1.554 | −14.347 | −34.285 | 1.00 | 12.76 | L |
| ATOM | 1794 CB | THR | L | 74 | 1.182 | −15.517 | −33.337 | 1.00 | 11.52 | L |
| ATOM | 1795 OG1 | THR | L | 74 | 2.251 | −15.739 | −32.410 | 1.00 | 9.59 | L |
| ATOM | 1796 CG2 | THR | L | 74 | 0.942 | −16.779 | −34.112 | 1.00 | 11.42 | L |
| ATOM | 1797 C | THR | L | 74 | 0.431 | −14.157 | −35.302 | 1.00 | 14.52 | L |
| ATOM | 1798 O | THR | L | 74 | −0.611 | −13.566 | −34.999 | 1.00 | 13.39 | L |
| ATOM | 1799 N | ILE | L | 75 | 0.655 | −14.664 | −36.507 | 1.00 | 16.24 | L |
| ATOM | 1800 CA | ILE | L | 75 | −0.324 | −14.575 | −37.575 | 1.00 | 19.83 | L |
| ATOM | 1801 CB | ILE | L | 75 | 0.263 | −13.885 | −38.825 | 1.00 | 19.67 | L |
| ATOM | 1802 CG2 | ILE | L | 75 | −0.818 | −13.745 | −39.902 | 1.00 | 18.59 | L |
| ATOM | 1803 CG1 | ILE | L | 75 | 0.850 | −12.533 | −38.437 | 1.00 | 19.11 | L |
| ATOM | 1804 CD1 | ILE | L | 75 | 1.501 | −11.807 | −39.572 | 1.00 | 17.61 | L |
| ATOM | 1805 C | ILE | L | 75 | −0.678 | −16.002 | −37.944 | 1.00 | 21.94 | L |
| ATOM | 1806 O | ILE | L | 75 | 0.164 | −16.729 | −38.452 | 1.00 | 24.70 | L |
| ATOM | 1807 N | SER | L | 76 | −1.914 | −16.408 | −37.713 | 1.00 | 23.66 | L |
| ATOM | 1808 CA | SER | L | 76 | −2.287 | −17.778 | −38.016 | 1.00 | 26.41 | L |
| ATOM | 1809 CB | SER | L | 76 | −3.609 | −18.105 | −37.334 | 1.00 | 26.86 | L |
| ATOM | 1810 OG | SER | L | 76 | −3.430 | −18.113 | −35.939 | 1.00 | 28.66 | L |
| ATOM | 1811 C | SER | L | 76 | −2.358 | −18.135 | −39.491 | 1.00 | 27.72 | L |
| ATOM | 1812 O | SER | L | 76 | −1.348 | −18.468 | −40.109 | 1.00 | 26.56 | L |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 1813 | N | SER | L | 77 | −3.563 | −18.071 | −40.048 | 1.00 | 29.97 | L |
| ATOM | 1814 | CA | SER | L | 77 | −3.790 | −18.392 | −41.458 | 1.00 | 31.58 | L |
| ATOM | 1815 | CB | SER | L | 77 | −5.293 | −18.554 | −41.711 | 1.00 | 33.53 | L |
| ATOM | 1816 | OG | SER | L | 77 | −5.886 | −19.442 | −40.766 | 1.00 | 35.88 | L |
| ATOM | 1817 | C | SER | L | 77 | −3.240 | −17.287 | −42.368 | 1.00 | 30.85 | L |
| ATOM | 1818 | O | SER | L | 77 | −3.999 | −16.466 | −42.864 | 1.00 | 30.63 | L |
| ATOM | 1819 | N | LEU | L | 78 | −1.928 | −17.278 | −42.596 | 1.00 | 30.53 | L |
| ATOM | 1820 | CA | LEU | L | 78 | −1.301 | −16.258 | −43.429 | 1.00 | 30.15 | L |
| ATOM | 1821 | CB | LEU | L | 78 | 0.170 | −16.605 | −43.668 | 1.00 | 28.83 | L |
| ATOM | 1822 | CG | LEU | L | 78 | 1.088 | −15.437 | −44.047 | 1.00 | 28.76 | L |
| ATOM | 1823 | CD1 | LEU | L | 78 | 1.268 | −14.518 | −42.853 | 1.00 | 28.55 | L |
| ATOM | 1824 | CD2 | LEU | L | 78 | 2.440 | −15.956 | −44.511 | 1.00 | 28.72 | L |
| ATOM | 1825 | C | LEU | L | 78 | −2.015 | −16.083 | −44.765 | 1.00 | 31.57 | L |
| ATOM | 1826 | O | LEU | L | 78 | −2.232 | −17.044 | −45.496 | 1.00 | 32.52 | L |
| ATOM | 1827 | N | GLN | L | 79 | −2.393 | −14.850 | −45.079 | 1.00 | 32.63 | L |
| ATOM | 1828 | CA | GLN | L | 79 | −3.073 | −14.576 | −46.335 | 1.00 | 33.55 | L |
| ATOM | 1829 | CB | GLN | L | 79 | −4.296 | −13.709 | −46.086 | 1.00 | 33.63 | L |
| ATOM | 1830 | CG | GLN | L | 79 | −5.243 | −14.244 | −45.029 | 1.00 | 35.38 | L |
| ATOM | 1831 | CD | GLN | L | 79 | −5.963 | −15.507 | −45.450 | 1.00 | 36.55 | L |
| ATOM | 1832 | OE1 | GLN | L | 79 | −6.674 | −15.531 | −46.457 | 1.00 | 38.30 | L |
| ATOM | 1833 | NE2 | GLN | L | 79 | −5.796 | −16.564 | −44.668 | 1.00 | 37.18 | L |
| ATOM | 1834 | C | GLN | L | 79 | −2.125 | −13.863 | −47.304 | 1.00 | 34.40 | L |
| ATOM | 1835 | O | GLN | L | 79 | −1.092 | −13.315 | −46.905 | 1.00 | 33.83 | L |
| ATOM | 1836 | N | PRO | L | 80 | −2.473 | −13.850 | −48.596 | 1.00 | 34.60 | L |
| ATOM | 1837 | CD | PRO | L | 80 | −3.736 | −14.323 | −49.186 | 1.00 | 34.49 | L |
| ATOM | 1838 | CA | PRO | L | 80 | −1.641 | −13.202 | −49.611 | 1.00 | 34.81 | L |
| ATOM | 1839 | CB | PRO | L | 80 | −2.377 | −13.516 | −50.901 | 1.00 | 35.12 | L |
| ATOM | 1840 | CG | PRO | L | 80 | −3.816 | −13.495 | −50.448 | 1.00 | 35.60 | L |
| ATOM | 1841 | C | PRO | L | 80 | −1.511 | −11.705 | −49.383 | 1.00 | 34.93 | L |
| ATOM | 1842 | O | PRO | L | 80 | −0.559 | −11.091 | −49.858 | 1.00 | 36.49 | L |
| ATOM | 1843 | N | GLU | L | 81 | −2.466 | −11.119 | −48.663 | 1.00 | 34.01 | L |
| ATOM | 1844 | CA | GLU | L | 81 | −2.442 | −9.687 | −48.386 | 1.00 | 32.18 | L |
| ATOM | 1845 | CB | GLU | L | 81 | −3.841 | −9.089 | −48.569 | 1.00 | 33.65 | L |
| ATOM | 1846 | CG | GLU | L | 81 | −4.969 | −10.115 | −48.665 | 1.00 | 36.06 | L |
| ATOM | 1847 | CD | GLU | L | 81 | −5.402 | −10.622 | −47.322 | 1.00 | 36.33 | L |
| ATOM | 1848 | OE1 | GLU | L | 81 | −6.230 | −11.567 | −47.274 | 1.00 | 35.64 | L |
| ATOM | 1849 | OE2 | GLU | L | 81 | −4.908 | −10.059 | −46.320 | 1.00 | 37.30 | L |
| ATOM | 1850 | C | GLU | L | 81 | −1.885 | −9.342 | −47.007 | 1.00 | 30.05 | L |
| ATOM | 1851 | O | GLU | L | 81 | −1.886 | −8.182 | −46.611 | 1.00 | 30.43 | L |
| ATOM | 1852 | N | ASP | L | 82 | −1.403 | −10.354 | −46.291 | 1.00 | 27.93 | L |
| ATOM | 1853 | CA | ASP | L | 82 | −0.807 | −10.142 | −44.985 | 1.00 | 26.19 | L |
| ATOM | 1854 | CB | ASP | L | 82 | −0.855 | −11.425 | −44.150 | 1.00 | 26.09 | L |
| ATOM | 1855 | CG | ASP | L | 82 | −2.219 | −11.665 | −43.540 | 1.00 | 26.98 | L |
| ATOM | 1856 | OD1 | ASP | L | 82 | −3.016 | −10.704 | −43.500 | 1.00 | 27.12 | L |
| ATOM | 1857 | OD2 | ASP | L | 82 | −2.498 | −12.799 | −43.086 | 1.00 | 26.87 | L |
| ATOM | 1858 | C | ASP | L | 82 | 0.639 | −9.684 | −45.164 | 1.00 | 25.38 | L |
| ATOM | 1859 | O | ASP | L | 82 | 1.377 | −9.507 | −44.191 | 1.00 | 25.53 | L |
| ATOM | 1860 | N | PHE | L | 83 | 1.034 | −9.513 | −46.423 | 1.00 | 24.11 | L |
| ATOM | 1861 | CA | PHE | L | 83 | 2.373 | −9.055 | −46.791 | 1.00 | 22.21 | L |
| ATOM | 1862 | CB | PHE | L | 83 | 2.555 | −9.135 | −48.304 | 1.00 | 24.70 | L |
| ATOM | 1863 | CG | PHE | L | 83 | 3.496 | −8.112 | −48.854 | 1.00 | 27.07 | L |
| ATOM | 1864 | CD1 | PHE | L | 83 | 4.852 | −8.143 | −48.535 | 1.00 | 29.04 | L |
| ATOM | 1865 | CD2 | PHE | L | 83 | 3.021 | −7.095 | −49.676 | 1.00 | 27.98 | L |
| ATOM | 1866 | CE1 | PHE | L | 83 | 5.729 | −7.169 | −49.031 | 1.00 | 29.51 | L |
| ATOM | 1867 | CE2 | PHE | L | 83 | 3.885 | −6.115 | −50.179 | 1.00 | 28.81 | L |
| ATOM | 1868 | CZ | PHE | L | 83 | 5.245 | −6.150 | −49.856 | 1.00 | 28.92 | L |
| ATOM | 1869 | C | PHE | L | 83 | 2.539 | −7.611 | −46.345 | 1.00 | 19.13 | L |
| ATOM | 1870 | O | PHE | L | 83 | 1.738 | −6.748 | −46.694 | 1.00 | 17.37 | L |
| ATOM | 1871 | N | ALA | L | 84 | 3.586 | −7.348 | −45.577 | 1.00 | 17.11 | L |
| ATOM | 1872 | CA | ALA | L | 84 | 3.829 | −5.998 | −45.083 | 1.00 | 14.54 | L |
| ATOM | 1873 | CB | ALA | L | 84 | 2.576 | −5.475 | −44.393 | 1.00 | 14.75 | L |
| ATOM | 1874 | C | ALA | L | 84 | 4.990 | −5.969 | −44.109 | 1.00 | 12.00 | L |
| ATOM | 1875 | O | ALA | L | 84 | 5.614 | −6.993 | −43.853 | 1.00 | 11.20 | L |
| ATOM | 1876 | N | THR | L | 85 | 5.287 | −4.787 | −43.580 | 1.00 | 10.99 | L |
| ATOM | 1877 | CA | THR | L | 85 | 6.343 | −4.662 | −42.576 | 1.00 | 9.98 | L |
| ATOM | 1878 | CB | THR | L | 85 | 7.239 | −3.431 | −42.768 | 1.00 | 10.55 | L |
| ATOM | 1879 | OG1 | THR | L | 85 | 7.894 | −3.485 | −44.042 | 1.00 | 12.19 | L |
| ATOM | 1880 | CG2 | THR | L | 85 | 8.290 | −3.401 | −41.656 | 1.00 | 9.30 | L |
| ATOM | 1881 | C | THR | L | 85 | 5.623 | −4.495 | −41.241 | 1.00 | 8.43 | L |
| ATOM | 1882 | O | THR | L | 85 | 4.729 | −3.673 | −41.120 | 1.00 | 6.48 | L |
| ATOM | 1883 | N | TYR | L | 86 | 5.997 | −5.306 | −40.259 | 1.00 | 8.48 | L |
| ATOM | 1884 | CA | TYR | L | 86 | 5.391 | −5.245 | −38.949 | 1.00 | 7.21 | L |
| ATOM | 1885 | CB | TYR | L | 86 | 5.028 | −6.649 | −38.460 | 1.00 | 6.82 | L |
| ATOM | 1886 | CG | TYR | L | 86 | 3.949 | −7.290 | −39.306 | 1.00 | 6.34 | L |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 1887 | CD1 | TYR | L | 86 | 4.243 | −7.762 | −40.588 | 1.00 | 6.20 | L |
| ATOM | 1888 | CE1 | TYR | L | 86 | 3.253 | −8.227 | −41.429 | 1.00 | 6.26 | L |
| ATOM | 1889 | CD2 | TYR | L | 86 | 2.617 | −7.319 | −38.877 | 1.00 | 4.76 | L |
| ATOM | 1890 | CE2 | TYR | L | 86 | 1.602 | −7.785 | −39.714 | 1.00 | 5.10 | L |
| ATOM | 1891 | CZ | TYR | L | 86 | 1.929 | −8.236 | −40.996 | 1.00 | 7.14 | L |
| ATOM | 1892 | OH | TYR | L | 86 | 0.941 | −8.659 | −41.866 | 1.00 | 6.72 | L |
| ATOM | 1893 | C | TYR | L | 86 | 6.373 | −4.579 | −37.995 | 1.00 | 7.26 | L |
| ATOM | 1894 | O | TYR | L | 86 | 7.579 | −4.870 | −38.005 | 1.00 | 4.91 | L |
| ATOM | 1895 | N | TYR | L | 87 | 5.845 | −3.677 | −37.174 | 1.00 | 6.41 | L |
| ATOM | 1896 | CA | TYR | L | 87 | 6.652 | −2.933 | −36.225 | 1.00 | 7.18 | L |
| ATOM | 1897 | CB | TYR | L | 87 | 6.676 | −1.444 | −36.575 | 1.00 | 8.52 | L |
| ATOM | 1898 | CG | TYR | L | 87 | 7.429 | −1.033 | −37.814 | 1.00 | 8.46 | L |
| ATOM | 1899 | CD1 | TYR | L | 87 | 6.774 | −0.864 | −39.030 | 1.00 | 9.06 | L |
| ATOM | 1900 | CE1 | TYR | L | 87 | 7.469 | −0.430 | −40.166 | 1.00 | 9.29 | L |
| ATOM | 1901 | CD2 | TYR | L | 87 | 8.800 | −0.765 | −37.761 | 1.00 | 8.75 | L |
| ATOM | 1902 | CE2 | TYR | L | 87 | 9.497 | −0.336 | −38.887 | 1.00 | 8.41 | L |
| ATOM | 1903 | CZ | TYR | L | 87 | 8.831 | −0.172 | −40.080 | 1.00 | 8.83 | L |
| ATOM | 1904 | OH | TYR | L | 87 | 9.539 | 0.236 | −41.185 | 1.00 | 11.80 | L |
| ATOM | 1905 | C | TYR | L | 87 | 6.099 | −3.031 | −34.825 | 1.00 | 7.93 | L |
| ATOM | 1906 | O | TYR | L | 87 | 4.885 | −2.992 | −34.632 | 1.00 | 7.55 | L |
| ATOM | 1907 | N | CYS | L | 88 | 6.977 | −3.152 | −33.840 | 1.00 | 8.98 | L |
| ATOM | 1908 | CA | CYS | L | 88 | 6.499 | −3.166 | −32.469 | 1.00 | 11.08 | L |
| ATOM | 1909 | C | CYS | L | 88 | 6.912 | −1.822 | −31.879 | 1.00 | 9.49 | L |
| ATOM | 1910 | O | CYS | L | 88 | 7.922 | −1.246 | −32.288 | 1.00 | 8.19 | L |
| ATOM | 1911 | CB | CYS | L | 88 | 7.086 | −4.336 | −31.669 | 1.00 | 13.87 | L |
| ATOM | 1912 | SG | CYS | L | 88 | 8.894 | −4.471 | −31.607 | 1.00 | 20.10 | L |
| ATOM | 1913 | N | GLN | L | 89 | 6.116 | −1.308 | −30.948 | 1.00 | 7.20 | L |
| ATOM | 1914 | CA | GLN | L | 89 | 6.407 | −0.018 | −30.327 | 1.00 | 6.74 | L |
| ATOM | 1915 | CB | GLN | L | 89 | 5.560 | 1.069 | −31.001 | 1.00 | 6.69 | L |
| ATOM | 1916 | CG | GLN | L | 89 | 5.789 | 2.460 | −30.496 | 1.00 | 6.01 | L |
| ATOM | 1917 | CD | GLN | L | 89 | 4.544 | 3.052 | −29.902 | 1.00 | 6.62 | L |
| ATOM | 1918 | OE1 | GLN | L | 89 | 3.475 | 3.034 | −30.516 | 1.00 | 7.04 | L |
| ATOM | 1919 | NE2 | GLN | L | 89 | 4.669 | 3.591 | −28.699 | 1.00 | 6.50 | L |
| ATOM | 1920 | C | GLN | L | 89 | 6.122 | −0.056 | −28.827 | 1.00 | 6.25 | L |
| ATOM | 1921 | O | GLN | L | 89 | 5.090 | −0.584 | −28.414 | 1.00 | 6.91 | L |
| ATOM | 1922 | N | GLN | L | 90 | 7.033 | 0.467 | −28.002 | 1.00 | 4.40 | L |
| ATOM | 1923 | CA | GLN | L | 90 | 6.784 | 0.480 | −26.556 | 1.00 | 2.66 | L |
| ATOM | 1924 | CB | GLN | L | 90 | 8.018 | 0.016 | −25.758 | 1.00 | 2.41 | L |
| ATOM | 1925 | CG | GLN | L | 90 | 9.279 | 0.918 | −25.727 | 1.00 | 1.00 | L |
| ATOM | 1926 | CD | GLN | L | 90 | 9.148 | 2.183 | −24.860 | 1.00 | 1.97 | L |
| ATOM | 1927 | OE1 | GLN | L | 90 | 8.495 | 2.190 | −23.802 | 1.00 | 1.00 | L |
| ATOM | 1928 | NE2 | GLN | L | 90 | 9.788 | 3.262 | −25.311 | 1.00 | 1.00 | L |
| ATOM | 1929 | C | GLN | L | 90 | 6.359 | 1.865 | −26.082 | 1.00 | 3.53 | L |
| ATOM | 1930 | O | GLN | L | 90 | 6.774 | 2.889 | −26.635 | 1.00 | 1.89 | L |
| ATOM | 1931 | N | TYR | L | 91 | 5.507 | 1.893 | −25.068 | 1.00 | 4.57 | L |
| ATOM | 1932 | CA | TYR | L | 91 | 5.053 | 3.153 | −24.516 | 1.00 | 5.80 | L |
| ATOM | 1933 | CB | TYR | L | 91 | 3.646 | 3.498 | −25.013 | 1.00 | 5.04 | L |
| ATOM | 1934 | CG | TYR | L | 91 | 2.594 | 2.439 | −24.830 | 1.00 | 3.81 | L |
| ATOM | 1935 | CD1 | TYR | L | 91 | 1.726 | 2.476 | −23.745 | 1.00 | 2.40 | L |
| ATOM | 1936 | CE1 | TYR | L | 91 | 0.722 | 1.522 | −23.601 | 1.00 | 3.37 | L |
| ATOM | 1937 | CD2 | TYR | L | 91 | 2.438 | 1.418 | −25.774 | 1.00 | 4.35 | L |
| ATOM | 1938 | CE2 | TYR | L | 91 | 1.433 | 0.450 | −25.643 | 1.00 | 4.21 | L |
| ATOM | 1939 | CZ | TYR | L | 91 | 0.576 | 0.512 | −24.548 | 1.00 | 4.57 | L |
| ATOM | 1940 | OH | TYR | L | 91 | −0.437 | −0.423 | −24.391 | 1.00 | 5.24 | L |
| ATOM | 1941 | C | TYR | L | 91 | 5.106 | 3.122 | −23.001 | 1.00 | 6.62 | L |
| ATOM | 1942 | O | TYR | L | 91 | 4.224 | 3.610 | −22.314 | 1.00 | 6.77 | L |
| ATOM | 1943 | N | HIS | L | 92 | 6.187 | 2.565 | −22.486 | 1.00 | 8.26 | L |
| ATOM | 1944 | CA | HIS | L | 92 | 6.379 | 2.482 | −21.055 | 1.00 | 9.83 | L |
| ATOM | 1945 | CB | HIS | L | 92 | 7.304 | 1.307 | −20.732 | 1.00 | 10.19 | L |
| ATOM | 1946 | CG | HIS | L | 92 | 7.597 | 1.157 | −19.277 | 1.00 | 13.25 | L |
| ATOM | 1947 | CD2 | HIS | L | 92 | 8.751 | 1.290 | −18.579 | 1.00 | 14.04 | L |
| ATOM | 1948 | ND1 | HIS | L | 92 | 6.617 | 0.877 | −18.351 | 1.00 | 15.26 | L |
| ATOM | 1949 | CE1 | HIS | L | 92 | 7.153 | 0.846 | −17.143 | 1.00 | 15.88 | L |
| ATOM | 1950 | NE2 | HIS | L | 92 | 8.446 | 1.095 | −17.254 | 1.00 | 14.69 | L |
| ATOM | 1951 | C | HIS | L | 92 | 6.992 | 3.797 | −20.592 | 1.00 | 9.20 | L |
| ATOM | 1952 | O | HIS | L | 92 | 6.559 | 4.372 | −19.608 | 1.00 | 10.88 | L |
| ATOM | 1953 | N | SER | L | 93 | 8.020 | 4.257 | −21.291 | 1.00 | 9.19 | L |
| ATOM | 1954 | CA | SER | L | 93 | 8.664 | 5.515 | −20.936 | 1.00 | 10.15 | L |
| ATOM | 1955 | CB | SER | L | 93 | 9.917 | 5.274 | −20.075 | 1.00 | 9.91 | L |
| ATOM | 1956 | OG | SER | L | 93 | 10.867 | 4.497 | −20.754 | 1.00 | 9.93 | L |
| ATOM | 1957 | C | SER | L | 93 | 9.037 | 6.274 | −22.212 | 1.00 | 11.08 | L |
| ATOM | 1958 | O | SER | L | 93 | 9.094 | 5.699 | −23.300 | 1.00 | 13.59 | L |
| ATOM | 1959 | N | TYR | L | 94 | 9.258 | 7.575 | −22.080 | 1.00 | 11.16 | L |
| ATOM | 1960 | CA | TYR | L | 94 | 9.645 | 8.405 | −23.207 | 1.00 | 10.67 | L |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 1961 | CB | TYR | L | 94 | 9.220 | 9.831 | −22.952 | 1.00 | 10.20 | L |
| ATOM | 1962 | CG | TYR | L | 94 | 7.750 | 10.031 | −23.055 | 1.00 | 11.98 | L |
| ATOM | 1963 | CD1 | TYR | L | 94 | 7.126 | 10.063 | −24.299 | 1.00 | 13.10 | L |
| ATOM | 1964 | CE1 | TYR | L | 94 | 5.764 | 10.284 | −24.409 | 1.00 | 12.68 | L |
| ATOM | 1965 | CD2 | TYR | L | 94 | 6.970 | 10.214 | −21.913 | 1.00 | 12.34 | L |
| ATOM | 1966 | CE2 | TYR | L | 94 | 5.606 | 10.434 | −22.019 | 1.00 | 11.24 | L |
| ATOM | 1967 | CZ | TYR | L | 94 | 5.017 | 10.473 | −23.272 | 1.00 | 10.97 | L |
| ATOM | 1968 | OH | TYR | L | 94 | 3.683 | 10.752 | −23.393 | 1.00 | 12.39 | L |
| ATOM | 1969 | C | TYR | L | 94 | 11.152 | 8.359 | −23.350 | 1.00 | 10.75 | L |
| ATOM | 1970 | O | TYR | L | 94 | 11.864 | 8.329 | −22.339 | 1.00 | 12.12 | L |
| ATOM | 1971 | N | PRO | L | 95 | 11.659 | 8.378 | −24.599 | 1.00 | 10.12 | L |
| ATOM | 1972 | CD | PRO | L | 95 | 13.096 | 8.523 | −24.881 | 1.00 | 10.42 | L |
| ATOM | 1973 | CA | PRO | L | 95 | 10.891 | 8.452 | −25.845 | 1.00 | 9.23 | L |
| ATOM | 1974 | CB | PRO | L | 95 | 11.939 | 8.828 | −26.890 | 1.00 | 10.36 | L |
| ATOM | 1975 | CG | PRO | L | 95 | 13.074 | 9.396 | −26.088 | 1.00 | 11.18 | L |
| ATOM | 1976 | C | PRO | L | 95 | 10.259 | 7.125 | −26.181 | 1.00 | 9.78 | L |
| ATOM | 1977 | O | PRO | L | 95 | 10.742 | 6.054 | −25.786 | 1.00 | 9.82 | L |
| ATOM | 1978 | N | TRP | L | 96 | 9.171 | 7.189 | −26.926 | 1.00 | 9.66 | L |
| ATOM | 1979 | CA | TRP | L | 96 | 8.516 | 5.961 | −27.329 | 1.00 | 8.38 | L |
| ATOM | 1980 | CB | TRP | L | 96 | 7.080 | 6.265 | −27.733 | 1.00 | 6.22 | L |
| ATOM | 1981 | CG | TRP | L | 96 | 6.222 | 6.675 | −26.553 | 1.00 | 6.85 | L |
| ATOM | 1982 | CD2 | TRP | L | 96 | 4.985 | 7.388 | −26.614 | 1.00 | 5.61 | L |
| ATOM | 1983 | CE2 | TRP | L | 96 | 4.444 | 7.404 | −25.307 | 1.00 | 5.12 | L |
| ATOM | 1984 | CE3 | TRP | L | 96 | 4.276 | 8.003 | −27.649 | 1.00 | 5.94 | L |
| ATOM | 1985 | CD1 | TRP | L | 96 | 6.390 | 6.310 | −25.232 | 1.00 | 5.28 | L |
| ATOM | 1986 | NE1 | TRP | L | 96 | 5.319 | 6.743 | −24.486 | 1.00 | 5.09 | L |
| ATOM | 1987 | CZ2 | TRP | L | 96 | 3.226 | 8.011 | −25.012 | 1.00 | 4.95 | L |
| ATOM | 1988 | CZ3 | TRP | L | 96 | 3.063 | 8.607 | −27.360 | 1.00 | 6.82 | L |
| ATOM | 1989 | CH2 | TRP | L | 96 | 2.546 | 8.603 | −26.045 | 1.00 | 6.87 | L |
| ATOM | 1990 | C | TRP | L | 96 | 9.331 | 5.389 | −28.481 | 1.00 | 7.69 | L |
| ATOM | 1991 | O | TRP | L | 96 | 9.669 | 6.098 | −29.427 | 1.00 | 8.74 | L |
| ATOM | 1992 | N | THR | L | 97 | 9.648 | 4.105 | −28.400 | 1.00 | 6.85 | L |
| ATOM | 1993 | CA | THR | L | 97 | 10.472 | 3.511 | −29.424 | 1.00 | 5.66 | L |
| ATOM | 1994 | CB | THR | L | 97 | 11.755 | 2.906 | −28.839 | 1.00 | 5.83 | L |
| ATOM | 1995 | OG1 | THR | L | 97 | 12.374 | 3.857 | −27.979 | 1.00 | 5.11 | L |
| ATOM | 1996 | CG2 | THR | L | 97 | 12.736 | 2.559 | −29.969 | 1.00 | 9.74 | L |
| ATOM | 1997 | C | THR | L | 97 | 9.827 | 2.448 | −30.254 | 1.00 | 5.70 | L |
| ATOM | 1998 | O | THR | L | 97 | 8.964 | 1.712 | −29.784 | 1.00 | 5.77 | L |
| ATOM | 1999 | N | PHE | L | 98 | 10.268 | 2.377 | −31.503 | 1.00 | 5.71 | L |
| ATOM | 2000 | CA | PHE | L | 98 | 9.779 | 1.385 | −32.417 | 1.00 | 5.89 | L |
| ATOM | 2001 | CB | PHE | L | 98 | 9.439 | 2.032 | −33.739 | 1.00 | 5.15 | L |
| ATOM | 2002 | CG | PHE | L | 98 | 8.181 | 2.801 | −33.716 | 1.00 | 4.13 | L |
| ATOM | 2003 | CD1 | PHE | L | 98 | 8.177 | 4.124 | −33.316 | 1.00 | 5.60 | L |
| ATOM | 2004 | CD2 | PHE | L | 98 | 6.988 | 2.196 | −34.091 | 1.00 | 4.22 | L |
| ATOM | 2005 | CE1 | PHE | L | 98 | 6.989 | 4.857 | −33.293 | 1.00 | 7.42 | L |
| ATOM | 2006 | CE2 | PHE | L | 98 | 5.793 | 2.907 | −34.075 | 1.00 | 6.81 | L |
| ATOM | 2007 | CZ | PHE | L | 98 | 5.789 | 4.244 | −33.673 | 1.00 | 7.48 | L |
| ATOM | 2008 | C | PHE | L | 98 | 10.838 | 0.332 | −32.625 | 1.00 | 7.27 | L |
| ATOM | 2009 | O | PHE | L | 98 | 11.988 | 0.502 | −32.219 | 1.00 | 8.89 | L |
| ATOM | 2010 | N | GLY | L | 99 | 10.434 | −0.780 | −33.218 | 1.00 | 7.92 | L |
| ATOM | 2011 | CA | GLY | L | 99 | 11.389 | −1.824 | −33.490 | 1.00 | 9.17 | L |
| ATOM | 2012 | C | GLY | L | 99 | 11.865 | −1.576 | −34.911 | 1.00 | 9.56 | L |
| ATOM | 2013 | O | GLY | L | 99 | 11.177 | −0.905 | −35.682 | 1.00 | 10.42 | L |
| ATOM | 2014 | N | GLN | L | 100 | 13.028 | −2.109 | −35.267 | 1.00 | 9.40 | L |
| ATOM | 2015 | CA | GLN | L | 100 | 13.551 | −1.937 | −36.604 | 1.00 | 9.59 | L |
| ATOM | 2016 | CB | GLN | L | 100 | 14.878 | −2.691 | −36.751 | 1.00 | 8.63 | L |
| ATOM | 2017 | CG | GLN | L | 100 | 14.688 | −4.183 | −36.949 | 1.00 | 13.79 | L |
| ATOM | 2018 | CD | GLN | L | 100 | 14.906 | −4.984 | −35.693 | 1.00 | 15.52 | L |
| ATOM | 2019 | OE1 | GLN | L | 100 | 14.629 | −4.519 | −34.583 | 1.00 | 16.85 | L |
| ATOM | 2020 | NE2 | GLN | L | 100 | 15.397 | −6.213 | −35.860 | 1.00 | 16.25 | L |
| ATOM | 2021 | C | GLN | L | 100 | 12.527 | −2.468 | −37.621 | 1.00 | 9.72 | L |
| ATOM | 2022 | O | GLN | L | 100 | 12.577 | −2.128 | −38.793 | 1.00 | 11.02 | L |
| ATOM | 2023 | N | GLY | L | 101 | 11.600 | −3.308 | −37.179 | 1.00 | 8.67 | L |
| ATOM | 2024 | CA | GLY | L | 101 | 10.612 | −3.835 | −38.108 | 1.00 | 10.14 | L |
| ATOM | 2025 | C | GLY | L | 101 | 10.929 | −5.179 | −38.768 | 1.00 | 10.68 | L |
| ATOM | 2026 | O | GLY | L | 101 | 12.091 | −5.550 | −38.941 | 1.00 | 10.81 | L |
| ATOM | 2027 | N | THR | L | 102 | 9.882 | −5.907 | −39.145 | 1.00 | 10.02 | L |
| ATOM | 2028 | CA | THR | L | 102 | 10.019 | −7.212 | −39.782 | 1.00 | 10.68 | L |
| ATOM | 2029 | CB | THR | L | 102 | 9.391 | −8.306 | −38.919 | 1.00 | 10.47 | L |
| ATOM | 2030 | OG1 | THR | L | 102 | 10.062 | −8.363 | −37.657 | 1.00 | 12.78 | L |
| ATOM | 2031 | CG2 | THR | L | 102 | 9.482 | −9.642 | −39.605 | 1.00 | 9.34 | L |
| ATOM | 2032 | C | THR | L | 102 | 9.302 | −7.227 | −41.125 | 1.00 | 12.44 | L |
| ATOM | 2033 | O | THR | L | 102 | 8.083 | −7.049 | −41.176 | 1.00 | 12.34 | L |
| ATOM | 2034 | N | LYS | L | 103 | 10.038 | −7.460 | −42.207 | 1.00 | 12.98 | L |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 2035 CA | LYS | L | 103 | 9.422 | −7.471 | −43.528 | 1.00 | 14.84 | L |
| ATOM | 2036 CB | LYS | L | 103 | 10.385 | −6.893 | −44.567 | 1.00 | 15.63 | L |
| ATOM | 2037 CG | LYS | L | 103 | 9.767 | −6.747 | −45.945 | 1.00 | 18.74 | L |
| ATOM | 2038 CD | LYS | L | 103 | 10.845 | −6.785 | −47.009 | 1.00 | 21.41 | L |
| ATOM | 2039 CE | LYS | L | 103 | 10.264 | −6.625 | −48.396 | 1.00 | 22.44 | L |
| ATOM | 2040 NZ | LYS | L | 103 | 9.589 | −5.300 | −48.528 | 1.00 | 23.85 | L |
| ATOM | 2041 C | LYS | L | 103 | 8.974 | −8.871 | −43.943 | 1.00 | 14.71 | L |
| ATOM | 2042 O | LYS | L | 103 | 9.794 | −9.778 | −44.132 | 1.00 | 15.12 | L |
| ATOM | 2043 N | LEU | L | 104 | 7.666 | −9.031 | −44.112 | 1.00 | 14.45 | L |
| ATOM | 2044 CA | LEU | L | 104 | 7.091 | −10.325 | −44.468 | 1.00 | 14.60 | L |
| ATOM | 2045 CB | LEU | L | 104 | 5.972 | −10.670 | −43.481 | 1.00 | 11.99 | L |
| ATOM | 2046 CG | LEU | L | 104 | 5.099 | −11.881 | −43.764 | 1.00 | 11.10 | L |
| ATOM | 2047 CD1 | LEU | L | 104 | 5.932 | −13.135 | −43.663 | 1.00 | 11.33 | L |
| ATOM | 2048 CD2 | LEU | L | 104 | 3.942 | −11.917 | −42.770 | 1.00 | 11.59 | L |
| ATOM | 2049 C | LEU | L | 104 | 6.562 | −10.423 | −45.892 | 1.00 | 15.97 | L |
| ATOM | 2050 O | LEU | L | 104 | 5.579 | −9.775 | −46.258 | 1.00 | 16.90 | L |
| ATOM | 2051 N | GLU | L | 105 | 7.223 | −11.236 | −46.701 | 1.00 | 16.86 | L |
| ATOM | 2052 CA | GLU | L | 105 | 6.762 | −11.411 | −48.063 | 1.00 | 19.59 | L |
| ATOM | 2053 CB | GLU | L | 105 | 7.919 | −11.295 | −49.046 | 1.00 | 20.51 | L |
| ATOM | 2054 CG | GLU | L | 105 | 8.883 | −12.420 | −48.980 | 1.00 | 20.99 | L |
| ATOM | 2055 CD | GLU | L | 105 | 8.948 | −13.134 | −50.299 | 1.00 | 21.61 | L |
| ATOM | 2056 OE1 | GLU | L | 105 | 9.142 | −12.436 | −51.313 | 1.00 | 22.37 | L |
| ATOM | 2057 OE2 | GLU | L | 105 | 8.809 | −14.376 | −50.328 | 1.00 | 21.64 | L |
| ATOM | 2058 C | GLU | L | 105 | 6.094 | −12.771 | −48.168 | 1.00 | 20.32 | L |
| ATOM | 2059 O | GLU | L | 105 | 6.404 | −13.685 | −47.398 | 1.00 | 20.09 | L |
| ATOM | 2060 N | ILE | L | 106 | 5.169 | −12.898 | −49.111 | 1.00 | 21.44 | L |
| ATOM | 2061 CA | ILE | L | 106 | 4.446 | −14.143 | −49.276 | 1.00 | 23.43 | L |
| ATOM | 2062 CB | ILE | L | 106 | 3.028 | −13.889 | −49.771 | 1.00 | 22.83 | L |
| ATOM | 2063 CG2 | ILE | L | 106 | 2.236 | −15.179 | −49.698 | 1.00 | 22.89 | L |
| ATOM | 2064 CG1 | ILE | L | 106 | 2.389 | −12.769 | −48.945 | 1.00 | 20.99 | L |
| ATOM | 2065 CD1 | ILE | L | 106 | 2.379 | −13.024 | −47.451 | 1.00 | 20.39 | L |
| ATOM | 2066 C | ILE | L | 106 | 5.121 | −15.103 | −50.230 | 1.00 | 24.93 | L |
| ATOM | 2067 O | ILE | L | 106 | 5.380 | −14.771 | −51.387 | 1.00 | 24.17 | L |
| ATOM | 2068 N | LYS | L | 107 | 5.409 | −16.296 | −49.722 | 1.00 | 28.03 | L |
| ATOM | 2069 CA | LYS | L | 107 | 6.045 | −17.327 | −50.515 | 1.00 | 30.61 | L |
| ATOM | 2070 CB | LYS | L | 107 | 6.328 | −18.571 | −49.679 | 1.00 | 32.10 | L |
| ATOM | 2071 CG | LYS | L | 107 | 7.301 | −19.534 | −50.336 | 1.00 | 34.09 | L |
| ATOM | 2072 CD | LYS | L | 107 | 8.721 | −19.326 | −49.823 | 1.00 | 36.04 | L |
| ATOM | 2073 CE | LYS | L | 107 | 8.846 | −19.791 | −48.369 | 1.00 | 36.60 | L |
| ATOM | 2074 NZ | LYS | L | 107 | 10.213 | −19.608 | −47.801 | 1.00 | 37.56 | L |
| ATOM | 2075 C | LYS | L | 107 | 5.041 | −17.670 | −51.579 | 1.00 | 31.41 | L |
| ATOM | 2076 O | LYS | L | 107 | 3.827 | −17.614 | −51.373 | 1.00 | 31.92 | L |
| ATOM | 2077 N | ARG | L | 108 | 5.536 | −18.025 | −52.734 | 1.00 | 31.09 | L |
| ATOM | 2078 CA | ARG | L | 108 | 4.608 | −18.351 | −53.773 | 1.00 | 30.67 | L |
| ATOM | 2079 CB | ARG | L | 108 | 4.218 | −17.065 | −54.487 | 1.00 | 29.56 | L |
| ATOM | 2080 CG | ARG | L | 108 | 2.983 | −17.166 | −55.316 | 1.00 | 29.55 | L |
| ATOM | 2081 CD | ARG | L | 108 | 3.044 | −16.154 | −56.428 | 1.00 | 29.00 | L |
| ATOM | 2082 NE | ARG | L | 108 | 3.220 | −16.825 | −57.705 | 1.00 | 30.73 | L |
| ATOM | 2083 CZ | ARG | L | 108 | 2.221 | −17.208 | −58.491 | 1.00 | 31.28 | L |
| ATOM | 2084 NH1 | ARG | L | 108 | 0.967 | −16.966 | −58.125 | 1.00 | 32.82 | L |
| ATOM | 2085 NH2 | ARG | L | 108 | 2.473 | −17.856 | −59.628 | 1.00 | 30.38 | L |
| ATOM | 2086 C | ARG | L | 108 | 5.292 | −19.314 | −54.710 | 1.00 | 30.78 | L |
| ATOM | 2087 O | ARG | L | 108 | 6.516 | −19.477 | −54.662 | 1.00 | 30.73 | L |
| ATOM | 2885 CB | GLN | H | 1 | −17.228 | 9.372 | −41.991 | 1.00 | 38.03 | H |
| ATOM | 2886 CG | GLN | H | 1 | −17.154 | 10.882 | −41.725 | 1.00 | 41.63 | H |
| ATOM | 2887 CD | GLN | H | 1 | −18.494 | 11.453 | −41.221 | 1.00 | 44.22 | H |
| ATOM | 2888 OE1 | GLN | H | 1 | −19.539 | 11.258 | −41.860 | 1.00 | 45.30 | H |
| ATOM | 2889 NE2 | GLN | H | 1 | −18.464 | 12.166 | −40.083 | 1.00 | 44.03 | H |
| ATOM | 2890 C | GLN | H | 1 | −14.757 | 9.019 | −41.817 | 1.00 | 31.13 | H |
| ATOM | 2891 O | GLN | H | 1 | −14.172 | 10.095 | −41.886 | 1.00 | 31.51 | H |
| ATOM | 2892 N | GLN | H | 1 | −16.184 | 7.270 | −42.783 | 1.00 | 34.00 | H |
| ATOM | 2893 CA | GLN | H | 1 | −15.992 | 8.747 | −42.656 | 1.00 | 34.12 | H |
| ATOM | 2894 N | VAL | H | 2 | −14.367 | 8.024 | −41.031 | 1.00 | 26.54 | H |
| ATOM | 2895 CA | VAL | H | 2 | −13.212 | 8.138 | −40.155 | 1.00 | 23.34 | H |
| ATOM | 2896 CB | VAL | H | 2 | −13.245 | 7.012 | −39.131 | 1.00 | 22.59 | H |
| ATOM | 2897 CG1 | VAL | H | 2 | −13.829 | 5.784 | −39.774 | 1.00 | 21.51 | H |
| ATOM | 2898 CG2 | VAL | H | 2 | −11.850 | 6.738 | −38.596 | 1.00 | 22.41 | H |
| ATOM | 2899 C | VAL | H | 2 | −11.892 | 8.101 | −40.926 | 1.00 | 21.85 | H |
| ATOM | 2900 O | VAL | H | 2 | −11.568 | 7.107 | −41.560 | 1.00 | 22.10 | H |
| ATOM | 2901 N | SER | H | 3 | −11.121 | 9.179 | −40.868 | 1.00 | 20.36 | H |
| ATOM | 2902 CA | SER | H | 3 | −9.858 | 9.213 | −41.596 | 1.00 | 18.47 | H |
| ATOM | 2903 CB | SER | H | 3 | −10.141 | 9.399 | −43.095 | 1.00 | 18.64 | H |
| ATOM | 2904 OG | SER | H | 3 | −10.823 | 10.625 | −43.336 | 1.00 | 18.79 | H |
| ATOM | 2905 C | SER | H | 3 | −8.909 | 10.315 | −41.108 | 1.00 | 16.35 | H |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 2906 | O | SER | H | 3 | −9.301 | 11.207 | −40.349 | 1.00 | 14.67 | H |
| ATOM | 2907 | N | LEU | H | 4 | −7.655 | 10.245 | −41.545 | 1.00 | 14.24 | H |
| ATOM | 2908 | CA | LEU | H | 4 | −6.668 | 11.258 | −41.184 | 1.00 | 14.54 | H |
| ATOM | 2909 | CB | LEU | H | 4 | −5.672 | 10.723 | −40.157 | 1.00 | 13.53 | H |
| ATOM | 2910 | CG | LEU | H | 4 | −6.211 | 10.379 | −38.766 | 1.00 | 13.76 | H |
| ATOM | 2911 | CD1 | LEU | H | 4 | −5.092 | 9.717 | −37.965 | 1.00 | 12.35 | H |
| ATOM | 2912 | CD2 | LEU | H | 4 | −6.742 | 11.635 | −38.063 | 1.00 | 11.54 | H |
| ATOM | 2913 | C | LEU | H | 4 | −5.913 | 11.687 | −42.427 | 1.00 | 14.67 | H |
| ATOM | 2914 | O | LEU | H | 4 | −5.243 | 10.867 | −43.049 | 1.00 | 15.74 | H |
| ATOM | 2915 | N | ARG | H | 5 | −6.024 | 12.964 | −42.788 | 1.00 | 15.44 | H |
| ATOM | 2916 | CA | ARG | H | 5 | −5.350 | 13.478 | −43.975 | 1.00 | 17.23 | H |
| ATOM | 2917 | CB | ARG | H | 5 | −6.361 | 14.004 | −45.003 | 1.00 | 20.91 | H |
| ATOM | 2918 | CG | ARG | H | 5 | −7.130 | 12.917 | −45.748 | 1.00 | 26.83 | H |
| ATOM | 2919 | CD | ARG | H | 5 | −7.934 | 13.525 | −46.904 | 1.00 | 34.28 | H |
| ATOM | 2920 | NE | ARG | H | 5 | −9.324 | 13.826 | −46.553 | 1.00 | 38.31 | H |
| ATOM | 2921 | CZ | ARG | H | 5 | −10.294 | 12.916 | −46.470 | 1.00 | 41.05 | H |
| ATOM | 2922 | NH1 | ARG | H | 5 | −10.030 | 11.638 | −46.708 | 1.00 | 41.35 | H |
| ATOM | 2923 | NH2 | ARG | H | 5 | −11.537 | 13.283 | −46.169 | 1.00 | 42.82 | H |
| ATOM | 2924 | C | ARG | H | 5 | −4.358 | 14.567 | −43.655 | 1.00 | 15.33 | H |
| ATOM | 2925 | O | ARG | H | 5 | −4.731 | 15.672 | −43.252 | 1.00 | 15.11 | H |
| ATOM | 2926 | N | GLU | H | 6 | −3.082 | 14.252 | −43.830 | 1.00 | 14.48 | H |
| ATOM | 2927 | CA | GLU | H | 6 | −2.043 | 15.240 | −43.555 | 1.00 | 13.53 | H |
| ATOM | 2928 | CB | GLU | H | 6 | −0.837 | 14.591 | −42.848 | 1.00 | 10.37 | H |
| ATOM | 2929 | CG | GLU | H | 6 | −0.242 | 13.379 | −43.502 | 1.00 | 10.69 | H |
| ATOM | 2930 | CD | GLU | H | 6 | −0.904 | 12.053 | −43.105 | 1.00 | 12.25 | H |
| ATOM | 2931 | OE1 | GLU | H | 6 | −1.689 | 11.509 | −43.910 | 1.00 | 11.59 | H |
| ATOM | 2932 | OE2 | GLU | H | 6 | −0.622 | 11.540 | −41.999 | 1.00 | 11.51 | H |
| ATOM | 2933 | C | GLU | H | 6 | −1.595 | 16.021 | −44.790 | 1.00 | 11.79 | H |
| ATOM | 2934 | O | GLU | H | 6 | −1.707 | 15.556 | −45.914 | 1.00 | 11.18 | H |
| ATOM | 2935 | N | SER | H | 7 | −1.120 | 17.236 | −44.576 | 1.00 | 12.26 | H |
| ATOM | 2936 | CA | SER | H | 7 | −0.672 | 18.049 | −45.684 | 1.00 | 12.42 | H |
| ATOM | 2937 | CB | SER | H | 7 | −1.867 | 18.735 | −46.366 | 1.00 | 9.88 | H |
| ATOM | 2938 | OG | SER | H | 7 | −2.516 | 19.601 | −45.461 | 1.00 | 8.60 | H |
| ATOM | 2939 | C | SER | H | 7 | 0.302 | 19.099 | −45.169 | 1.00 | 13.19 | H |
| ATOM | 2940 | O | SER | H | 7 | 0.463 | 19.295 | −43.950 | 1.00 | 11.90 | H |
| ATOM | 2941 | N | GLY | H | 8 | 0.934 | 19.777 | −46.120 | 1.00 | 13.68 | H |
| ATOM | 2942 | CA | GLY | H | 8 | 1.892 | 20.813 | −45.801 | 1.00 | 13.72 | H |
| ATOM | 2943 | C | GLY | H | 8 | 3.277 | 20.422 | −46.251 | 1.00 | 13.27 | H |
| ATOM | 2944 | O | GLY | H | 8 | 4.133 | 21.279 | −46.429 | 1.00 | 14.46 | H |
| ATOM | 2945 | N | GLY | H | 9 | 3.493 | 19.125 | −46.446 | 1.00 | 13.04 | H |
| ATOM | 2946 | CA | GLY | H | 9 | 4.802 | 18.651 | −46.855 | 1.00 | 13.75 | H |
| ATOM | 2947 | C | GLY | H | 9 | 5.258 | 19.190 | −48.193 | 1.00 | 14.12 | H |
| ATOM | 2948 | O | GLY | H | 9 | 4.449 | 19.475 | −49.070 | 1.00 | 14.64 | H |
| ATOM | 2949 | N | GLY | H | 10 | 6.569 | 19.324 | −48.335 | 1.00 | 12.90 | H |
| ATOM | 2950 | CA | GLY | H | 10 | 7.147 | 19.815 | −49.562 | 1.00 | 11.12 | H |
| ATOM | 2951 | C | GLY | H | 10 | 8.640 | 19.951 | −49.395 | 1.00 | 12.16 | H |
| ATOM | 2952 | O | GLY | H | 10 | 9.231 | 19.397 | −48.460 | 1.00 | 14.47 | H |
| ATOM | 2953 | N | LEU | H | 11 | 9.254 | 20.695 | −50.301 | 1.00 | 11.81 | H |
| ATOM | 2954 | CA | LEU | H | 11 | 10.695 | 20.902 | −50.264 | 1.00 | 11.20 | H |
| ATOM | 2955 | CB | LEU | H | 11 | 11.194 | 21.229 | −51.666 | 1.00 | 11.52 | H |
| ATOM | 2956 | CG | LEU | H | 11 | 12.655 | 21.626 | −51.772 | 1.00 | 9.91 | H |
| ATOM | 2957 | CD1 | LEU | H | 11 | 13.531 | 20.399 | −51.735 | 1.00 | 9.46 | H |
| ATOM | 2958 | CD2 | LEU | H | 11 | 12.840 | 22.394 | −53.039 | 1.00 | 11.08 | H |
| ATOM | 2959 | C | LEU | H | 11 | 10.970 | 22.065 | −49.336 | 1.00 | 10.64 | H |
| ATOM | 2960 | O | LEU | H | 11 | 10.341 | 23.103 | −49.445 | 1.00 | 11.74 | H |
| ATOM | 2961 | N | VAL | H | 12 | 11.895 | 21.898 | −48.412 | 1.00 | 11.07 | H |
| ATOM | 2962 | CA | VAL | H | 12 | 12.199 | 22.984 | −47.500 | 1.00 | 11.68 | H |
| ATOM | 2963 | CB | VAL | H | 12 | 11.525 | 22.744 | −46.117 | 1.00 | 11.62 | H |
| ATOM | 2964 | CG1 | VAL | H | 12 | 11.994 | 21.426 | −45.533 | 1.00 | 11.18 | H |
| ATOM | 2965 | CG2 | VAL | H | 12 | 11.831 | 23.881 | −45.177 | 1.00 | 10.48 | H |
| ATOM | 2966 | C | VAL | H | 12 | 13.714 | 23.124 | −47.362 | 1.00 | 11.68 | H |
| ATOM | 2967 | O | VAL | H | 12 | 14.449 | 22.135 | −47.333 | 1.00 | 11.18 | H |
| ATOM | 2968 | N | GLN | H | 13 | 14.178 | 24.364 | −47.284 | 1.00 | 13.31 | H |
| ATOM | 2969 | CA | GLN | H | 13 | 15.606 | 24.628 | −47.187 | 1.00 | 15.00 | H |
| ATOM | 2970 | CB | GLN | H | 13 | 15.919 | 26.019 | −47.755 | 1.00 | 15.90 | H |
| ATOM | 2971 | CG | GLN | H | 13 | 16.193 | 26.029 | −49.271 | 1.00 | 16.90 | H |
| ATOM | 2972 | CD | GLN | H | 13 | 16.243 | 27.430 | −49.863 | 1.00 | 18.00 | H |
| ATOM | 2973 | OE1 | GLN | H | 13 | 16.870 | 28.332 | −49.308 | 1.00 | 18.96 | H |
| ATOM | 2974 | NE2 | GLN | H | 13 | 15.597 | 27.611 | −51.009 | 1.00 | 18.93 | H |
| ATOM | 2975 | C | GLN | H | 13 | 16.152 | 24.501 | −45.777 | 1.00 | 13.89 | H |
| ATOM | 2976 | O | GLN | H | 13 | 15.469 | 24.805 | −44.806 | 1.00 | 14.83 | H |
| ATOM | 2977 | N | PRO | H | 14 | 17.402 | 24.044 | −45.647 | 1.00 | 13.23 | H |
| ATOM | 2978 | CD | PRO | H | 14 | 18.348 | 23.638 | −46.699 | 1.00 | 13.82 | H |
| ATOM | 2979 | CA | PRO | H | 14 | 18.001 | 23.893 | −44.319 | 1.00 | 12.61 | H |

TABLE VIII-continued

Structure coordinates of the epitopes of allergenic beta-lactoglobulin in an antibody-beta-lactoglobulin immunocomplex;

| | | Atom type | Resid | # | X | Y | Z | OCC | B | |
|---|---|---|---|---|---|---|---|---|---|---|
| ATOM | 2980 | CB | PRO | H | 14 | 19.445 | 23.511 | −44.630 | 1.00 | 11.95 | H |
| ATOM | 2981 | CG | PRO | H | 14 | 19.321 | 22.762 | −45.916 | 1.00 | 13.51 | H |
| ATOM | 2982 | C | PRO | H | 14 | 17.895 | 25.206 | −43.561 | 1.00 | 12.29 | H |
| ATOM | 2983 | O | PRO | H | 14 | 18.215 | 26.265 | −44.089 | 1.00 | 13.56 | H |
| ATOM | 2984 | N | GLY | H | 15 | 17.415 | 25.127 | −42.329 | 1.00 | 11.52 | H |
| ATOM | 2985 | CA | GLY | H | 15 | 17.278 | 26.320 | −41.529 | 1.00 | 10.23 | H |
| ATOM | 2986 | C | GLY | H | 15 | 15.918 | 26.977 | −41.625 | 1.00 | 11.22 | H |
| ATOM | 2987 | O | GLY | H | 15 | 15.526 | 27.715 | −40.724 | 1.00 | 9.73 | H |
| ATOM | 2988 | N | ARG | H | 16 | 15.186 | 26.719 | −42.702 | 1.00 | 12.69 | H |
| ATOM | 2989 | CA | ARG | H | 16 | 13.877 | 27.342 | −42.854 | 1.00 | 14.66 | H |
| ATOM | 2990 | CB | ARG | H | 16 | 13.435 | 27.319 | −44.314 | 1.00 | 18.56 | H |
| ATOM | 2991 | CG | ARG | H | 16 | 14.241 | 28.208 | −45.227 | 1.00 | 21.98 | H |
| ATOM | 2992 | CD | ARG | H | 16 | 13.934 | 29.663 | −44.974 | 1.00 | 25.86 | H |
| ATOM | 2993 | NE | ARG | H | 16 | 14.396 | 30.485 | −46.095 | 1.00 | 32.22 | H |
| ATOM | 2994 | CZ | ARG | H | 16 | 13.815 | 30.518 | −47.295 | 1.00 | 34.94 | H |
| ATOM | 2995 | NH1 | ARG | H | 16 | 12.732 | 29.783 | −47.529 | 1.00 | 36.64 | H |
| ATOM | 2996 | NH2 | ARG | H | 16 | 14.333 | 31.255 | −48.274 | 1.00 | 36.71 | H |
| ATOM | 2997 | C | ARG | H | 16 | 12.875 | 26.594 | −42.005 | 1.00 | 14.25 | H |
| ATOM | 2998 | O | ARG | H | 16 | 13.233 | 25.638 | −41.321 | 1.00 | 14.28 | H |
| ATOM | 2999 | N | SER | H | 17 | 11.623 | 27.037 | −42.029 | 1.00 | 13.56 | H |
| ATOM | 3000 | CA | SER | H | 17 | 10.585 | 26.376 | −41.248 | 1.00 | 12.76 | H |
| ATOM | 3001 | CB | SER | H | 17 | 10.251 | 27.185 | −39.976 | 1.00 | 10.97 | H |
| ATOM | 3002 | OG | SER | H | 17 | 9.880 | 28.517 | −40.261 | 1.00 | 10.44 | H |
| ATOM | 3003 | C | SER | H | 17 | 9.338 | 26.116 | −42.083 | 1.00 | 12.50 | H |
| ATOM | 3004 | O | SER | H | 17 | 8.999 | 26.880 | −42.990 | 1.00 | 11.82 | H |
| ATOM | 3005 | N | LEU | H | 18 | 8.672 | 25.012 | −41.763 | 1.00 | 12.08 | H |
| ATOM | 3006 | CA | LEU | H | 18 | 7.480 | 24.574 | −42.471 | 1.00 | 12.12 | H |
| ATOM | 3007 | CB | LEU | H | 18 | 7.854 | 23.397 | −43.366 | 1.00 | 12.29 | H |
| ATOM | 3008 | CG | LEU | H | 18 | 6.806 | 22.856 | −44.314 | 1.00 | 15.26 | H |
| ATOM | 3009 | CD1 | LEU | H | 18 | 6.544 | 23.892 | −45.426 | 1.00 | 16.99 | H |
| ATOM | 3010 | CD2 | LEU | H | 18 | 7.298 | 21.565 | −44.932 | 1.00 | 14.85 | H |
| ATOM | 3011 | C | LEU | H | 18 | 6.409 | 24.131 | −41.469 | 1.00 | 12.46 | H |
| ATOM | 3012 | O | LEU | H | 18 | 6.740 | 23.668 | −40.376 | 1.00 | 13.86 | H |
| ATOM | 3013 | N | ARG | H | 19 | 5.134 | 24.269 | −41.837 | 1.00 | 11.69 | H |
| ATOM | 3014 | CA | ARG | H | 19 | 4.053 | 23.858 | −40.949 | 1.00 | 11.63 | H |
| ATOM | 3015 | CB | ARG | H | 19 | 3.108 | 25.010 | −40.584 | 1.00 | 13.15 | H |
| ATOM | 3016 | CG | ARG | H | 19 | 2.323 | 24.705 | −39.311 | 1.00 | 17.79 | H |
| ATOM | 3017 | CD | ARG | H | 19 | 1.220 | 25.700 | −39.011 | 1.00 | 20.71 | H |
| ATOM | 3018 | NE | ARG | H | 19 | 0.145 | 25.586 | −39.985 | 1.00 | 24.55 | H |
| ATOM | 3019 | CZ | ARG | H | 19 | −1.106 | 25.997 | −39.786 | 1.00 | 26.15 | H |
| ATOM | 3020 | NH1 | ARG | H | 19 | −1.453 | 26.559 | −38.629 | 1.00 | 27.90 | H |
| ATOM | 3021 | NH2 | ARG | H | 19 | −2.011 | 25.833 | −40.750 | 1.00 | 23.19 | H |
| ATOM | 3022 | C | ARG | H | 19 | 3.232 | 22.752 | −41.554 | 1.00 | 10.59 | H |
| ATOM | 3023 | O | ARG | H | 19 | 2.636 | 22.908 | −42.622 | 1.00 | 11.48 | H |
| ATOM | 3024 | N | LEU | H | 20 | 3.195 | 21.625 | −40.856 | 1.00 | 8.72 | H |
| ATOM | 3025 | CA | LEU | H | 20 | 2.431 | 20.459 | −41.299 | 1.00 | 6.73 | H |
| ATOM | 3026 | CB | LEU | H | 20 | 3.193 | 19.198 | −40.933 | 1.00 | 5.77 | H |
| ATOM | 3027 | CG | LEU | H | 20 | 3.855 | 18.376 | −42.018 | 1.00 | 6.73 | H |
| ATOM | 3028 | CD1 | LEU | H | 20 | 4.504 | 19.241 | −43.114 | 1.00 | 5.43 | H |
| ATOM | 3029 | CD2 | LEU | H | 20 | 4.875 | 17.511 | −41.312 | 1.00 | 4.29 | H |
| ATOM | 3030 | C | LEU | H | 20 | 1.076 | 20.433 | −40.599 | 1.00 | 5.76 | H |
| ATOM | 3031 | O | LEU | H | 20 | 0.984 | 20.689 | −39.406 | 1.00 | 6.95 | H |
| ATOM | 3032 | N | SER | H | 21 | 0.026 | 20.111 | −41.329 | 1.00 | 5.05 | H |
| ATOM | 3033 | CA | SER | H | 21 | −1.271 | 20.061 | −40.691 | 1.00 | 5.74 | H |
| ATOM | 3034 | CB | SER | H | 21 | −2.160 | 21.227 | −41.124 | 1.00 | 5.27 | H |
| ATOM | 3035 | OG | SER | H | 21 | −2.582 | 21.072 | −42.462 | 1.00 | 8.84 | H |
| ATOM | 3036 | C | SER | H | 21 | −1.929 | 18.744 | −41.036 | 1.00 | 5.36 | H |
| ATOM | 3037 | O | SER | H | 21 | −1.707 | 18.214 | −42.121 | 1.00 | 2.68 | H |
| ATOM | 3038 | N | CYS | H | 22 | −2.698 | 18.215 | −40.083 | 1.00 | 7.14 | H |
| ATOM | 3039 | CA | CYS | H | 22 | −3.415 | 16.950 | −40.221 | 1.00 | 9.56 | H |
| ATOM | 3040 | C | CYS | H | 22 | −4.910 | 17.166 | −39.980 | 1.00 | 9.14 | H |
| ATOM | 3041 | O | CYS | H | 22 | −5.308 | 17.596 | −38.894 | 1.00 | 7.69 | H |
| ATOM | 3042 | CB | CYS | H | 22 | −2.922 | 15.911 | −39.204 | 1.00 | 11.39 | H |
| ATOM | 3043 | SG | CYS | H | 22 | −3.763 | 14.298 | −39.439 | 1.00 | 13.19 | H |
| ATOM | 3044 | N | THR | H | 23 | −5.731 | 16.873 | −40.989 | 1.00 | 8.90 | H |
| ATOM | 3045 | CA | THR | H | 23 | −7.184 | 17.020 | −40.872 | 1.00 | 9.76 | H |
| ATOM | 3046 | CB | THR | H | 23 | −7.819 | 17.476 | −42.177 | 1.00 | 10.09 | H |
| ATOM | 3047 | OG1 | THR | H | 23 | −7.296 | 18.758 | −42.534 | 1.00 | 12.65 | H |
| ATOM | 3048 | CG2 | THR | H | 23 | −9.335 | 17.552 | −42.022 | 1.00 | 8.41 | H |
| ATOM | 3049 | C | THR | H | 23 | −7.862 | 15.714 | −40.488 | 1.00 | 9.51 | H |
| ATOM | 3050 | O | THR | H | 23 | −7.682 | 14.686 | −41.152 | 1.00 | 9.77 | H |
| ATOM | 3051 | N | ALA | H | 24 | −8.664 | 15.771 | −39.430 | 1.00 | 7.58 | H |
| ATOM | 3052 | CA | ALA | H | 24 | −9.375 | 14.601 | −38.941 | 1.00 | 6.53 | H |
| ATOM | 3053 | CB | ALA | H | 24 | −9.189 | 14.512 | −37.453 | 1.00 | 5.54 | H |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 3054 | C | ALA | H | 24 | −10.873 | 14.590 | −39.280 | 1.00 | 6.84 | H |
| ATOM | 3055 | O | ALA | H | 24 | −11.472 | 15.630 | −39.561 | 1.00 | 6.30 | H |
| ATOM | 3056 | N | SER | H | 25 | −11.468 | 13.402 | −39.268 | 1.00 | 7.53 | H |
| ATOM | 3057 | CA | SER | H | 25 | −12.891 | 13.275 | −39.529 | 1.00 | 9.12 | H |
| ATOM | 3058 | CB | SER | H | 25 | −13.207 | 13.521 | −41.003 | 1.00 | 10.49 | H |
| ATOM | 3059 | OG | SER | H | 25 | −12.900 | 12.376 | −41.778 | 1.00 | 13.85 | H |
| ATOM | 3060 | C | SER | H | 25 | −13.392 | 11.900 | −39.138 | 1.00 | 8.68 | H |
| ATOM | 3061 | O | SER | H | 25 | −12.610 | 10.959 | −39.071 | 1.00 | 9.15 | H |
| ATOM | 3062 | N | GLY | H | 26 | −14.694 | 11.803 | −38.863 | 1.00 | 7.31 | H |
| ATOM | 3063 | CA | GLY | H | 26 | −15.294 | 10.534 | −38.512 | 1.00 | 5.63 | H |
| ATOM | 3064 | C | GLY | H | 26 | −15.259 | 10.129 | −37.052 | 1.00 | 6.29 | H |
| ATOM | 3065 | O | GLY | H | 26 | −15.746 | 9.043 | −36.718 | 1.00 | 6.85 | H |
| ATOM | 3066 | N | PHE | H | 27 | −14.676 | 10.970 | −36.195 | 1.00 | 5.39 | H |
| ATOM | 3067 | CA | PHE | H | 27 | −14.602 | 10.703 | −34.764 | 1.00 | 3.21 | H |
| ATOM | 3068 | CB | PHE | H | 27 | −13.394 | 9.836 | −34.430 | 1.00 | 3.38 | H |
| ATOM | 3069 | CG | PHE | H | 27 | −12.069 | 10.493 | −34.681 | 1.00 | 6.17 | H |
| ATOM | 3070 | CD1 | PHE | H | 27 | −11.388 | 11.128 | −33.649 | 1.00 | 7.13 | H |
| ATOM | 3071 | CD2 | PHE | H | 27 | −11.485 | 10.459 | −35.948 | 1.00 | 8.80 | H |
| ATOM | 3072 | CE1 | PHE | H | 27 | −10.129 | 11.725 | −33.872 | 1.00 | 8.38 | H |
| ATOM | 3073 | CE2 | PHE | H | 27 | −10.224 | 11.053 | −36.192 | 1.00 | 7.26 | H |
| ATOM | 3074 | CZ | PHE | H | 27 | −9.546 | 11.687 | −35.145 | 1.00 | 7.99 | H |
| ATOM | 3075 | C | PHE | H | 27 | −14.534 | 12.027 | −34.038 | 1.00 | 3.40 | H |
| ATOM | 3076 | O | PHE | H | 27 | −14.437 | 13.059 | −34.677 | 1.00 | 2.87 | H |
| ATOM | 3077 | N | THR | H | 28 | −14.622 | 12.007 | −32.710 | 1.00 | 5.40 | H |
| ATOM | 3078 | CA | THR | H | 28 | −14.601 | 13.243 | −31.932 | 1.00 | 6.21 | H |
| ATOM | 3079 | CB | THR | H | 28 | −15.466 | 13.120 | −30.668 | 1.00 | 6.55 | H |
| ATOM | 3080 | OG1 | THR | H | 28 | −16.790 | 12.732 | −31.047 | 1.00 | 7.06 | H |
| ATOM | 3081 | CG2 | THR | H | 28 | −15.537 | 14.448 | −29.940 | 1.00 | 5.57 | H |
| ATOM | 3082 | C | THR | H | 28 | −13.178 | 13.618 | −31.539 | 1.00 | 8.34 | H |
| ATOM | 3083 | O | THR | H | 28 | −12.650 | 13.174 | −30.513 | 1.00 | 7.70 | H |
| ATOM | 3084 | N | PHE | H | 29 | −12.586 | 14.471 | −32.366 | 1.00 | 9.20 | H |
| ATOM | 3085 | CA | PHE | H | 29 | −11.219 | 14.939 | −32.223 | 1.00 | 8.64 | H |
| ATOM | 3086 | CB | PHE | H | 29 | −11.023 | 16.179 | −33.108 | 1.00 | 6.86 | H |
| ATOM | 3087 | CG | PHE | H | 29 | −9.588 | 16.496 | −33.401 | 1.00 | 5.50 | H |
| ATOM | 3088 | CD1 | PHE | H | 29 | −8.792 | 15.590 | −34.095 | 1.00 | 4.60 | H |
| ATOM | 3089 | CD2 | PHE | H | 29 | −9.033 | 17.706 | −32.999 | 1.00 | 4.43 | H |
| ATOM | 3090 | CE1 | PHE | H | 29 | −7.466 | 15.879 | −34.382 | 1.00 | 5.04 | H |
| ATOM | 3091 | CE2 | PHE | H | 29 | −7.706 | 18.005 | −33.281 | 1.00 | 4.00 | H |
| ATOM | 3092 | CZ | PHE | H | 29 | −6.923 | 17.089 | −33.977 | 1.00 | 5.16 | H |
| ATOM | 3093 | C | PHE | H | 29 | −10.706 | 15.231 | −30.821 | 1.00 | 9.74 | H |
| ATOM | 3094 | O | PHE | H | 29 | −9.661 | 14.697 | −30.422 | 1.00 | 8.35 | H |
| ATOM | 3095 | N | ARG | H | 30 | −11.421 | 16.073 | −30.077 | 1.00 | 12.71 | H |
| ATOM | 3096 | CA | ARG | H | 30 | −10.984 | 16.465 | −28.728 | 1.00 | 14.89 | H |
| ATOM | 3097 | CB | ARG | H | 30 | −11.880 | 17.577 | −28.172 | 1.00 | 18.34 | H |
| ATOM | 3098 | CG | ARG | H | 30 | −13.328 | 17.141 | −28.001 | 1.00 | 25.22 | H |
| ATOM | 3099 | CD | ARG | H | 30 | −14.242 | 18.281 | −27.550 | 1.00 | 30.89 | H |
| ATOM | 3100 | NE | ARG | H | 30 | −14.174 | 18.521 | −26.112 | 1.00 | 34.44 | H |
| ATOM | 3101 | CZ | ARG | H | 30 | −14.768 | 19.538 | −25.477 | 1.00 | 37.44 | H |
| ATOM | 3102 | NH1 | ARG | H | 30 | −15.486 | 20.435 | −26.150 | 1.00 | 36.31 | H |
| ATOM | 3103 | NH2 | ARG | H | 30 | −14.647 | 19.660 | −24.153 | 1.00 | 37.84 | H |
| ATOM | 3104 | C | ARG | H | 30 | −10.960 | 15.307 | −27.739 | 1.00 | 14.44 | H |
| ATOM | 3105 | O | ARG | H | 30 | −10.426 | 15.442 | −26.641 | 1.00 | 14.72 | H |
| ATOM | 3106 | N | HIS | H | 31 | −11.522 | 14.170 | −28.134 | 1.00 | 13.78 | H |
| ATOM | 3107 | CA | HIS | H | 31 | −11.580 | 13.006 | −27.263 | 1.00 | 13.18 | H |
| ATOM | 3108 | CB | HIS | H | 31 | −12.850 | 12.186 | −27.530 | 1.00 | 14.12 | H |
| ATOM | 3109 | CG | HIS | H | 31 | −14.089 | 12.735 | −26.899 | 1.00 | 14.52 | H |
| ATOM | 3110 | CD2 | HIS | H | 31 | −14.314 | 13.900 | −26.247 | 1.00 | 14.13 | H |
| ATOM | 3111 | ND1 | HIS | H | 31 | −15.279 | 12.046 | −26.883 | 1.00 | 13.70 | H |
| ATOM | 3112 | CE1 | HIS | H | 31 | −16.190 | 12.761 | −26.244 | 1.00 | 15.24 | H |
| ATOM | 3113 | NE2 | HIS | H | 31 | −15.628 | 13.888 | −25.850 | 1.00 | 14.50 | H |
| ATOM | 3114 | C | HIS | H | 31 | −10.408 | 12.073 | −27.426 | 1.00 | 12.58 | H |
| ATOM | 3115 | O | HIS | H | 31 | −10.392 | 10.995 | −26.834 | 1.00 | 14.16 | H |
| ATOM | 3116 | N | HIS | H | 32 | −9.434 | 12.467 | −28.229 | 1.00 | 12.49 | H |
| ATOM | 3117 | CA | HIS | H | 32 | −8.304 | 11.585 | −28.478 | 1.00 | 12.89 | H |
| ATOM | 3118 | CB | HIS | H | 32 | −8.545 | 10.851 | −29.808 | 1.00 | 13.05 | H |
| ATOM | 3119 | CG | HIS | H | 32 | −9.697 | 9.889 | −29.761 | 1.00 | 12.70 | H |
| ATOM | 3120 | CD2 | HIS | H | 32 | −10.988 | 10.023 | −30.149 | 1.00 | 12.40 | H |
| ATOM | 3121 | ND1 | HIS | H | 32 | −9.592 | 8.631 | −29.209 | 1.00 | 12.19 | H |
| ATOM | 3122 | CE1 | HIS | H | 32 | −10.768 | 8.029 | −29.258 | 1.00 | 13.35 | H |
| ATOM | 3123 | NE2 | HIS | H | 32 | −11.633 | 8.852 | −29.822 | 1.00 | 12.35 | H |
| ATOM | 3124 | C | HIS | H | 32 | −6.976 | 12.326 | −28.504 | 1.00 | 12.49 | H |
| ATOM | 3125 | O | HIS | H | 32 | −6.920 | 13.476 | −28.918 | 1.00 | 14.67 | H |
| ATOM | 3126 | N | GLY | H | 33 | −5.914 | 11.687 | −28.026 | 1.00 | 11.48 | H |
| ATOM | 3127 | CA | GLY | H | 33 | −4.611 | 12.327 | −28.063 | 1.00 | 10.32 | H |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 3128 C | GLY | H | 33 | −4.052 | 12.137 | −29.461 | 1.00 | 8.82 | H |
| ATOM | 3129 O | GLY | H | 33 | −4.339 | 11.127 | −30.101 | 1.00 | 10.42 | H |
| ATOM | 3130 N | MET | H | 34 | −3.276 | 13.086 | −29.965 | 1.00 | 7.85 | H |
| ATOM | 3131 CA | MET | H | 34 | −2.721 | 12.935 | −31.320 | 1.00 | 6.64 | H |
| ATOM | 3132 CB | MET | H | 34 | −3.173 | 14.090 | −32.218 | 1.00 | 4.40 | H |
| ATOM | 3133 CG | MET | H | 34 | −4.710 | 14.204 | −32.374 | 1.00 | 4.44 | H |
| ATOM | 3134 SD | MET | H | 34 | −5.426 | 12.756 | −33.283 | 1.00 | 3.13 | H |
| ATOM | 3135 CE | MET | H | 34 | −4.669 | 12.931 | −34.869 | 1.00 | 3.16 | H |
| ATOM | 3136 C | MET | H | 34 | −1.201 | 12.896 | −31.281 | 1.00 | 6.08 | H |
| ATOM | 3137 O | MET | H | 34 | −0.575 | 13.439 | −30.381 | 1.00 | 5.25 | H |
| ATOM | 3138 N | THR | H | 35 | −0.607 | 12.267 | −32.274 | 1.00 | 6.01 | H |
| ATOM | 3139 CA | THR | H | 35 | 0.828 | 12.175 | −32.290 | 1.00 | 7.01 | H |
| ATOM | 3140 CB | THR | H | 35 | 1.292 | 10.851 | −31.608 | 1.00 | 9.35 | H |
| ATOM | 3141 OG1 | THR | H | 35 | 2.719 | 10.707 | −31.709 | 1.00 | 10.60 | H |
| ATOM | 3142 CG2 | THR | H | 35 | 0.633 | 9.661 | −32.289 | 1.00 | 10.35 | H |
| ATOM | 3143 C | THR | H | 35 | 1.383 | 12.231 | −33.710 | 1.00 | 5.93 | H |
| ATOM | 3144 O | THR | H | 35 | 0.672 | 11.965 | −34.690 | 1.00 | 4.87 | H |
| ATOM | 3145 N | TRP | H | 36 | 2.659 | 12.591 | −33.812 | 1.00 | 5.33 | H |
| ATOM | 3146 CA | TRP | H | 36 | 3.335 | 12.655 | −35.097 | 1.00 | 3.82 | H |
| ATOM | 3147 CB | TRP | H | 36 | 4.005 | 14.005 | −35.327 | 1.00 | 1.93 | H |
| ATOM | 3148 CG | TRP | H | 36 | 3.059 | 15.064 | −35.776 | 1.00 | 3.01 | H |
| ATOM | 3149 CD2 | TRP | H | 36 | 2.500 | 15.209 | −37.090 | 1.00 | 2.59 | H |
| ATOM | 3150 CE2 | TRP | H | 36 | 1.656 | 16.338 | −37.063 | 1.00 | 1.00 | H |
| ATOM | 3151 CE3 | TRP | H | 36 | 2.632 | 14.491 | −38.285 | 1.00 | 2.19 | H |
| ATOM | 3152 CD1 | TRP | H | 36 | 2.540 | 16.079 | −35.029 | 1.00 | 1.86 | H |
| ATOM | 3153 NE1 | TRP | H | 36 | 1.699 | 16.849 | −35.796 | 1.00 | 1.16 | H |
| ATOM | 3154 CZ2 | TRP | H | 36 | 0.953 | 16.773 | −38.178 | 1.00 | 1.00 | H |
| ATOM | 3155 CZ3 | TRP | H | 36 | 1.930 | 14.923 | −39.395 | 1.00 | 1.00 | H |
| ATOM | 3156 CH2 | TRP | H | 36 | 1.100 | 16.057 | −39.334 | 1.00 | 1.00 | H |
| ATOM | 3157 C | TRP | H | 36 | 4.406 | 11.617 | −35.091 | 1.00 | 3.68 | H |
| ATOM | 3158 O | TRP | H | 36 | 5.195 | 11.544 | −34.152 | 1.00 | 4.93 | H |
| ATOM | 3159 N | VAL | H | 37 | 4.429 | 10.803 | −36.130 | 1.00 | 3.07 | H |
| ATOM | 3160 CA | VAL | H | 37 | 5.465 | 9.794 | −36.254 | 1.00 | 4.69 | H |
| ATOM | 3161 CB | VAL | H | 37 | 4.895 | 8.340 | −36.114 | 1.00 | 5.17 | H |
| ATOM | 3162 CG1 | VAL | H | 37 | 5.994 | 7.335 | −36.345 | 1.00 | 4.96 | H |
| ATOM | 3163 CG2 | VAL | H | 37 | 4.315 | 8.126 | −34.732 | 1.00 | 4.23 | H |
| ATOM | 3164 C | VAL | H | 37 | 6.075 | 10.005 | −37.645 | 1.00 | 4.66 | H |
| ATOM | 3165 O | VAL | H | 37 | 5.371 | 10.340 | −38.593 | 1.00 | 5.19 | H |
| ATOM | 3166 N | ARG | H | 38 | 7.383 | 9.846 | −37.776 | 1.00 | 5.35 | H |
| ATOM | 3167 CA | ARG | H | 38 | 8.000 | 10.039 | −39.082 | 1.00 | 5.57 | H |
| ATOM | 3168 CB | ARG | H | 38 | 8.897 | 11.272 | −39.068 | 1.00 | 7.67 | H |
| ATOM | 3169 CG | ARG | H | 38 | 10.129 | 11.136 | −38.196 | 1.00 | 6.25 | H |
| ATOM | 3170 CD | ARG | H | 38 | 10.940 | 12.385 | −38.305 | 1.00 | 6.36 | H |
| ATOM | 3171 NE | ARG | H | 38 | 12.058 | 12.368 | −37.388 | 1.00 | 9.42 | H |
| ATOM | 3172 CZ | ARG | H | 38 | 12.969 | 13.319 | −37.330 | 1.00 | 8.80 | H |
| ATOM | 3173 NH1 | ARG | H | 38 | 12.879 | 14.351 | −38.151 | 1.00 | 9.68 | H |
| ATOM | 3174 NH2 | ARG | H | 38 | 13.947 | 13.249 | −36.439 | 1.00 | 9.99 | H |
| ATOM | 3175 C | ARG | H | 38 | 8.822 | 8.842 | −39.497 | 1.00 | 4.93 | H |
| ATOM | 3176 O | ARG | H | 38 | 9.135 | 7.964 | −38.693 | 1.00 | 4.06 | H |
| ATOM | 3177 N | GLN | H | 39 | 9.203 | 8.840 | −40.759 | 1.00 | 5.54 | H |
| ATOM | 3178 CA | GLN | H | 39 | 9.986 | 7.751 | −41.295 | 1.00 | 7.45 | H |
| ATOM | 3179 CB | GLN | H | 39 | 9.056 | 6.716 | −41.914 | 1.00 | 6.58 | H |
| ATOM | 3180 CG | GLN | H | 39 | 9.751 | 5.495 | −42.440 | 1.00 | 6.23 | H |
| ATOM | 3181 CD | GLN | H | 39 | 8.780 | 4.490 | −42.991 | 1.00 | 7.57 | H |
| ATOM | 3182 OE1 | GLN | H | 39 | 8.002 | 4.790 | −43.895 | 1.00 | 9.72 | H |
| ATOM | 3183 NE2 | GLN | H | 39 | 8.809 | 3.288 | −42.446 | 1.00 | 7.92 | H |
| ATOM | 3184 C | GLN | H | 39 | 10.949 | 8.280 | −42.342 | 1.00 | 8.66 | H |
| ATOM | 3185 O | GLN | H | 39 | 10.532 | 8.690 | −43.433 | 1.00 | 9.98 | H |
| ATOM | 3186 N | ALA | H | 40 | 12.237 | 8.275 | −42.001 | 1.00 | 10.55 | H |
| ATOM | 3187 CA | ALA | H | 40 | 13.281 | 8.761 | −42.901 | 1.00 | 11.32 | H |
| ATOM | 3188 CB | ALA | H | 40 | 14.598 | 8.882 | −42.161 | 1.00 | 9.49 | H |
| ATOM | 3189 C | ALA | H | 40 | 13.412 | 7.792 | −44.062 | 1.00 | 12.45 | H |
| ATOM | 3190 O | ALA | H | 40 | 13.185 | 6.595 | −43.904 | 1.00 | 12.06 | H |
| ATOM | 3191 N | PRO | H | 41 | 13.774 | 8.298 | −45.250 | 1.00 | 14.18 | H |
| ATOM | 3192 CD | PRO | H | 41 | 14.084 | 9.704 | −45.562 | 1.00 | 13.94 | H |
| ATOM | 3193 CA | PRO | H | 41 | 13.926 | 7.458 | −46.440 | 1.00 | 14.90 | H |
| ATOM | 3194 CB | PRO | H | 41 | 14.757 | 8.333 | −47.364 | 1.00 | 13.64 | H |
| ATOM | 3195 CG | PRO | H | 41 | 14.172 | 9.691 | −47.081 | 1.00 | 13.81 | H |
| ATOM | 3196 C | PRO | H | 41 | 14.565 | 6.108 | −46.165 | 1.00 | 16.86 | H |
| ATOM | 3197 O | PRO | H | 41 | 15.683 | 6.018 | −45.644 | 1.00 | 16.32 | H |
| ATOM | 3198 N | GLY | H | 42 | 13.830 | 5.053 | −46.508 | 1.00 | 18.46 | H |
| ATOM | 3199 CA | GLY | H | 42 | 14.317 | 3.699 | −46.294 | 1.00 | 19.28 | H |
| ATOM | 3200 C | GLY | H | 42 | 14.764 | 3.427 | −44.863 | 1.00 | 20.26 | H |
| ATOM | 3201 O | GLY | H | 42 | 15.795 | 2.798 | −44.637 | 1.00 | 21.03 | H |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 3202 N | LYS | H | 43 | 14.000 | 3.899 | −43.884 | 1.00 | 20.62 | H |
| ATOM | 3203 CA | LYS | H | 43 | 14.351 | 3.665 | −42.487 | 1.00 | 19.70 | H |
| ATOM | 3204 CB | LYS | H | 43 | 14.981 | 4.923 | −41.890 | 1.00 | 20.93 | H |
| ATOM | 3205 CG | LYS | H | 43 | 16.185 | 5.411 | −42.686 | 1.00 | 22.44 | H |
| ATOM | 3206 CD | LYS | H | 43 | 17.345 | 4.434 | −42.632 | 1.00 | 23.53 | H |
| ATOM | 3207 CE | LYS | H | 43 | 17.977 | 4.468 | −41.247 | 1.00 | 27.18 | H |
| ATOM | 3208 NZ | LYS | H | 43 | 19.111 | 3.504 | −41.050 | 1.00 | 28.98 | H |
| ATOM | 3209 C | LYS | H | 43 | 13.071 | 3.280 | −41.758 | 1.00 | 17.81 | H |
| ATOM | 3210 O | LYS | H | 43 | 11.991 | 3.297 | −42.361 | 1.00 | 17.97 | H |
| ATOM | 3211 N | GLY | H | 44 | 13.189 | 2.923 | −40.483 | 1.00 | 15.15 | H |
| ATOM | 3212 CA | GLY | H | 44 | 12.023 | 2.520 | −39.718 | 1.00 | 13.55 | H |
| ATOM | 3213 C | GLY | H | 44 | 11.220 | 3.666 | −39.138 | 1.00 | 12.70 | H |
| ATOM | 3214 O | GLY | H | 44 | 11.564 | 4.831 | −39.331 | 1.00 | 13.60 | H |
| ATOM | 3215 N | LEU | H | 45 | 10.150 | 3.342 | −38.418 | 1.00 | 10.34 | H |
| ATOM | 3216 CA | LEU | H | 45 | 9.312 | 4.371 | −37.823 | 1.00 | 8.11 | H |
| ATOM | 3217 CB | LEU | H | 45 | 8.006 | 3.765 | −37.319 | 1.00 | 6.67 | H |
| ATOM | 3218 CG | LEU | H | 45 | 7.016 | 3.285 | −38.384 | 1.00 | 6.00 | H |
| ATOM | 3219 CD1 | LEU | H | 45 | 5.807 | 2.634 | −37.700 | 1.00 | 6.82 | H |
| ATOM | 3220 CD2 | LEU | H | 45 | 6.567 | 4.447 | −39.220 | 1.00 | 4.53 | H |
| ATOM | 3221 C | LEU | H | 45 | 10.010 | 5.088 | −36.680 | 1.00 | 8.20 | H |
| ATOM | 3222 O | LEU | H | 45 | 10.840 | 4.514 | −35.975 | 1.00 | 8.35 | H |
| ATOM | 3223 N | GLU | H | 46 | 9.683 | 6.361 | −36.516 | 1.00 | 6.89 | H |
| ATOM | 3224 CA | GLU | H | 46 | 10.261 | 7.134 | −35.440 | 1.00 | 5.45 | H |
| ATOM | 3225 CB | GLU | H | 46 | 11.459 | 7.906 | −35.946 | 1.00 | 6.53 | H |
| ATOM | 3226 CG | GLU | H | 46 | 12.370 | 8.384 | −34.853 | 1.00 | 8.96 | H |
| ATOM | 3227 CD | GLU | H | 46 | 13.090 | 9.655 | −35.223 | 1.00 | 11.41 | H |
| ATOM | 3228 OE1 | GLU | H | 46 | 13.534 | 9.759 | −36.407 | 1.00 | 7.77 | H |
| ATOM | 3229 OE2 | GLU | H | 46 | 13.211 | 10.539 | −34.320 | 1.00 | 13.45 | H |
| ATOM | 3230 C | GLU | H | 46 | 9.241 | 8.109 | −34.864 | 1.00 | 5.60 | H |
| ATOM | 3231 O | GLU | H | 46 | 8.712 | 8.967 | −35.575 | 1.00 | 6.68 | H |
| ATOM | 3232 N | TRP | H | 47 | 8.978 | 7.981 | −33.571 | 1.00 | 4.36 | H |
| ATOM | 3233 CA | TRP | H | 47 | 8.028 | 8.841 | −32.886 | 1.00 | 3.67 | H |
| ATOM | 3234 CB | TRP | H | 47 | 7.788 | 8.320 | −31.481 | 1.00 | 4.95 | H |
| ATOM | 3235 CG | TRP | H | 47 | 6.989 | 9.246 | −30.659 | 1.00 | 4.60 | H |
| ATOM | 3236 CD2 | TRP | H | 47 | 7.482 | 10.057 | −29.587 | 1.00 | 4.44 | H |
| ATOM | 3237 CE2 | TRP | H | 47 | 6.387 | 10.818 | −29.102 | 1.00 | 4.11 | H |
| ATOM | 3238 CE3 | TRP | H | 47 | 8.748 | 10.217 | −28.989 | 1.00 | 2.69 | H |
| ATOM | 3239 CD1 | TRP | H | 47 | 5.649 | 9.529 | −30.784 | 1.00 | 3.52 | H |
| ATOM | 3240 NE1 | TRP | H | 47 | 5.285 | 10.475 | −29.846 | 1.00 | 5.11 | H |
| ATOM | 3241 CZ2 | TRP | H | 47 | 6.520 | 11.730 | −28.042 | 1.00 | 1.81 | H |
| ATOM | 3242 CZ3 | TRP | H | 47 | 8.883 | 11.122 | −27.938 | 1.00 | 1.00 | H |
| ATOM | 3243 CH2 | TRP | H | 47 | 7.770 | 11.869 | −27.475 | 1.00 | 1.00 | H |
| ATOM | 3244 C | TRP | H | 47 | 8.579 | 10.237 | −32.816 | 1.00 | 2.64 | H |
| ATOM | 3245 O | TRP | H | 47 | 9.745 | 10.425 | −32.486 | 1.00 | 5.55 | H |
| ATOM | 3246 N | VAL | H | 48 | 7.744 | 11.227 | −33.084 | 1.00 | 2.44 | H |
| ATOM | 3247 CA | VAL | H | 48 | 8.222 | 12.605 | −33.075 | 1.00 | 1.81 | H |
| ATOM | 3248 CB | VAL | H | 48 | 7.825 | 13.292 | −34.408 | 1.00 | 1.31 | H |
| ATOM | 3249 CG1 | VAL | H | 48 | 8.401 | 14.689 | −34.498 | 1.00 | 1.00 | H |
| ATOM | 3250 CG2 | VAL | H | 48 | 8.286 | 12.444 | −35.562 | 1.00 | 1.00 | H |
| ATOM | 3251 C | VAL | H | 48 | 7.708 | 13.413 | −31.883 | 1.00 | 3.22 | H |
| ATOM | 3252 O | VAL | H | 48 | 8.488 | 13.833 | −31.032 | 1.00 | 2.46 | H |
| ATOM | 3253 N | ALA | H | 49 | 6.398 | 13.621 | −31.823 | 1.00 | 3.27 | H |
| ATOM | 3254 CA | ALA | H | 49 | 5.802 | 14.384 | −30.745 | 1.00 | 4.78 | H |
| ATOM | 3255 CB | ALA | H | 49 | 5.819 | 15.866 | −31.110 | 1.00 | 3.76 | H |
| ATOM | 3256 C | ALA | H | 49 | 4.356 | 13.912 | −30.505 | 1.00 | 5.83 | H |
| ATOM | 3257 O | ALA | H | 49 | 3.700 | 13.365 | −31.406 | 1.00 | 4.82 | H |
| ATOM | 3258 N | SER | H | 50 | 3.874 | 14.135 | −29.285 | 1.00 | 4.82 | H |
| ATOM | 3259 CA | SER | H | 50 | 2.526 | 13.768 | −28.922 | 1.00 | 4.97 | H |
| ATOM | 3260 CB | SER | H | 50 | 2.516 | 12.512 | −28.059 | 1.00 | 5.14 | H |
| ATOM | 3261 OG | SER | H | 50 | 2.568 | 11.365 | −28.878 | 1.00 | 6.92 | H |
| ATOM | 3262 C | SER | H | 50 | 1.815 | 14.898 | −28.220 | 1.00 | 5.98 | H |
| ATOM | 3263 O | SER | H | 50 | 2.435 | 15.801 | −27.670 | 1.00 | 5.57 | H |
| ATOM | 3264 N | LEU | H | 51 | 0.495 | 14.816 | −28.224 | 1.00 | 7.39 | H |
| ATOM | 3265 CA | LEU | H | 51 | −0.340 | 15.847 | −27.652 | 1.00 | 8.22 | H |
| ATOM | 3266 CB | LEU | H | 51 | −0.651 | 16.828 | −28.769 | 1.00 | 9.05 | H |
| ATOM | 3267 CG | LEU | H | 51 | −1.506 | 18.005 | −28.376 | 1.00 | 10.34 | H |
| ATOM | 3268 CD1 | LEU | H | 51 | −0.678 | 18.875 | −27.452 | 1.00 | 11.80 | H |
| ATOM | 3269 CD2 | LEU | H | 51 | −1.934 | 18.776 | −29.592 | 1.00 | 10.62 | H |
| ATOM | 3270 C | LEU | H | 51 | −1.646 | 15.252 | −27.116 | 1.00 | 9.09 | H |
| ATOM | 3271 O | LEU | H | 51 | −2.244 | 14.386 | −27.757 | 1.00 | 11.36 | H |
| ATOM | 3272 N | SER | H | 52 | −2.112 | 15.730 | −25.970 | 1.00 | 7.37 | H |
| ATOM | 3273 CA | SER | H | 52 | −3.364 | 15.220 | −25.428 | 1.00 | 7.34 | H |
| ATOM | 3274 CB | SER | H | 52 | −3.453 | 15.487 | −23.920 | 1.00 | 6.67 | H |
| ATOM | 3275 OG | SER | H | 52 | −3.234 | 16.851 | −23.580 | 1.00 | 6.96 | H |

TABLE VIII-continued

Structure coordinates of the epitopes of allergenic beta-lactoglobulin in an antibody-beta-lactoglobulin immunocomplex;

| | | Atom type | Resid | | # | X | Y | Z | OCC | B | |
|---|---|---|---|---|---|---|---|---|---|---|---|
| ATOM | 3276 | C | SER | H | 52 | −4.573 | 15.823 | −26.142 | 1.00 | 8.92 | H |
| ATOM | 3277 | O | SER | H | 52 | −4.423 | 16.691 | −27.009 | 1.00 | 9.13 | H |
| ATOM | 3278 | N | GLY | H | 53 | −5.769 | 15.369 | −25.764 | 1.00 | 8.62 | H |
| ATOM | 3279 | CA | GLY | H | 53 | −6.986 | 15.856 | −26.388 | 1.00 | 6.90 | H |
| ATOM | 3280 | C | GLY | H | 53 | −7.165 | 17.339 | −26.198 | 1.00 | 5.00 | H |
| ATOM | 3281 | O | GLY | H | 53 | −7.542 | 18.062 | −27.120 | 1.00 | 4.67 | H |
| ATOM | 3282 | N | SER | H | 54 | −6.900 | 17.800 | −24.990 | 1.00 | 4.14 | H |
| ATOM | 3283 | CA | SER | H | 54 | −7.025 | 19.224 | −24.690 | 1.00 | 6.17 | H |
| ATOM | 3284 | CB | SER | H | 54 | −7.028 | 19.434 | −23.173 | 1.00 | 6.62 | H |
| ATOM | 3285 | OG | SER | H | 54 | −5.841 | 18.929 | −22.561 | 1.00 | 4.64 | H |
| ATOM | 3286 | C | SER | H | 54 | −5.842 | 19.957 | −25.320 | 1.00 | 7.53 | H |
| ATOM | 3287 | O | SER | H | 54 | −5.965 | 21.101 | −25.751 | 1.00 | 6.08 | H |
| ATOM | 3288 | N | GLY | H | 55 | −4.697 | 19.277 | −25.368 | 1.00 | 8.59 | H |
| ATOM | 3289 | CA | GLY | H | 55 | −3.516 | 19.868 | −25.956 | 1.00 | 9.92 | H |
| ATOM | 3290 | C | GLY | H | 55 | −2.648 | 20.537 | −24.916 | 1.00 | 10.79 | H |
| ATOM | 3291 | O | GLY | H | 55 | −1.634 | 21.174 | −25.232 | 1.00 | 8.31 | H |
| ATOM | 3292 | N | THR | H | 56 | −3.050 | 20.398 | −23.659 | 1.00 | 12.24 | H |
| ATOM | 3293 | CA | THR | H | 56 | −2.303 | 20.999 | −22.558 | 1.00 | 12.50 | H |
| ATOM | 3294 | CB | THR | H | 56 | −3.195 | 21.164 | −21.302 | 1.00 | 11.85 | H |
| ATOM | 3295 | OG1 | THR | H | 56 | −3.497 | 19.879 | −20.739 | 1.00 | 11.11 | H |
| ATOM | 3296 | CG2 | THR | H | 56 | −4.483 | 21.866 | −21.670 | 1.00 | 11.04 | H |
| ATOM | 3297 | C | THR | H | 56 | −1.089 | 20.152 | −22.191 | 1.00 | 11.96 | H |
| ATOM | 3298 | O | THR | H | 56 | −0.203 | 20.601 | −21.466 | 1.00 | 11.88 | H |
| ATOM | 3299 | N | LYS | H | 57 | −1.052 | 18.924 | −22.695 | 1.00 | 11.02 | H |
| ATOM | 3300 | CA | LYS | H | 57 | 0.062 | 18.047 | −22.407 | 1.00 | 9.97 | H |
| ATOM | 3301 | CB | LYS | H | 57 | −0.400 | 16.818 | −21.626 | 1.00 | 8.17 | H |
| ATOM | 3302 | CG | LYS | H | 57 | −1.011 | 17.145 | −20.277 | 1.00 | 9.71 | H |
| ATOM | 3303 | CD | LYS | H | 57 | −1.297 | 15.893 | −19.467 | 1.00 | 10.00 | H |
| ATOM | 3304 | CE | LYS | H | 57 | −2.760 | 15.785 | −19.084 | 1.00 | 11.05 | H |
| ATOM | 3305 | NZ | LYS | H | 57 | −3.188 | 16.841 | −18.138 | 1.00 | 12.83 | H |
| ATOM | 3306 | C | LYS | H | 57 | 0.698 | 17.628 | −23.707 | 1.00 | 9.96 | H |
| ATOM | 3307 | O | LYS | H | 57 | 0.085 | 16.933 | −24.507 | 1.00 | 11.40 | H |
| ATOM | 3308 | N | THR | H | 58 | 1.930 | 18.069 | −23.929 | 1.00 | 9.40 | H |
| ATOM | 3309 | CA | THR | H | 58 | 2.626 | 17.714 | −25.154 | 1.00 | 8.99 | H |
| ATOM | 3310 | CB | THR | H | 58 | 2.922 | 18.939 | −26.023 | 1.00 | 8.49 | H |
| ATOM | 3311 | OG1 | THR | H | 58 | 4.147 | 19.530 | −25.596 | 1.00 | 9.58 | H |
| ATOM | 3312 | CG2 | THR | H | 58 | 1.826 | 19.960 | −25.889 | 1.00 | 6.38 | H |
| ATOM | 3313 | C | THR | H | 58 | 3.938 | 17.060 | −24.777 | 1.00 | 9.30 | H |
| ATOM | 3314 | O | THR | H | 58 | 4.415 | 17.236 | −23.663 | 1.00 | 8.22 | H |
| ATOM | 3315 | N | HIS | H | 59 | 4.508 | 16.305 | −25.717 | 1.00 | 9.24 | H |
| ATOM | 3316 | CA | HIS | H | 59 | 5.769 | 15.595 | −25.519 | 1.00 | 8.03 | H |
| ATOM | 3317 | CB | HIS | H | 59 | 5.499 | 14.189 | −24.981 | 1.00 | 11.10 | H |
| ATOM | 3318 | CG | HIS | H | 59 | 5.068 | 14.158 | −23.547 | 1.00 | 14.76 | H |
| ATOM | 3319 | CD2 | HIS | H | 59 | 3.838 | 14.042 | −22.991 | 1.00 | 16.75 | H |
| ATOM | 3320 | ND1 | HIS | H | 59 | 5.960 | 14.219 | −22.500 | 1.00 | 15.55 | H |
| ATOM | 3321 | CE1 | HIS | H | 59 | 5.300 | 14.135 | −21.355 | 1.00 | 16.99 | H |
| ATOM | 3322 | NE2 | HIS | H | 59 | 4.012 | 14.026 | −21.626 | 1.00 | 16.44 | H |
| ATOM | 3323 | C | HIS | H | 59 | 6.534 | 15.505 | −26.841 | 1.00 | 6.73 | H |
| ATOM | 3324 | O | HIS | H | 59 | 5.947 | 15.238 | −27.892 | 1.00 | 4.86 | H |
| ATOM | 3325 | N | PHE | H | 60 | 7.844 | 15.735 | −26.776 | 1.00 | 6.24 | H |
| ATOM | 3326 | CA | PHE | H | 60 | 8.691 | 15.707 | −27.963 | 1.00 | 6.73 | H |
| ATOM | 3327 | CB | PHE | H | 60 | 9.258 | 17.098 | −28.259 | 1.00 | 6.25 | H |
| ATOM | 3328 | CG | PHE | H | 60 | 8.223 | 18.165 | −28.368 | 1.00 | 8.88 | H |
| ATOM | 3329 | CD1 | PHE | H | 60 | 7.732 | 18.795 | −27.226 | 1.00 | 10.51 | H |
| ATOM | 3330 | CD2 | PHE | H | 60 | 7.700 | 18.516 | −29.604 | 1.00 | 10.03 | H |
| ATOM | 3331 | CE1 | PHE | H | 60 | 6.724 | 19.760 | −27.311 | 1.00 | 9.17 | H |
| ATOM | 3332 | CE2 | PHE | H | 60 | 6.697 | 19.474 | −29.701 | 1.00 | 10.91 | H |
| ATOM | 3333 | CZ | PHE | H | 60 | 6.207 | 20.099 | −28.543 | 1.00 | 11.27 | H |
| ATOM | 3334 | C | PHE | H | 60 | 9.851 | 14.743 | −27.810 | 1.00 | 6.57 | H |
| ATOM | 3335 | O | PHE | H | 60 | 10.119 | 14.263 | −26.720 | 1.00 | 6.46 | H |
| ATOM | 3336 | N | ALA | H | 61 | 10.524 | 14.469 | −28.922 | 1.00 | 8.14 | H |
| ATOM | 3337 | CA | ALA | H | 61 | 11.684 | 13.589 | −28.956 | 1.00 | 10.25 | H |
| ATOM | 3338 | CB | ALA | H | 61 | 11.711 | 12.818 | −30.262 | 1.00 | 9.23 | H |
| ATOM | 3339 | C | ALA | H | 61 | 12.891 | 14.521 | −28.863 | 1.00 | 11.89 | H |
| ATOM | 3340 | O | ALA | H | 61 | 12.857 | 15.623 | −29.413 | 1.00 | 13.75 | H |
| ATOM | 3341 | N | ASP | H | 62 | 13.953 | 14.094 | −28.188 | 1.00 | 13.51 | H |
| ATOM | 3342 | CA | ASP | H | 62 | 15.124 | 14.953 | −28.047 | 1.00 | 15.64 | H |
| ATOM | 3343 | CB | ASP | H | 62 | 16.236 | 14.230 | −27.277 | 1.00 | 18.66 | H |
| ATOM | 3344 | CG | ASP | H | 62 | 16.077 | 14.365 | −25.771 | 1.00 | 23.55 | H |
| ATOM | 3345 | OD1 | ASP | H | 62 | 16.797 | 13.650 | −25.022 | 1.00 | 26.30 | H |
| ATOM | 3346 | OD2 | ASP | H | 62 | 15.234 | 15.197 | −25.333 | 1.00 | 25.44 | H |
| ATOM | 3347 | C | ASP | H | 62 | 15.657 | 15.493 | −29.364 | 1.00 | 14.78 | H |
| ATOM | 3348 | O | ASP | H | 62 | 15.992 | 16.672 | −29.464 | 1.00 | 16.08 | H |
| ATOM | 3349 | N | SER | H | 63 | 15.706 | 14.648 | −30.379 | 1.00 | 13.12 | H |

TABLE VIII-continued

Structure coordinates of the epitopes of allergenic beta-lactoglobulin in an antibody-beta-lactoglobulin immunocomplex;

|   | Atom type | Resid | | # | X | Y | Z | OCC | B | |
|---|---|---|---|---|---|---|---|---|---|---|
| ATOM | 3350 CA | SER | H | 63 | 16.222 | 15.072 | −31.667 | 1.00 | 13.50 | H |
| ATOM | 3351 CB | SER | H | 63 | 16.283 | 13.885 | −32.615 | 1.00 | 14.56 | H |
| ATOM | 3352 OG | SER | H | 63 | 14.980 | 13.365 | −32.822 | 1.00 | 18.30 | H |
| ATOM | 3353 C | SER | H | 63 | 15.397 | 16.165 | −32.326 | 1.00 | 13.14 | H |
| ATOM | 3354 O | SER | H | 63 | 15.734 | 16.635 | −33.411 | 1.00 | 12.97 | H |
| ATOM | 3355 N | VAL | H | 64 | 14.325 | 16.594 | −31.686 | 1.00 | 12.76 | H |
| ATOM | 3356 CA | VAL | H | 64 | 13.498 | 17.595 | −32.324 | 1.00 | 13.21 | H |
| ATOM | 3357 CB | VAL | H | 64 | 12.316 | 16.857 | −33.044 | 1.00 | 12.72 | H |
| ATOM | 3358 CG1 | VAL | H | 64 | 10.991 | 17.103 | −32.335 | 1.00 | 13.63 | H |
| ATOM | 3359 CG2 | VAL | H | 64 | 12.269 | 17.237 | −34.479 | 1.00 | 10.90 | H |
| ATOM | 3360 C | VAL | H | 64 | 13.021 | 18.673 | −31.340 | 1.00 | 13.76 | H |
| ATOM | 3361 O | VAL | H | 64 | 12.543 | 19.749 | −31.732 | 1.00 | 11.87 | H |
| ATOM | 3362 N | LYS | H | 65 | 13.172 | 18.384 | −30.052 | 1.00 | 16.05 | H |
| ATOM | 3363 CA | LYS | H | 65 | 12.772 | 19.323 | −29.013 | 1.00 | 17.75 | H |
| ATOM | 3364 CB | LYS | H | 65 | 13.103 | 18.787 | −27.617 | 1.00 | 20.48 | H |
| ATOM | 3365 CG | LYS | H | 65 | 12.768 | 19.806 | −26.531 | 1.00 | 24.24 | H |
| ATOM | 3366 CD | LYS | H | 65 | 12.539 | 19.177 | −25.177 | 1.00 | 26.75 | H |
| ATOM | 3367 CE | LYS | H | 65 | 12.065 | 20.228 | −24.186 | 1.00 | 29.20 | H |
| ATOM | 3368 NZ | LYS | H | 65 | 11.806 | 19.649 | −22.835 | 1.00 | 30.30 | H |
| ATOM | 3369 C | LYS | H | 65 | 13.467 | 20.654 | −29.196 | 1.00 | 16.93 | H |
| ATOM | 3370 O | LYS | H | 65 | 14.672 | 20.707 | −29.452 | 1.00 | 17.42 | H |
| ATOM | 3371 N | GLY | H | 66 | 12.701 | 21.725 | −29.040 | 1.00 | 15.98 | H |
| ATOM | 3372 CA | GLY | H | 66 | 13.255 | 23.047 | −29.210 | 1.00 | 15.03 | H |
| ATOM | 3373 C | GLY | H | 66 | 13.106 | 23.481 | −30.652 | 1.00 | 15.31 | H |
| ATOM | 3374 O | GLY | H | 66 | 13.118 | 24.669 | −30.945 | 1.00 | 17.76 | H |
| ATOM | 3375 N | ARG | H | 67 | 12.972 | 22.540 | −31.574 | 1.00 | 12.33 | H |
| ATOM | 3376 CA | ARG | H | 67 | 12.823 | 22.955 | −32.950 | 1.00 | 11.57 | H |
| ATOM | 3377 CB | ARG | H | 67 | 13.784 | 22.198 | −33.856 | 1.00 | 11.70 | H |
| ATOM | 3378 CG | ARG | H | 67 | 15.254 | 22.497 | −33.600 | 1.00 | 9.21 | H |
| ATOM | 3379 CD | ARG | H | 67 | 16.113 | 21.818 | −34.641 | 1.00 | 6.92 | H |
| ATOM | 3380 NE | ARG | H | 67 | 15.869 | 20.379 | −34.681 | 1.00 | 6.37 | H |
| ATOM | 3381 CZ | ARG | H | 67 | 15.526 | 19.713 | −35.778 | 1.00 | 7.25 | H |
| ATOM | 3382 NH1 | ARG | H | 67 | 15.386 | 20.350 | −36.934 | 1.00 | 9.14 | H |
| ATOM | 3383 NH2 | ARG | H | 67 | 15.300 | 18.413 | −35.719 | 1.00 | 6.47 | H |
| ATOM | 3384 C | ARG | H | 67 | 11.402 | 22.732 | −33.415 | 1.00 | 12.38 | H |
| ATOM | 3385 O | ARG | H | 67 | 10.849 | 23.543 | −34.143 | 1.00 | 13.55 | H |
| ATOM | 3386 N | PHE | H | 68 | 10.804 | 21.632 | −32.983 | 1.00 | 12.18 | H |
| ATOM | 3387 CA | PHE | H | 68 | 9.448 | 21.319 | −33.381 | 1.00 | 11.31 | H |
| ATOM | 3388 CB | PHE | H | 68 | 9.351 | 19.850 | −33.769 | 1.00 | 11.86 | H |
| ATOM | 3389 CG | PHE | H | 68 | 9.971 | 19.516 | −35.099 | 1.00 | 12.06 | H |
| ATOM | 3390 CD1 | PHE | H | 68 | 10.973 | 20.313 | −35.653 | 1.00 | 11.71 | H |
| ATOM | 3391 CD2 | PHE | H | 68 | 9.583 | 18.351 | −35.776 | 1.00 | 11.05 | H |
| ATOM | 3392 CE1 | PHE | H | 68 | 11.584 | 19.953 | −36.859 | 1.00 | 11.42 | H |
| ATOM | 3393 CE2 | PHE | H | 68 | 10.186 | 17.981 | −36.980 | 1.00 | 9.57 | H |
| ATOM | 3394 CZ | PHE | H | 68 | 11.188 | 18.779 | −37.527 | 1.00 | 9.82 | H |
| ATOM | 3395 C | PHE | H | 68 | 8.436 | 21.611 | −32.291 | 1.00 | 12.02 | H |
| ATOM | 3396 O | PHE | H | 68 | 8.684 | 21.376 | −31.110 | 1.00 | 12.67 | H |
| ATOM | 3397 N | THR | H | 69 | 7.283 | 22.127 | −32.693 | 1.00 | 11.69 | H |
| ATOM | 3398 CA | THR | H | 69 | 6.233 | 22.416 | −31.735 | 1.00 | 10.64 | H |
| ATOM | 3399 CB | THR | H | 69 | 6.103 | 23.948 | −31.456 | 1.00 | 10.59 | H |
| ATOM | 3400 OG1 | THR | H | 69 | 4.719 | 24.297 | −31.351 | 1.00 | 14.40 | H |
| ATOM | 3401 CG2 | THR | H | 69 | 6.737 | 24.771 | −32.569 | 1.00 | 11.79 | H |
| ATOM | 3402 C | THR | H | 69 | 4.910 | 21.841 | −32.244 | 1.00 | 9.62 | H |
| ATOM | 3403 O | THR | H | 69 | 4.450 | 22.170 | −33.337 | 1.00 | 9.39 | H |
| ATOM | 3404 N | ILE | H | 70 | 4.316 | 20.962 | −31.440 | 1.00 | 7.95 | H |
| ATOM | 3405 CA | ILE | H | 70 | 3.044 | 20.325 | −31.773 | 1.00 | 6.64 | H |
| ATOM | 3406 CB | ILE | H | 70 | 2.937 | 18.914 | −31.124 | 1.00 | 5.97 | H |
| ATOM | 3407 CG2 | ILE | H | 70 | 2.930 | 19.046 | −29.621 | 1.00 | 3.75 | H |
| ATOM | 3408 CG1 | ILE | H | 70 | 1.667 | 18.200 | −31.605 | 1.00 | 5.93 | H |
| ATOM | 3409 CD1 | ILE | H | 70 | 1.677 | 16.710 | −31.399 | 1.00 | 5.04 | H |
| ATOM | 3410 C | ILE | H | 70 | 1.897 | 21.189 | −31.254 | 1.00 | 5.92 | H |
| ATOM | 3411 O | ILE | H | 70 | 2.041 | 21.831 | −30.219 | 1.00 | 7.78 | H |
| ATOM | 3412 N | SER | H | 71 | 0.775 | 21.205 | −31.970 | 1.00 | 4.08 | H |
| ATOM | 3413 CA | SER | H | 71 | −0.408 | 21.972 | −31.570 | 1.00 | 3.29 | H |
| ATOM | 3414 CB | SER | H | 71 | −0.267 | 23.449 | −31.943 | 1.00 | 1.76 | H |
| ATOM | 3415 OG | SER | H | 71 | 0.300 | 23.593 | −33.232 | 1.00 | 5.75 | H |
| ATOM | 3416 C | SER | H | 71 | −1.645 | 21.384 | −32.230 | 1.00 | 2.94 | H |
| ATOM | 3417 O | SER | H | 71 | −1.545 | 20.614 | −33.185 | 1.00 | 1.59 | H |
| ATOM | 3418 N | ARG | H | 72 | −2.812 | 21.764 | −31.728 | 1.00 | 3.54 | H |
| ATOM | 3419 CA | ARG | H | 72 | −4.081 | 21.231 | −32.216 | 1.00 | 4.48 | H |
| ATOM | 3420 CB | ARG | H | 72 | −4.441 | 20.016 | −31.343 | 1.00 | 4.63 | H |
| ATOM | 3421 CG | ARG | H | 72 | −5.849 | 19.970 | −30.810 | 1.00 | 5.35 | H |
| ATOM | 3422 CD | ARG | H | 72 | −5.940 | 19.277 | −29.466 | 1.00 | 4.98 | H |
| ATOM | 3423 NE | ARG | H | 72 | −5.546 | 17.865 | −29.437 | 1.00 | 6.58 | H |

TABLE VIII-continued

Structure coordinates of the epitopes of allergenic beta-lactoglobulin in an antibody-beta-lactoglobulin immunocomplex;

|  |  | Atom type | Resid |  | # | X | Y | Z | OCC | B |  |
|---|---|---|---|---|---|---|---|---|---|---|---|
| ATOM | 3424 | CZ | ARG | H | 72 | −6.289 | 16.841 | −29.867 | 1.00 | 7.67 | H |
| ATOM | 3425 | NH1 | ARG | H | 72 | −7.484 | 17.035 | −30.386 | 1.00 | 7.98 | H |
| ATOM | 3426 | NH2 | ARG | H | 72 | −5.854 | 15.598 | −29.742 | 1.00 | 9.34 | H |
| ATOM | 3427 | C | ARG | H | 72 | −5.167 | 22.289 | −32.161 | 1.00 | 5.09 | H |
| ATOM | 3428 | O | ARG | H | 72 | −5.086 | 23.194 | −31.351 | 1.00 | 5.98 | H |
| ATOM | 3429 | N | ASP | H | 73 | −6.164 | 22.196 | −33.036 | 1.00 | 7.54 | H |
| ATOM | 3430 | CA | ASP | H | 73 | −7.261 | 23.166 | −33.032 | 1.00 | 10.50 | H |
| ATOM | 3431 | CB | ASP | H | 73 | −7.214 | 24.030 | −34.297 | 1.00 | 12.67 | H |
| ATOM | 3432 | CG | ASP | H | 73 | −8.309 | 25.111 | −34.327 | 1.00 | 13.54 | H |
| ATOM | 3433 | OD1 | ASP | H | 73 | −9.429 | 24.831 | −33.863 | 1.00 | 12.69 | H |
| ATOM | 3434 | OD2 | ASP | H | 73 | −8.049 | 26.231 | −34.832 | 1.00 | 14.66 | H |
| ATOM | 3435 | C | ASP | H | 73 | −8.613 | 22.447 | −32.957 | 1.00 | 11.07 | H |
| ATOM | 3436 | O | ASP | H | 73 | −9.191 | 22.093 | −33.983 | 1.00 | 11.19 | H |
| ATOM | 3437 | N | ASN | H | 74 | −9.122 | 22.262 | −31.748 | 1.00 | 11.92 | H |
| ATOM | 3438 | CA | ASN | H | 74 | −10.390 | 21.589 | −31.565 | 1.00 | 13.93 | H |
| ATOM | 3439 | CB | ASN | H | 74 | −10.538 | 21.139 | −30.115 | 1.00 | 13.39 | H |
| ATOM | 3440 | CG | ASN | H | 74 | −9.502 | 20.112 | −29.727 | 1.00 | 15.07 | H |
| ATOM | 3441 | OD1 | ASN | H | 74 | −9.020 | 19.368 | −30.581 | 1.00 | 15.70 | H |
| ATOM | 3442 | ND2 | ASN | H | 74 | −9.163 | 20.045 | −28.444 | 1.00 | 14.48 | H |
| ATOM | 3443 | C | ASN | H | 74 | −11.579 | 22.456 | −31.962 | 1.00 | 16.05 | H |
| ATOM | 3444 | O | ASN | H | 74 | −12.340 | 22.924 | −31.116 | 1.00 | 18.94 | H |
| ATOM | 3445 | N | SER | H | 75 | −11.727 | 22.683 | −33.257 | 1.00 | 16.45 | H |
| ATOM | 3446 | CA | SER | H | 75 | −12.820 | 23.484 | −33.786 | 1.00 | 16.17 | H |
| ATOM | 3447 | CB | SER | H | 75 | −12.491 | 24.974 | −33.745 | 1.00 | 17.32 | H |
| ATOM | 3448 | OG | SER | H | 75 | −11.878 | 25.333 | −32.521 | 1.00 | 20.43 | H |
| ATOM | 3449 | C | SER | H | 75 | −12.884 | 23.070 | −35.223 | 1.00 | 17.41 | H |
| ATOM | 3450 | O | SER | H | 75 | −13.954 | 22.830 | −35.774 | 1.00 | 19.91 | H |
| ATOM | 3451 | N | ASN | H | 76 | −11.703 | 22.992 | −35.825 | 1.00 | 16.64 | H |
| ATOM | 3452 | CA | ASN | H | 76 | −11.568 | 22.611 | −37.217 | 1.00 | 15.45 | H |
| ATOM | 3453 | CB | ASN | H | 76 | −10.637 | 23.590 | −37.947 | 1.00 | 17.04 | H |
| ATOM | 3454 | CG | ASN | H | 76 | −9.302 | 23.775 | −37.232 | 1.00 | 20.41 | H |
| ATOM | 3455 | OD1 | ASN | H | 76 | −8.938 | 23.003 | −36.336 | 1.00 | 21.95 | H |
| ATOM | 3456 | ND2 | ASN | H | 76 | −8.558 | 24.796 | −37.636 | 1.00 | 21.39 | H |
| ATOM | 3457 | C | ASN | H | 76 | −11.019 | 21.196 | −37.340 | 1.00 | 13.63 | H |
| ATOM | 3458 | O | ASN | H | 76 | −10.672 | 20.771 | −38.436 | 1.00 | 11.77 | H |
| ATOM | 3459 | N | ASN | H | 77 | −10.934 | 20.479 | −36.222 | 1.00 | 11.14 | H |
| ATOM | 3460 | CA | ASN | H | 77 | −10.419 | 19.112 | −36.239 | 1.00 | 11.22 | H |
| ATOM | 3461 | CB | ASN | H | 77 | −11.383 | 18.193 | −36.977 | 1.00 | 12.73 | H |
| ATOM | 3462 | CG | ASN | H | 77 | −12.674 | 17.980 | −36.224 | 1.00 | 16.20 | H |
| ATOM | 3463 | OD1 | ASN | H | 77 | −13.517 | 17.176 | −36.630 | 1.00 | 17.08 | H |
| ATOM | 3464 | ND2 | ASN | H | 77 | −12.840 | 18.702 | −35.109 | 1.00 | 18.52 | H |
| ATOM | 3465 | C | ASN | H | 77 | −9.064 | 19.001 | −36.919 | 1.00 | 11.03 | H |
| ATOM | 3466 | O | ASN | H | 77 | −8.846 | 18.114 | −37.748 | 1.00 | 10.80 | H |
| ATOM | 3467 | N | THR | H | 78 | −8.157 | 19.900 | −36.565 | 1.00 | 8.71 | H |
| ATOM | 3468 | CA | THR | H | 78 | −6.852 | 19.919 | −37.178 | 1.00 | 7.47 | H |
| ATOM | 3469 | CB | THR | H | 78 | −6.651 | 21.223 | −37.953 | 1.00 | 9.54 | H |
| ATOM | 3470 | OG1 | THR | H | 78 | −7.779 | 21.447 | −38.801 | 1.00 | 11.42 | H |
| ATOM | 3471 | CG2 | THR | H | 78 | −5.401 | 21.149 | −38.813 | 1.00 | 9.06 | H |
| ATOM | 3472 | C | THR | H | 78 | −5.704 | 19.757 | −36.208 | 1.00 | 7.12 | H |
| ATOM | 3473 | O | THR | H | 78 | −5.692 | 20.332 | −35.119 | 1.00 | 4.88 | H |
| ATOM | 3474 | N | LEU | H | 79 | −4.728 | 18.959 | −36.626 | 1.00 | 6.47 | H |
| ATOM | 3475 | CA | LEU | H | 79 | −3.548 | 18.700 | −35.823 | 1.00 | 6.13 | H |
| ATOM | 3476 | CB | LEU | H | 79 | −3.339 | 17.188 | −35.672 | 1.00 | 3.73 | H |
| ATOM | 3477 | CG | LEU | H | 79 | −2.217 | 16.691 | −34.754 | 1.00 | 2.93 | H |
| ATOM | 3478 | CD1 | LEU | H | 79 | −0.978 | 16.427 | −35.533 | 1.00 | 1.00 | H |
| ATOM | 3479 | CD2 | LEU | H | 79 | −1.970 | 17.684 | −33.647 | 1.00 | 2.62 | H |
| ATOM | 3480 | C | LEU | H | 79 | −2.385 | 19.345 | −36.562 | 1.00 | 6.55 | H |
| ATOM | 3481 | O | LEU | H | 79 | −2.199 | 19.119 | −37.743 | 1.00 | 6.69 | H |
| ATOM | 3482 | N | TYR | H | 80 | −1.621 | 20.167 | −35.863 | 1.00 | 6.40 | H |
| ATOM | 3483 | CA | TYR | H | 80 | −0.495 | 20.836 | −36.469 | 1.00 | 7.17 | H |
| ATOM | 3484 | CB | TYR | H | 80 | −0.607 | 22.341 | −36.206 | 1.00 | 6.40 | H |
| ATOM | 3485 | CG | TYR | H | 80 | −1.840 | 22.956 | −36.818 | 1.00 | 7.53 | H |
| ATOM | 3486 | CD1 | TYR | H | 80 | −1.955 | 23.089 | −38.195 | 1.00 | 7.52 | H |
| ATOM | 3487 | CE1 | TYR | H | 80 | −3.110 | 23.592 | −38.784 | 1.00 | 7.14 | H |
| ATOM | 3488 | CD2 | TYR | H | 80 | −2.920 | 23.351 | −36.028 | 1.00 | 7.68 | H |
| ATOM | 3489 | CE2 | TYR | H | 80 | −4.083 | 23.855 | −36.607 | 1.00 | 8.61 | H |
| ATOM | 3490 | CZ | TYR | H | 80 | −4.169 | 23.970 | −37.994 | 1.00 | 8.93 | H |
| ATOM | 3491 | OH | TYR | H | 80 | −5.332 | 24.446 | −38.576 | 1.00 | 10.76 | H |
| ATOM | 3492 | C | TYR | H | 80 | 0.859 | 20.317 | −35.945 | 1.00 | 9.01 | H |
| ATOM | 3493 | O | TYR | H | 80 | 0.945 | 19.633 | −34.909 | 1.00 | 7.86 | H |
| ATOM | 3494 | N | LEU | H | 81 | 1.906 | 20.667 | −36.691 | 1.00 | 9.72 | H |
| ATOM | 3495 | CA | LEU | H | 81 | 3.289 | 20.356 | −36.370 | 1.00 | 9.06 | H |
| ATOM | 3496 | CB | LEU | H | 81 | 3.706 | 18.993 | −36.914 | 1.00 | 8.70 | H |
| ATOM | 3497 | CG | LEU | H | 81 | 5.192 | 18.669 | −36.656 | 1.00 | 7.92 | H |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 3498 CD1 | LEU | H | 81 | 5.449 | 18.645 | −35.145 | 1.00 | 7.49 | H |
| ATOM | 3499 CD2 | LEU | H | 81 | 5.574 | 17.343 | −37.284 | 1.00 | 3.90 | H |
| ATOM | 3500 C | LEU | H | 81 | 4.127 | 21.444 | −37.021 | 1.00 | 10.37 | H |
| ATOM | 3501 O | LEU | H | 81 | 4.178 | 21.552 | −38.256 | 1.00 | 9.62 | H |
| ATOM | 3502 N | GLN | H | 82 | 4.756 | 22.259 | −36.172 | 1.00 | 11.89 | H |
| ATOM | 3503 CA | GLN | H | 82 | 5.627 | 23.362 | −36.590 | 1.00 | 12.40 | H |
| ATOM | 3504 CB | GLN | H | 82 | 5.477 | 24.554 | −35.643 | 1.00 | 11.73 | H |
| ATOM | 3505 CG | GLN | H | 82 | 6.116 | 25.822 | −36.160 | 1.00 | 13.56 | H |
| ATOM | 3506 CD | GLN | H | 82 | 5.432 | 26.305 | −37.406 | 1.00 | 13.55 | H |
| ATOM | 3507 OE1 | GLN | H | 82 | 4.204 | 26.380 | −37.451 | 1.00 | 13.14 | H |
| ATOM | 3508 NE2 | GLN | H | 82 | 6.214 | 26.645 | −38.426 | 1.00 | 12.96 | H |
| ATOM | 3509 C | GLN | H | 82 | 7.081 | 22.901 | −36.562 | 1.00 | 12.65 | H |
| ATOM | 3510 O | GLN | H | 82 | 7.633 | 22.606 | −35.497 | 1.00 | 11.89 | H |
| ATOM | 3511 N | MET | H | 83 | 7.685 | 22.850 | −37.742 | 1.00 | 13.04 | H |
| ATOM | 3512 CA | MET | H | 83 | 9.072 | 22.442 | −37.893 | 1.00 | 13.26 | H |
| ATOM | 3513 CB | MET | H | 83 | 9.203 | 21.476 | −39.076 | 1.00 | 13.61 | H |
| ATOM | 3514 CG | MET | H | 83 | 8.251 | 20.267 | −39.014 | 1.00 | 13.89 | H |
| ATOM | 3515 SD | MET | H | 83 | 8.630 | 18.987 | −40.303 | 1.00 | 10.43 | H |
| ATOM | 3516 CE | MET | H | 83 | 7.431 | 19.442 | −41.574 | 1.00 | 10.13 | H |
| ATOM | 3517 C | MET | H | 83 | 9.944 | 23.664 | −38.135 | 1.00 | 12.74 | H |
| ATOM | 3518 O | MET | H | 83 | 9.885 | 24.244 | −39.221 | 1.00 | 12.35 | H |
| ATOM | 3519 N | ASP | H | 84 | 10.726 | 24.064 | −37.129 | 1.00 | 12.16 | H |
| ATOM | 3520 CA | ASP | H | 84 | 11.614 | 25.219 | −37.276 | 1.00 | 13.74 | H |
| ATOM | 3521 CB | ASP | H | 84 | 11.416 | 26.247 | −36.155 | 1.00 | 15.64 | H |
| ATOM | 3522 CG | ASP | H | 84 | 9.972 | 26.738 | −36.035 | 1.00 | 19.86 | H |
| ATOM | 3523 OD1 | ASP | H | 84 | 9.331 | 27.059 | −37.079 | 1.00 | 19.64 | H |
| ATOM | 3524 OD2 | ASP | H | 84 | 9.480 | 26.817 | −34.875 | 1.00 | 22.08 | H |
| ATOM | 3525 C | ASP | H | 84 | 13.066 | 24.762 | −37.284 | 1.00 | 14.11 | H |
| ATOM | 3526 O | ASP | H | 84 | 13.414 | 23.741 | −36.691 | 1.00 | 13.48 | H |
| ATOM | 3527 N | ASN | H | 85 | 13.907 | 25.541 | −37.956 | 1.00 | 14.96 | H |
| ATOM | 3528 CA | ASN | H | 85 | 15.328 | 25.250 | −38.101 | 1.00 | 14.80 | H |
| ATOM | 3529 CB | ASN | H | 85 | 16.078 | 25.539 | −36.798 | 1.00 | 16.03 | H |
| ATOM | 3530 CG | ASN | H | 85 | 17.589 | 25.441 | −36.957 | 1.00 | 17.56 | H |
| ATOM | 3531 OD1 | ASN | H | 85 | 18.199 | 26.153 | −37.758 | 1.00 | 20.22 | H |
| ATOM | 3532 ND2 | ASN | H | 85 | 18.199 | 24.552 | −36.196 | 1.00 | 20.29 | H |
| ATOM | 3533 C | ASN | H | 85 | 15.508 | 23.795 | −38.510 | 1.00 | 14.22 | H |
| ATOM | 3534 O | ASN | H | 85 | 16.154 | 23.012 | −37.800 | 1.00 | 15.62 | H |
| ATOM | 3535 N | VAL | H | 86 | 14.941 | 23.442 | −39.666 | 1.00 | 12.38 | H |
| ATOM | 3536 CA | VAL | H | 86 | 15.013 | 22.073 | −40.172 | 1.00 | 10.44 | H |
| ATOM | 3537 CB | VAL | H | 86 | 14.026 | 21.831 | −41.351 | 1.00 | 8.45 | H |
| ATOM | 3538 CG1 | VAL | H | 86 | 12.606 | 22.045 | −40.891 | 1.00 | 3.18 | H |
| ATOM | 3539 CG2 | VAL | H | 86 | 14.357 | 22.741 | −42.521 | 1.00 | 8.04 | H |
| ATOM | 3540 C | VAL | H | 86 | 16.388 | 21.635 | −40.632 | 1.00 | 10.36 | H |
| ATOM | 3541 O | VAL | H | 86 | 17.037 | 22.310 | −41.426 | 1.00 | 10.28 | H |
| ATOM | 3542 N | ARG | H | 87 | 16.819 | 20.493 | −40.116 | 1.00 | 11.49 | H |
| ATOM | 3543 CA | ARG | H | 87 | 18.094 | 19.917 | −40.487 | 1.00 | 13.66 | H |
| ATOM | 3544 CB | ARG | H | 87 | 18.714 | 19.147 | −39.319 | 1.00 | 14.95 | H |
| ATOM | 3545 CG | ARG | H | 87 | 18.626 | 19.789 | −37.937 | 1.00 | 17.51 | H |
| ATOM | 3546 CD | ARG | H | 87 | 19.444 | 18.934 | −36.976 | 1.00 | 19.96 | H |
| ATOM | 3547 NE | ARG | H | 87 | 19.129 | 19.055 | −35.552 | 1.00 | 22.00 | H |
| ATOM | 3548 CZ | ARG | H | 87 | 19.207 | 20.173 | −34.840 | 1.00 | 24.13 | H |
| ATOM | 3549 NH1 | ARG | H | 87 | 19.579 | 21.315 | −35.415 | 1.00 | 26.64 | H |
| ATOM | 3550 NH2 | ARG | H | 87 | 18.951 | 20.135 | −33.537 | 1.00 | 23.82 | H |
| ATOM | 3551 C | ARG | H | 87 | 17.815 | 18.929 | −41.619 | 1.00 | 15.16 | H |
| ATOM | 3552 O | ARG | H | 87 | 16.659 | 18.641 | −41.938 | 1.00 | 15.01 | H |
| ATOM | 3553 N | ASP | H | 88 | 18.881 | 18.392 | −42.201 | 1.00 | 17.98 | H |
| ATOM | 3554 CA | ASP | H | 88 | 18.781 | 17.421 | −43.289 | 1.00 | 20.08 | H |
| ATOM | 3555 CB | ASP | H | 88 | 20.197 | 17.139 | −43.812 | 1.00 | 23.69 | H |
| ATOM | 3556 CG | ASP | H | 88 | 21.061 | 18.413 | −43.875 | 1.00 | 29.04 | H |
| ATOM | 3557 OD1 | ASP | H | 88 | 20.911 | 19.212 | −44.842 | 1.00 | 30.25 | H |
| ATOM | 3558 OD2 | ASP | H | 88 | 21.887 | 18.620 | −42.944 | 1.00 | 31.49 | H |
| ATOM | 3559 C | ASP | H | 88 | 18.110 | 16.141 | −42.770 | 1.00 | 19.34 | H |
| ATOM | 3560 O | ASP | H | 88 | 17.316 | 15.507 | −43.471 | 1.00 | 17.14 | H |
| ATOM | 3561 N | GLU | H | 89 | 18.435 | 15.802 | −41.524 | 1.00 | 20.05 | H |
| ATOM | 3562 CA | GLU | H | 89 | 17.928 | 14.626 | −40.835 | 1.00 | 20.41 | H |
| ATOM | 3563 CB | GLU | H | 89 | 18.623 | 14.491 | −39.484 | 1.00 | 23.61 | H |
| ATOM | 3564 CG | GLU | H | 89 | 20.141 | 14.591 | −39.567 | 1.00 | 30.26 | H |
| ATOM | 3565 CD | GLU | H | 89 | 20.637 | 16.031 | −39.604 | 1.00 | 33.35 | H |
| ATOM | 3566 OE1 | GLU | H | 89 | 20.360 | 16.764 | −38.625 | 1.00 | 36.26 | H |
| ATOM | 3567 OE2 | GLU | H | 89 | 21.304 | 16.423 | −40.595 | 1.00 | 34.20 | H |
| ATOM | 3568 C | GLU | H | 89 | 16.415 | 14.647 | −40.636 | 1.00 | 18.53 | H |
| ATOM | 3569 O | GLU | H | 89 | 15.821 | 13.677 | −40.171 | 1.00 | 18.64 | H |
| ATOM | 3570 N | ASP | H | 90 | 15.783 | 15.757 | −40.968 | 1.00 | 16.04 | H |
| ATOM | 3571 CA | ASP | H | 90 | 14.350 | 15.813 | −40.832 | 1.00 | 13.47 | H |

TABLE VIII-continued

Structure coordinates of the epitopes of allergenic beta-lactoglobulin in an antibody-beta-lactoglobulin immunocomplex;

| | | Atom type | | Resid | # | X | Y | Z | OCC | B | |
|---|---|---|---|---|---|---|---|---|---|---|---|
| ATOM | 3572 | CB | ASP | H | 90 | 13.901 | 17.237 | −40.509 | 1.00 | 13.36 | H |
| ATOM | 3573 | CG | ASP | H | 90 | 14.319 | 17.678 | −39.111 | 1.00 | 13.47 | H |
| ATOM | 3574 | OD1 | ASP | H | 90 | 14.207 | 16.875 | −38.153 | 1.00 | 12.70 | H |
| ATOM | 3575 | OD2 | ASP | H | 90 | 14.747 | 18.841 | −38.960 | 1.00 | 13.27 | H |
| ATOM | 3576 | C | ASP | H | 90 | 13.639 | 15.296 | −42.083 | 1.00 | 11.74 | H |
| ATOM | 3577 | O | ASP | H | 90 | 12.421 | 15.162 | −42.082 | 1.00 | 11.55 | H |
| ATOM | 3578 | N | THR | H | 91 | 14.379 | 15.000 | −43.150 | 1.00 | 10.83 | H |
| ATOM | 3579 | CA | THR | H | 91 | 13.739 | 14.477 | −44.359 | 1.00 | 9.48 | H |
| ATOM | 3580 | CB | THR | H | 91 | 14.758 | 14.316 | −45.534 | 1.00 | 7.81 | H |
| ATOM | 3581 | OG1 | THR | H | 91 | 15.200 | 15.615 | −45.947 | 1.00 | 7.57 | H |
| ATOM | 3582 | CG2 | THR | H | 91 | 14.111 | 13.659 | −46.748 | 1.00 | 6.29 | H |
| ATOM | 3583 | C | THR | H | 91 | 13.084 | 13.138 | −44.019 | 1.00 | 8.73 | H |
| ATOM | 3584 | O | THR | H | 91 | 13.738 | 12.204 | −43.531 | 1.00 | 8.19 | H |
| ATOM | 3585 | N | ALA | H | 92 | 11.776 | 13.068 | −44.241 | 1.00 | 8.36 | H |
| ATOM | 3586 | CA | ALA | H | 92 | 11.017 | 11.852 | −43.951 | 1.00 | 8.03 | H |
| ATOM | 3587 | CB | ALA | H | 92 | 11.149 | 11.491 | −42.471 | 1.00 | 6.60 | H |
| ATOM | 3588 | C | ALA | H | 92 | 9.548 | 12.009 | −44.290 | 1.00 | 6.21 | H |
| ATOM | 3589 | O | ALA | H | 92 | 9.092 | 13.092 | −44.669 | 1.00 | 3.46 | H |
| ATOM | 3590 | N | ILE | H | 93 | 8.823 | 10.905 | −44.157 | 1.00 | 6.09 | H |
| ATOM | 3591 | CA | ILE | H | 93 | 7.399 | 10.905 | −44.390 | 1.00 | 6.84 | H |
| ATOM | 3592 | CB | ILE | H | 93 | 6.920 | 9.571 | −44.932 | 1.00 | 6.37 | H |
| ATOM | 3593 | CG2 | ILE | H | 93 | 5.416 | 9.615 | −45.139 | 1.00 | 6.16 | H |
| ATOM | 3594 | CG1 | ILE | H | 93 | 7.606 | 9.289 | −46.259 | 1.00 | 7.33 | H |
| ATOM | 3595 | CD1 | ILE | H | 93 | 7.328 | 7.897 | −46.781 | 1.00 | 8.98 | H |
| ATOM | 3596 | C | ILE | H | 93 | 6.796 | 11.126 | −43.023 | 1.00 | 6.45 | H |
| ATOM | 3597 | O | ILE | H | 93 | 6.982 | 10.309 | −42.134 | 1.00 | 7.71 | H |
| ATOM | 3598 | N | TYR | H | 94 | 6.127 | 12.254 | −42.828 | 1.00 | 7.32 | H |
| ATOM | 3599 | CA | TYR | H | 94 | 5.536 | 12.521 | −41.527 | 1.00 | 8.20 | H |
| ATOM | 3600 | CB | TYR | H | 94 | 5.547 | 14.022 | −41.207 | 1.00 | 7.72 | H |
| ATOM | 3601 | CG | TYR | H | 94 | 6.930 | 14.526 | −40.868 | 1.00 | 6.95 | H |
| ATOM | 3602 | CD1 | TYR | H | 94 | 7.942 | 14.513 | −41.825 | 1.00 | 6.29 | H |
| ATOM | 3603 | CE1 | TYR | H | 94 | 9.235 | 14.867 | −41.513 | 1.00 | 6.51 | H |
| ATOM | 3604 | CD2 | TYR | H | 94 | 7.252 | 14.927 | −39.569 | 1.00 | 7.60 | H |
| ATOM | 3605 | CE2 | TYR | H | 94 | 8.552 | 15.290 | −39.241 | 1.00 | 8.06 | H |
| ATOM | 3606 | CZ | TYR | H | 94 | 9.544 | 15.250 | −40.232 | 1.00 | 7.37 | H |
| ATOM | 3607 | OH | TYR | H | 94 | 10.844 | 15.565 | −39.926 | 1.00 | 7.51 | H |
| ATOM | 3608 | C | TYR | H | 94 | 4.128 | 11.974 | −41.467 | 1.00 | 8.37 | H |
| ATOM | 3609 | O | TYR | H | 94 | 3.231 | 12.385 | −42.217 | 1.00 | 8.36 | H |
| ATOM | 3610 | N | TYR | H | 95 | 3.950 | 11.015 | −40.572 | 1.00 | 7.89 | H |
| ATOM | 3611 | CA | TYR | H | 95 | 2.658 | 10.387 | −40.373 | 1.00 | 7.44 | H |
| ATOM | 3612 | CB | TYR | H | 95 | 2.824 | 8.887 | −40.112 | 1.00 | 7.20 | H |
| ATOM | 3613 | CG | TYR | H | 95 | 3.349 | 8.085 | −41.279 | 1.00 | 6.80 | H |
| ATOM | 3614 | CD1 | TYR | H | 95 | 2.508 | 7.660 | −42.295 | 1.00 | 6.39 | H |
| ATOM | 3615 | CE1 | TYR | H | 95 | 2.994 | 6.925 | −43.365 | 1.00 | 8.93 | H |
| ATOM | 3616 | CD2 | TYR | H | 95 | 4.689 | 7.757 | −41.360 | 1.00 | 6.07 | H |
| ATOM | 3617 | CE2 | TYR | H | 95 | 5.186 | 7.027 | −42.419 | 1.00 | 8.64 | H |
| ATOM | 3618 | CZ | TYR | H | 95 | 4.336 | 6.608 | −43.425 | 1.00 | 10.04 | H |
| ATOM | 3619 | OH | TYR | H | 95 | 4.834 | 5.866 | −44.482 | 1.00 | 13.38 | H |
| ATOM | 3620 | C | TYR | H | 95 | 1.888 | 10.998 | −39.209 | 1.00 | 6.27 | H |
| ATOM | 3621 | O | TYR | H | 95 | 2.431 | 11.316 | −38.153 | 1.00 | 4.94 | H |
| ATOM | 3622 | N | CYS | H | 96 | 0.593 | 11.129 | −39.431 | 1.00 | 8.19 | H |
| ATOM | 3623 | CA | CYS | H | 96 | −0.370 | 11.655 | −38.470 | 1.00 | 7.75 | H |
| ATOM | 3624 | C | CYS | H | 96 | −1.075 | 10.462 | −37.805 | 1.00 | 6.55 | H |
| ATOM | 3625 | O | CYS | H | 96 | −1.678 | 9.647 | −38.505 | 1.00 | 6.33 | H |
| ATOM | 3626 | CB | CYS | H | 96 | −1.396 | 12.450 | −39.250 | 1.00 | 8.73 | H |
| ATOM | 3627 | SG | CYS | H | 96 | −2.753 | 13.021 | −38.248 | 1.00 | 18.02 | H |
| ATOM | 3628 | N | ALA | H | 97 | −1.024 | 10.343 | −36.482 | 1.00 | 5.62 | H |
| ATOM | 3629 | CA | ALA | H | 97 | −1.708 | 9.217 | −35.842 | 1.00 | 6.65 | H |
| ATOM | 3630 | CB | ALA | H | 97 | −0.705 | 8.135 | −35.433 | 1.00 | 4.88 | H |
| ATOM | 3631 | C | ALA | H | 97 | −2.591 | 9.600 | −34.652 | 1.00 | 7.14 | H |
| ATOM | 3632 | O | ALA | H | 97 | −2.270 | 10.525 | −33.889 | 1.00 | 6.80 | H |
| ATOM | 3633 | N | LYS | H | 98 | −3.706 | 8.876 | −34.504 | 1.00 | 7.33 | H |
| ATOM | 3634 | CA | LYS | H | 98 | −4.695 | 9.107 | −33.435 | 1.00 | 6.92 | H |
| ATOM | 3635 | CB | LYS | H | 98 | −6.118 | 9.141 | −34.047 | 1.00 | 7.96 | H |
| ATOM | 3636 | CG | LYS | H | 98 | −7.243 | 8.683 | −33.099 | 1.00 | 8.65 | H |
| ATOM | 3637 | CD | LYS | H | 98 | −8.577 | 8.713 | −33.793 | 1.00 | 7.93 | H |
| ATOM | 3638 | CE | LYS | H | 98 | −9.632 | 8.044 | −32.957 | 1.00 | 8.38 | H |
| ATOM | 3639 | NZ | LYS | H | 98 | −9.289 | 6.614 | −32.781 | 1.00 | 11.17 | H |
| ATOM | 3640 | C | LYS | H | 98 | −4.631 | 8.081 | −32.291 | 1.00 | 5.55 | H |
| ATOM | 3641 | O | LYS | H | 98 | −4.677 | 6.876 | −32.522 | 1.00 | 4.02 | H |
| ATOM | 3642 | N | ALA | H | 99 | −4.526 | 8.582 | −31.063 | 1.00 | 5.94 | H |
| ATOM | 3643 | CA | ALA | H | 99 | −4.466 | 7.744 | −29.870 | 1.00 | 6.05 | H |
| ATOM | 3644 | CB | ALA | H | 99 | −3.893 | 8.530 | −28.713 | 1.00 | 5.32 | H |
| ATOM | 3645 | C | ALA | H | 99 | −5.851 | 7.215 | −29.498 | 1.00 | 6.38 | H |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 3646 O | ALA | H | 99 | −6.880 | 7.829 | −29.806 | 1.00 | 6.74 | H |
| ATOM | 3647 N | LYS | H | 100 | −5.863 | 6.073 | −28.823 | 1.00 | 6.25 | H |
| ATOM | 3648 CA | LYS | H | 100 | −7.109 | 5.446 | −28.432 | 1.00 | 6.98 | H |
| ATOM | 3649 CB | LYS | H | 100 | −6.862 | 4.012 | −27.966 | 1.00 | 7.85 | H |
| ATOM | 3650 CG | LYS | H | 100 | −8.137 | 3.260 | −27.666 | 1.00 | 8.20 | H |
| ATOM | 3651 CD | LYS | H | 100 | −7.854 | 1.843 | −27.230 | 1.00 | 10.16 | H |
| ATOM | 3652 CE | LYS | H | 100 | −7.573 | 0.930 | −28.401 | 1.00 | 11.45 | H |
| ATOM | 3653 NZ | LYS | H | 100 | −8.683 | 0.917 | −29.389 | 1.00 | 10.69 | H |
| ATOM | 3654 C | LYS | H | 100 | −7.833 | 6.209 | −27.337 | 1.00 | 7.43 | H |
| ATOM | 3655 O | LYS | H | 100 | −9.067 | 6.222 | −27.292 | 1.00 | 7.57 | H |
| ATOM | 3656 N | ARG | H | 101 | −7.068 | 6.848 | −26.455 | 1.00 | 6.66 | H |
| ATOM | 3657 CA | ARG | H | 101 | −7.667 | 7.591 | −25.355 | 1.00 | 5.82 | H |
| ATOM | 3658 CB | ARG | H | 101 | −7.125 | 7.080 | −24.033 | 1.00 | 7.35 | H |
| ATOM | 3659 CG | ARG | H | 101 | −6.901 | 5.583 | −24.024 | 1.00 | 8.88 | H |
| ATOM | 3660 CD | ARG | H | 101 | −6.708 | 5.089 | −22.605 | 1.00 | 10.61 | H |
| ATOM | 3661 NE | ARG | H | 101 | −7.985 | 4.767 | −21.985 | 1.00 | 11.45 | H |
| ATOM | 3662 CZ | ARG | H | 101 | −8.324 | 5.114 | −20.755 | 1.00 | 13.93 | H |
| ATOM | 3663 NH1 | ARG | H | 101 | −7.479 | 5.808 | −19.996 | 1.00 | 17.72 | H |
| ATOM | 3664 NH2 | ARG | H | 101 | −9.504 | 4.753 | −20.281 | 1.00 | 12.33 | H |
| ATOM | 3665 C | ARG | H | 101 | −7.432 | 9.085 | −25.459 | 1.00 | 4.76 | H |
| ATOM | 3666 O | ARG | H | 101 | −6.777 | 9.534 | −26.393 | 1.00 | 6.34 | H |
| ATOM | 3667 N | VAL | H | 102 | −7.960 | 9.848 | −24.501 | 1.00 | 3.31 | H |
| ATOM | 3668 CA | VAL | H | 102 | −7.815 | 11.302 | −24.516 | 1.00 | 1.00 | H |
| ATOM | 3669 CB | VAL | H | 102 | −8.656 | 12.030 | −23.457 | 1.00 | 2.44 | H |
| ATOM | 3670 CG1 | VAL | H | 102 | −9.799 | 12.724 | −24.127 | 1.00 | 1.07 | H |
| ATOM | 3671 CG2 | VAL | H | 102 | −9.099 | 11.083 | −22.353 | 1.00 | 1.00 | H |
| ATOM | 3672 C | VAL | H | 102 | −6.434 | 11.817 | −24.301 | 1.00 | 1.00 | H |
| ATOM | 3673 O | VAL | H | 102 | −6.142 | 12.932 | −24.688 | 1.00 | 1.36 | H |
| ATOM | 3674 N | GLY | H | 103 | −5.592 | 11.034 | −23.650 | 1.00 | 1.00 | H |
| ATOM | 3675 CA | GLY | H | 103 | −4.246 | 11.501 | −23.422 | 1.00 | 2.80 | H |
| ATOM | 3676 C | GLY | H | 103 | −3.334 | 10.895 | −24.457 | 1.00 | 5.14 | H |
| ATOM | 3677 O | GLY | H | 103 | −3.778 | 10.171 | −25.335 | 1.00 | 5.99 | H |
| ATOM | 3678 N | ALA | H | 104 | −2.057 | 11.224 | −24.381 | 1.00 | 7.98 | H |
| ATOM | 3679 CA | ALA | H | 104 | −1.081 | 10.647 | −25.281 | 1.00 | 11.22 | H |
| ATOM | 3680 CB | ALA | H | 104 | 0.259 | 11.310 | −25.052 | 1.00 | 12.12 | H |
| ATOM | 3681 C | ALA | H | 104 | −1.080 | 9.230 | −24.730 | 1.00 | 13.71 | H |
| ATOM | 3682 O | ALA | H | 104 | −0.454 | 8.956 | −23.703 | 1.00 | 16.89 | H |
| ATOM | 3683 N | THR | H | 105 | −1.808 | 8.339 | −25.383 | 1.00 | 12.18 | H |
| ATOM | 3684 CA | THR | H | 105 | −1.913 | 6.979 | −24.889 | 1.00 | 10.87 | H |
| ATOM | 3685 CB | THR | H | 105 | −3.137 | 6.300 | −25.540 | 1.00 | 11.27 | H |
| ATOM | 3686 OG1 | THR | H | 105 | −4.258 | 7.186 | −25.458 | 1.00 | 11.02 | H |
| ATOM | 3687 CG2 | THR | H | 105 | −3.497 | 5.020 | −24.828 | 1.00 | 11.22 | H |
| ATOM | 3688 C | THR | H | 105 | −0.646 | 6.143 | −25.097 | 1.00 | 10.95 | H |
| ATOM | 3689 O | THR | H | 105 | −0.193 | 5.472 | −24.173 | 1.00 | 11.18 | H |
| ATOM | 3690 N | GLY | H | 106 | −0.080 | 6.193 | −26.303 | 1.00 | 9.89 | H |
| ATOM | 3691 CA | GLY | H | 106 | 1.108 | 5.422 | −26.610 | 1.00 | 8.03 | H |
| ATOM | 3692 C | GLY | H | 106 | 0.873 | 4.532 | −27.821 | 1.00 | 9.08 | H |
| ATOM | 3693 O | GLY | H | 106 | 1.806 | 4.189 | −28.551 | 1.00 | 8.94 | H |
| ATOM | 3694 N | TYR | H | 107 | −0.381 | 4.152 | −28.041 | 1.00 | 9.04 | H |
| ATOM | 3695 CA | TYR | H | 107 | −0.722 | 3.318 | −29.178 | 1.00 | 7.70 | H |
| ATOM | 3696 CB | TYR | H | 107 | −1.167 | 1.918 | −28.728 | 1.00 | 7.28 | H |
| ATOM | 3697 CG | TYR | H | 107 | −2.176 | 1.870 | −27.621 | 1.00 | 6.75 | H |
| ATOM | 3698 CD1 | TYR | H | 107 | −3.531 | 1.704 | −27.889 | 1.00 | 7.50 | H |
| ATOM | 3699 CE1 | TYR | H | 107 | −4.461 | 1.622 | −26.868 | 1.00 | 9.33 | H |
| ATOM | 3700 CD2 | TYR | H | 107 | −1.773 | 1.954 | −26.308 | 1.00 | 7.00 | H |
| ATOM | 3701 CE2 | TYR | H | 107 | −2.680 | 1.871 | −25.281 | 1.00 | 8.83 | H |
| ATOM | 3702 CZ | TYR | H | 107 | −4.029 | 1.706 | −25.552 | 1.00 | 11.18 | H |
| ATOM | 3703 OH | TYR | H | 107 | −4.940 | 1.646 | −24.498 | 1.00 | 13.47 | H |
| ATOM | 3704 C | TYR | H | 107 | −1.793 | 4.036 | −29.970 | 1.00 | 8.28 | H |
| ATOM | 3705 O | TYR | H | 107 | −2.670 | 4.694 | −29.404 | 1.00 | 8.79 | H |
| ATOM | 3706 N | PHE | H | 108 | −1.707 | 3.904 | −31.290 | 1.00 | 8.59 | H |
| ATOM | 3707 CA | PHE | H | 108 | −2.618 | 4.594 | −32.194 | 1.00 | 7.43 | H |
| ATOM | 3708 CB | PHE | H | 108 | −1.803 | 5.633 | −32.928 | 1.00 | 6.07 | H |
| ATOM | 3709 CG | PHE | H | 108 | −0.641 | 6.100 | −32.138 | 1.00 | 3.15 | H |
| ATOM | 3710 CD1 | PHE | H | 108 | −0.828 | 6.931 | −31.033 | 1.00 | 3.84 | H |
| ATOM | 3711 CD2 | PHE | H | 108 | 0.631 | 5.640 | −32.428 | 1.00 | 1.87 | H |
| ATOM | 3712 CE1 | PHE | H | 108 | 0.251 | 7.304 | −30.206 | 1.00 | 1.62 | H |
| ATOM | 3713 CE2 | PHE | H | 108 | 1.720 | 5.998 | −31.621 | 1.00 | 2.47 | H |
| ATOM | 3714 CZ | PHE | H | 108 | 1.529 | 6.834 | −30.503 | 1.00 | 1.15 | H |
| ATOM | 3715 C | PHE | H | 108 | −3.343 | 3.712 | −33.189 | 1.00 | 7.78 | H |
| ATOM | 3716 O | PHE | H | 108 | −2.716 | 3.093 | −34.041 | 1.00 | 7.98 | H |
| ATOM | 3717 N | ASP | H | 109 | −4.671 | 3.703 | −33.092 | 1.00 | 7.48 | H |
| ATOM | 3718 CA | ASP | H | 109 | −5.522 | 2.904 | −33.958 | 1.00 | 6.76 | H |
| ATOM | 3719 CB | ASP | H | 109 | −6.827 | 2.525 | −33.251 | 1.00 | 8.37 | H |

TABLE VIII-continued

Structure coordinates of the epitopes of allergenic beta-lactoglobulin in an antibody-beta-lactoglobulin immunocomplex;

| | | Atom type | Resid | # | X | Y | Z | OCC | B | |
|---|---|---|---|---|---|---|---|---|---|---|
| ATOM | 3720 | CG | ASP | H | 109 | −7.497 | 3.708 | −32.566 | 1.00 | 9.76 | H |
| ATOM | 3721 | OD1 | ASP | H | 109 | −7.446 | 4.836 | −33.080 | 1.00 | 12.11 | H |
| ATOM | 3722 | OD2 | ASP | H | 109 | −8.092 | 3.513 | −31.496 | 1.00 | 11.64 | H |
| ATOM | 3723 | C | ASP | H | 109 | −5.867 | 3.540 | −35.287 | 1.00 | 6.63 | H |
| ATOM | 3724 | O | ASP | H | 109 | −6.497 | 2.904 | −36.137 | 1.00 | 7.36 | H |
| ATOM | 3725 | N | LEU | H | 110 | −5.466 | 4.782 | −35.500 | 1.00 | 5.24 | H |
| ATOM | 3726 | CA | LEU | H | 110 | −5.786 | 5.398 | −36.781 | 1.00 | 5.19 | H |
| ATOM | 3727 | CB | LEU | H | 110 | −7.013 | 6.295 | −36.650 | 1.00 | 4.04 | H |
| ATOM | 3728 | CG | LEU | H | 110 | −7.465 | 6.907 | −37.979 | 1.00 | 4.58 | H |
| ATOM | 3729 | CD1 | LEU | H | 110 | −7.936 | 5.827 | −38.912 | 1.00 | 1.00 | H |
| ATOM | 3730 | CD2 | LEU | H | 110 | −8.592 | 7.914 | −37.717 | 1.00 | 6.43 | H |
| ATOM | 3731 | C | LEU | H | 110 | −4.624 | 6.200 | −37.298 | 1.00 | 5.51 | H |
| ATOM | 3732 | O | LEU | H | 110 | −4.076 | 7.038 | −36.592 | 1.00 | 6.65 | H |
| ATOM | 3733 | N | TRP | H | 111 | −4.247 | 5.957 | −38.538 | 1.00 | 4.26 | H |
| ATOM | 3734 | CA | TRP | H | 111 | −3.132 | 6.702 | −39.088 | 1.00 | 4.57 | H |
| ATOM | 3735 | CB | TRP | H | 111 | −1.912 | 5.790 | −39.296 | 1.00 | 3.02 | H |
| ATOM | 3736 | CG | TRP | H | 111 | −1.291 | 5.208 | −38.059 | 1.00 | 1.95 | H |
| ATOM | 3737 | CD2 | TRP | H | 111 | 0.081 | 5.316 | −37.665 | 1.00 | 1.00 | H |
| ATOM | 3738 | CE2 | TRP | H | 111 | 0.246 | 4.528 | −36.503 | 1.00 | 1.00 | H |
| ATOM | 3739 | CE3 | TRP | H | 111 | 1.189 | 6.001 | −38.187 | 1.00 | 1.00 | H |
| ATOM | 3740 | CD1 | TRP | H | 111 | −1.890 | 4.389 | −37.140 | 1.00 | 2.44 | H |
| ATOM | 3741 | NE1 | TRP | H | 111 | −0.971 | 3.975 | −36.206 | 1.00 | 1.00 | H |
| ATOM | 3742 | CZ2 | TRP | H | 111 | 1.482 | 4.401 | −35.851 | 1.00 | 1.00 | H |
| ATOM | 3743 | CZ3 | TRP | H | 111 | 2.412 | 5.882 | −37.549 | 1.00 | 1.00 | H |
| ATOM | 3744 | CH2 | TRP | H | 111 | 2.553 | 5.084 | −36.387 | 1.00 | 2.97 | H |
| ATOM | 3745 | C | TRP | H | 111 | −3.534 | 7.310 | −40.423 | 1.00 | 5.19 | H |
| ATOM | 3746 | O | TRP | H | 111 | −4.602 | 7.016 | −40.963 | 1.00 | 4.62 | H |
| ATOM | 3747 | N | GLY | H | 112 | −2.669 | 8.178 | −40.933 | 1.00 | 6.36 | H |
| ATOM | 3748 | CA | GLY | H | 112 | −2.917 | 8.808 | −42.209 | 1.00 | 7.94 | H |
| ATOM | 3749 | C | GLY | H | 112 | −1.848 | 8.270 | −43.134 | 1.00 | 9.94 | H |
| ATOM | 3750 | O | GLY | H | 112 | −0.962 | 7.545 | −42.674 | 1.00 | 7.59 | H |
| ATOM | 3751 | N | ARG | H | 113 | −1.911 | 8.609 | −44.420 | 1.00 | 12.17 | H |
| ATOM | 3752 | CA | ARG | H | 113 | −0.918 | 8.130 | −45.387 | 1.00 | 14.63 | H |
| ATOM | 3753 | CB | ARG | H | 113 | −1.415 | 8.357 | −46.821 | 1.00 | 19.69 | H |
| ATOM | 3754 | CG | ARG | H | 113 | −2.716 | 7.645 | −47.220 | 1.00 | 26.76 | H |
| ATOM | 3755 | CD | ARG | H | 113 | −3.136 | 7.992 | −48.682 | 1.00 | 32.39 | H |
| ATOM | 3756 | NE | ARG | H | 113 | −3.098 | 9.435 | −48.981 | 1.00 | 36.17 | H |
| ATOM | 3757 | CZ | ARG | H | 113 | −3.435 | 9.974 | −50.154 | 1.00 | 39.14 | H |
| ATOM | 3758 | NH1 | ARG | H | 113 | −3.844 | 9.194 | −51.153 | 1.00 | 40.77 | H |
| ATOM | 3759 | NH2 | ARG | H | 113 | −3.348 | 11.291 | −50.334 | 1.00 | 39.73 | H |
| ATOM | 3760 | C | ARG | H | 113 | 0.459 | 8.801 | −45.236 | 1.00 | 13.93 | H |
| ATOM | 3761 | O | ARG | H | 113 | 1.454 | 8.288 | −45.747 | 1.00 | 14.13 | H |
| ATOM | 3762 | N | GLY | H | 114 | 0.508 | 9.949 | −44.560 | 1.00 | 12.46 | H |
| ATOM | 3763 | CA | GLY | H | 114 | 1.763 | 10.660 | −44.373 | 1.00 | 10.52 | H |
| ATOM | 3764 | C | GLY | H | 114 | 2.053 | 11.683 | −45.468 | 1.00 | 9.35 | H |
| ATOM | 3765 | O | GLY | H | 114 | 1.436 | 11.642 | −46.527 | 1.00 | 8.23 | H |
| ATOM | 3766 | N | THR | H | 115 | 2.963 | 12.618 | −45.192 | 1.00 | 8.71 | H |
| ATOM | 3767 | CA | THR | H | 115 | 3.398 | 13.635 | −46.151 | 1.00 | 6.50 | H |
| ATOM | 3768 | CB | THR | H | 115 | 3.021 | 15.043 | −45.753 | 1.00 | 7.27 | H |
| ATOM | 3769 | OG1 | THR | H | 115 | 1.952 | 14.999 | −44.822 | 1.00 | 9.76 | H |
| ATOM | 3770 | CG2 | THR | H | 115 | 2.636 | 15.855 | −46.966 | 1.00 | 7.54 | H |
| ATOM | 3771 | C | THR | H | 115 | 4.925 | 13.624 | −46.129 | 1.00 | 7.01 | H |
| ATOM | 3772 | O | THR | H | 115 | 5.554 | 13.574 | −45.055 | 1.00 | 2.98 | H |
| ATOM | 3773 | N | LEU | H | 116 | 5.511 | 13.699 | −47.318 | 1.00 | 6.85 | H |
| ATOM | 3774 | CA | LEU | H | 116 | 6.953 | 13.701 | −47.463 | 1.00 | 6.07 | H |
| ATOM | 3775 | CB | LEU | H | 116 | 7.352 | 13.132 | −48.812 | 1.00 | 5.44 | H |
| ATOM | 3776 | CG | LEU | H | 116 | 8.812 | 13.352 | −49.199 | 1.00 | 5.58 | H |
| ATOM | 3777 | CD1 | LEU | H | 116 | 9.727 | 12.426 | −48.399 | 1.00 | 3.24 | H |
| ATOM | 3778 | CD2 | LEU | H | 116 | 8.941 | 13.099 | −50.685 | 1.00 | 5.27 | H |
| ATOM | 3779 | C | LEU | H | 116 | 7.531 | 15.082 | −47.350 | 1.00 | 7.43 | H |
| ATOM | 3780 | O | LEU | H | 116 | 7.132 | 15.997 | −48.059 | 1.00 | 9.44 | H |
| ATOM | 3781 | N | VAL | H | 117 | 8.481 | 15.228 | −46.443 | 1.00 | 9.93 | H |
| ATOM | 3782 | CA | VAL | H | 117 | 9.151 | 16.500 | −46.275 | 1.00 | 11.48 | H |
| ATOM | 3783 | CB | VAL | H | 117 | 9.107 | 16.966 | −44.817 | 1.00 | 11.24 | H |
| ATOM | 3784 | CG1 | VAL | H | 117 | 9.929 | 18.231 | −44.648 | 1.00 | 11.87 | H |
| ATOM | 3785 | CG2 | VAL | H | 117 | 7.675 | 17.217 | −44.418 | 1.00 | 11.74 | H |
| ATOM | 3786 | C | VAL | H | 117 | 10.587 | 16.250 | −46.706 | 1.00 | 11.33 | H |
| ATOM | 3787 | O | VAL | H | 117 | 11.247 | 15.342 | −46.187 | 1.00 | 10.03 | H |
| ATOM | 3788 | N | THR | H | 118 | 11.049 | 17.032 | −47.677 | 1.00 | 11.55 | H |
| ATOM | 3789 | CA | THR | H | 118 | 12.412 | 16.898 | −48.182 | 1.00 | 13.80 | H |
| ATOM | 3790 | CB | THR | H | 118 | 12.469 | 16.720 | −49.714 | 1.00 | 12.54 | H |
| ATOM | 3791 | OG1 | THR | H | 118 | 11.597 | 15.658 | −50.113 | 1.00 | 17.37 | H |
| ATOM | 3792 | CG2 | THR | H | 118 | 13.880 | 16.398 | −50.147 | 1.00 | 11.46 | H |
| ATOM | 3793 | C | THR | H | 118 | 13.156 | 18.177 | −47.889 | 1.00 | 15.05 | H |

TABLE VIII-continued

Structure coordinates of the epitopes of allergenic beta-lactoglobulin in an antibody-beta-lactoglobulin immunocomplex;

| | Atom type | Resid | | # | X | Y | Z | OCC | B | |
|---|---|---|---|---|---|---|---|---|---|---|
| ATOM | 3794 O | THR | H | 118 | 12.809 | 19.235 | −48.422 | 1.00 | 16.32 | H |
| ATOM | 3795 N | VAL | H | 119 | 14.176 | 18.102 | −47.048 | 1.00 | 14.62 | H |
| ATOM | 3796 CA | VAL | H | 119 | 14.932 | 19.302 | −46.763 | 1.00 | 15.25 | H |
| ATOM | 3797 CB | VAL | H | 119 | 15.212 | 19.441 | −45.249 | 1.00 | 15.70 | H |
| ATOM | 3798 CG1 | VAL | H | 119 | 15.740 | 18.137 | −44.684 | 1.00 | 18.79 | H |
| ATOM | 3799 CG2 | VAL | H | 119 | 16.205 | 20.559 | −45.013 | 1.00 | 14.10 | H |
| ATOM | 3800 C | VAL | H | 119 | 16.242 | 19.309 | −47.544 | 1.00 | 15.85 | H |
| ATOM | 3801 O | VAL | H | 119 | 17.170 | 18.567 | −47.232 | 1.00 | 15.88 | H |
| ATOM | 3802 N | SER | H | 120 | 16.297 | 20.129 | −48.589 | 1.00 | 17.32 | H |
| ATOM | 3803 CA | SER | H | 120 | 17.511 | 20.245 | −49.385 | 1.00 | 18.51 | H |
| ATOM | 3804 CB | SER | H | 120 | 17.491 | 19.307 | −50.597 | 1.00 | 18.68 | H |
| ATOM | 3805 OG | SER | H | 120 | 17.034 | 19.984 | −51.754 | 1.00 | 16.68 | H |
| ATOM | 3806 C | SER | H | 120 | 17.669 | 21.665 | −49.879 | 1.00 | 19.18 | H |
| ATOM | 3807 O | SER | H | 120 | 16.789 | 22.509 | −49.698 | 1.00 | 16.51 | H |
| ATOM | 3808 N | SER | H | 121 | 18.808 | 21.908 | −50.518 | 1.00 | 21.95 | H |
| ATOM | 3809 CA | SER | H | 121 | 19.120 | 23.215 | −51.069 | 1.00 | 23.17 | H |
| ATOM | 3810 CB | SER | H | 121 | 20.568 | 23.602 | −50.719 | 1.00 | 22.76 | H |
| ATOM | 3811 OG | SER | H | 121 | 20.655 | 24.126 | −49.404 | 1.00 | 23.27 | H |
| ATOM | 3812 C | SER | H | 121 | 18.890 | 23.299 | −52.584 | 1.00 | 23.84 | H |
| ATOM | 3813 O | SER | H | 121 | 18.862 | 24.394 | −53.122 | 1.00 | 24.66 | H |

REMARK A = monomer A of allergen;
REMARK L = light chain of antibody, variable domain;
REMARK H = heavy chain of antibody, variable domain

TABLE IX

Amino acid sequences of the rBLG-His6, rBLG-His6 T18Y and rBLG-His6 T18Y/E45Y/L57Y are shown. The His6 tag is in italics, mutated amino acids are bolded and underlined.

rBLG-His6:
(SEQ ID NO: 9)
```
  1 LIVTQTMKGL DIQKVAGTWY SLAMAASDIS LLDAQSABLR
 41 VYVEELKBTB EGDLEILLQK WENGECAQKK IIAEKTKIPA
 81 VFKIDALNEN KVLVLDTDYK KYLLFCMENS AEBEQSLVCQ
121 CLVRTBEVDD EALEKFDKAL KALBMHIRLS FNBTQLEEQC
161 HI*HHHHHH*
``` rBLG-His6 T18Y:
(SEQ ID NO: 10)
```
  1 LIVTQTMKGL DIQKVAGYWY SLAMAASDIS LLDAQSABLR
 41 VYVEELKBTB EGDLEILLQK WENGECAQKK IIAEKTKIPA
 81 VFKIDALNEN KVLVLDTDYK KYLLFCMENS AEBEQSLVCQ
121 CLVRTPEVDD EALEKFDKAL KALBMHIRLS FNPTQLEEQC
161 HI*HHHHHH*
``` rBLG-His6 T18Y/E45Y/L57Y:
(SEQ ID NO: 11)
```
  1 LIVTQTMKGL DIQKVAGYWY SLAMAASDIS LLDAQSAPLR
 41 VYVEYLKPTP EGDLEIYLQK WENGECAQKK IIAEKTKIPA
 81 VFKIDALNEN KVLVLDTDYK KYLLFCMENS AEPEQSLVCQ
121 CLVRTPEVDD EALEKFDKAL KALPMHIRLS FNPTQLEEQC
161 HI*HHHHHH*
```

TABLE X

The primers used for the PCR amplification of rBLG-His6, rBLG-His6 T18Y and rBLG-His6 T18Y/E45Y/L57Y mutant. Restriction enzyme sites are shown in italics. Overlapping areas and stop codons are underlined. Mutated codons are bolded, underlined and in italics.

```
                    SfiI              NcoI
Primer 1. GAA TCC GC*G* *GCC CAG CCG* *GCC* ATG *GCC* CTG ATT GTG
          ACC (SEQ ID NO: 124)

HindIII    Stop
Primer 2. TTA CTC *AAG CTT* TTA ATG GTG ATG GTG ATG ATG AAT ATG
          GCA CTG TTC TTC CAG C (SEQ ID NO: 125)

StuI
Primer 3. CC ATG AAA *GGC CTG* GAT ATT CAG AAA GTG GCG GGC *TAC*
          TGG TAT AGC C (SEQ ID NO: 126)

Overlapping area with the primer 5
Primer 4. *ATA* AAT TTC CAG ATC GCC TTC CGG GGT CGG TTT CAG *ATA*
          TTC CAC ATA CAC ACG C (SEQ ID NO: 127)
```

TABLE X-continued

The primers used for the PCR amplification of rBLG-His6,
rBLG-His6 T18Y and rBLG-His6 T18Y/E45Y/L57Y mutant.
Restriction enzyme sites are shown in italics.
Overlapping areas and stop codons are underlined.
Mutated codons are bolded, underlined and in italics.

```
           Overlapping area with the primer 4
Primer 5.  GGC GAT CTG GAA ATT TAT CTG CAG AAA TGG G
           (SEQ ID NO: 124)
```

TABLE XI

The association and dissociation constants of the D1 IgE Fab
to nBLG, rBLG-His6 and its mutants (see FIG. 24).

|  | nBLG | rBLGhis | T18Y | Triple mutant |
|---|---|---|---|---|
| Kd (1/s) | $4.8e^{-3}$ | $8.2e^{-3}$ | $8.2e^{-2}$ | — |
| Ka (1/Ms) | $1.8e^{6}$ | $9.61e^{5}$ | $1.3e^{5}$ | — |
| KD (M) | $2.7e^{-9}$ | $8.5e^{-9}$ | $6.1e^{-7}$ | — |
| KA (1/M) | $3.2e^{8}$ | $1.2e^{8}$ | $1.6e^{6}$ | — |

REFERENCES

Argos, P. (1988) *Protein Engineering*, 2, 101-113.
Banerjee, B., Wang, X., Kelly, K. J., Fink, J. N., Sussman, G. L., and Kurup, V. P. (1997) *J. Immunol.* 159, 5724-5732.
Barbas III, C. F., Kang, A. S., Lerner, R. A., and Benkovic, S. J. (1991) *Proc. Natl. Acad. Sci. U.S.A.* 88, 7978-7982.
Brownlow, S., Cabral, J. H. M, Cooper, R., Flower, D. R., Yewdall, S. J., Polikarpov, I., North, A. C. T., Sawyer, L. (1997) *Structure* 5, 481-495
Corry, D. B., and Kheradmand, F. (1999) *Nature* 402, B18-B23.
De Genst, E., Silence, K., Decanniere, K., Conrath, K., Loris, R., Kinne, J., Muyldermans, S, and Wyns, L. (2006) *Proc. Natl. Acad. Sci. U.S.A.* 103, 4586-4591.
Desplancq, D., King, D. J., Lawson, A. D. G., and Mountain, A. (1994) *Protein Eng.* 7, 1027-1033.
Godovac-Zimmermann J. and Braunitzer G. (1987) *Milchwissenchaft* 42(5), 294-297.
Hill, D. J., Hosking, C. S. and Heine, R. G. (1999) *Ann. Med.* 31, 272-281.
Holliger, P., Prospero, T., and Winter, G. (1993) *Proc. Natl. Acad. Sci. U.S.A.* 90, 6444-6448.
Hoogenboom, H. R., de Bruïne, A. P., Hufton, S. E., Hoet, R. M., Arends, J.-W. and Roovers, R. C. (1998) *Immunotechnolgy* 4, 1-20.
Host, A. and Halken, S. (1990) *Allergy* 45, 587-596.
Kabat, E. A., Wu, T. T., Reid-Miller, M., Perry, H. M., and Gottesman, K. S. (1991) *Sequences of Proteins of Immunological Interest*, 4th Ed., U.S. Dept. of Health and Human Services, Bethesda, Md.
McCafferty, J., Griffiths, A. D., Winter, G., and Chiswell, F. J. (1990) *Nature* 348, 552-554.
Nevanen, T. K, Söderholm, L., Kukkonen, K., Suortti, T., Teerinen, T., Linder, M., Söderlund, H., Teeri, T. T. (2001) *J. Chromatogr. A* 925, 89-97.
Rouvinen, J., Virtanen, T., Mäntyjärvi, R. (2001) *J. Chromatogr. B* 756, 199-206.
Saarinen, K. M., Juntunen-Backman, K., Jarvenpaa, A. L., Kuitunen, P., Lope, L., Renlund, M., Siivola, M. and Savilahti, E. (1999) *J. Allergy Clin. Immunol.* 104, 457-461.
Saarinen, K. M. (2000) *Risk factors and characteristics of cow's milk allergy*. In. Helsinki University, Helsinki, Finland.
Sampson, H. A. and Scanlon, S. M. (1989) *J Pediatr* 115, 23-7.
Sanger, F., Nicklen, S., and Coulson, A. R. (1977) *Proc. Natl. Acad. Sci. U.S.A.* 74, 5463-5467.
Savilahti, E. (1981) *Allergy* 36, 73-88.
Sawyer, L., Papiz, M. Z., North, A., Eliopoulos, E (1985) *Biochemical Society Transactions* 13(1), 265-6
Schrander, J. J., van den Bogart, J. P., Forget, P. P., Schrander-Stumpel, C. T., Kuijten, R. H. and Kester, A. D. (1993) *Eur. J. Pediatr.* 152, 640-644.
Steinberger, P., Kraft, D., and Valenta, R. (1996) *J. Biol. Chem.* 271, 10967-10972.
Vaarala, O., Saukkonen, T., Savilahti, E., Klemola, T. and Akerblom, H. K. (1995) *J. Allergy Clin. Immunol.* 96, 917-23.

The invention claimed is:

1. A method for selecting a modified β-lactoglobulin as a hypoallergen candidate, the method comprising the steps of:
   (a) modifying an unmodified nucleic acid sequence encoding unmodified β-lactoglobulin represented by SEQ ID NO: 8 to produce a modified nucleic acid sequence encoding a modified β-lactoglobulin, wherein the modified β-lactoglobulin comprises an amino acid mutation in 1-5 amino acids in one or more of the following amino acid regions of SEQ ID NO:8: 18-20, 42-47, 55-59, 65-70, 125-127, and 154-161;
   (b) expressing or producing the modified β-lactoglobulin from the modified nucleic acid sequence;
   (c) contacting the modified β-lactoglobulin with an IgE antibody specific for unmodified β-lactoglobulin;
   (d) comparing binding affinity of the modified β-lactoglobulin to the IgE antibody to binding affinity of unmodified β-lactoglobulin to the IgE antibody; and
   (e) selecting the modified β-lactoglobulin as a hypoallergen candidate if the binding affinity of the modified β-lactoglobulin to the IgE antibody is decreased by at least tenfold compared to the binding affinity of the IgE antibody to the unmodified β-lactoglobulin.

2. A method for producing a modified allergenic polypeptide, the method comprising the steps of:
   (a) modifying an unmodified nucleic acid sequence encoding an unmodified β-lactoglobulin polypeptide (SEQ ID NO:8) to produce a modified nucleic acid sequence encoding a modified β-lactoglobulin polypeptide wherein the modified β-lactoglobulin polypeptide comprises a T18Y mutation or a T18Y/E45Y/L57Y mutation; and
   (b) expressing or producing the modified β-lactoglobulin polypeptide from the modified nucleic acid.

3. A method according to claim 1, wherein the modified β-lactoglobulin comprises an amino acid mutation in at least amino acid region 18-20.

4. A method according to claim 1, wherein the modified β-lactoglobulin comprises an amino acid mutation in at least amino acid region 42-47.

5. A method according to claim 1, wherein the modified β-lactoglobulin comprises an amino acid mutation in at least amino acid region 55-59.

6. A method according to claim 1, wherein the modified β-lactoglobulin comprises an amino acid mutation in at least amino acid region 65-70.

7. A method according to claim 1, wherein the modified β-lactoglobulin comprises an amino acid mutation in at least amino acid region 154-161.

* * * * *